(12) United States Patent
Hamblin et al.

(10) Patent No.: US 9,394,374 B2
(45) Date of Patent: Jul. 19, 2016

(54) ANTIGEN-BINDING PROTEINS

(75) Inventors: Paul Andrew Hamblin, Stevenage (GB); Alan Peter Lewis, Stevenage (GB); Martin Anibal Orecchia, Stevenage (GB); Radha Shah Parmar, Stevenage (GB)

(73) Assignee: Glaxo Group Limited, Brentford, Middlesex (GB)

( * ) Notice: Subject to any disclaimer, the term of this patent is extended or adjusted under 35 U.S.C. 154(b) by 1076 days.

(21) Appl. No.: 13/322,224

(22) PCT Filed: May 26, 2010

(86) PCT No.: PCT/EP2010/057231
§ 371 (c)(1),
(2), (4) Date: Nov. 23, 2011

(87) PCT Pub. No.: WO2010/136483
PCT Pub. Date: Dec. 2, 2010

(65) Prior Publication Data
US 2012/0070439 A1    Mar. 22, 2012

Related U.S. Application Data

(60) Provisional application No. 61/181,893, filed on May 28, 2009.

(51) Int. Cl.
*C07K 16/00* (2006.01)
*C07K 16/46* (2006.01)
*C07K 16/22* (2006.01)
*C07K 16/24* (2006.01)
*C07K 16/28* (2006.01)

(52) U.S. Cl.
CPC ............... *C07K 16/468* (2013.01); *C07K 16/22* (2013.01); *C07K 16/241* (2013.01); *C07K 16/244* (2013.01); *C07K 16/247* (2013.01); *C07K 16/2863* (2013.01); *C07K 16/2866* (2013.01); *C07K 2317/31* (2013.01); *C07K 2317/52* (2013.01); *C07K 2317/569* (2013.01); *C07K 2318/20* (2013.01); *C07K 2319/30* (2013.01)

(58) Field of Classification Search
None
See application file for complete search history.

(56) References Cited

FOREIGN PATENT DOCUMENTS

| WO | WO2007/066106 | * | 6/2007 |
|----|---------------|---|--------|
| WO | WO 2007/066106 A1 | | 6/2007 |
| WO | WO2007/085814 | * | 8/2007 |
| WO | WO 2007/085814 A1 | | 8/2007 |
| WO | WO 2007/085815 | | 8/2007 |
| WO | WO 2009/068649 A2 | | 6/2009 |

OTHER PUBLICATIONS

Shen et al. (Journal of Immunological Methods, vol. 318, No. 1-2,3, p. 65-74, Jan. 2007).*
Shen, et al., J. Immunol. Meth., vol. 318, No. 1-2, 3 Jan. 2007, pp. 65-74.

* cited by examiner

*Primary Examiner* — Laura B Goddard
*Assistant Examiner* — Meera Natarajan
(74) *Attorney, Agent, or Firm* — Leah M. Octavio; Andrea V. Lockenour

(57) ABSTRACT

The invention relates to linkers suitable for use in antigen-binding proteins, certain antigen binding proteins and methods of making such proteins and uses thereof.

40 Claims, 14 Drawing Sheets

SEQUENCE LISTING

<160> NUMBER OF SEQ ID NOS: 114

<210> SEQ ID NO 1
<211> LENGTH: 118

```
<212> TYPE: PRT
<213> ORGANISM: Homo Sapiens

<400> SEQUENCE: 1

Gly Val Gln Leu Leu Glu Ser Gly Gly Gly Leu Val Gln Pro Gly Gly
 1               5                  10                  15

Ser Leu Arg Leu Ser Cys Ala Ala Ser Gly Phe Val Phe Pro Trp Tyr
            20                  25                  30

Asp Met Gly Trp Val Arg Gln Ala Pro Gly Lys Gly Leu Glu Trp Val
        35                  40                  45

Ser Ser Ile Asp Trp His Gly Lys Ile Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ala Glu Asp Glu Pro Gly Tyr Asp Tyr Trp Gly Gln Gly Thr
            100                 105                 110

Leu Val Thr Val Ser Ser
        115

<210> SEQ ID NO 2
<211> LENGTH: 445
<212> TYPE: PRT
<213> ORGANISM: Artificial Sequence
<220> FEATURE:
<223> OTHER INFORMATION: Humanised

<400> SEQUENCE: 2

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
```

```
                 210                 215                 220
Thr His Thr Cys Pro Pro Cys Pro Ala Pro Glu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                    325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                    405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys
            435                 440                 445

<210> SEQ ID NO 3
<211> LENGTH: 216
<212> TYPE: PRT
<213> ORGANISM: Artificial Sequence
<220> FEATURE:
<223> OTHER INFORMATION: Humanised

<400> SEQUENCE: 3

Asp Ile Val Leu Thr Gln Ser Pro Ser Ser Leu Ser Ala Ser Val Gly
 1               5                  10                  15

Asp Arg Val Thr Ile Thr Cys Lys Ala Ser Gln Ser Val Asp Tyr Asp
                20                  25                  30

Gly Asp Ser Tyr Met Asn Trp Tyr Gln Gln Lys Pro Gly Lys Ala Pro
            35                  40                  45

Lys Leu Leu Ile Tyr Ala Asn Leu Glu Ser Gly Ile Pro Ser Arg Phe
    50                  55                  60

Ser Gly Ser Gly Ser Gly Thr Asp Phe Thr Phe Thr Ile Ser Ser Leu
65                  70                  75                  80

Gln Pro Glu Asp Ile Ala Thr Tyr Tyr Cys Gln Gln Ser Asn Glu Asp
                85                  90                  95

Pro Pro Thr Phe Gly Gln Gly Thr Lys Val Glu Ile Lys Arg Thr Val
                100                 105                 110

Ala Ala Pro Ser Val Phe Ile Phe Pro Pro Ser Asp Glu Gln Leu Lys
            115                 120                 125

Ser Gly Thr Ala Ser Val Val Cys Leu Leu Asn Asn Phe Tyr Pro Arg
```

```
                    130                 135                 140
Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
                180                 185                 190

Val Tyr Ala Cys Glu Val Thr His Gln Gly Leu Ser Ser Pro Val Thr
                195                 200                 205

Lys Ser Phe Asn Arg Gly Glu Cys
    210                 215

<210> SEQ ID NO 4
<211> LENGTH: 565
<212> TYPE: PRT
<213> ORGANISM: Homo Sapiens

<400> SEQUENCE: 4

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285
```

```
Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Gly Ser Gly
            435                 440                 445

Val Gln Leu Leu Glu Ser Gly Gly Gly Leu Val Gln Pro Gly Gly Ser
    450                 455                 460

Leu Arg Leu Ser Cys Ala Ala Ser Gly Phe Val Phe Pro Trp Tyr Asp
465                 470                 475                 480

Met Gly Trp Val Arg Gln Ala Pro Gly Lys Gly Leu Glu Trp Val Ser
                485                 490                 495

Ser Ile Asp Trp His Gly Lys Ile Thr Tyr Tyr Ala Asp Ser Val Lys
                500                 505                 510

Gly Arg Phe Thr Ile Ser Arg Asp Asn Ser Lys Asn Thr Leu Tyr Leu
            515                 520                 525

Gln Met Asn Ser Leu Arg Ala Glu Asp Thr Ala Val Tyr Tyr Cys Ala
    530                 535                 540

Thr Ala Glu Asp Glu Pro Gly Tyr Asp Tyr Trp Gly Gln Gly Thr Leu
545                 550                 555                 560

Val Thr Val Ser Ser
                565

<210> SEQ ID NO 5
<211> LENGTH: 573
<212> TYPE: PRT
<213> ORGANISM: Artificial Sequence
<220> FEATURE:
<223> OTHER INFORMATION: Fusion protein

<400> SEQUENCE: 5

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80
```

```
Val Leu Thr Met Thr Asn Met Asp Pro Val Asp Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Ser Thr
        435                 440                 445

Val Ala Ala Pro Ser Gly Ser Gly Val Gln Leu Leu Glu Ser Gly Gly
    450                 455                 460

Gly Leu Val Gln Pro Gly Gly Ser Leu Arg Leu Ser Cys Ala Ala Ser
465                 470                 475                 480

Gly Phe Val Phe Pro Trp Tyr Asp Met Gly Trp Val Arg Gln Ala Pro
                485                 490                 495

Gly Lys Gly Leu Glu Trp Val Ser Ser Ile Asp Trp His Gly Lys Ile
```

```
                    500                 505                 510
Thr Tyr Tyr Ala Asp Ser Val Lys Gly Arg Phe Thr Ile Ser Arg Asp
            515                 520                 525

Asn Ser Lys Asn Thr Leu Tyr Leu Gln Met Asn Ser Leu Arg Ala Glu
        530                 535                 540

Asp Thr Ala Val Tyr Tyr Cys Ala Thr Ala Glu Asp Glu Pro Gly Tyr
545                 550                 555                 560

Asp Tyr Trp Gly Gln Gly Thr Leu Val Thr Val Ser Ser
                565                 570

<210> SEQ ID NO 6
<211> LENGTH: 581
<212> TYPE: PRT
<213> ORGANISM: Artificial Sequence
<220> FEATURE:
<223> OTHER INFORMATION: Fusion protein

<400> SEQUENCE: 6

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
```

```
                      290                 295                 300
Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Ser Thr
        435                 440                 445

Val Ala Ala Pro Ser Gly Ser Thr Val Ala Ala Pro Ser Gly Ser Gly
    450                 455                 460

Val Gln Leu Leu Glu Ser Gly Gly Leu Val Gln Pro Gly Gly Ser
465                 470                 475                 480

Leu Arg Leu Ser Cys Ala Ala Ser Gly Phe Val Phe Pro Trp Tyr Asp
                485                 490                 495

Met Gly Trp Val Arg Gln Ala Pro Gly Lys Gly Leu Glu Trp Val Ser
            500                 505                 510

Ser Ile Asp Trp His Gly Lys Ile Thr Tyr Tyr Ala Asp Ser Val Lys
        515                 520                 525

Gly Arg Phe Thr Ile Ser Arg Asp Asn Ser Lys Asn Thr Leu Tyr Leu
    530                 535                 540

Gln Met Asn Ser Leu Arg Ala Glu Asp Thr Ala Val Tyr Tyr Cys Ala
545                 550                 555                 560

Thr Ala Glu Asp Glu Pro Gly Tyr Asp Tyr Trp Gly Gln Gly Thr Leu
                565                 570                 575

Val Thr Val Ser Ser
            580

<210> SEQ ID NO 7
<211> LENGTH: 589
<212> TYPE: PRT
<213> ORGANISM: Artificial Sequence
<220> FEATURE:
<223> OTHER INFORMATION: Fusion protein

<400> SEQUENCE: 7

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
                 20                  25                  30

Gly Met Gly Val Ser Trp Ile Arg Gln Pro Pro Gly Lys Gly Leu Glu
             35                  40                  45

Trp Leu Ala His Ile Tyr Trp Asp Asp Asp Lys Arg Tyr Asn Pro Ser
         50                  55                  60

Leu Lys Ser Arg Leu Thr Ile Ser Lys Asp Thr Ser Arg Asn Gln Val
```

-continued

```
                65                  70                  75                  80
        Val Leu Thr Met Thr Asn Met Asp Pro Val Asp Thr Ala Thr Tyr Tyr
                        85                  90                  95
        Cys Ala Arg Arg Glu Thr Val Phe Tyr Trp Tyr Phe Asp Val Trp Gly
                       100                 105                 110
        Arg Gly Thr Leu Val Thr Val Ser Ser Ala Ser Thr Lys Gly Pro Ser
                       115                 120                 125
        Val Phe Pro Leu Ala Pro Ser Ser Lys Ser Thr Ser Gly Gly Thr Ala
                       130                 135                 140
        Ala Leu Gly Cys Leu Val Lys Asp Tyr Phe Pro Glu Pro Val Thr Val
        145                 150                 155                 160
        Ser Trp Asn Ser Gly Ala Leu Thr Ser Gly Val His Thr Phe Pro Ala
                       165                 170                 175
        Val Leu Gln Ser Ser Gly Ser Leu Ser Ser Val Val Thr Val Pro Ser
                       180                 185                 190
        Ser Ser Leu Gly Thr Gln Thr Tyr Ile Cys Asn Val Asn His Lys Pro
                       195                 200                 205
        Ser Asn Thr Lys Val Asp Lys Lys Val Glu Pro Lys Ser Cys Asp Lys
                       210                 215                 220
        Thr His Thr Cys Pro Pro Cys Pro Ala Pro Glu Leu Leu Gly Gly Pro
        225                 230                 235                 240
        Ser Val Phe Leu Phe Pro Pro Lys Pro Lys Asp Thr Leu Met Ile Ser
                       245                 250                 255
        Arg Thr Pro Glu Val Thr Cys Val Val Val Asp Val Ser His Glu Asp
                       260                 265                 270
        Pro Glu Val Lys Phe Asn Trp Tyr Val Asp Gly Val Glu Val His Asn
                       275                 280                 285
        Ala Lys Thr Lys Pro Arg Glu Glu Gln Tyr Asn Ser Tyr Val Val Ser
                       290                 295                 300
        Val Leu Thr Val Leu His Gln Asp Trp Leu Asn Gly Lys Glu Tyr Lys
        305                 310                 315                 320
        Cys Lys Val Ser Asn Lys Ala Leu Pro Ala Pro Ile Glu Lys Thr Ile
                       325                 330                 335
        Ser Lys Ala Lys Gly Gln Pro Arg Glu Pro Gln Val Tyr Thr Leu Pro
                       340                 345                 350
        Pro Ser Arg Asp Glu Leu Thr Lys Asn Gln Val Ser Leu Thr Cys Leu
                       355                 360                 365
        Val Lys Gly Phe Tyr Pro Ser Asp Ile Ala Val Glu Trp Glu Ser Asn
                       370                 375                 380
        Gly Gln Pro Glu Asn Asn Tyr Lys Thr Thr Pro Pro Val Leu Asp Ser
        385                 390                 395                 400
        Asp Gly Ser Phe Phe Lys Lys Leu Thr Val Asp Lys Ser Arg Trp Gln
                       405                 410                 415
        Gln Gly Asn Val Phe Ser Cys Ser Val Met His Glu Ala Leu His Asn
                       420                 425                 430
        His Tyr Thr Gln Lys Ser Leu Ser Leu Ser Pro Gly Lys Gly Ser Thr
                       435                 440                 445
        Val Ala Ala Pro Ser Gly Ser Thr Val Ala Ala Pro Ser Gly Ser Thr
                       450                 455                 460
        Val Ala Ala Pro Ser Gly Ser Gly Val Gln Leu Leu Glu Ser Gly Gly
        465                 470                 475                 480
        Gly Leu Val Gln Pro Gly Gly Ser Leu Arg Leu Ser Cys Ala Ala Ser
                       485                 490                 495
```

-continued

Gly Phe Val Phe Pro Trp Tyr Asp Met Gly Trp Val Arg Gln Ala Pro
            500                 505                 510

Gly Lys Gly Leu Glu Trp Val Ser Ser Ile Asp Trp His Gly Lys Ile
        515                 520                 525

Thr Tyr Tyr Ala Asp Ser Val Lys Gly Arg Phe Thr Ile Ser Arg Asp
    530                 535                 540

Asn Ser Lys Asn Thr Leu Tyr Leu Gln Met Asn Ser Leu Arg Ala Glu
545                 550                 555                 560

Asp Thr Ala Val Tyr Tyr Cys Ala Thr Ala Glu Asp Glu Pro Gly Tyr
                565                 570                 575

Asp Tyr Trp Gly Gln Gly Thr Leu Val Thr Val Ser Ser
            580                 585

<210> SEQ ID NO 8
<211> LENGTH: 597
<212> TYPE: PRT
<213> ORGANISM: Artificial Sequence
<220> FEATURE:
<223> OTHER INFORMATION: Fusion protein

<400> SEQUENCE: 8

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Tyr Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Ser Thr
        435                 440                 445

Val Ala Ala Pro Ser Gly Ser Thr Val Ala Ala Pro Ser Gly Ser Thr
450                 455                 460

Val Ala Ala Pro Ser Gly Ser Thr Val Ala Ala Pro Ser Gly Ser Gly
465                 470                 475                 480

Val Gln Leu Leu Glu Ser Gly Gly Gly Leu Val Gln Pro Gly Gly Ser
                485                 490                 495

Leu Arg Leu Ser Cys Ala Ala Ser Gly Phe Val Phe Pro Trp Tyr Asp
            500                 505                 510

Met Gly Trp Val Arg Gln Ala Pro Gly Lys Gly Leu Glu Trp Val Ser
        515                 520                 525

Ser Ile Asp Trp His Gly Lys Ile Thr Tyr Tyr Ala Asp Ser Val Lys
530                 535                 540

Gly Arg Phe Thr Ile Ser Arg Asp Asn Ser Lys Asn Thr Leu Tyr Leu
545                 550                 555                 560

Gln Met Asn Ser Leu Arg Ala Glu Asp Thr Ala Val Tyr Tyr Cys Ala
                565                 570                 575

Thr Ala Glu Asp Glu Pro Gly Tyr Asp Tyr Trp Gly Gln Gly Thr Leu
            580                 585                 590

Val Thr Val Ser Ser
        595

<210> SEQ ID NO 9
<211> LENGTH: 605
<212> TYPE: PRT
<213> ORGANISM: Artificial Sequence
<220> FEATURE:
<223> OTHER INFORMATION: Fusion protein

<400> SEQUENCE: 9

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

```
Gly Met Gly Val Ser Trp Ile Arg Gln Pro Gly Lys Gly Leu Glu
         35                  40                  45

Trp Leu Ala His Ile Tyr Trp Asp Asp Asp Lys Arg Tyr Asn Pro Ser
50                      55                  60

Leu Lys Ser Arg Leu Thr Ile Ser Lys Asp Thr Ser Arg Asn Gln Val
65                      70                  75                  80

Val Leu Thr Met Thr Asn Met Asp Pro Val Asp Thr Ala Thr Tyr Tyr
                    85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ser Ala Ser Thr Lys Gly Pro Ser
                115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                    165                 170                 175

Val Leu Gln Ser Ser Gly Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Tyr Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                    325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Gly Ser Thr
            435                 440                 445
```

Val Ala Ala Pro Ser Gly Ser Thr Val Ala Ala Pro Ser Gly Ser Thr
450                 455                 460

Val Ala Ala Pro Ser Gly Ser Thr Val Ala Ala Pro Ser Gly Ser Thr
465                 470                 475                 480

Val Ala Ala Pro Ser Gly Ser Gly Val Gln Leu Leu Glu Ser Gly Gly
                485                 490                 495

Gly Leu Val Gln Pro Gly Gly Ser Leu Arg Leu Ser Cys Ala Ala Ser
                500                 505                 510

Gly Phe Val Phe Pro Trp Tyr Asp Met Gly Trp Val Arg Gln Ala Pro
                515                 520                 525

Gly Lys Gly Leu Glu Trp Val Ser Ser Ile Asp Trp His Gly Lys Ile
530                 535                 540

Thr Tyr Tyr Ala Asp Ser Val Lys Gly Arg Phe Thr Ile Ser Arg Asp
545                 550                 555                 560

Asn Ser Lys Asn Thr Leu Tyr Leu Gln Met Asn Ser Leu Arg Ala Glu
                565                 570                 575

Asp Thr Ala Val Tyr Tyr Cys Ala Thr Ala Glu Asp Glu Pro Gly Tyr
                580                 585                 590

Asp Tyr Trp Gly Gln Gly Thr Leu Val Thr Val Ser Ser
                595                 600                 605

<210> SEQ ID NO 10
<211> LENGTH: 613
<212> TYPE: PRT
<213> ORGANISM: Artificial Sequence
<220> FEATURE:
<223> OTHER INFORMATION: Fusion protein

<400> SEQUENCE: 10

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Tyr Trp Asp Asp Asp Lys Arg Tyr Asn Pro Ser
        50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

```
Ser Asn Thr Lys Val Asp Lys Lys Val Glu Pro Lys Ser Cys Asp Lys
210                 215                 220
Thr His Thr Cys Pro Pro Cys Pro Ala Pro Glu Leu Leu Gly Gly Pro
225                 230                 235                 240
Ser Val Phe Leu Phe Pro Pro Lys Pro Lys Asp Thr Leu Met Ile Ser
            245                 250                 255
Arg Thr Pro Glu Val Thr Cys Val Val Val Asp Val Ser His Glu Asp
            260                 265                 270
Pro Glu Val Lys Phe Asn Trp Tyr Val Asp Gly Val Glu Val His Asn
                275                 280                 285
Ala Lys Thr Lys Pro Arg Glu Glu Gln Tyr Asn Ser Tyr Val Val Ser
290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Pro Ile Glu Lys Thr Ile
                325                 330                 335
Ser Lys Ala Lys Gly Gln Pro Arg Glu Pro Gln Val Tyr Thr Leu Pro
                340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
370                 375                 380
Gly Gln Pro Glu Asn Asn Tyr Lys Thr Thr Pro Pro Val Leu Asp Ser
385                 390                 395                 400
Asp Gly Ser Phe Phe Lys Lys Leu Thr Val Asp Lys Ser Arg Trp Gln
                405                 410                 415
Gln Gly Asn Val Phe Ser Cys Ser Val Met His Glu Ala Leu His Asn
                420                 425                 430
His Tyr Thr Gln Lys Ser Leu Ser Leu Ser Pro Gly Lys Gly Ser Thr
            435                 440                 445
Val Ala Ala Pro Ser Gly Ser Thr Val Ala Ala Pro Ser Gly Ser Thr
450                 455                 460
Val Ala Ala Pro Ser Gly Ser Thr Val Ala Ala Pro Ser Gly Ser Thr
465                 470                 475                 480
Val Ala Ala Pro Ser Gly Ser Thr Val Ala Ala Pro Ser Gly Ser Gly
                485                 490                 495
Val Gln Leu Leu Glu Ser Gly Gly Gly Leu Val Gln Pro Gly Gly Ser
                500                 505                 510
Leu Arg Leu Ser Cys Ala Ala Ser Gly Phe Val Phe Pro Trp Tyr Asp
            515                 520                 525
Met Gly Trp Val Arg Gln Ala Pro Gly Lys Gly Leu Glu Trp Val Ser
            530                 535                 540
Ser Ile Asp Trp His Gly Lys Ile Thr Tyr Tyr Ala Asp Ser Val Lys
545                 550                 555                 560
Gly Arg Phe Thr Ile Ser Arg Asp Asn Ser Lys Asn Thr Leu Tyr Leu
                565                 570                 575
Gln Met Asn Ser Leu Arg Ala Glu Asp Thr Ala Val Tyr Tyr Cys Ala
                580                 585                 590
Thr Ala Glu Asp Glu Pro Gly Tyr Asp Tyr Trp Gly Gln Gly Thr Leu
            595                 600                 605
Val Thr Val Ser Ser
610
```

<210> SEQ ID NO 11
<211> LENGTH: 568
<212> TYPE: PRT
<213> ORGANISM: Artificial Sequence
<220> FEATURE:
<223> OTHER INFORMATION: Fusion protein

<400> SEQUENCE: 11

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Lys Arg Tyr Asn Pro Ser
     50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
```

```
                    370                 375                 380
Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Pro Ala Ser
                435                 440                 445

Gly Ser Gly Val Gln Leu Leu Glu Ser Gly Gly Leu Val Gln Pro
            450                 455                 460

Gly Gly Ser Leu Arg Leu Ser Cys Ala Ala Ser Gly Phe Val Phe Pro
465                 470                 475                 480

Trp Tyr Asp Met Gly Trp Val Arg Gln Ala Pro Gly Lys Gly Leu Glu
                485                 490                 495

Trp Val Ser Ser Ile Asp Trp His Gly Lys Ile Thr Tyr Tyr Ala Asp
                500                 505                 510

Ser Val Lys Gly Arg Phe Thr Ile Ser Arg Asp Asn Ser Lys Asn Thr
                515                 520                 525

Leu Tyr Leu Gln Met Asn Ser Leu Arg Ala Glu Asp Thr Ala Val Tyr
            530                 535                 540

Tyr Cys Ala Thr Ala Glu Asp Glu Pro Gly Tyr Asp Tyr Trp Gly Gln
545                 550                 555                 560

Gly Thr Leu Val Thr Val Ser Ser
                565

<210> SEQ ID NO 12
<211> LENGTH: 569
<212> TYPE: PRT
<213> ORGANISM: Artificial Sequence
<220> FEATURE:
<223> OTHER INFORMATION: Fusion protein

<400> SEQUENCE: 12

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Tyr Trp Asp Asp Asp Lys Arg Tyr Asn Pro Ser
50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
            130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
            165                 170                 175
Val Leu Gln Ser Ser Gly Ser Leu Ser Ser Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                    245                 250                 255

Arg Thr Pro Glu Val Thr Cys Val Val Val Asp Val Ser His Glu Asp
                    260                 265                 270

Pro Glu Val Lys Phe Asn Trp Tyr Val Asp Gly Val Glu Val His Asn
                    275                 280                 285

Ala Lys Thr Lys Pro Arg Glu Glu Gln Tyr Asn Ser Tyr Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                    325                 330                 335

Ser Lys Ala Lys Gly Gln Pro Arg Glu Pro Gln Val Tyr Thr Leu Pro
                    340                 345                 350

Pro Ser Arg Asp Glu Leu Thr Lys Asn Gln Val Ser Leu Thr Cys Leu
                    355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                    405                 410                 415

Gln Gly Asn Val Phe Ser Cys Ser Val Met His Glu Ala Leu His Asn
                    420                 425                 430

His Tyr Thr Gln Lys Ser Leu Ser Leu Ser Pro Gly Lys Pro Asp Ala
            435                 440                 445

Ser Gly Ser Gly Val Gln Leu Leu Glu Ser Gly Gly Gly Leu Val Gln
            450                 455                 460

Pro Gly Gly Ser Leu Arg Leu Ser Cys Ala Ala Ser Gly Phe Val Phe
465                 470                 475                 480

Pro Trp Tyr Asp Met Gly Trp Val Arg Gln Ala Pro Gly Lys Gly Leu
                    485                 490                 495

Glu Trp Val Ser Ser Ile Asp Trp His Gly Lys Ile Thr Tyr Tyr Ala
                    500                 505                 510

Asp Ser Val Lys Gly Arg Phe Thr Ile Ser Arg Asp Asn Ser Lys Asn
                    515                 520                 525

Thr Leu Tyr Leu Gln Met Asn Ser Leu Arg Ala Glu Asp Thr Ala Val
            530                 535                 540

Tyr Tyr Cys Ala Thr Ala Glu Asp Glu Pro Gly Tyr Asp Tyr Trp Gly
545                 550                 555                 560

Gln Gly Thr Leu Val Thr Val Ser Ser
                    565

<210> SEQ ID NO 13
```

<211> LENGTH: 570
<212> TYPE: PRT
<213> ORGANISM: Artificial Sequence
<220> FEATURE:
<223> OTHER INFORMATION: Fusion protein

<400> SEQUENCE: 13

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Lys Arg Tyr Asn Pro Ser
 50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380
```

```
Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Pro Asp Asp
                435                 440                 445

Ala Ser Gly Ser Gly Val Gln Leu Leu Glu Ser Gly Gly Gly Leu Val
450                 455                 460

Gln Pro Gly Gly Ser Leu Arg Leu Ser Cys Ala Ala Ser Gly Phe Val
465                 470                 475                 480

Phe Pro Trp Tyr Asp Met Gly Trp Val Arg Gln Ala Pro Gly Lys Gly
                485                 490                 495

Leu Glu Trp Val Ser Ser Ile Asp Trp His Gly Lys Ile Thr Tyr Tyr
                500                 505                 510

Ala Asp Ser Val Lys Gly Arg Phe Thr Ile Ser Arg Asp Asn Ser Lys
                515                 520                 525

Asn Thr Leu Tyr Leu Gln Met Asn Ser Leu Arg Ala Glu Asp Thr Ala
530                 535                 540

Val Tyr Tyr Cys Ala Thr Ala Glu Asp Glu Pro Gly Tyr Asp Tyr Trp
545                 550                 555                 560

Gly Gln Gly Thr Leu Val Thr Val Ser Ser
                565                 570

<210> SEQ ID NO 14
<211> LENGTH: 568
<212> TYPE: PRT
<213> ORGANISM: Artificial Sequence
<220> FEATURE:
<223> OTHER INFORMATION: Fusion protein

<400> SEQUENCE: 14

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Tyr Trp Asp Asp Asp Lys Arg Tyr Asn Pro Ser
50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

Val Leu Gln Ser Ser Gly Ser Leu Ser Ser Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
            245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Tyr Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
            405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
            435                 440                 445

Gly Ser Gly Val Gln Leu Leu Glu Ser Gly Gly Gly Leu Val Gln Pro
450                 455                 460

Gly Gly Ser Leu Arg Leu Ser Cys Ala Ala Ser Gly Phe Val Phe Pro
465                 470                 475                 480

Trp Tyr Asp Met Gly Trp Val Arg Gln Ala Pro Gly Lys Gly Leu Glu
            485                 490                 495

Trp Val Ser Ser Ile Asp Trp His Gly Lys Ile Thr Tyr Tyr Ala Asp
            500                 505                 510

Ser Val Lys Gly Arg Phe Thr Ile Ser Arg Asp Asn Ser Lys Asn Thr
            515                 520                 525

Leu Tyr Leu Gln Met Asn Ser Leu Arg Ala Glu Asp Thr Ala Val Tyr
            530                 535                 540

Tyr Cys Ala Thr Ala Glu Asp Glu Pro Gly Tyr Asp Tyr Trp Gly Gln
545                 550                 555                 560

Gly Thr Leu Val Thr Val Ser Ser
            565

<210> SEQ ID NO 15
<211> LENGTH: 573

<212> TYPE: PRT
<213> ORGANISM: Artificial Sequence
<220> FEATURE:
<223> OTHER INFORMATION: Fusion protein

<400> SEQUENCE: 15

```
Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Asp Lys Arg Tyr Asn Pro Ser
 50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380
```

-continued

```
Gly Gln Pro Glu Asn Asn Tyr Lys Thr Thr Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
        435                 440                 445

Gly Ser Gly Gly Gly Gly Ser Gly Val Gln Leu Leu Glu Ser Gly Gly
450                 455                 460

Gly Leu Val Gln Pro Gly Gly Ser Leu Arg Leu Ser Cys Ala Ala Ser
465                 470                 475                 480

Gly Phe Val Phe Pro Trp Tyr Asp Met Gly Trp Val Arg Gln Ala Pro
            485                 490                 495

Gly Lys Gly Leu Glu Trp Val Ser Ser Ile Asp Trp His Gly Lys Ile
        500                 505                 510

Thr Tyr Tyr Ala Asp Ser Val Lys Gly Arg Phe Thr Ile Ser Arg Asp
    515                 520                 525

Asn Ser Lys Asn Thr Leu Tyr Leu Gln Met Asn Ser Leu Arg Ala Glu
530                 535                 540

Asp Thr Ala Val Tyr Tyr Cys Ala Thr Ala Glu Asp Glu Pro Gly Tyr
545                 550                 555                 560

Asp Tyr Trp Gly Gln Gly Thr Leu Val Thr Val Ser Ser
            565                 570
```

```
<210> SEQ ID NO 16
<211> LENGTH: 578
<212> TYPE: PRT
<213> ORGANISM: Artificial Sequence
<220> FEATURE:
<223> OTHER INFORMATION: Fusion protein

<400> SEQUENCE: 16
```

```
Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

Val Leu Gln Ser Ser Gly Leu Ser Ser Val Thr Val Pro Ser
            180             185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Gly Gly Gly
        435                 440                 445

Gly Ser Gly Gly Gly Ser Gly Gly Gly Ser Gly Val Gln Leu
450                 455                 460

Leu Glu Ser Gly Gly Gly Leu Val Gln Pro Gly Gly Ser Leu Arg Leu
465                 470                 475                 480

Ser Cys Ala Ala Ser Gly Phe Val Phe Pro Trp Tyr Asp Met Gly Trp
                485                 490                 495

Val Arg Gln Ala Pro Gly Lys Gly Leu Glu Trp Val Ser Ser Ile Asp
            500                 505                 510

Trp His Gly Lys Ile Thr Tyr Tyr Ala Asp Ser Val Lys Gly Arg Phe
        515                 520                 525

Thr Ile Ser Arg Asp Asn Ser Lys Asn Thr Leu Tyr Leu Gln Met Asn
530                 535                 540

Ser Leu Arg Ala Glu Asp Thr Ala Val Tyr Tyr Cys Ala Thr Ala Glu
545                 550                 555                 560

Asp Glu Pro Gly Tyr Asp Tyr Trp Gly Gln Gly Thr Leu Val Thr Val
                565                 570                 575

Ser Ser

<210> SEQ ID NO 17

```
<211> LENGTH: 571
<212> TYPE: PRT
<213> ORGANISM: Artificial Sequence
<220> FEATURE:
<223> OTHER INFORMATION: Fusion protein

<400> SEQUENCE: 17

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Asp Lys Arg Tyr Asn Pro Ser
 50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380
```

```
Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Pro Ala Val
                435                 440                 445

Pro Pro Pro Gly Ser Gly Val Gln Leu Leu Glu Ser Gly Gly Gly Leu
            450                 455                 460

Val Gln Pro Gly Gly Ser Leu Arg Leu Ser Cys Ala Ala Ser Gly Phe
465                 470                 475                 480

Val Phe Pro Trp Tyr Asp Met Gly Trp Val Arg Gln Ala Pro Gly Lys
                485                 490                 495

Gly Leu Glu Trp Val Ser Ser Ile Asp Trp His Gly Lys Ile Thr Tyr
                500                 505                 510

Tyr Ala Asp Ser Val Lys Gly Arg Phe Thr Ile Ser Arg Asp Asn Ser
                515                 520                 525

Lys Asn Thr Leu Tyr Leu Gln Met Asn Ser Leu Arg Ala Glu Asp Thr
530                 535                 540

Ala Val Tyr Tyr Cys Ala Thr Ala Glu Asp Glu Pro Gly Tyr Asp Tyr
545                 550                 555                 560

Trp Gly Gln Gly Thr Leu Val Thr Val Ser Ser
                565                 570

<210> SEQ ID NO 18
<211> LENGTH: 577
<212> TYPE: PRT
<213> ORGANISM: Artificial Sequence
<220> FEATURE:
<223> OTHER INFORMATION: Fusion protein

<400> SEQUENCE: 18

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Ser Leu Ser Ser Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Pro Ala Val
        435                 440                 445

Pro Pro Pro Pro Ala Val Pro Pro Gly Ser Gly Val Gln Leu Leu
450                 455                 460

Glu Ser Gly Gly Gly Leu Val Gln Pro Gly Gly Ser Leu Arg Leu Ser
465                 470                 475                 480

Cys Ala Ala Ser Gly Phe Val Phe Pro Trp Tyr Asp Met Gly Trp Val
                485                 490                 495

Arg Gln Ala Pro Gly Lys Gly Leu Glu Trp Val Ser Ser Ile Asp Trp
            500                 505                 510

His Gly Lys Ile Thr Tyr Tyr Ala Asp Ser Val Lys Gly Arg Phe Thr
        515                 520                 525

Ile Ser Arg Asp Asn Ser Lys Asn Thr Leu Tyr Leu Gln Met Asn Ser
        530                 535                 540

Leu Arg Ala Glu Asp Thr Ala Val Tyr Tyr Cys Ala Thr Ala Glu Asp
545                 550                 555                 560

Glu Pro Gly Tyr Asp Tyr Trp Gly Gln Gly Thr Leu Val Thr Val Ser
                565                 570                 575

Ser
```

-continued

```
<210> SEQ ID NO 19
<211> LENGTH: 583
<212> TYPE: PRT
<213> ORGANISM: Artificial Sequence
<220> FEATURE:
<223> OTHER INFORMATION: Fusion protein

<400> SEQUENCE: 19

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
```

```
                370                 375                 380
Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Pro Ala Val
                435                 440                 445

Pro Pro Pro Pro Ala Val Pro Pro Pro Ala Val Pro Pro Gly
                450                 455                 460

Ser Gly Val Gln Leu Leu Glu Ser Gly Gly Gly Leu Val Gln Pro Gly
465                 470                 475                 480

Gly Ser Leu Arg Leu Ser Cys Ala Ala Ser Gly Phe Val Phe Pro Trp
                485                 490                 495

Tyr Asp Met Gly Trp Val Arg Gln Ala Pro Gly Lys Gly Leu Glu Trp
                500                 505                 510

Val Ser Ser Ile Asp Trp His Gly Lys Ile Thr Tyr Tyr Ala Asp Ser
                515                 520                 525

Val Lys Gly Arg Phe Thr Ile Ser Arg Asp Asn Ser Lys Asn Thr Leu
                530                 535                 540

Tyr Leu Gln Met Asn Ser Leu Arg Ala Glu Asp Thr Ala Val Tyr Tyr
545                 550                 555                 560

Cys Ala Thr Ala Glu Asp Glu Pro Gly Tyr Asp Tyr Trp Gly Gln Gly
                565                 570                 575

Thr Leu Val Thr Val Ser Ser
                580

<210> SEQ ID NO 20
<211> LENGTH: 571
<212> TYPE: PRT
<213> ORGANISM: Artificial Sequence
<220> FEATURE:
<223> OTHER INFORMATION: Fusion protein

<400> SEQUENCE: 20

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
                35                  40                  45

Trp Leu Ala His Ile Tyr Trp Asp Asp Asp Lys Arg Tyr Asn Pro Ser
                50                  55                  60

Leu Lys Ser Arg Leu Thr Ile Ser Lys Asp Thr Ser Arg Asn Gln Val
65              70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ala Ser Thr Lys Gly Pro Ser
                115                 120                 125

Val Phe Pro Leu Ala Pro Ser Ser Lys Ser Thr Ser Gly Gly Thr Ala
                130                 135                 140

Ala Leu Gly Cys Leu Val Lys Asp Tyr Phe Pro Glu Pro Val Thr Val
```

```
                145                 150                 155                 160
Ser Trp Asn Ser Gly Ala Leu Thr Ser Gly Val His Thr Phe Pro Ala
                165                 170                 175

Val Leu Gln Ser Ser Gly Ser Leu Ser Ser Val Thr Val Pro Ser
        180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Thr Val Ser
            435                 440                 445

Asp Val Pro Gly Ser Gly Val Gln Leu Leu Glu Ser Gly Gly Gly Leu
    450                 455                 460

Val Gln Pro Gly Gly Ser Leu Arg Leu Ser Cys Ala Ala Ser Gly Phe
465                 470                 475                 480

Val Phe Pro Trp Tyr Asp Met Gly Trp Val Arg Gln Ala Pro Gly Lys
                485                 490                 495

Gly Leu Glu Trp Val Ser Ser Ile Asp Trp His Gly Lys Ile Thr Tyr
                500                 505                 510

Tyr Ala Asp Ser Val Lys Gly Arg Phe Thr Ile Ser Arg Asp Asn Ser
            515                 520                 525

Lys Asn Thr Leu Tyr Leu Gln Met Asn Ser Leu Arg Ala Glu Asp Thr
    530                 535                 540

Ala Val Tyr Tyr Cys Ala Thr Ala Glu Asp Glu Pro Gly Tyr Asp Tyr
545                 550                 555                 560

Trp Gly Gln Gly Thr Leu Val Thr Val Ser Ser
                565                 570
```

<210> SEQ ID NO 21
<211> LENGTH: 577
<212> TYPE: PRT
<213> ORGANISM: Artificial Sequence
<220> FEATURE:
<223> OTHER INFORMATION: Fusion protein

<400> SEQUENCE: 21

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Lys Arg Tyr Asn Pro Ser
     50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Thr Val Ser
            435                 440                 445

Asp Val Pro Thr Val Ser Asp Val Pro Gly Ser Gly Val Gln Leu Leu
    450                 455                 460

Glu Ser Gly Gly Gly Leu Val Gln Pro Gly Gly Ser Leu Arg Leu Ser
465                 470                 475                 480

Cys Ala Ala Ser Gly Phe Val Phe Pro Trp Tyr Asp Met Gly Trp Val
                485                 490                 495

Arg Gln Ala Pro Gly Lys Gly Leu Glu Trp Val Ser Ser Ile Asp Trp
                500                 505                 510

His Gly Lys Ile Thr Tyr Ala Asp Ser Val Lys Gly Arg Phe Thr
            515                 520                 525

Ile Ser Arg Asp Asn Ser Lys Asn Thr Leu Tyr Leu Gln Met Asn Ser
    530                 535                 540

Leu Arg Ala Glu Asp Thr Ala Val Tyr Tyr Cys Ala Thr Ala Glu Asp
545                 550                 555                 560

Glu Pro Gly Tyr Asp Tyr Trp Gly Gln Gly Thr Leu Val Thr Val Ser
                565                 570                 575

Ser

<210> SEQ ID NO 22
<211> LENGTH: 583
<212> TYPE: PRT
<213> ORGANISM: Artificial Sequence
<220> FEATURE:
<223> OTHER INFORMATION: Fusion protein

<400> SEQUENCE: 22

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Ser Leu Ser Ser Val Val Thr Val Pro Ser
        180                 185                 190

Ser Ser Leu Gly Thr Gln Thr Tyr Ile Cys Asn Val Asn His Lys Pro
    195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Tyr Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Thr Val Ser
        435                 440                 445

Asp Val Pro Thr Val Ser Asp Val Pro Thr Val Ser Asp Val Pro Gly
    450                 455                 460

Ser Gly Val Gln Leu Leu Glu Ser Gly Gly Gly Leu Val Gln Pro Gly
465                 470                 475                 480

Gly Ser Leu Arg Leu Ser Cys Ala Ala Ser Gly Phe Val Phe Pro Trp
                485                 490                 495

Tyr Asp Met Gly Trp Val Arg Gln Ala Pro Gly Lys Gly Leu Glu Trp
            500                 505                 510

Val Ser Ser Ile Asp Trp His Gly Lys Ile Thr Tyr Tyr Ala Asp Ser
        515                 520                 525

Val Lys Gly Arg Phe Thr Ile Ser Arg Asp Asn Ser Lys Asn Thr Leu
    530                 535                 540

Tyr Leu Gln Met Asn Ser Leu Arg Ala Glu Asp Thr Ala Val Tyr Tyr
545                 550                 555                 560

Cys Ala Thr Ala Glu Asp Glu Pro Gly Tyr Asp Tyr Trp Gly Gln Gly
```

-continued

```
                  565                 570                 575
Thr Leu Val Thr Val Ser Ser
            580

<210> SEQ ID NO 23
<211> LENGTH: 571
<212> TYPE: PRT
<213> ORGANISM: Artificial Sequence
<220> FEATURE:
<223> OTHER INFORMATION: Fusion protein

<400> SEQUENCE: 23

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Asp Lys Arg Tyr Asn Pro Ser
     50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
```

```
              340                 345                 350
Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Thr Gly Leu
        435                 440                 445

Asp Ser Pro Gly Ser Gly Val Gln Leu Leu Glu Ser Gly Gly Gly Leu
    450                 455                 460

Val Gln Pro Gly Gly Ser Leu Arg Leu Ser Cys Ala Ala Ser Gly Phe
465                 470                 475                 480

Val Phe Pro Trp Tyr Asp Met Gly Trp Val Arg Gln Ala Pro Gly Lys
                485                 490                 495

Gly Leu Glu Trp Val Ser Ser Ile Asp Trp His Gly Lys Ile Thr Tyr
            500                 505                 510

Tyr Ala Asp Ser Val Lys Gly Arg Phe Thr Ile Ser Arg Asp Asn Ser
        515                 520                 525

Lys Asn Thr Leu Tyr Leu Gln Met Asn Ser Leu Arg Ala Glu Asp Thr
    530                 535                 540

Ala Val Tyr Tyr Cys Ala Thr Ala Glu Asp Glu Pro Gly Tyr Asp Tyr
545                 550                 555                 560

Trp Gly Gln Gly Thr Leu Val Thr Val Ser Ser
                565                 570

<210> SEQ ID NO 24
<211> LENGTH: 577
<212> TYPE: PRT
<213> ORGANISM: Artificial Sequence
<220> FEATURE:
<223> OTHER INFORMATION: Fusion protein

<400> SEQUENCE: 24

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
                20                  25                  30

Gly Met Gly Val Ser Trp Ile Arg Gln Pro Pro Gly Lys Gly Leu Glu
            35                  40                  45

Trp Leu Ala His Ile Tyr Trp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
                100                 105                 110

Arg Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
```

```
            130                 135                 140
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Tyr Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Thr Gly Leu
            435                 440                 445

Asp Ser Pro Thr Gly Leu Asp Ser Pro Gly Ser Gly Val Gln Leu Leu
        450                 455                 460

Glu Ser Gly Gly Gly Leu Val Gln Pro Gly Gly Ser Leu Arg Leu Ser
465                 470                 475                 480

Cys Ala Ala Ser Gly Phe Val Phe Pro Trp Tyr Asp Met Gly Trp Val
                485                 490                 495

Arg Gln Ala Pro Gly Lys Gly Leu Glu Trp Val Ser Ser Ile Asp Trp
                500                 505                 510

His Gly Lys Ile Thr Tyr Tyr Ala Asp Ser Val Lys Gly Arg Phe Thr
            515                 520                 525

Ile Ser Arg Asp Asn Ser Lys Asn Thr Leu Tyr Leu Gln Met Asn Ser
        530                 535                 540

Leu Arg Ala Glu Asp Thr Ala Val Tyr Tyr Cys Ala Thr Ala Glu Asp
545                 550                 555                 560
```

```
Glu Pro Gly Tyr Asp Tyr Trp Gly Gln Gly Thr Leu Val Thr Val Ser
            565                 570                 575
Ser

<210> SEQ ID NO 25
<211> LENGTH: 583
<212> TYPE: PRT
<213> ORGANISM: Artificial Sequence
<220> FEATURE:
<223> OTHER INFORMATION: Fusion protein

<400> SEQUENCE: 25

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
 50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ala Ser Thr Lys Gly Pro Ser
            115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335
```

```
Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Thr Gly Leu
        435                 440                 445

Asp Ser Pro Thr Gly Leu Asp Ser Pro Thr Gly Leu Asp Ser Pro Gly
    450                 455                 460

Ser Gly Val Gln Leu Leu Glu Ser Gly Gly Leu Val Gln Pro Gly Gly
465                 470                 475                 480

Gly Ser Leu Arg Leu Ser Cys Ala Ala Ser Gly Phe Val Phe Pro Trp
                485                 490                 495

Tyr Asp Met Gly Trp Val Arg Gln Ala Pro Gly Lys Gly Leu Glu Trp
            500                 505                 510

Val Ser Ser Ile Asp Trp His Gly Lys Ile Thr Tyr Tyr Ala Asp Ser
        515                 520                 525

Val Lys Gly Arg Phe Thr Ile Ser Arg Asp Asn Ser Lys Asn Thr Leu
    530                 535                 540

Tyr Leu Gln Met Asn Ser Leu Arg Ala Glu Asp Thr Ala Val Tyr Tyr
545                 550                 555                 560

Cys Ala Thr Ala Glu Asp Pro Gly Tyr Asp Tyr Trp Gly Gln Gly
                565                 570                 575

Thr Leu Val Thr Val Ser Ser
            580

<210> SEQ ID NO 26
<211> LENGTH: 108
<212> TYPE: PRT
<213> ORGANISM: Homo Sapiens

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Ser Asp Trp
            20                  25                  30

Leu His Trp Tyr Gln Gln Lys Pro Gly Lys Ala Pro Lys Leu Leu Ile
        35                  40                  45

Ala Trp Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Glu Gly Trp Gly Pro Pro
                85                  90                  95

Thr Phe Gly Gln Gly Thr Lys Val Glu Ile Lys Arg
            100                 105

<210> SEQ ID NO 27
```

```
<211> LENGTH: 219
<212> TYPE: PRT
<213> ORGANISM: Artificial Sequence
<220> FEATURE:
<223> OTHER INFORMATION: Humanised

<400> SEQUENCE: 27

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Asn Ile Val His Ile
             20                  25                  30

Asn Gly Asn Thr Tyr Leu Glu Trp Tyr Leu Gln Lys Pro Gly Gln Ser
         35                  40                  45

Pro Arg Leu Leu Ile Tyr Lys Ile Ser Asp Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Asp Asp Val Gly Ile Tyr Tyr Cys Phe Gln Gly
                 85                  90                  95

Ser His Val Pro Trp Thr Phe Gly Gln Gly Thr Lys Leu Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 28
<211> LENGTH: 449
<212> TYPE: PRT
<213> ORGANISM: Artificial Sequence
<220> FEATURE:
<223> OTHER INFORMATION: Humanised

<400> SEQUENCE: 28

Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Tyr Asp Asp Tyr Tyr Ala Met
```

```
            100                 105                 110
Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Ser Ser Val Val
                    180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Val Glu Pro Lys
                210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 29
<211> LENGTH: 559
<212> TYPE: PRT
<213> ORGANISM: Artificial Sequence
<220> FEATURE:
<223> OTHER INFORMATION: Fusion protein

<400> SEQUENCE: 29

Gln Val Gln Leu Val Gln Ser Gly Ala Glu Val Lys Lys Pro Gly Ser
1               5                   10                  15
```

```
Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
 50                  55                  60

Gln Gly Arg Val Thr Ile Thr Ala Asp Glu Ser Thr Ser Thr Ala Tyr
65                   70                  75                  80

Met Glu Leu Ser Ser Leu Arg Ser Glu Asp Thr Ala Val Tyr Tyr Cys
             85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Ser Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
            405                 410                 415

Ser Arg Trp Gln Gln Gly Asn Val Phe Ser Cys Ser Val Met His Glu
        420                 425                 430
```

```
Ala Leu His Asn His Tyr Thr Gln Lys Ser Leu Ser Leu Ser Pro Gly
            435                 440                 445

Lys Gly Ser Asp Ile Gln Met Thr Gln Ser Pro Ser Ser Leu Ser Ala
450                 455                 460

Ser Val Gly Asp Arg Val Thr Ile Thr Cys Arg Ala Ser Arg Pro Ile
465                 470                 475                 480

Ser Asp Trp Leu His Trp Tyr Gln Gln Lys Pro Gly Lys Ala Pro Lys
                485                 490                 495

Leu Leu Ile Ala Trp Ala Ser Ser Leu Gln Gly Gly Val Pro Ser Arg
            500                 505                 510

Phe Ser Gly Ser Gly Ser Gly Thr Asp Phe Thr Leu Thr Ile Ser Ser
            515                 520                 525

Leu Gln Pro Glu Asp Phe Ala Thr Tyr Tyr Cys Leu Gln Glu Gly Trp
530                 535                 540

Gly Pro Pro Thr Phe Gly Gln Gly Thr Lys Val Glu Ile Lys Arg
545                 550                 555

<210> SEQ ID NO 30
<211> LENGTH: 567
<212> TYPE: PRT
<213> ORGANISM: Artificial Sequence
<220> FEATURE:
<223> OTHER INFORMATION: Fusion protein

<400> SEQUENCE: 30

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240
```

```
Leu Gly Gly Pro Ser Val Phe Leu Phe Pro Pro Lys Pro Lys Asp Thr
                    245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Gly Ser Thr Val Ala Ala Pro Ser Gly Ser Asp Ile Gln Met Thr
        450                 455                 460

Gln Ser Pro Ser Ser Leu Ser Ala Ser Val Gly Asp Arg Val Thr Ile
465                 470                 475                 480

Thr Cys Arg Ala Ser Arg Pro Ile Ser Asp Trp Leu His Trp Tyr Gln
                485                 490                 495

Gln Lys Pro Gly Lys Ala Pro Lys Leu Leu Ile Ala Trp Ala Ser Ser
                500                 505                 510

Leu Gln Gly Gly Val Pro Ser Arg Phe Ser Gly Ser Gly Ser Gly Thr
            515                 520                 525

Asp Phe Thr Leu Thr Ile Ser Ser Leu Gln Pro Glu Asp Phe Ala Thr
        530                 535                 540

Tyr Tyr Cys Leu Gln Glu Gly Trp Gly Pro Pro Thr Phe Gly Gln Gly
545                 550                 555                 560

Thr Lys Val Glu Ile Lys Arg
                565

<210> SEQ ID NO 31
<211> LENGTH: 575
<212> TYPE: PRT
<213> ORGANISM: Artificial Sequence
<220> FEATURE:
<223> OTHER INFORMATION: Fusion protein

<400> SEQUENCE: 31

Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
                 20                  25                  30
```

```
Tyr Met His Trp Val Arg Gln Ala Pro Gly Gln Gly Leu Glu Trp Met
        35                  40                  45
Gly Thr Ile Asp Pro Ala Asn Gly Asn Thr Lys Tyr Val Pro Lys Phe
 50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Ile Tyr Asp Asp Tyr His Tyr Asp Asp Tyr Ala Met
                100                 105                 110
Asp Tyr Trp Gly Gln Gly Thr Leu Val Thr Val Ser Ser Ala Ser Thr
            115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Tyr Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Lys Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Ser Thr Val Ala Ala Pro Ser Gly Ser Thr Val Ala Ala Pro
```

```
                   450                 455                 460
Ser Gly Ser Asp Ile Gln Met Thr Gln Ser Pro Ser Ser Leu Ser Ala
465                 470                 475                 480

Ser Val Gly Asp Arg Val Thr Ile Thr Cys Arg Ala Ser Arg Pro Ile
                485                 490                 495

Ser Asp Trp Leu His Trp Tyr Gln Gln Lys Pro Gly Lys Ala Pro Lys
            500                 505                 510

Leu Leu Ile Ala Trp Ala Ser Ser Leu Gln Gly Gly Val Pro Ser Arg
        515                 520                 525

Phe Ser Gly Ser Gly Ser Gly Thr Asp Phe Thr Leu Thr Ile Ser Ser
    530                 535                 540

Leu Gln Pro Glu Asp Phe Ala Thr Tyr Tyr Cys Leu Gln Glu Gly Trp
545                 550                 555                 560

Gly Pro Pro Thr Phe Gly Gln Gly Thr Lys Val Glu Ile Lys Arg
                565                 570                 575

<210> SEQ ID NO 32
<211> LENGTH: 583
<212> TYPE: PRT
<213> ORGANISM: Artificial Sequence
<220> FEATURE:
<223> OTHER INFORMATION: Fusion protein

<400> SEQUENCE: 32

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
```

```
                    245                 250                 255
Leu Met Ile Ser Arg Thr Pro Glu Val Thr Cys Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
    290                 295                 300

Tyr Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
    435                 440                 445

Lys Gly Ser Thr Val Ala Ala Pro Ser Gly Ser Thr Val Ala Ala Pro
450                 455                 460

Ser Gly Ser Thr Val Ala Ala Pro Ser Gly Ser Asp Ile Gln Met Thr
465                 470                 475                 480

Gln Ser Pro Ser Ser Leu Ser Ala Ser Val Gly Asp Arg Val Thr Ile
                485                 490                 495

Thr Cys Arg Ala Ser Arg Pro Ile Ser Asp Trp Leu His Trp Tyr Gln
            500                 505                 510

Gln Lys Pro Gly Lys Ala Pro Lys Leu Leu Ile Ala Trp Ala Ser Ser
    515                 520                 525

Leu Gln Gly Gly Val Pro Ser Arg Phe Ser Gly Ser Gly Ser Gly Thr
530                 535                 540

Asp Phe Thr Leu Thr Ile Ser Ser Leu Gln Pro Glu Asp Phe Ala Thr
545                 550                 555                 560

Tyr Tyr Cys Leu Gln Glu Gly Trp Gly Pro Pro Thr Phe Gly Gln Gly
                565                 570                 575

Thr Lys Val Glu Ile Lys Arg
            580

<210> SEQ ID NO 33
<211> LENGTH: 591
<212> TYPE: PRT
<213> ORGANISM: Artificial Sequence
<220> FEATURE:
<223> OTHER INFORMATION: Fusion protein

<400> SEQUENCE: 33

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
```

```
                    20                  25                  30
Tyr Met His Trp Val Arg Gln Ala Pro Gly Gln Gly Leu Glu Trp Met
                35                  40                  45
Gly Thr Ile Asp Pro Ala Asn Gly Asn Thr Lys Tyr Val Pro Lys Phe
        50                  55                  60
Gln Gly Arg Val Thr Ile Thr Ala Asp Glu Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Ile Tyr Asp Asp Tyr His Tyr Asp Asp Tyr Tyr Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
        130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Ser Ser Val Val
            180                 185                 190
Thr Val Pro Ser Ser Leu Gly Thr Gln Thr Tyr Ile Cys Asn Val
            195                 200                 205
Asn His Lys Pro Ser Asn Thr Lys Val Asp Lys Val Glu Pro Lys
        210                 215                 220
Ser Cys Asp Lys Thr His Thr Cys Pro Pro Cys Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
        290                 295                 300
Tyr Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
        370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
```

```
Lys Gly Ser Thr Val Ala Ala Pro Ser Gly Ser Thr Val Ala Ala Pro
    450                 455                 460
Ser Gly Ser Thr Val Ala Ala Pro Ser Gly Ser Thr Val Ala Ala Pro
465                 470                 475                 480
Ser Gly Ser Asp Ile Gln Met Thr Gln Ser Pro Ser Ser Leu Ser Ala
                485                 490                 495
Ser Val Gly Asp Arg Val Thr Ile Thr Cys Arg Ala Ser Arg Pro Ile
            500                 505                 510
Ser Asp Trp Leu His Trp Tyr Gln Gln Lys Pro Gly Lys Ala Pro Lys
        515                 520                 525
Leu Leu Ile Ala Trp Ala Ser Ser Leu Gln Gly Gly Val Pro Ser Arg
    530                 535                 540
Phe Ser Gly Ser Gly Ser Gly Thr Asp Phe Thr Leu Thr Ile Ser Ser
545                 550                 555                 560
Leu Gln Pro Glu Asp Phe Ala Thr Tyr Tyr Cys Leu Gln Glu Gly Trp
                565                 570                 575
Gly Pro Pro Thr Phe Gly Gln Gly Thr Lys Val Glu Ile Lys Arg
            580                 585                 590
```

<210> SEQ ID NO 34
<211> LENGTH: 599
<212> TYPE: PRT
<213> ORGANISM: Artificial Sequence
<220> FEATURE:
<223> OTHER INFORMATION: Fusion protein

<400> SEQUENCE: 34

```
Gln Val Gln Leu Val Gln Ser Gly Ala Glu Val Lys Lys Pro Gly Ser
  1               5                  10                  15
Ser Val Lys Val Ser Cys Lys Ala Ser Gly Phe Tyr Ile Lys Asp Thr
             20                  25                  30
Tyr Met His Trp Val Arg Gln Ala Pro Gly Gln Gly Leu Glu Trp Met
         35                  40                  45
Gly Thr Ile Asp Pro Ala Asn Gly Asn Thr Lys Tyr Val Pro Lys Phe
     50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Ile Tyr Asp Asp Tyr His Tyr Asp Asp Tyr Tyr Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
    130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
    210                 215                 220
```

```
Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
275                 280                 285

Glu Val His Asn Ala Lys Thr Lys Pro Arg Glu Glu Gln Tyr Asn Ser
    290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
435                 440                 445

Lys Gly Ser Thr Val Ala Ala Pro Ser Gly Ser Thr Val Ala Ala Pro
    450                 455                 460

Ser Gly Ser Thr Val Ala Ala Pro Ser Gly Ser Thr Val Ala Ala Pro
465                 470                 475                 480

Ser Gly Ser Thr Val Ala Ala Pro Ser Gly Ser Asp Ile Gln Met Thr
            485                 490                 495

Gln Ser Pro Ser Ser Leu Ser Ala Ser Val Gly Asp Arg Val Thr Ile
        500                 505                 510

Thr Cys Arg Ala Ser Arg Pro Ile Ser Asp Trp Leu His Trp Tyr Gln
515                 520                 525

Gln Lys Pro Gly Lys Ala Pro Lys Leu Leu Ile Ala Trp Ala Ser Ser
    530                 535                 540

Leu Gln Gly Gly Val Pro Ser Arg Phe Ser Gly Ser Gly Ser Gly Thr
545                 550                 555                 560

Asp Phe Thr Leu Thr Ile Ser Ser Leu Gln Pro Glu Asp Phe Ala Thr
            565                 570                 575

Tyr Tyr Cys Leu Gln Glu Gly Trp Gly Pro Pro Thr Phe Gly Gln Gly
        580                 585                 590

Thr Lys Val Glu Ile Lys Arg
        595

<210> SEQ ID NO 35
<211> LENGTH: 607
<212> TYPE: PRT
<213> ORGANISM: Artificial Sequence
<220> FEATURE:
```

<223> OTHER INFORMATION: Fusion protein

<400> SEQUENCE: 35

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400
```

```
Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Ser Thr Val Ala Ala Pro Ser Gly Ser Thr Val Ala Ala Pro
    450                 455                 460

Ser Gly Ser Thr Val Ala Ala Pro Ser Gly Ser Thr Val Ala Ala Pro
465                 470                 475                 480

Ser Gly Ser Thr Val Ala Ala Pro Ser Gly Ser Thr Val Ala Ala Pro
            485                 490                 495

Ser Gly Ser Asp Ile Gln Met Thr Gln Ser Pro Ser Ser Leu Ser Ala
            500                 505                 510

Ser Val Gly Asp Arg Val Thr Ile Thr Cys Arg Ala Ser Arg Pro Ile
            515                 520                 525

Ser Asp Trp Leu His Trp Tyr Gln Gln Lys Pro Gly Lys Ala Pro Lys
            530                 535                 540

Leu Leu Ile Ala Trp Ala Ser Ser Leu Gln Gly Gly Val Pro Ser Arg
545                 550                 555                 560

Phe Ser Gly Ser Gly Ser Gly Thr Asp Phe Thr Leu Thr Ile Ser Ser
                565                 570                 575

Leu Gln Pro Glu Asp Phe Ala Thr Tyr Tyr Cys Leu Gln Glu Gly Trp
            580                 585                 590

Gly Pro Pro Thr Phe Gly Gln Gly Thr Lys Val Glu Ile Lys Arg
            595                 600                 605

<210> SEQ ID NO 36
<211> LENGTH: 562
<212> TYPE: PRT
<213> ORGANISM: Artificial Sequence
<220> FEATURE:
<223> OTHER INFORMATION: Fusion protein

<400> SEQUENCE: 36

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160
```

```
Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Pro Ala Ser Gly Ser Asp Ile Gln Met Thr Gln Ser Pro Ser Ser
    450                 455                 460

Leu Ser Ala Ser Val Gly Asp Arg Val Thr Ile Thr Cys Arg Ala Ser
465                 470                 475                 480

Arg Pro Ile Ser Asp Trp Leu His Trp Tyr Gln Gln Lys Pro Gly Lys
                485                 490                 495

Ala Pro Lys Leu Leu Ile Ala Trp Ala Ser Ser Leu Gln Gly Val
            500                 505                 510

Pro Ser Arg Phe Ser Gly Ser Gly Ser Gly Thr Asp Phe Thr Leu Thr
        515                 520                 525

Ile Ser Ser Leu Gln Pro Glu Asp Phe Ala Thr Tyr Tyr Cys Leu Gln
    530                 535                 540

Glu Gly Trp Gly Pro Pro Thr Phe Gly Gln Gly Thr Lys Val Glu Ile
545                 550                 555                 560

Lys Arg

<210> SEQ ID NO 37
```

```
<211> LENGTH: 563
<212> TYPE: PRT
<213> ORGANISM: Artificial Sequence
<220> FEATURE:
<223> OTHER INFORMATION: Fusion protein

<400> SEQUENCE: 37

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
                20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Gln Tyr Asn Ser
290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380
```

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Pro Asp Ala Ser Gly Ser Asp Ile Gln Met Thr Gln Ser Pro Ser
450                 455                 460

Ser Leu Ser Ala Ser Val Gly Asp Arg Val Thr Ile Thr Cys Arg Ala
465                 470                 475                 480

Ser Arg Pro Ile Ser Asp Trp Leu His Trp Tyr Gln Gln Lys Pro Gly
            485                 490                 495

Lys Ala Pro Lys Leu Leu Ile Ala Trp Ala Ser Ser Leu Gln Gly Gly
            500                 505                 510

Val Pro Ser Arg Phe Ser Gly Ser Gly Ser Gly Thr Asp Phe Thr Leu
            515                 520                 525

Thr Ile Ser Ser Leu Gln Pro Glu Asp Phe Ala Thr Tyr Tyr Cys Leu
530                 535                 540

Gln Glu Gly Trp Gly Pro Pro Thr Phe Gly Gln Gly Thr Lys Val Glu
545                 550                 555                 560

Ile Lys Arg

<210> SEQ ID NO 38
<211> LENGTH: 564
<212> TYPE: PRT
<213> ORGANISM: Artificial Sequence
<220> FEATURE:
<223> OTHER INFORMATION: Fusion protein

<400> SEQUENCE: 38

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175
```

Thr Phe Pro Ala Val Leu Gln Ser Ser Gly Ser Leu Ser Val Val
            180                 185                 190

Thr Val Pro Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Tyr Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Pro Asp Asp Ala Ser Gly Ser Asp Ile Gln Met Thr Gln Ser Pro
    450                 455                 460

Ser Ser Leu Ser Ala Ser Val Gly Asp Arg Val Thr Ile Thr Cys Arg
465                 470                 475                 480

Ala Ser Arg Pro Ile Ser Asp Trp Leu His Trp Tyr Gln Gln Lys Pro
                485                 490                 495

Gly Lys Ala Pro Lys Leu Leu Ile Ala Trp Ala Ser Ser Leu Gln Gly
            500                 505                 510

Gly Val Pro Ser Arg Phe Ser Gly Ser Gly Ser Gly Thr Asp Phe Thr
        515                 520                 525

Leu Thr Ile Ser Ser Leu Gln Pro Glu Asp Phe Ala Thr Tyr Tyr Cys
    530                 535                 540

Leu Gln Glu Gly Trp Gly Pro Pro Thr Phe Gly Gln Gly Thr Lys Val
545                 550                 555                 560

Glu Ile Lys Arg

<210> SEQ ID NO 39
<211> LENGTH: 562
<212> TYPE: PRT
<213> ORGANISM: Artificial Sequence
<220> FEATURE:
<223> OTHER INFORMATION: Fusion protein

<400> SEQUENCE: 39

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400
```

Val Leu Asp Ser Asp Gly Ser Phe Phe Lys Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Asp Ile Gln Met Thr Gln Ser Pro Ser Ser
450                 455                 460

Leu Ser Ala Ser Val Gly Asp Arg Val Thr Ile Thr Cys Arg Ala Ser
465                 470                 475                 480

Arg Pro Ile Ser Asp Trp Leu His Trp Tyr Gln Gln Lys Pro Gly Lys
            485                 490                 495

Ala Pro Lys Leu Leu Ile Ala Trp Ala Ser Ser Leu Gln Gly Gly Val
            500                 505                 510

Pro Ser Arg Phe Ser Gly Ser Gly Ser Gly Thr Asp Phe Thr Leu Thr
            515                 520                 525

Ile Ser Ser Leu Gln Pro Glu Asp Phe Ala Thr Tyr Tyr Cys Leu Gln
            530                 535                 540

Glu Gly Trp Gly Pro Pro Thr Phe Gly Gln Gly Thr Lys Val Glu Ile
545                 550                 555                 560

Lys Arg

<210> SEQ ID NO 40
<211> LENGTH: 567
<212> TYPE: PRT
<213> ORGANISM: Artificial Sequence
<220> FEATURE:
<223> OTHER INFORMATION: Fusion protein

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
            245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
            290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
            405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Gly Ser Gly Gly Gly Gly Ser Asp Ile Gln Met Thr
450                 455                 460

Gln Ser Pro Ser Ser Leu Ser Ala Ser Val Gly Asp Arg Val Thr Ile
465                 470                 475                 480

Thr Cys Arg Ala Ser Arg Pro Ile Ser Asp Trp Leu His Trp Tyr Gln
            485                 490                 495

Gln Lys Pro Gly Lys Ala Pro Lys Leu Leu Ile Ala Trp Ala Ser Ser
            500                 505                 510

Leu Gln Gly Gly Val Pro Ser Arg Phe Ser Gly Ser Gly Ser Gly Thr
            515                 520                 525

Asp Phe Thr Leu Thr Ile Ser Ser Leu Gln Pro Glu Asp Phe Ala Thr
            530                 535                 540

Tyr Tyr Cys Leu Gln Glu Gly Trp Gly Pro Pro Thr Phe Gly Gln Gly
545                 550                 555                 560

Thr Lys Val Glu Ile Lys Arg
                565

<210> SEQ ID NO 41
<211> LENGTH: 572
<212> TYPE: PRT
<213> ORGANISM: Artificial Sequence
<220> FEATURE:
<223> OTHER INFORMATION: Fusion protein

<400> SEQUENCE: 41

```
Gln Val Gln Leu Val Gln Ser Gly Ala Glu Val Lys Lys Pro Gly Ser
  1               5                  10                  15
Ser Val Lys Val Ser Cys Lys Ala Ser Gly Phe Tyr Ile Lys Asp Thr
             20                  25                  30
Tyr Met His Trp Val Arg Gln Ala Pro Gly Gln Gly Leu Glu Trp Met
         35                  40                  45
Gly Thr Ile Asp Pro Ala Asn Gly Asn Thr Lys Tyr Val Pro Lys Phe
     50                  55                  60
Gln Gly Arg Val Thr Ile Thr Ala Asp Glu Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Ile Tyr Asp Asp Tyr His Tyr Asp Asp Tyr Tyr Ala Met
            100                 105                 110
Asp Tyr Trp Gly Gln Gly Thr Leu Val Thr Val Ser Ser Ala Ser Thr
        115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Ser Leu Ser Ser Val Val
            180                 185                 190
Thr Val Pro Ser Ser Ser Leu Gly Thr Gln Thr Tyr Ile Cys Asn Val
        195                 200                 205
Asn His Lys Pro Ser Asn Thr Lys Val Asp Lys Lys Val Glu Pro Lys
210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
        275                 280                 285
Glu Val His Asn Ala Lys Thr Lys Pro Arg Glu Glu Gln Tyr Asn Ser
    290                 295                 300
Tyr Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
        355                 360                 365
Leu Thr Cys Leu Val Lys Gly Phe Tyr Pro Ser Asp Ile Ala Val Glu
    370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Lys Lys Leu Thr Val Asp Lys
```

```
                405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Gly Gly Gly Ser Gly Gly Gly Ser Gly Gly Gly Ser
450                 455                 460

Asp Ile Gln Met Thr Gln Ser Pro Ser Ser Leu Ser Ala Ser Val Gly
465                 470                 475                 480

Asp Arg Val Thr Ile Thr Cys Arg Ala Ser Arg Pro Ile Ser Asp Trp
            485                 490                 495

Leu His Trp Tyr Gln Gln Lys Pro Gly Lys Ala Pro Lys Leu Leu Ile
            500                 505                 510

Ala Trp Ala Ser Ser Leu Gln Gly Gly Val Pro Ser Arg Phe Ser Gly
            515                 520                 525

Ser Gly Ser Gly Thr Asp Phe Thr Leu Thr Ile Ser Ser Leu Gln Pro
530                 535                 540

Glu Asp Phe Ala Thr Tyr Tyr Cys Leu Gln Glu Gly Trp Gly Pro Pro
545                 550                 555                 560

Thr Phe Gly Gln Gly Thr Lys Val Glu Ile Lys Arg
            565                 570

<210> SEQ ID NO 42
<211> LENGTH: 565
<212> TYPE: PRT
<213> ORGANISM: Artificial Sequence
<220> FEATURE:
<223> OTHER INFORMATION: Fusion protein

<400> SEQUENCE: 42

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
```

```
                195                 200                 205
Asn His Lys Pro Ser Asn Thr Lys Val Asp Lys Lys Val Glu Pro Lys
            210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Pro Ala Val Pro Pro Gly Ser Asp Ile Gln Met Thr Gln Ser
    450                 455                 460

Pro Ser Ser Leu Ser Ala Ser Val Gly Asp Arg Val Thr Ile Thr Cys
465                 470                 475                 480

Arg Ala Ser Arg Pro Ile Ser Asp Trp Leu His Trp Tyr Gln Gln Lys
                485                 490                 495

Pro Gly Lys Ala Pro Lys Leu Leu Ile Ala Trp Ala Ser Ser Leu Gln
            500                 505                 510

Gly Gly Val Pro Ser Arg Phe Ser Gly Ser Gly Ser Gly Thr Asp Phe
        515                 520                 525

Thr Leu Thr Ile Ser Ser Leu Gln Pro Glu Asp Phe Ala Thr Tyr Tyr
    530                 535                 540

Cys Leu Gln Glu Gly Trp Gly Pro Pro Thr Phe Gly Gln Gly Thr Lys
545                 550                 555                 560

Val Glu Ile Lys Arg
                565

<210> SEQ ID NO 43
<211> LENGTH: 571
<212> TYPE: PRT
<213> ORGANISM: Artificial Sequence
<220> FEATURE:
<223> OTHER INFORMATION: Fusion protein
```

```
<400> SEQUENCE: 43

Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
 50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Pro Ala Val Pro Pro Pro Ala Val Pro Pro Pro Gly Ser Asp
450                 455                 460

Ile Gln Met Thr Gln Ser Pro Ser Ser Leu Ser Ala Ser Val Gly Asp
465                 470                 475                 480

Arg Val Thr Ile Thr Cys Arg Ala Ser Arg Pro Ile Ser Asp Trp Leu
                485                 490                 495

His Trp Tyr Gln Gln Lys Pro Gly Lys Ala Pro Lys Leu Leu Ile Ala
            500                 505                 510

Trp Ala Ser Ser Leu Gln Gly Gly Val Pro Ser Arg Phe Ser Gly Ser
            515                 520                 525

Gly Ser Gly Thr Asp Phe Thr Leu Thr Ile Ser Ser Leu Gln Pro Glu
530                 535                 540

Asp Phe Ala Thr Tyr Tyr Cys Leu Gln Glu Gly Trp Gly Pro Pro Thr
545                 550                 555                 560

Phe Gly Gln Gly Thr Lys Val Glu Ile Lys Arg
                565                 570
```

<210> SEQ ID NO 44
<211> LENGTH: 577
<212> TYPE: PRT
<213> ORGANISM: Artificial Sequence
<220> FEATURE:
<223> OTHER INFORMATION: Fusion protein

<400> SEQUENCE: 44

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205
```

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                    245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Pro Ala Val Pro Pro Pro Ala Val Pro Pro Pro Ala Val
        450                 455                 460

Pro Pro Pro Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
        515                 520                 525

Ser Arg Phe Ser Gly Ser Gly Ser Gly Thr Asp Phe Thr Leu Thr Ile
530                 535                 540

Ser Ser Leu Gln Pro Glu Asp Phe Ala Thr Tyr Tyr Cys Leu Gln Glu
545                 550                 555                 560

Gly Trp Gly Pro Pro Thr Phe Gly Gln Gly Thr Lys Val Glu Ile Lys
                565                 570                 575

Arg

<210> SEQ ID NO 45
<211> LENGTH: 565
<212> TYPE: PRT
<213> ORGANISM: Artificial Sequence
<220> FEATURE:
<223> OTHER INFORMATION: Fusion protein

<400> SEQUENCE: 45

```
Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
```

```
              405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Thr Val Ser Asp Val Pro Gly Ser Asp Ile Gln Met Thr Gln Ser
            450                 455                 460

Pro Ser Ser Leu Ser Ala Ser Val Gly Asp Arg Val Thr Ile Thr Cys
465                 470                 475                 480

Arg Ala Ser Arg Pro Ile Ser Asp Trp Leu His Trp Tyr Gln Gln Lys
            485                 490                 495

Pro Gly Lys Ala Pro Lys Leu Leu Ile Ala Trp Ala Ser Ser Leu Gln
            500                 505                 510

Gly Gly Val Pro Ser Arg Phe Ser Gly Ser Gly Ser Gly Thr Asp Phe
            515                 520                 525

Thr Leu Thr Ile Ser Ser Leu Gln Pro Glu Asp Phe Ala Thr Tyr Tyr
            530                 535                 540

Cys Leu Gln Glu Gly Trp Gly Pro Pro Thr Phe Gly Gln Gly Thr Lys
545                 550                 555                 560

Val Glu Ile Lys Arg
            565

<210> SEQ ID NO 46
<211> LENGTH: 571
<212> TYPE: PRT
<213> ORGANISM: Artificial Sequence
<220> FEATURE:
<223> OTHER INFORMATION: Fusion protein

<400> SEQUENCE: 46

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
```

```
                195                 200                 205
Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Thr Val Ser Asp Val Pro Thr Val Ser Asp Val Pro Gly Ser Asp
        450                 455                 460

Ile Gln Met Thr Gln Ser Pro Ser Ser Leu Ser Ala Ser Val Gly Asp
465                 470                 475                 480

Arg Val Thr Ile Thr Cys Arg Ala Ser Arg Pro Ile Ser Asp Trp Leu
                485                 490                 495

His Trp Tyr Gln Gln Lys Pro Gly Lys Ala Pro Lys Leu Leu Ile Ala
                500                 505                 510

Trp Ala Ser Ser Leu Gln Gly Gly Val Pro Ser Arg Phe Ser Gly Ser
            515                 520                 525

Gly Ser Gly Thr Asp Phe Thr Leu Thr Ile Ser Ser Leu Gln Pro Glu
        530                 535                 540

Asp Phe Ala Thr Tyr Tyr Cys Leu Gln Glu Gly Trp Gly Pro Pro Thr
545                 550                 555                 560

Phe Gly Gln Gly Thr Lys Val Glu Ile Lys Arg
                565                 570

<210> SEQ ID NO 47
<211> LENGTH: 577
<212> TYPE: PRT
<213> ORGANISM: Artificial Sequence
<220> FEATURE:
<223> OTHER INFORMATION: Fusion protein
```

```
<400> SEQUENCE: 47

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415
```

```
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Thr Val Ser Asp Val Pro Thr Val Ser Asp Val Pro Thr Val Ser
450                 455                 460

Asp Val Pro Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
            485                 490                 495

Pro Ile Ser Asp Trp Leu His Trp Tyr Gln Gln Lys Pro Gly Lys Ala
            500                 505                 510

Pro Lys Leu Leu Ile Ala Trp Ala Ser Ser Leu Gln Gly Gly Val Pro
            515                 520                 525

Ser Arg Phe Ser Gly Ser Gly Ser Gly Thr Asp Phe Thr Leu Thr Ile
            530                 535                 540

Ser Ser Leu Gln Pro Glu Asp Phe Ala Thr Tyr Tyr Cys Leu Gln Glu
545                 550                 555                 560

Gly Trp Gly Pro Pro Thr Phe Gly Gln Gly Thr Lys Val Glu Ile Lys
            565                 570                 575

Arg

<210> SEQ ID NO 48
<211> LENGTH: 565
<212> TYPE: PRT
<213> ORGANISM: Artificial Sequence
<220> FEATURE:
<223> OTHER INFORMATION: Fusion protein

<400> SEQUENCE: 48

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65              70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Tyr Tyr Ala Met
            100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
            130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Ser Leu Ser Ser Val Val
            180                 185                 190
```

```
Thr Val Pro Ser Ser Ser Leu Gly Thr Gln Thr Tyr Ile Cys Asn Val
        195                 200                 205

Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
            275                 280                 285

Glu Val His Asn Ala Lys Thr Lys Pro Arg Glu Glu Gln Tyr Asn Ser
        290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
            355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Thr Gly Leu Asp Ser Pro Gly Ser Asp Ile Gln Met Thr Gln Ser
450                 455                 460

Pro Ser Ser Leu Ser Ala Ser Val Gly Asp Arg Val Thr Ile Thr Cys
465                 470                 475                 480

Arg Ala Ser Arg Pro Ile Ser Asp Trp Leu His Trp Tyr Gln Gln Lys
                485                 490                 495

Pro Gly Lys Ala Pro Lys Leu Leu Ile Ala Trp Ala Ser Ser Leu Gln
                500                 505                 510

Gly Gly Val Pro Ser Arg Phe Ser Gly Ser Gly Ser Gly Thr Asp Phe
            515                 520                 525

Thr Leu Thr Ile Ser Ser Leu Gln Pro Glu Asp Phe Ala Thr Tyr Tyr
530                 535                 540

Cys Leu Gln Glu Gly Trp Gly Pro Pro Thr Phe Gly Gln Gly Thr Lys
545                 550                 555                 560

Val Glu Ile Lys Arg
            565
```

<210> SEQ ID NO 49
<211> LENGTH: 571
<212> TYPE: PRT
<213> ORGANISM: Artificial Sequence
<220> FEATURE:
<223> OTHER INFORMATION: Fusion protein

<400> SEQUENCE: 49

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys

-continued

```
                405                 410                 415
Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys Thr Gly Leu Asp Ser Pro Thr Gly Leu Asp Ser Pro Gly Ser Asp
            450                 455                 460

Ile Gln Met Thr Gln Ser Pro Ser Ser Leu Ser Ala Ser Val Gly Asp
465                 470                 475                 480

Arg Val Thr Ile Thr Cys Arg Ala Ser Arg Pro Ile Ser Asp Trp Leu
            485                 490                 495

His Trp Tyr Gln Gln Lys Pro Gly Lys Ala Pro Lys Leu Leu Ile Ala
            500                 505                 510

Trp Ala Ser Ser Leu Gln Gly Gly Val Pro Ser Arg Phe Ser Gly Ser
            515                 520                 525

Gly Ser Gly Thr Asp Phe Thr Leu Thr Ile Ser Ser Leu Gln Pro Glu
            530                 535                 540

Asp Phe Ala Thr Tyr Tyr Cys Leu Gln Glu Gly Trp Gly Pro Pro Thr
545                 550                 555                 560

Phe Gly Gln Gly Thr Lys Val Glu Ile Lys Arg
            565                 570

<210> SEQ ID NO 50
<211> LENGTH: 577
<212> TYPE: PRT
<213> ORGANISM: Artificial Sequence
<220> FEATURE:
<223> OTHER INFORMATION: Fusion protein

<400> SEQUENCE: 50

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Ile Tyr Asp Asp Tyr His Tyr Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
            165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
```

```
                195                 200                 205
Asn His Lys Pro Ser Asn Thr Lys Val Asp Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
                290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys Thr Gly Leu Asp Ser Pro Thr Gly Leu Asp Ser Pro Thr Gly Leu
450                 455                 460

Asp Ser Pro Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
                485                 490                 495

Pro Ile Ser Asp Trp Leu His Trp Tyr Gln Gln Lys Pro Gly Lys Ala
                500                 505                 510

Pro Lys Leu Leu Ile Ala Trp Ala Ser Ser Leu Gln Gly Gly Val Pro
                515                 520                 525

Ser Arg Phe Ser Gly Ser Gly Ser Gly Thr Asp Phe Thr Leu Thr Ile
                530                 535                 540

Ser Ser Leu Gln Pro Glu Asp Phe Ala Thr Tyr Tyr Cys Leu Gln Glu
545                 550                 555                 560

Gly Trp Gly Pro Pro Thr Phe Gly Gln Gly Thr Lys Val Glu Ile Lys
                565                 570                 575

Arg

<210> SEQ ID NO 51
<211> LENGTH: 2
<212> TYPE: PRT
<213> ORGANISM: Artificial Sequence
<220> FEATURE:
```

<223> OTHER INFORMATION: Linker

<400> SEQUENCE: 51

Gly Ser
1

<210> SEQ ID NO 52
<211> LENGTH: 10
<212> TYPE: PRT
<213> ORGANISM: Artificial Sequence
<220> FEATURE:
<223> OTHER INFORMATION: Linker

<400> SEQUENCE: 52

Gly Ser Thr Val Ala Ala Pro Ser Gly Ser
1               5                   10

<210> SEQ ID NO 53
<211> LENGTH: 18
<212> TYPE: PRT
<213> ORGANISM: Artificial Sequence
<220> FEATURE:
<223> OTHER INFORMATION: Linker

<400> SEQUENCE: 53

Gly Ser Thr Val Ala Ala Pro Ser Gly Ser Thr Val Ala Ala Pro Ser
1               5                   10                  15

Gly Ser

<210> SEQ ID NO 54
<211> LENGTH: 26
<212> TYPE: PRT
<213> ORGANISM: Artificial Sequence
<220> FEATURE:
<223> OTHER INFORMATION: Linker

<400> SEQUENCE: 54

Gly Ser Thr Val Ala Ala Pro Ser Gly Ser Thr Val Ala Ala Pro Ser
1               5                   10                  15

Gly Ser Thr Val Ala Ala Pro Ser Gly Ser
            20                  25

<210> SEQ ID NO 55
<211> LENGTH: 34
<212> TYPE: PRT
<213> ORGANISM: Artificial Sequence
<220> FEATURE:
<223> OTHER INFORMATION: Linker

<400> SEQUENCE: 55

Gly Ser Thr Val Ala Ala Pro Ser Gly Ser Thr Val Ala Ala Pro Ser
1               5                   10                  15

Gly Ser Thr Val Ala Ala Pro Ser Gly Ser Thr Val Ala Ala Pro Ser
            20                  25                  30

Gly Ser

<210> SEQ ID NO 56
<211> LENGTH: 42
<212> TYPE: PRT
<213> ORGANISM: Artificial Sequence
<220> FEATURE:
<223> OTHER INFORMATION: Linker

<400> SEQUENCE: 56

Gly Ser Thr Val Ala Ala Pro Ser Gly Ser Thr Val Ala Ala Pro Ser
1               5                   10                  15

Gly Ser Thr Val Ala Ala Pro Ser Gly Ser Thr Val Ala Ala Pro Ser
                20                  25                  30

Gly Ser Thr Val Ala Ala Pro Ser Gly Ser
        35                  40

<210> SEQ ID NO 57
<211> LENGTH: 50
<212> TYPE: PRT
<213> ORGANISM: Artificial Sequence
<220> FEATURE:
<223> OTHER INFORMATION: Linker

<400> SEQUENCE: 57

Gly Ser Thr Val Ala Ala Pro Ser Gly Ser Thr Val Ala Ala Pro Ser
1               5                   10                  15

Gly Ser Thr Val Ala Ala Pro Ser Gly Ser Thr Val Ala Ala Pro Ser
                20                  25                  30

Gly Ser Thr Val Ala Ala Pro Ser Gly Ser Thr Val Ala Ala Pro Ser
        35                  40                  45

Gly Ser
    50

<210> SEQ ID NO 58
<211> LENGTH: 5
<212> TYPE: PRT
<213> ORGANISM: Artificial Sequence
<220> FEATURE:
<223> OTHER INFORMATION: Linker

<400> SEQUENCE: 58

Pro Ala Ser Gly Ser
1               5

<210> SEQ ID NO 59
<211> LENGTH: 6
<212> TYPE: PRT
<213> ORGANISM: Artificial Sequence
<220> FEATURE:
<223> OTHER INFORMATION: Linker

<400> SEQUENCE: 59

Pro Asp Ala Ser Gly Ser
1               5

<210> SEQ ID NO 60
<211> LENGTH: 7
<212> TYPE: PRT
<213> ORGANISM: Artificial Sequence
<220> FEATURE:
<223> OTHER INFORMATION: Linker

<400> SEQUENCE: 60

Pro Asp Asp Ala Ser Gly Ser
1               5

<210> SEQ ID NO 61
<211> LENGTH: 5
<212> TYPE: PRT
<213> ORGANISM: Artificial Sequence
<220> FEATURE:
<223> OTHER INFORMATION: Linker

<400> SEQUENCE: 61

```
Gly Gly Gly Gly Ser
1               5

<210> SEQ ID NO 62
<211> LENGTH: 10
<212> TYPE: PRT
<213> ORGANISM: Artificial Sequence
<220> FEATURE:
<223> OTHER INFORMATION: Linker

<400> SEQUENCE: 62

Gly Gly Gly Gly Ser Gly Gly Gly Gly Ser
1               5                   10

<210> SEQ ID NO 63
<211> LENGTH: 15
<212> TYPE: PRT
<213> ORGANISM: Artificial Sequence
<220> FEATURE:
<223> OTHER INFORMATION: Linker

<400> SEQUENCE: 63

Gly Gly Gly Gly Ser Gly Gly Gly Gly Ser Gly Gly Gly Gly Ser
1               5                   10                  15

<210> SEQ ID NO 64
<211> LENGTH: 8
<212> TYPE: PRT
<213> ORGANISM: Artificial Sequence
<220> FEATURE:
<223> OTHER INFORMATION: Linker

<400> SEQUENCE: 64

Pro Ala Val Pro Pro Pro Gly Ser
1               5

<210> SEQ ID NO 65
<211> LENGTH: 14
<212> TYPE: PRT
<213> ORGANISM: Artificial Sequence
<220> FEATURE:
<223> OTHER INFORMATION: Linker

<400> SEQUENCE: 65

Pro Ala Val Pro Pro Pro Ala Val Pro Pro Pro Gly Ser
1               5                   10

<210> SEQ ID NO 66
<211> LENGTH: 20
<212> TYPE: PRT
<213> ORGANISM: Artificial Sequence
<220> FEATURE:
<223> OTHER INFORMATION: Linker

<400> SEQUENCE: 66

Pro Ala Val Pro Pro Pro Ala Val Pro Pro Pro Ala Val Pro
1               5                   10                  15

Pro Pro Gly Ser
            20

<210> SEQ ID NO 67
<211> LENGTH: 8
<212> TYPE: PRT
<213> ORGANISM: Artificial Sequence
<220> FEATURE:
<223> OTHER INFORMATION: Linker
```

<400> SEQUENCE: 67

Thr Val Ser Asp Val Pro Gly Ser
1               5

<210> SEQ ID NO 68
<211> LENGTH: 14
<212> TYPE: PRT
<213> ORGANISM: Artificial Sequence
<220> FEATURE:
<223> OTHER INFORMATION: Linker

<400> SEQUENCE: 68

Thr Val Ser Asp Val Pro Thr Val Ser Asp Val Pro Gly Ser
1               5                   10

<210> SEQ ID NO 69
<211> LENGTH: 20
<212> TYPE: PRT
<213> ORGANISM: Artificial Sequence
<220> FEATURE:
<223> OTHER INFORMATION: Linker

<400> SEQUENCE: 69

Thr Val Ser Asp Val Pro Thr Val Ser Asp Val Pro Thr Val Ser Asp
1               5                   10                  15

Val Pro Gly Ser
            20

<210> SEQ ID NO 70
<211> LENGTH: 8
<212> TYPE: PRT
<213> ORGANISM: Artificial Sequence
<220> FEATURE:
<223> OTHER INFORMATION: Linker

<400> SEQUENCE: 70

Thr Gly Leu Asp Ser Pro Gly Ser
1               5

<210> SEQ ID NO 71
<211> LENGTH: 14
<212> TYPE: PRT
<213> ORGANISM: Artificial Sequence
<220> FEATURE:
<223> OTHER INFORMATION: Linker

<400> SEQUENCE: 71

Thr Gly Leu Asp Ser Pro Thr Gly Leu Asp Ser Pro Gly Ser
1               5                   10

<210> SEQ ID NO 72
<211> LENGTH: 20
<212> TYPE: PRT
<213> ORGANISM: Artificial Sequence
<220> FEATURE:
<223> OTHER INFORMATION: Linker

<400> SEQUENCE: 72

Thr Gly Leu Asp Ser Pro Thr Gly Leu Asp Ser Pro Thr Gly Leu Asp
1               5                   10                  15

Ser Pro Gly Ser
            20

<210> SEQ ID NO 73

```
<211> LENGTH: 8
<212> TYPE: PRT
<213> ORGANISM: Artificial Sequence
<220> FEATURE:
<223> OTHER INFORMATION: Linker

<400> SEQUENCE: 73

Thr Val Ala Ala Pro Ser Gly Ser
1               5

<210> SEQ ID NO 74
<211> LENGTH: 3
<212> TYPE: PRT
<213> ORGANISM: Artificial Sequence
<220> FEATURE:
<223> OTHER INFORMATION: Linker

<400> SEQUENCE: 74

Pro Ala Ser
1

<210> SEQ ID NO 75
<211> LENGTH: 6
<212> TYPE: PRT
<213> ORGANISM: Artificial Sequence
<220> FEATURE:
<223> OTHER INFORMATION: Linker

<400> SEQUENCE: 75

Thr Val Ala Ala Pro Ser
1               5

<210> SEQ ID NO 76
<211> LENGTH: 6
<212> TYPE: PRT
<213> ORGANISM: Artificial Sequence
<220> FEATURE:
<223> OTHER INFORMATION: Linker

<400> SEQUENCE: 76

Pro Ala Val Pro Pro Pro
1               5

<210> SEQ ID NO 77
<211> LENGTH: 6
<212> TYPE: PRT
<213> ORGANISM: Artificial Sequence
<220> FEATURE:
<223> OTHER INFORMATION: Linker

<400> SEQUENCE: 77

Thr Val Ser Asp Val Pro
1               5

<210> SEQ ID NO 78
<211> LENGTH: 6
<212> TYPE: PRT
<213> ORGANISM: Artificial Sequence
<220> FEATURE:
<223> OTHER INFORMATION: Linker

<400> SEQUENCE: 78

Thr Gly Leu Asp Ser Pro
1               5

<210> SEQ ID NO 79
<211> LENGTH: 565
```

```
<212> TYPE: PRT
<213> ORGANISM: Artificial Sequence
<220> FEATURE:
<223> OTHER INFORMATION: Fusion protein

<400> SEQUENCE: 79
```

| | | | | | | | | | | | | | | |
|---|---|---|---|---|---|---|---|---|---|---|---|---|---|---|
| Gln | Val | Gln | Leu | Val | Gln | Ser | Gly | Ala | Glu | Val | Lys | Lys | Pro | Gly | Ser |
| 1 | | | | 5 | | | | | 10 | | | | | 15 |
| Ser | Val | Lys | Val | Ser | Cys | Lys | Ala | Ser | Gly | Phe | Tyr | Ile | Lys | Asp | Thr |
| | | | 20 | | | | | 25 | | | | | 30 | |
| Tyr | Met | His | Trp | Val | Arg | Gln | Ala | Pro | Gly | Gln | Gly | Leu | Glu | Trp | Met |
| | | 35 | | | | | 40 | | | | | 45 | | |
| Gly | Thr | Ile | Asp | Pro | Ala | Asn | Gly | Asn | Thr | Lys | Tyr | Val | Pro | Lys | Phe |
| | 50 | | | | | 55 | | | | | 60 | | | | |
| Gln | Gly | Arg | Val | Thr | Ile | Thr | Ala | Asp | Glu | Ser | Thr | Ser | Thr | Ala | Tyr |
| 65 | | | | | 70 | | | | | 75 | | | | | 80 |
| Met | Glu | Leu | Ser | Ser | Leu | Arg | Ser | Glu | Asp | Thr | Ala | Val | Tyr | Tyr | Cys |
| | | | | 85 | | | | | 90 | | | | | 95 | |
| Ala | Arg | Ser | Ile | Tyr | Asp | Asp | Tyr | His | Tyr | Asp | Asp | Tyr | Tyr | Ala | Met |
| | | | 100 | | | | | 105 | | | | | 110 | | |
| Asp | Tyr | Trp | Gly | Gln | Gly | Thr | Leu | Val | Thr | Val | Ser | Ser | Ala | Ser | Thr |
| | | | 115 | | | | | 120 | | | | | 125 | | |
| Lys | Gly | Pro | Ser | Val | Phe | Pro | Leu | Ala | Pro | Ser | Ser | Lys | Ser | Thr | Ser |
| 130 | | | | | 135 | | | | | 140 | | | | | |
| Gly | Gly | Thr | Ala | Ala | Leu | Gly | Cys | Leu | Val | Lys | Asp | Tyr | Phe | Pro | Glu |
| 145 | | | | | 150 | | | | | 155 | | | | | 160 |
| Pro | Val | Thr | Val | Ser | Trp | Asn | Ser | Gly | Ala | Leu | Thr | Ser | Gly | Val | His |
| | | | | 165 | | | | | 170 | | | | | 175 | |
| Thr | Phe | Pro | Ala | Val | Leu | Gln | Ser | Ser | Gly | Ser | Leu | Ser | Ser | Val | Val |
| | | 180 | | | | | 185 | | | | | 190 | | | |
| Thr | Val | Pro | Ser | Ser | Ser | Leu | Gly | Thr | Gln | Thr | Tyr | Ile | Cys | Asn | Val |
| | | 195 | | | | | 200 | | | | | 205 | | | |
| Asn | His | Lys | Pro | Ser | Asn | Thr | Lys | Val | Asp | Lys | Lys | Val | Glu | Pro | Lys |
| 210 | | | | | 215 | | | | | 220 | | | | | |
| Ser | Cys | Asp | Lys | Thr | His | Thr | Cys | Pro | Pro | Cys | Pro | Ala | Pro | Glu | Leu |
| 225 | | | | | 230 | | | | | 235 | | | | | 240 |
| Leu | Gly | Gly | Pro | Ser | Val | Phe | Leu | Phe | Pro | Pro | Lys | Pro | Lys | Asp | Thr |
| | | | | 245 | | | | | 250 | | | | | 255 | |
| Leu | Met | Ile | Ser | Arg | Thr | Pro | Glu | Val | Thr | Cys | Val | Val | Val | Asp | Val |
| | | | 260 | | | | | 265 | | | | | 270 | | |
| Ser | His | Glu | Asp | Pro | Glu | Val | Lys | Phe | Asn | Trp | Tyr | Val | Asp | Gly | Val |
| | | 275 | | | | | 280 | | | | | 285 | | | |
| Glu | Val | His | Asn | Ala | Lys | Thr | Lys | Pro | Arg | Glu | Glu | Gln | Tyr | Asn | Ser |
| | | 290 | | | | | 295 | | | | | 300 | | | |
| Tyr | Val | Val | Ser | Val | Leu | Thr | Val | Leu | His | Gln | Asp | Trp | Leu | Asn | Gly |
| 305 | | | | | 310 | | | | | 315 | | | | | 320 |
| Lys | Glu | Tyr | Lys | Cys | Lys | Val | Ser | Asn | Lys | Ala | Leu | Pro | Ala | Pro | Ile |
| | | | 325 | | | | | 330 | | | | | 335 | | |
| Glu | Lys | Thr | Ile | Ser | Lys | Ala | Lys | Gly | Gln | Pro | Arg | Glu | Pro | Gln | Val |
| | | | 340 | | | | | 345 | | | | | 350 | | |
| Tyr | Thr | Leu | Pro | Pro | Ser | Arg | Asp | Glu | Leu | Thr | Lys | Asn | Gln | Val | Ser |
| | | 355 | | | | | 360 | | | | | 365 | | | |
| Leu | Thr | Cys | Leu | Val | Lys | Gly | Phe | Tyr | Pro | Ser | Asp | Ile | Ala | Val | Glu |
| | | 370 | | | | | 375 | | | | | 380 | | | |

```
Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
            435                 440                 445

Lys Thr Val Ala Ala Pro Ser Gly Ser Asp Ile Gln Met Thr Gln Ser
        450                 455                 460

Pro Ser Ser Leu Ser Ala Ser Val Gly Asp Arg Val Thr Ile Thr Cys
465                 470                 475                 480

Arg Ala Ser Arg Pro Ile Ser Asp Trp Leu His Trp Tyr Gln Gln Lys
            485                 490                 495

Pro Gly Lys Ala Pro Lys Leu Leu Ile Ala Trp Ala Ser Ser Leu Gln
        500                 505                 510

Gly Gly Val Pro Ser Arg Phe Ser Gly Ser Gly Ser Gly Thr Asp Phe
            515                 520                 525

Thr Leu Thr Ile Ser Ser Leu Gln Pro Glu Asp Phe Ala Thr Tyr Tyr
        530                 535                 540

Cys Leu Gln Glu Gly Trp Gly Pro Pro Thr Phe Gly Gln Gly Thr Lys
545                 550                 555                 560

Val Glu Ile Lys Arg
            565

<210> SEQ ID NO 80
<211> LENGTH: 108
<212> TYPE: PRT
<213> ORGANISM: Homo Sapiens

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Ser Asp Trp
            20                  25                  30

Leu His Trp Tyr Gln Gln Lys Pro Gly Lys Ala Pro Lys Leu Leu Ile
        35                  40                  45

Ala Trp Ala Ser Thr Leu Asp Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Glu Gly Trp Gly Pro Pro
                85                  90                  95

Thr Phe Gly Gln Gly Thr Lys Val Glu Ile Lys Arg
            100                 105

<210> SEQ ID NO 81
<211> LENGTH: 108
<212> TYPE: PRT
<213> ORGANISM: Homo Sapiens

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Ser Asp Trp
            20                  25                  30
```

```
Leu His Trp Tyr Gln Gln Lys Pro Gly Lys Ala Pro Lys Leu Leu Ile
        35                  40                  45

Ala Trp Ala Ser Ser Leu Tyr Glu Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Leu Gln Glu Gly Trp Gly Pro Pro
                 85                  90                  95

Thr Phe Gly Gln Gly Thr Lys Val Glu Ile Lys Arg
            100                 105
```

<210> SEQ ID NO 82
<211> LENGTH: 116
<212> TYPE: PRT
<213> ORGANISM: Homo Sapiens

<400> SEQUENCE: 82

```
Glu Val Gln Leu Leu Glu Ser Gly Gly Leu Val Gln Pro Gly Gly
 1               5                   10                  15

Ser Leu Arg Leu Ser Cys Ala Ala Ser Gly Phe Thr Phe Arg Asn Phe
            20                  25                  30

Gly Met Gly Trp Val Arg Gln Ala Pro Gly Lys Gly Leu Glu Trp Val
        35                  40                  45

Ser Trp Ile Ile Ser Ser Gly Thr Glu Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Ser Leu Gly Arg Phe Asp Tyr Trp Gly Gln Gly Thr Leu Val
            100                 105                 110

Thr Val Ser Ser
        115
```

<210> SEQ ID NO 83
<211> LENGTH: 118
<212> TYPE: PRT
<213> ORGANISM: Homo Sapiens

<400> SEQUENCE: 83

```
Gly Val Gln Leu Leu Glu Ser Gly Gly Leu Val Gln Pro Gly Gly
 1               5                   10                  15

Ser Leu Arg Leu Ser Cys Ala Ala Ser Gly Phe Thr Phe Ala Trp Tyr
            20                  25                  30

Asp Met Gly Trp Val Arg Gln Ala Pro Gly Lys Gly Leu Glu Trp Val
        35                  40                  45

Ser Ser Ile Asp Trp His Gly Glu Val Thr Tyr Tyr Ala Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Ala Glu Asp Glu Pro Gly Tyr Asp Tyr Trp Gly Gln Gly Thr
            100                 105                 110

Leu Val Thr Val Ser Ser
            115
```

```
<210> SEQ ID NO 84
<211> LENGTH: 19
<212> TYPE: PRT
<213> ORGANISM: Artificial Sequence
<220> FEATURE:
<223> OTHER INFORMATION: Signal sequence

<400> SEQUENCE: 84

Met Gly Trp Ser Cys Ile Ile Leu Phe Leu Val Ala Thr Ala Thr Gly
 1               5                  10                  15

Val His Ser

<210> SEQ ID NO 85
<211> LENGTH: 571
<212> TYPE: PRT
<213> ORGANISM: Artificial Sequence
<220> FEATURE:
<223> OTHER INFORMATION: Fusion protein

<400> SEQUENCE: 85

Gly Val Gln Leu Leu Glu Ser Gly Gly Gly Leu Val Gln Pro Gly Gly
 1               5                  10                  15

Ser Leu Arg Leu Ser Cys Ala Ala Ser Gly Phe Val Phe Pro Trp Tyr
             20                  25                  30

Asp Met Gly Trp Val Arg Gln Ala Pro Gly Lys Gly Leu Glu Trp Val
         35                  40                  45

Ser Ser Ile Asp Trp His Gly Lys Ile Thr Tyr Tyr Ala Asp Ser Val
     50                  55                  60

Lys Gly Arg Phe Thr Ile Ser Arg Asp Asn Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Thr Ala Glu Asp Glu Pro Gly Tyr Asp Tyr Trp Gly Gln Gly Thr
            100                 105                 110

Leu Val Thr Val Ser Ser Gly Ser Thr Val Ala Ala Pro Ser Gln Val
        115                 120                 125

Thr Leu Arg Glu Ser Gly Pro Ala Leu Val Lys Pro Thr Gln Thr Leu
    130                 135                 140

Thr Leu Thr Cys Thr Phe Ser Gly Phe Ser Leu Ser Thr Ser Gly Met
145                 150                 155                 160

Gly Val Ser Trp Ile Arg Gln Pro Pro Gly Lys Gly Leu Glu Trp Leu
                165                 170                 175

Ala His Ile Tyr Trp Asp Asp Lys Arg Tyr Asn Pro Ser Leu Lys
            180                 185                 190

Ser Arg Leu Thr Ile Ser Lys Asp Thr Ser Arg Asn Gln Val Val Leu
        195                 200                 205

Thr Met Thr Asn Met Asp Pro Val Asp Thr Ala Thr Tyr Tyr Cys Ala
    210                 215                 220

Arg Arg Glu Thr Val Phe Tyr Trp Tyr Phe Asp Val Trp Gly Arg Gly
225                 230                 235                 240

Thr Leu Val Thr Val Ser Ser Ala Ser Thr Lys Gly Pro Ser Val Phe
                245                 250                 255

Pro Leu Ala Pro Ser Ser Lys Ser Thr Ser Gly Gly Thr Ala Ala Leu
            260                 265                 270

Gly Cys Leu Val Lys Asp Tyr Phe Pro Glu Pro Val Thr Val Ser Trp
        275                 280                 285
```

```
Asn Ser Gly Ala Leu Thr Ser Gly Val His Thr Phe Pro Ala Val Leu
    290                 295                 300

Gln Ser Ser Gly Ser Leu Ser Ser Val Val Thr Val Pro Ser Ser Ser
305                 310                 315                 320

Leu Gly Thr Gln Thr Tyr Ile Cys Asn Val Asn His Lys Pro Ser Asn
                325                 330                 335

Thr Lys Val Asp Lys Lys Val Glu Pro Lys Ser Cys Asp Lys Thr His
            340                 345                 350

Thr Cys Pro Pro Cys Pro Ala Pro Glu Leu Leu Gly Gly Pro Ser Val
        355                 360                 365

Phe Leu Phe Pro Pro Lys Pro Lys Asp Thr Leu Met Ile Ser Arg Thr
370                 375                 380

Pro Glu Val Thr Cys Val Val Val Asp Val Ser His Glu Asp Pro Glu
385                 390                 395                 400

Val Lys Phe Asn Trp Tyr Val Asp Gly Val Glu Val His Asn Ala Lys
                405                 410                 415

Thr Lys Pro Arg Glu Glu Gln Tyr Asn Ser Tyr Val Val Ser Val Leu
            420                 425                 430

Thr Val Leu His Gln Asp Trp Leu Asn Gly Lys Glu Tyr Lys Cys Lys
        435                 440                 445

Val Ser Asn Lys Ala Leu Pro Ala Pro Ile Glu Lys Thr Ile Ser Lys
450                 455                 460

Ala Lys Gly Gln Pro Arg Glu Pro Gln Val Tyr Thr Leu Pro Pro Ser
465                 470                 475                 480

Arg Asp Glu Leu Thr Lys Asn Gln Val Ser Leu Thr Cys Leu Val Lys
                485                 490                 495

Gly Phe Tyr Pro Ser Asp Ile Ala Val Glu Trp Glu Ser Asn Gly Gln
            500                 505                 510

Pro Glu Asn Asn Tyr Lys Thr Thr Pro Pro Val Leu Asp Ser Asp Gly
        515                 520                 525

Ser Phe Phe Lys Lys Leu Thr Val Asp Lys Ser Arg Trp Gln Gln Gly
530                 535                 540

Asn Val Phe Ser Cys Ser Val Met His Glu Ala Leu His Asn His Tyr
545                 550                 555                 560

Thr Gln Lys Ser Leu Ser Leu Ser Pro Gly Lys
                565                 570

<210> SEQ ID NO 86
<211> LENGTH: 572
<212> TYPE: PRT
<213> ORGANISM: Artificial Sequence
<220> FEATURE:
<223> OTHER INFORMATION: Fusion protein

<400> SEQUENCE: 86

Gly Val Gln Leu Leu Glu Ser Gly Gly Gly Leu Val Gln Pro Gly Gly
  1               5                  10                  15

Ser Leu Arg Leu Ser Cys Ala Ala Ser Gly Phe Val Phe Pro Trp Tyr
                 20                  25                  30

Asp Met Gly Trp Val Arg Gln Ala Pro Gly Lys Gly Leu Glu Trp Val
             35                  40                  45

Ser Ser Ile Asp Trp His Gly Lys Ile Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                 85                  90                  95

Ala Thr Ala Glu Asp Glu Pro Gly Tyr Asp Tyr Trp Gly Gln Gly Thr
            100                 105                 110

Leu Val Thr Val Ser Ser Gly Ser Ala Ser Thr Lys Gly Pro Ser Gln
        115                 120                 125

Val Thr Leu Arg Glu Ser Gly Pro Ala Leu Val Lys Pro Thr Gln Thr
    130                 135                 140

Leu Thr Leu Thr Cys Thr Phe Ser Gly Phe Ser Leu Ser Thr Ser Gly
145                 150                 155                 160

Met Gly Val Ser Trp Ile Arg Gln Pro Pro Gly Lys Gly Leu Glu Trp
                165                 170                 175

Leu Ala His Ile Tyr Trp Asp Asp Lys Arg Tyr Asn Pro Ser Leu
            180                 185                 190

Lys Ser Arg Leu Thr Ile Ser Lys Asp Thr Ser Arg Asn Gln Val Val
        195                 200                 205

Leu Thr Met Thr Asn Met Asp Pro Val Asp Thr Ala Thr Tyr Tyr Cys
    210                 215                 220

Ala Arg Arg Glu Thr Val Phe Tyr Trp Tyr Phe Asp Val Trp Gly Arg
225                 230                 235                 240

Gly Thr Leu Val Thr Val Ser Ser Ala Ser Thr Lys Gly Pro Ser Val
                245                 250                 255

Phe Pro Leu Ala Pro Ser Ser Lys Ser Thr Ser Gly Gly Thr Ala Ala
            260                 265                 270

Leu Gly Cys Leu Val Lys Asp Tyr Phe Pro Glu Pro Val Thr Val Ser
        275                 280                 285

Trp Asn Ser Gly Ala Leu Thr Ser Gly Val His Thr Phe Pro Ala Val
    290                 295                 300

Leu Gln Ser Ser Gly Ser Leu Ser Ser Val Val Thr Val Pro Ser Ser
305                 310                 315                 320

Ser Leu Gly Thr Gln Thr Tyr Ile Cys Asn Val Asn His Lys Pro Ser
                325                 330                 335

Asn Thr Lys Val Asp Lys Lys Val Glu Pro Lys Ser Cys Asp Lys Thr
            340                 345                 350

His Thr Cys Pro Pro Cys Pro Ala Pro Glu Leu Leu Gly Gly Pro Ser
        355                 360                 365

Val Phe Leu Phe Pro Pro Lys Pro Lys Asp Thr Leu Met Ile Ser Arg
    370                 375                 380

Thr Pro Glu Val Thr Cys Val Val Val Asp Val Ser His Glu Asp Pro
385                 390                 395                 400

Glu Val Lys Phe Asn Trp Tyr Val Asp Gly Val Glu Val His Asn Ala
                405                 410                 415

Lys Thr Lys Pro Arg Glu Glu Gln Tyr Asn Ser Tyr Val Val Ser Val
            420                 425                 430

Leu Thr Val Leu His Gln Asp Trp Leu Asn Gly Lys Glu Tyr Lys Cys
        435                 440                 445

Lys Val Ser Asn Lys Ala Leu Pro Ala Pro Ile Glu Lys Thr Ile Ser
    450                 455                 460

Lys Ala Lys Gly Gln Pro Arg Glu Pro Gln Val Tyr Thr Leu Pro Pro
465                 470                 475                 480

Ser Arg Asp Glu Leu Thr Lys Asn Gln Val Ser Leu Thr Cys Leu Val
                485                 490                 495

Lys Gly Phe Tyr Pro Ser Asp Ile Ala Val Glu Trp Glu Ser Asn Gly
```

```
                   500                 505                 510
Gln Pro Glu Asn Asn Tyr Lys Thr Thr Pro Val Leu Asp Ser Asp
            515                 520                 525
Gly Ser Phe Phe Lys Lys Leu Thr Val Asp Lys Ser Arg Trp Gln Gln
    530                 535                 540
Gly Asn Val Phe Ser Cys Ser Val Met His Glu Ala Leu His Asn His
545                 550                 555                 560
Tyr Thr Gln Lys Ser Leu Ser Leu Ser Pro Gly Lys
                565                 570
```

<210> SEQ ID NO 87
<211> LENGTH: 342
<212> TYPE: PRT
<213> ORGANISM: Artificial Sequence
<220> FEATURE:
<223> OTHER INFORMATION: Fusion protein

<400> SEQUENCE: 87

```
Gly Val Gln Leu Leu Glu Ser Gly Gly Gly Leu Val Gln Pro Gly Gly
  1               5                   10                  15
Ser Leu Arg Leu Ser Cys Ala Ala Ser Gly Phe Val Phe Pro Trp Tyr
                20                  25                  30
Asp Met Gly Trp Val Arg Gln Ala Pro Gly Lys Gly Leu Glu Trp Val
            35                  40                  45
Ser Ser Ile Asp Trp His Gly Lys Ile Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Thr Ala Glu Asp Glu Pro Gly Tyr Asp Tyr Trp Gly Gln Gly Thr
            100                 105                 110
Leu Val Thr Val Ser Ser Gly Ser Thr Val Ala Ala Pro Ser Asp Ile
        115                 120                 125
Val Leu Thr Gln Ser Pro Ser Ser Leu Ser Ala Ser Val Gly Asp Arg
130                 135                 140
Val Thr Ile Thr Cys Lys Ala Ser Gln Ser Val Asp Tyr Asp Gly Asp
145                 150                 155                 160
Ser Tyr Met Asn Trp Tyr Gln Gln Lys Pro Gly Lys Ala Pro Lys Leu
                165                 170                 175
Leu Ile Tyr Ala Asn Leu Glu Ser Gly Ile Pro Ser Arg Phe Ser Gly
            180                 185                 190
Ser Gly Ser Gly Thr Asp Phe Thr Phe Thr Ile Ser Ser Leu Gln Pro
        195                 200                 205
Glu Asp Ile Ala Thr Tyr Tyr Cys Gln Gln Ser Asn Glu Asp Pro Pro
    210                 215                 220
Thr Phe Gly Gln Gly Thr Lys Val Glu Ile Lys Arg Thr Val Ala Ala
225                 230                 235                 240
Pro Ser Val Phe Ile Phe Pro Pro Ser Asp Glu Gln Leu Lys Ser Gly
                245                 250                 255
Thr Ala Ser Val Val Cys Leu Leu Asn Asn Phe Tyr Pro Arg Glu Ala
            260                 265                 270
Lys Val Gln Trp Lys Val Asp Asn Ala Leu Gln Ser Gly Asn Ser Gln
        275                 280                 285
Glu Ser Val Thr Glu Gln Asp Ser Lys Asp Ser Thr Tyr Ser Leu Ser
```

```
            290                 295                 300
Ser Thr Leu Thr Leu Ser Lys Ala Asp Tyr Glu Lys His Lys Val Tyr
305                 310                 315                 320

Ala Cys Glu Val Thr His Gln Gly Leu Ser Ser Pro Val Thr Lys Ser
                325                 330                 335

Phe Asn Arg Gly Glu Cys
            340

<210> SEQ ID NO 88
<211> LENGTH: 343
<212> TYPE: PRT
<213> ORGANISM: Artificial Sequence
<220> FEATURE:
<223> OTHER INFORMATION: Fusion protein

<400> SEQUENCE: 88

Gly Val Gln Leu Leu Glu Ser Gly Gly Gly Leu Val Gln Pro Gly Gly
1               5                   10                  15

Ser Leu Arg Leu Ser Cys Ala Ala Ser Gly Phe Val Phe Pro Trp Tyr
            20                  25                  30

Asp Met Gly Trp Val Arg Gln Ala Pro Gly Lys Gly Leu Glu Trp Val
        35                  40                  45

Ser Ser Ile Asp Trp His Gly Lys Ile Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Thr Ala Glu Asp Glu Pro Gly Tyr Asp Tyr Trp Gly Gln Gly Thr
            100                 105                 110

Leu Val Thr Val Ser Ser Gly Ser Ala Ser Thr Lys Gly Pro Ser Asp
        115                 120                 125

Ile Val Leu Thr Gln Ser Pro Ser Ser Leu Ser Ala Ser Val Gly Asp
    130                 135                 140

Arg Val Thr Ile Thr Cys Lys Ala Ser Gln Ser Val Asp Tyr Asp Gly
145                 150                 155                 160

Asp Ser Tyr Met Asn Trp Tyr Gln Gln Lys Pro Gly Lys Ala Pro Lys
                165                 170                 175

Leu Leu Ile Tyr Ala Asn Leu Glu Ser Gly Ile Pro Ser Arg Phe Ser
            180                 185                 190

Gly Ser Gly Ser Gly Thr Asp Phe Thr Phe Thr Ile Ser Ser Leu Gln
        195                 200                 205

Pro Glu Asp Ile Ala Thr Tyr Tyr Cys Gln Gln Ser Asn Glu Asp Pro
    210                 215                 220

Pro Thr Phe Gly Gln Gly Thr Lys Val Glu Ile Lys Arg Thr Val Ala
225                 230                 235                 240

Ala Pro Ser Val Phe Ile Phe Pro Pro Ser Asp Glu Gln Leu Lys Ser
                245                 250                 255

Gly Thr Ala Ser Val Val Cys Leu Leu Asn Asn Phe Tyr Pro Arg Glu
            260                 265                 270

Ala Lys Val Gln Trp Lys Val Asp Asn Ala Leu Gln Ser Gly Asn Ser
        275                 280                 285

Gln Glu Ser Val Thr Glu Gln Asp Ser Lys Asp Ser Thr Tyr Ser Leu
    290                 295                 300

Ser Ser Thr Leu Thr Leu Ser Lys Ala Asp Tyr Glu Lys His Lys Val
```

```
             305                 310                 315                 320
Tyr Ala Cys Glu Val Thr His Gln Gly Leu Ser Ser Pro Val Thr Lys
                325                 330                 335
Ser Phe Asn Arg Gly Glu Cys
                340

<210> SEQ ID NO 89
<211> LENGTH: 340
<212> TYPE: PRT
<213> ORGANISM: Artificial Sequence
<220> FEATURE:
<223> OTHER INFORMATION: Fusion protein

<400> SEQUENCE: 89

Asp Ile Val Leu Thr Gln Ser Pro Ser Ser Leu Ser Ala Ser Val Gly
1               5                  10                  15

Asp Arg Val Thr Ile Thr Cys Lys Ala Ser Gln Ser Val Asp Tyr Asp
            20                  25                  30

Gly Asp Ser Tyr Met Asn Trp Tyr Gln Gln Lys Pro Gly Lys Ala Pro
        35                  40                  45

Lys Leu Leu Ile Tyr Ala Asn Leu Glu Ser Gly Ile Pro Ser Arg Phe
    50                  55                  60

Ser Gly Ser Gly Ser Gly Thr Asp Phe Thr Phe Thr Ile Ser Ser Leu
65                  70                  75                  80

Gln Pro Glu Asp Ile Ala Thr Tyr Tyr Cys Gln Gln Ser Asn Glu Asp
                85                  90                  95

Pro Pro Thr Phe Gly Gln Gly Thr Lys Val Glu Ile Lys Arg Thr Val
            100                 105                 110

Ala Ala Pro Ser Val Phe Ile Phe Pro Pro Ser Asp Glu Gln Leu Lys
        115                 120                 125

Ser Gly Thr Ala Ser Val Val Cys Leu Leu Asn Asn Phe Tyr Pro Arg
    130                 135                 140

Glu Ala Lys Val Gln Trp Lys Val Asp Asn Ala Leu Gln Ser Gly Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys Thr Val Ala Ala Pro Ser Gly Val
    210                 215                 220

Gln Leu Leu Glu Ser Gly Gly Gly Leu Val Gln Pro Gly Gly Ser Leu
225                 230                 235                 240

Arg Leu Ser Cys Ala Ala Ser Gly Phe Val Phe Pro Trp Tyr Asp Met
                245                 250                 255

Gly Trp Val Arg Gln Ala Pro Gly Lys Gly Leu Glu Trp Val Ser Ser
            260                 265                 270

Ile Asp Trp His Gly Lys Ile Thr Tyr Tyr Ala Asp Ser Val Lys Gly
        275                 280                 285

Arg Phe Thr Ile Ser Arg Asp Asn Ser Lys Asn Thr Leu Tyr Leu Gln
    290                 295                 300

Met Asn Ser Leu Arg Ala Glu Asp Thr Ala Val Tyr Tyr Cys Ala Thr
305                 310                 315                 320

Ala Glu Asp Glu Pro Gly Tyr Asp Tyr Trp Gly Gln Gly Thr Leu Val
```

```
                    325                 330                 335

Thr Val Ser Ser
            340

<210> SEQ ID NO 90
<211> LENGTH: 569
<212> TYPE: PRT
<213> ORGANISM: Artificial Sequence
<220> FEATURE:
<223> OTHER INFORMATION: Fusion protein

<400> SEQUENCE: 90

Gln Val Thr Leu Arg Glu Ser Gly Pro Ala Leu Val Lys Pro Thr Gln
  1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Lys Arg Tyr Asn Pro Ser
     50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
```

```
              340                 345                 350
Pro Ser Arg Asp Glu Leu Thr Lys Asn Gln Val Ser Leu Thr Cys Leu
            355                 360                 365
Val Lys Gly Phe Tyr Pro Ser Asp Ile Ala Val Glu Trp Glu Ser Asn
        370                 375                 380
Gly Gln Pro Glu Asn Asn Tyr Lys Thr Thr Pro Pro Val Leu Asp Ser
385                 390                 395                 400
Asp Gly Ser Phe Phe Lys Lys Leu Thr Val Asp Lys Ser Arg Trp Gln
            405                 410                 415
Gln Gly Asn Val Phe Ser Cys Ser Val Met His Glu Ala Leu His Asn
        420                 425                 430
His Tyr Thr Gln Lys Ser Leu Ser Leu Ser Pro Gly Lys Thr Val Ala
            435                 440                 445
Ala Pro Ser Gly Val Gln Leu Leu Glu Ser Gly Gly Gly Leu Val Gln
        450                 455                 460
Pro Gly Gly Ser Leu Arg Leu Ser Cys Ala Ala Ser Gly Phe Val Phe
465                 470                 475                 480
Pro Trp Tyr Asp Met Gly Trp Val Arg Gln Ala Pro Gly Lys Gly Leu
            485                 490                 495
Glu Trp Val Ser Ser Ile Asp Trp His Gly Lys Ile Thr Tyr Tyr Ala
        500                 505                 510
Asp Ser Val Lys Gly Arg Phe Thr Ile Ser Arg Asp Asn Ser Lys Asn
            515                 520                 525
Thr Leu Tyr Leu Gln Met Asn Ser Leu Arg Ala Glu Asp Thr Ala Val
        530                 535                 540
Tyr Tyr Cys Ala Thr Ala Glu Asp Glu Pro Gly Tyr Asp Tyr Trp Gly
545                 550                 555                 560
Gln Gly Thr Leu Val Thr Val Ser Ser
            565

<210> SEQ ID NO 91
<211> LENGTH: 443
<212> TYPE: PRT
<213> ORGANISM: Artificial Sequence
<220> FEATURE:
<223> OTHER INFORMATION: Humanised

<400> SEQUENCE: 91

Gln Val Thr Leu Arg Glu Ser Gly Pro Ala Leu Val Lys Pro Thr Gln
1               5                   10                  15
Thr Leu Thr Leu Thr Cys Thr Val Ser Gly Phe Ser Leu Thr Ser Tyr
            20                  25                  30
Ser Val His Trp Val Arg Gln Pro Pro Gly Lys Gly Leu Glu Trp Leu
        35                  40                  45
Gly Val Ile Trp Ala Ser Gly Thr Asp Tyr Asn Ser Ala Leu Met Ser
    50                  55                  60
Arg Leu Ser Ile Ser Lys Asp Thr Ser Arg Asn Gln Val Val Leu
65                  70                  75                  80
Thr Met Thr Asn Met Asp Pro Val Asp Thr Ala Thr Tyr Tyr Cys Ala
            85                  90                  95
Arg Asp Pro Pro Ser Ser Leu Leu Arg Leu Asp Tyr Trp Gly Arg Gly
        100                 105                 110
Thr Leu Val Thr Val Ser Ser Ala Ser Thr Lys Gly Pro Ser Val Phe
    115                 120                 125
Pro Leu Ala Pro Ser Ser Lys Ser Thr Ser Gly Gly Thr Ala Ala Leu
```

-continued

```
            130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Tyr Val Val Ser Val Leu
        290                 295                 300

Thr Val Leu His Gln Asp Trp Leu Asn Gly Lys Glu Tyr Lys Cys Lys
305                 310                 315                 320

Val Ser Asn Lys Ala Leu Pro Ala Pro Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Arg Asp Glu Leu Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Lys Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440
```

<210> SEQ ID NO 92
<211> LENGTH: 220
<212> TYPE: PRT
<213> ORGANISM: Artificial Sequence
<220> FEATURE:
<223> OTHER INFORMATION: Humanised

<400> SEQUENCE: 92

```
Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Leu Asn Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Glu Ser Gly Val
```

```
            50                  55                  60
Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Asn
                 85                  90                  95

Val His Ser Phe Pro Phe Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 93
<211> LENGTH: 449
<212> TYPE: PRT
<213> ORGANISM: Artificial Sequence
<220> FEATURE:
<223> OTHER INFORMATION: Humanised

<400> SEQUENCE: 93

Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
```

```
            195                 200                 205
Asn His Lys Pro Ser Asn Thr Lys Val Asp Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 94
<211> LENGTH: 571
<212> TYPE: PRT
<213> ORGANISM: Artificial Sequence
<220> FEATURE:
<223> OTHER INFORMATION: Fusion protein

<400> SEQUENCE: 94

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
                20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
            100                 105                 110
```

```
Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
    130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Ser Ser Val Val
            180                 185                 190

Thr Val Pro Ser Ser Ser Leu Gly Thr Gln Thr Tyr Ile Cys Asn Val
            195                 200                 205

Asn His Lys Pro Ser Asn Thr Lys Val Asp Lys Lys Val Glu Pro Lys
        210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
        290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Thr Val Ala Ala Pro Ser Thr Val Ala Ala Pro Ser Gly Ser Asp
    450                 455                 460

Ile Gln Met Thr Gln Ser Pro Ser Ser Leu Ser Ala Ser Val Gly Asp
465                 470                 475                 480

Arg Val Thr Ile Thr Cys Arg Ala Ser Arg Pro Ile Ser Asp Trp Leu
                485                 490                 495

His Trp Tyr Gln Gln Lys Pro Gly Lys Ala Pro Lys Leu Leu Ile Ala
            500                 505                 510

Trp Ala Ser Ser Leu Gln Gly Gly Val Pro Ser Arg Phe Ser Gly Ser
        515                 520                 525
```

Gly Ser Gly Thr Asp Phe Thr Leu Thr Ile Ser Ser Leu Gln Pro Glu
            530                 535                 540

Asp Phe Ala Thr Tyr Tyr Cys Gln Gln Glu Gly Trp Gly Pro Pro Thr
545                 550                 555                 560

Phe Gly Gln Gly Thr Lys Val Glu Ile Lys Arg
                565                 570

<210> SEQ ID NO 95
<211> LENGTH: 577
<212> TYPE: PRT
<213> ORGANISM: Artificial Sequence
<220> FEATURE:
<223> OTHER INFORMATION: Fusion protein

<400> SEQUENCE: 95

Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Ser Ser Val Val
        180                 185                 190

Thr Val Pro Ser Ser Ser Leu Gly Thr Gln Thr Tyr Ile Cys Asn Val
    195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
        260                 265                 270

Ser His Glu Asp Pro Glu Val Lys Phe Asn Trp Tyr Val Asp Gly Val
    275                 280                 285

Glu Val His Asn Ala Lys Thr Lys Pro Arg Glu Glu Gln Tyr Asn Ser
290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
             325                 330                 335

Glu Lys Thr Ile Ser Lys Ala Lys Gly Gln Pro Arg Glu Pro Gln Val
         340                 345                 350

Tyr Thr Leu Pro Pro Ser Arg Asp Glu Leu Thr Lys Asn Gln Val Ser
         355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
             405                 410                 415

Ser Arg Trp Gln Gln Gly Asn Val Phe Ser Cys Ser Val Met His Glu
         420                 425                 430

Ala Leu His Asn His Tyr Thr Gln Lys Ser Leu Ser Leu Ser Pro Gly
         435                 440                 445

Lys Thr Val Ala Ala Pro Ser Thr Val Ala Ala Pro Ser Thr Val Ala
     450                 455                 460

Ala Pro Ser Gly Ser Asp Ile Gln Met Thr Gln Ser Pro Ser Ser Leu
465                 470                 475                 480

Ser Ala Ser Val Gly Asp Arg Val Thr Ile Thr Cys Arg Ala Ser Arg
             485                 490                 495

Pro Ile Ser Asp Trp Leu His Trp Tyr Gln Gln Lys Pro Gly Lys Ala
         500                 505                 510

Pro Lys Leu Leu Ile Ala Trp Ala Ser Ser Leu Gln Gly Gly Val Pro
         515                 520                 525

Ser Arg Phe Ser Gly Ser Gly Ser Gly Thr Asp Phe Thr Leu Thr Ile
     530                 535                 540

Ser Ser Leu Gln Pro Glu Asp Phe Ala Thr Tyr Tyr Cys Gln Gln Glu
545                 550                 555                 560

Gly Trp Gly Pro Pro Thr Phe Gly Gln Gly Thr Lys Val Glu Ile Lys
             565                 570                 575

Arg

<210> SEQ ID NO 96
<211> LENGTH: 583
<212> TYPE: PRT
<213> ORGANISM: Artificial Sequence
<220> FEATURE:
<223> OTHER INFORMATION: Fusion protein

<400> SEQUENCE: 96

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
             85                  90                  95

Ala Arg Ser Ile Tyr Asp Asp Tyr His Val Asp Asp Tyr Tyr Ala Met

-continued

```
                100                 105                 110
Asp Tyr Trp Gly Gln Gly Thr Leu Val Thr Val Ser Ser Ala Ser Thr
            115                 120                 125
Lys Gly Pro Ser Val Phe Pro Leu Ala Pro Ser Ser Lys Ser Thr Ser
130                 135                 140
Gly Gly Thr Ala Ala Leu Gly Cys Leu Val Lys Asp Tyr Phe Pro Glu
145                 150                 155                 160
Pro Val Thr Val Ser Trp Asn Ser Gly Ala Leu Thr Ser Gly Val His
                165                 170                 175
Thr Phe Pro Ala Val Leu Gln Ser Ser Gly Leu Ser Ser Val Val
            180                 185                 190
Thr Val Pro Ser Ser Ser Leu Gly Thr Gln Thr Tyr Ile Cys Asn Val
            195                 200                 205
Asn His Lys Pro Ser Asn Thr Lys Val Asp Lys Val Glu Pro Lys
            210                 215                 220
Ser Cys Asp Lys Thr His Thr Cys Pro Pro Cys Pro Ala Pro Glu Leu
225                 230                 235                 240
Leu Gly Gly Pro Ser Val Phe Leu Phe Pro Pro Lys Pro Lys Asp Thr
                245                 250                 255
Leu Met Ile Ser Arg Thr Pro Glu Val Thr Cys Val Val Val Asp Val
            260                 265                 270
Ser His Glu Asp Pro Glu Val Lys Phe Asn Trp Tyr Val Asp Gly Val
            275                 280                 285
Glu Val His Asn Ala Lys Thr Lys Pro Arg Glu Glu Gln Tyr Asn Ser
            290                 295                 300
Tyr Val Val Ser Val Leu Thr Val Leu His Gln Asp Trp Leu Asn Gly
305                 310                 315                 320
Lys Glu Tyr Lys Cys Lys Val Ser Asn Lys Ala Leu Pro Ala Pro Ile
                325                 330                 335
Glu Lys Thr Ile Ser Lys Ala Lys Gly Gln Pro Arg Glu Pro Gln Val
            340                 345                 350
Tyr Thr Leu Pro Pro Ser Arg Asp Glu Leu Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Lys Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
            435                 440                 445
Lys Thr Val Ala Ala Pro Ser Thr Val Ala Ala Pro Ser Thr Val Ala
            450                 455                 460
Ala Pro Ser Thr Val Ala Ala Pro Ser Gly Ser Asp Ile Gln Met Thr
465                 470                 475                 480
Gln Ser Pro Ser Ser Leu Ser Ala Ser Val Gly Asp Arg Val Thr Ile
                485                 490                 495
Thr Cys Arg Ala Ser Arg Pro Ile Ser Asp Trp Leu His Trp Tyr Gln
            500                 505                 510
Gln Lys Pro Gly Lys Ala Pro Lys Leu Leu Ile Ala Trp Ala Ser Ser
            515                 520                 525
```

```
Leu Gln Gly Gly Val Pro Ser Arg Phe Ser Gly Ser Gly Ser Gly Thr
        530                 535                 540

Asp Phe Thr Leu Thr Ile Ser Ser Leu Gln Pro Glu Asp Phe Ala Thr
545                 550                 555                 560

Tyr Tyr Cys Gln Gln Glu Gly Trp Gly Pro Pro Thr Phe Gly Gln Gly
                565                 570                 575

Thr Lys Val Glu Ile Lys Arg
            580

<210> SEQ ID NO 97
<211> LENGTH: 108
<212> TYPE: PRT
<213> ORGANISM: Homo Sapiens

<400> SEQUENCE: 97

Asp Ile Gln Met Thr Gln Ser Pro Ser Ser Leu Ser Ala Ser Val Gly
  1               5                  10                  15

Asp Arg Val Thr Ile Thr Cys Arg Ala Ser Gln Trp Ile Gly Pro Tyr
            20                  25                  30

Leu Asn Trp Tyr Gln Gln Lys Pro Gly Lys Ala Pro Lys Pro Leu Ile
        35                  40                  45

Tyr Met Gly Tyr Trp Ala Pro Ser Gly Val Pro Ser Arg Phe Ser Gly
    50                  55                  60

Ser Gly Ser Gly Thr Asp Phe Thr Leu Thr Ile Ser Ser Leu Gln Pro
 65                 70                  75                  80

Glu Asp Phe Ala Thr Tyr Tyr Cys Gln Gln Asp Leu Tyr Pro Pro Phe
                85                  90                  95

Thr Phe Gly Gln Gly Thr Lys Val Glu Ile Lys Arg
            100                 105

<210> SEQ ID NO 98
<211> LENGTH: 575
<212> TYPE: PRT
<213> ORGANISM: Artificial Sequence
<220> FEATURE:
<223> OTHER INFORMATION: Fusion protein

<400> SEQUENCE: 98

Gln Val Gln Leu Val Gln Ser Gly Ala Glu Val Lys Lys Pro Gly Ser
  1               5                  10                  15

Ser Val Lys Val Ser Cys Lys Ala Ser Gly Phe Tyr Ile Lys Asp Thr
            20                  25                  30

Tyr Met His Trp Val Arg Gln Ala Pro Gly Gln Gly Leu Glu Trp Met
        35                  40                  45

Gly Thr Ile Asp Pro Ala Asn Gly Asn Thr Lys Tyr Val Pro Lys Phe
    50                  55                  60

Gln Gly Arg Val Thr Ile Thr Ala Asp Glu Ser Thr Ser Thr Ala Tyr
 65                 70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
        130                 135                 140
```

```
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Ser Thr Val Ala Ala Pro Ser Gly Ser Thr Val Ala Ala Pro
    450                 455                 460

Ser Gly Ser Asp Ile Gln Met Thr Gln Ser Pro Ser Ser Leu Ser Ala
465                 470                 475                 480

Ser Val Gly Asp Arg Val Thr Ile Thr Cys Arg Ala Ser Arg Pro Ile
                485                 490                 495

Ser Asp Trp Leu His Trp Tyr Gln Gln Lys Pro Gly Lys Ala Pro Lys
            500                 505                 510

Leu Leu Ile Ala Trp Ala Ser Ser Leu Gln Gly Gly Val Pro Ser Arg
        515                 520                 525

Phe Ser Gly Ser Gly Ser Gly Thr Asp Phe Thr Leu Thr Ile Ser Ser
    530                 535                 540

Leu Gln Pro Glu Asp Phe Ala Thr Tyr Tyr Cys Gln Gln Glu Gly Trp
545                 550                 555                 560

Gly Pro Pro Thr Phe Gly Gln Gly Thr Lys Val Glu Ile Lys Arg
```

<210> SEQ ID NO 99
<211> LENGTH: 583
<212> TYPE: PRT
<213> ORGANISM: Artificial Sequence
<220> FEATURE:
<223> OTHER INFORMATION: Fusion protein

<400> SEQUENCE: 99

```
Gln Val Gln Leu Val Gln Ser Gly Ala Glu Val Lys Lys Pro Gly Ser
 1               5                  10                  15

Ser Val Lys Val Ser Cys Lys Ala Ser Gly Phe Tyr Ile Lys Asp Thr
             20                  25                  30

Tyr Met His Trp Val Arg Gln Ala Pro Gly Gln Gly Leu Glu Trp Met
         35                  40                  45

Gly Thr Ile Asp Pro Ala Asn Gly Asn Thr Lys Tyr Val Pro Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Ile Tyr Asp Asp Tyr His Val Asp Asp Tyr Tyr Ala Met
            100                 105                 110

Asp Tyr Trp Gly Gln Gly Thr Leu Val Thr Val Ser Ser Ala Ser Thr
        115                 120                 125

Lys Gly Pro Ser Val Phe Pro Leu Ala Pro Ser Ser Lys Ser Thr Ser
130                 135                 140

Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Tyr Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
```

```
                355                 360                 365
Leu Thr Cys Leu Val Lys Gly Phe Tyr Pro Ser Asp Ile Ala Val Glu
            370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys Gly Ser Thr Val Ala Ala Pro Ser Gly Ser Thr Val Ala Ala Pro
            450                 455                 460

Ser Gly Ser Thr Val Ala Ala Pro Ser Gly Ser Asp Ile Gln Met Thr
465                 470                 475                 480

Gln Ser Pro Ser Ser Leu Ser Ala Ser Val Gly Asp Arg Val Thr Ile
                485                 490                 495

Thr Cys Arg Ala Ser Arg Pro Ile Ser Asp Trp Leu His Trp Tyr Gln
            500                 505                 510

Gln Lys Pro Gly Lys Ala Pro Lys Leu Leu Ile Ala Trp Ala Ser Ser
            515                 520                 525

Leu Gln Gly Gly Val Pro Ser Arg Phe Ser Gly Ser Gly Ser Gly Thr
            530                 535                 540

Asp Phe Thr Leu Thr Ile Ser Ser Leu Gln Pro Glu Asp Phe Ala Thr
545                 550                 555                 560

Tyr Tyr Cys Gln Gln Glu Gly Trp Gly Pro Thr Phe Gly Gln Gly
                565                 570                 575

Thr Lys Val Glu Ile Lys Arg
            580

<210> SEQ ID NO 100
<211> LENGTH: 591
<212> TYPE: PRT
<213> ORGANISM: Artificial Sequence
<220> FEATURE:
<223> OTHER INFORMATION: Fusion protein

<400> SEQUENCE: 100

Gln Val Gln Leu Val Gln Ser Gly Ala Glu Val Lys Lys Pro Gly Ser
1               5                   10                  15

Ser Val Lys Val Ser Cys Lys Ala Ser Gly Phe Tyr Ile Lys Asp Thr
                20                  25                  30

Tyr Met His Trp Val Arg Gln Ala Pro Gly Gln Gly Leu Glu Trp Met
            35                  40                  45

Gly Thr Ile Asp Pro Ala Asn Gly Asn Thr Lys Tyr Val Pro Lys Phe
        50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ile Tyr Asp Asp Tyr His Val Asp Tyr Tyr Ala Met
                100                 105                 110

Asp Tyr Trp Gly Gln Gly Thr Leu Val Thr Val Ser Ser Ala Ser Thr
            115                 120                 125

Lys Gly Pro Ser Val Phe Pro Leu Ala Pro Ser Ser Lys Ser Thr Ser
```

-continued

```
            130                 135                 140
Gly Gly Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Ser Leu Ser Ser Val Val
                180                 185                 190

Thr Val Pro Ser Ser Ser Leu Gly Thr Gln Thr Tyr Ile Cys Asn Val
                195                 200                 205

Asn His Lys Pro Ser Asn Thr Lys Val Asp Lys Lys Val Glu Pro Lys
                210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
                260                 265                 270

Ser His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn Ser
290                 295                 300

Tyr Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Asp Glu Leu Thr Lys Asn Gln Val Ser
                355                 360                 365

Leu Thr Cys Leu Val Lys Gly Phe Tyr Pro Ser Asp Ile Ala Val Glu
                370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Lys Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys Gly Ser Thr Val Ala Ala Pro Ser Gly Ser Thr Val Ala Ala Pro
450                 455                 460

Ser Gly Ser Thr Val Ala Ala Pro Ser Gly Ser Thr Val Ala Ala Pro
465                 470                 475                 480

Ser Gly Ser Asp Ile Gln Met Thr Gln Ser Pro Ser Ser Leu Ser Ala
                485                 490                 495

Ser Val Gly Asp Arg Val Thr Ile Thr Cys Arg Ala Ser Arg Pro Ile
                500                 505                 510

Ser Asp Trp Leu His Trp Tyr Gln Gln Lys Pro Gly Lys Ala Pro Lys
                515                 520                 525

Leu Leu Ile Ala Trp Ala Ser Ser Leu Gln Gly Gly Val Pro Ser Arg
                530                 535                 540

Phe Ser Gly Ser Gly Ser Gly Thr Asp Phe Thr Leu Thr Ile Ser Ser
545                 550                 555                 560
```

Leu Gln Pro Glu Asp Phe Ala Thr Tyr Tyr Cys Gln Gln Glu Gly Trp
                565                 570                 575

Gly Pro Pro Thr Phe Gly Gln Gly Thr Lys Val Glu Ile Lys Arg
            580                 585                 590

<210> SEQ ID NO 101
<211> LENGTH: 108
<212> TYPE: PRT
<213> ORGANISM: Homo Sapiens

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Pro Ile Ser Asp Trp
            20                  25                  30

Leu His Trp Tyr Gln Gln Lys Pro Gly Lys Ala Pro Lys Leu Leu Ile
        35                  40                  45

Ala Trp Ala Ser Ser Leu Gln Gly Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Glu Gly Trp Gly Pro Pro
                85                  90                  95

Thr Phe Gly Gln Gly Thr Lys Val Glu Ile Lys Arg
            100                 105

<210> SEQ ID NO 102
<211> LENGTH: 9
<212> TYPE: PRT
<213> ORGANISM: Homo Sapiens

<400> SEQUENCE: 102

Gln Gln Glu Gly Trp Gly Pro Pro Thr
1               5

<210> SEQ ID NO 103
<211> LENGTH: 1701
<212> TYPE: DNA
<213> ORGANISM: Artificial Sequence
<220> FEATURE:
<223> OTHER INFORMATION: Fusion protein

<400> SEQUENCE: 103
caggtgaccc tgagggagag cggcccccgcc ctggtgaagc ccacccagac cctgaccctg      60
acctgcacct tcagcggctt tagcctcagc acctccggca tgggcgtgag ctggatcagg     120
cagccacccg gcaaaggcct ggagtggctg gcccacatct actgggacga cgacaagagg     180
tacaacccca gcctgaagag ccggctgacc atcagcaagg ataccagcag gaaccaggtg     240
gtgctgacca tgaccaacat ggaccccgtg gacaccgcta cctactactg cgccaggagg     300
gagaccgtct tctactggta cttcgacgtg tggggaaggg gcacactagt gaccgtgtcc     360
agcgccagca ccaagggccc cagcgtgttc cccctggccc ccagcagcaa gagcaccagc     420
ggcggcacag ccgccctggg ctgcctggtg aaggactact cccccgaacc ggtgaccgtg     480
tcctggaaca gcggagccct gaccagcggc gtgcacacct tccccgccgt gctgcagagc     540
agcggcctgt acagcctgag cagcgtggtg accgtgccca gcagcagcct gggcacccag     600
acctacatct gtaacgtgaa ccacaagccc agcaacacca aggtggacaa gaaggtggag     660

```
cccaagagct gtgacaagac ccacacctgc cccccctgcc ctgcccccga gctgctggga    720
ggccccagcg tgttcctgtt ccccccaag cctaaggaca ccctgatgat cagcagaacc    780
cccgaggtga cctgtgtggt ggtggatgtg agccacgagg accctgaggt gaagttcaac    840
tggtacgtgg acggcgtgga ggtgcacaat gccaagacca gcccaggga ggagcagtac    900 aacagcacct accgggtggt gtccgtgctg accgtgctgc accaggattg gctgaacggc    960
aaggagtaca agtgtaaggt gtccaacaag gccctgcctg ccctatcga gaaaaccatc   1020 agcaaggcca agggccagcc cagagagccc caggtgtaca ccctgccccc tagcagagat   1080
gagctgacca gaaccaggt gtccctgacc tgcctggtga agggcttcta ccccagcgac   1140
atcgccgtgg agtgggagag caacggccag cccgagaaca actacaagac cacccccct    1200 gtgctggaca gcgatggcag cttcttcctg tacagcaagc tgaccgtgga caagagcaga   1260
tggcagcagg gcaacgtgtt cagctgctcc gtgatgcacg aggccctgca caatcactac   1320
acccagaaga gcctgagcct gtcccctggc aagaccgtgg ccgcccctc gggatccgac   1380 atccagatga ctcagagccc cagcagcctg agcgccagct gggcgatag ggtgaccatt   1440 acctgcaggg ccagccagag catcgacagc tacctgcact ggtaccagca gaagcccgga   1500
aaggccccca agctcctgat ctacagcgcc agcgagctgc agagcggcgt gcctagcagg   1560
ttttctggca gcggcagcgg caccgacttc accctgacca tctccagcct gcagcccgag   1620
gacttcgcca cctactactg ccagcaggtc gtgtggaggc ccttcacctt cggccagggc   1680
accaaggtgg agatcaagag g                                             1701
```

<210> SEQ ID NO 104
<211> LENGTH: 561
<212> TYPE: PRT
<213> ORGANISM: Artificial Sequence
<220> FEATURE:
<223> OTHER INFORMATION: Fusion protein

<400> SEQUENCE: 104

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Lys Arg Tyr Asn Pro Ser
     50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175
```

```
Val Leu Gln Ser Ser Gly Leu Ser Ser Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Tyr Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Lys Leu Thr Val Asp Lys Ser Arg Trp Gln
                405                 410                 415

Gln Gly Asn Val Phe Ser Cys Ser Val Met His Glu Ala Leu His Asn
            420                 425                 430

His Tyr Thr Gln Lys Ser Leu Ser Leu Ser Pro Gly Lys Thr Val Ala
        435                 440                 445

Ala Pro Ser Gly Ser Asp Ile Gln Met Thr Gln Ser Pro Ser Ser Leu
    450                 455                 460

Ser Ala Ser Val Gly Asp Arg Val Thr Ile Thr Cys Arg Ala Ser Gln
465                 470                 475                 480

Ser Ile Asp Ser Tyr Leu His Trp Tyr Gln Gln Lys Pro Gly Lys Ala
                485                 490                 495

Pro Lys Leu Leu Ile Tyr Ser Ala Ser Glu Leu Gln Ser Gly Val Pro
            500                 505                 510

Ser Arg Phe Ser Gly Ser Gly Ser Gly Thr Asp Phe Thr Leu Thr Ile
        515                 520                 525

Ser Ser Leu Gln Pro Glu Asp Phe Ala Thr Tyr Tyr Cys Gln Gln Val
        530                 535                 540

Val Trp Arg Pro Phe Thr Phe Gly Gln Gly Thr Lys Val Glu Ile Lys
545                 550                 555                 560

Arg

<210> SEQ ID NO 105
<211> LENGTH: 654
<212> TYPE: DNA
<213> ORGANISM: Artificial Sequence
```

```
<220> FEATURE:
<223> OTHER INFORMATION: Fusion protein

<400> SEQUENCE: 105
gacatcgtgc tgacccagag cccctcttcc ctgagcgcaa gcgtgggcga tagggtgacc    60
atcacctgca aggccagcca gagcgtggac tacgacggcg acagctacat gaactggtac   120
cagcagaagc ccggcaaggc ccccaaactg ctgatctacg ccgccagcaa cctcgagtca   180
ggcattccca gcaggtttag cggcagcggc agcggcaccg acttcacctt cacaatcagc   240
agcctgcagc ccgaggacat cgccacctac tactgccagc agagcaacga ggaccctccc   300
accttcggac agggcaccaa ggtcgagatc aagcgtacgg tggccgcccc cagcgtgttc   360
atcttccccc ccagcgatga gcagctgaag agcggcaccg ccagcgtggt gtgtctgctg   420
aacaacttct accccgggga ggccaaggtg cagtggaagg tggacaatgc cctgcagagc   480
ggcaacagcc aggagagcgt gaccgagcag gacagcaagg actccaccta cagcctgagc   540
agcaccctga ccctgagcaa ggccgactac gagaagcaca aggtgtacgc ctgtgaggtg   600
acccaccagg gcctgtccag ccccgtgacc aagagcttca accggggcga gtgc         654

<210> SEQ ID NO 106
<211> LENGTH: 1731
<212> TYPE: DNA
<213> ORGANISM: Artificial Sequence
<220> FEATURE:
<223> OTHER INFORMATION: Fusion protein

<400> SEQUENCE: 106
caggtgaccc tgagggagag cggccccgcc ctggtgaagc ccacccagac cctgaccctg    60
acctgcacct tcagcggctt tagcctcagc acctccggca tgggcgtgag ctggatcagg   120
cagccacccg gcaaaggcct ggagtggctg gcccacatct actgggacga cgacaagagg   180
tacaacccca agcctgaagag ccggctgacc atcagcaagg ataccagcag gaaccaggtg   240
gtgctgacca tgaccaacat ggacccccgtg gacaccgcta cctactactg cgccaggagg   300
gagaccgtct tctactggta cttcgacgtg tggggaaggg gcacactagt gaccgtgtcc   360
agcgccagca ccaagggccc cagcgtgttc cccctggccc ccagcagcaa gagcaccagc   420
ggcggcacag ccgccctggg ctgcctggtg aaggactact cccccgaacc ggtgaccgtg   480
tcctggaaca gcggagccct gaccagcggc gtgcacacct cccccgccgt gctgcagagc   540
agcggcctgt acagcctgag cagcgtggtg accgtgccca gcagcagcct gggcacccag   600
acctacatct gtaacgtgaa ccacaagccc agcaacacca aggtggacaa gaaggtggag   660
cccaagagct gtgacaagac ccacacctgc cccccctgcc ctgccccccga gctgctggga   720
ggccccagcg tgttcctgtt cccccccaag cctaaggaca cctgatgat cagcagaacc   780
cccgaggtga cctgtgtggg ggtggatgtg agccacgagg accctgaggt gaagttcaac   840
tggtacgtgg acggcgtgga ggtgcacaat gccaagacca gcccaggga ggagcagtac   900
aacagcacct accgggtggt gtccgtgctg accgtgctgc accaggattg gctgaacggc   960
aaggagtaca agtgtaaggt gtccaacaag gccctgcctg cccctatcga gaaaaccatc  1020
agcaaggcca agggccagcc cagagagccc caggtgtaca ccctgccccc tagcagagat  1080
gagctgacca gaaccaggt gtccctgacc tgcctggtga agggcttcta ccccagcgac  1140
atcgccgtgg agtgggagag caacggccag cccgagaaca actacaagac cacccccct   1200
gtgctggaca gcgatggcag cttcttcctg tacagcaagc tgaccgtgga caagagcaga  1260
```

```
tggcagcagg gcaacgtgtt cagctgctcc gtgatgcacg aggccctgca caatcactac      1320
acccagaaga gcctgagcct gtccctggc aagggatcta ccgtggcagc accatccgga       1380
tctaccgtag cagcaccatc cggatccgac atccagatga ctcagagccc cagcagcctg      1440
agcgccagcg tgggcgatag ggtgaccatt acctgcaggg ccagcagag catcgacagc      1500 tacctgcact ggtaccagca gaagcccgga aaggccccca agctcctgat ctacagcgcc      1560
agcgagctgc agagcggcgt gcctagcagg ttttctggca gcggcagcgg caccgacttc      1620
accctgacca tctccagcct gcagcccgag gacttcgcca cctactactg ccagcaggtc      1680
gtgtggaggc ccttcacctt cggccagggc accaaggtgg agatcaagag g               1731
```

<210> SEQ ID NO 107
<211> LENGTH: 571
<212> TYPE: PRT
<213> ORGANISM: Artificial Sequence
<220> FEATURE:
<223> OTHER INFORMATION: Fusion protein

<400> SEQUENCE: 107

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Asp Lys Arg Tyr Asn Pro Ser
     50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285
```

```
Ala Lys Thr Lys Pro Arg Glu Glu Gln Tyr Asn Ser Tyr Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Gly Ser Thr
            435                 440                 445

Val Ala Ala Pro Ser Gly Ser Thr Val Ala Ala Pro Ser Gly Ser Asp
450                 455                 460

Ile Gln Met Thr Gln Ser Pro Ser Ser Leu Ser Ala Ser Val Gly Asp
465                 470                 475                 480

Arg Val Thr Ile Thr Cys Arg Ala Ser Gln Ser Ile Asp Ser Tyr Leu
                485                 490                 495

His Trp Tyr Gln Gln Lys Pro Gly Lys Ala Pro Lys Leu Leu Ile Tyr
            500                 505                 510

Ser Ala Ser Glu Leu Gln Ser Gly Val Pro Ser Arg Phe Ser Gly Ser
            515                 520                 525

Gly Ser Gly Thr Asp Phe Thr Leu Thr Ile Ser Ser Leu Gln Pro Glu
            530                 535                 540

Asp Phe Ala Thr Tyr Tyr Cys Gln Gln Val Val Trp Arg Pro Phe Thr
545                 550                 555                 560

Phe Gly Gln Gly Thr Lys Val Glu Ile Lys Arg
                565                 570

<210> SEQ ID NO 108
<211> LENGTH: 1755
<212> TYPE: DNA
<213> ORGANISM: Artificial Sequence
<220> FEATURE:
<223> OTHER INFORMATION: Fusion protein

<400> SEQUENCE: 108
caggtgaccc tgagggagag cggccccgcc ctggtgaagc ccacccagac cctgaccctg      60
acctgcacct tcagcggctt tagcctcagc acctccggca tgggcgtgag ctggatcagg     120
cagccacccg gcaaaggcct ggagtggctg gcccacatct actgggacga cgacaagagg     180
tacaacccca gcctgaagag ccggctgacc atcagcaagg ataccagcag gaaccaggtg     240
gtgctgacca tgaccaacat ggaccccgtg gacaccgcta cctactactg cgccaggagg     300
gagaccgtct cctactggta cttcgacgtg tggggaaggg gcacactagt gaccgtgtcc     360
agcgccagca ccaagggccc cagcgtgttc cccctggccc ccagcagcaa gagcaccagc     420
```

```
ggcggcacag ccgccctggg ctgcctggtg aaggactact tccccgaacc ggtgaccgtg    480
tcctggaaca gcggagccct gaccagcggc gtgcacacct ccccgccgt gctgcagagc      540 agcggcctgt acagcctgag cagcgtggtg accgtgccca gcagcagcct gggcacccag    600
acctacatct gtaacgtgaa ccacaagccc agcaacacca aggtggacaa gaaggtggag    660
cccaagagct gtgacaagac ccacacctgc ccccctgcc ctgcccccga gctgctggga     720
ggccccagcg tgttcctgtt cccccccaag cctaaggaca ccctgatgat cagcagaacc    780
cccgaggtga cctgtgtggt ggtggatgtg agccacgagg accctgaggt gaagttcaac    840
tggtacgtgg acggcgtgga ggtgcacaat gccaagacca gcccaggga ggagcagtac     900 aacagcacct accgggtggt gtccgtgctg accgtgctgc accaggattg gctgaacggc    960
aaggagtaca agtgtaaggt gtccaacaag gccctgcctg ccctatcga aaaaccatc     1020 agcaaggcca agggccagcc cagagagccc caggtgtaca ccctgccccc tagcagagat   1080
gagctgacca gaaccaggt gtccctgacc tgcctggtga agggcttcta ccccagcgac    1140
atcgccgtgg agtgggagag caacggccag cccgagaaca actacaagac cacccccct    1200 gtgctggaca gcgatggcag cttcttcctg tacagcaagc tgaccgtgga caagagcaga   1260
tggcagcagg gcaacgtgtt cagctgctcc gtgatgcacg aggccctgca caatcactac   1320
acccagaaga gcctgagcct gtcccctggc aagggatcta ccgtggcagc accatcagga   1380
tctaccgtgg cagcaccatc aggttcaaca gtagctgctc cttctggatc cgacatccag   1440
atgactcaga gccccagcag cctgagcgcc agcgtgggcg ataggtgac cattacctgc    1500 agggccagcc agagcatcga cagctacctg cactggtacc agcagaagcc cggaaaggcc   1560
cccaagctcc tgatctacag cgccagcgag ctgcagagcg gcgtgcctag caggttttct   1620
ggcagcggca gcggcaccga cttcaccctg accatctcca gcctgcagcc cgaggacttc   1680
gccacctact actgccagca ggtcgtgtgg aggcccttca ccttcggcca gggcaccaag   1740
gtggagatca agagg                                                     1755
```

<210> SEQ ID NO 109
<211> LENGTH: 579
<212> TYPE: PRT
<213> ORGANISM: Artificial Sequence
<220> FEATURE:
<223> OTHER INFORMATION: Fusion protein

<400> SEQUENCE: 109

```
Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Thr Ser Arg Asn Gln Val
65                  70                  75                  80

Val Leu Thr Met Thr Asn Met Asp Pro Val Asp Thr Ala Thr Tyr Tyr
                85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125
```

```
Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Arg Asp Glu Leu Thr Lys Asn Gln Val Ser Leu Thr Cys Leu
                355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Gly Ser Thr
            435                 440                 445

Val Ala Ala Pro Ser Gly Ser Thr Val Ala Ala Pro Ser Gly Ser Thr
    450                 455                 460

Val Ala Ala Pro Ser Gly Ser Asp Ile Gln Met Thr Gln Ser Pro Ser
465                 470                 475                 480

Ser Leu Ser Ala Ser Val Gly Asp Arg Val Thr Ile Thr Cys Arg Ala
                485                 490                 495

Ser Gln Ser Ile Asp Ser Tyr Leu His Trp Tyr Gln Gln Lys Pro Gly
                500                 505                 510

Lys Ala Pro Lys Leu Leu Ile Tyr Ser Ala Ser Glu Leu Gln Ser Gly
                515                 520                 525

Val Pro Ser Arg Phe Ser Gly Ser Gly Ser Gly Thr Asp Phe Thr Leu
    530                 535                 540
```

Thr Ile Ser Ser Leu Gln Pro Glu Asp Phe Ala Thr Tyr Tyr Cys Gln
545                 550                 555                 560

Gln Val Val Trp Arg Pro Phe Thr Phe Gly Gln Gly Thr Lys Val Glu
            565                 570                 575

Ile Lys Arg

<210> SEQ ID NO 110
<211> LENGTH: 1779
<212> TYPE: DNA
<213> ORGANISM: Artificial Sequence
<220> FEATURE:
<223> OTHER INFORMATION: Fusion protein

<400> SEQUENCE: 110

| | | |
|---|---|---|
| caggtgaccc tgagggagag cggccccgcc ctggtgaagc ccacccagac cctgaccctg | 60 |
| acctgcacct tcagcggctt tagcctcagc acctccggca tgggcgtgag ctggatcagg | 120 |
| cagccacccg gcaaaggcct ggagtggctg gcccacatct actgggacga cgacaagagg | 180 |
| tacaacccca gcctgaagag ccggctgacc atcagcaagg ataccagcag gaaccaggtg | 240 |
| gtgctgacca tgaccaacat ggaccccgtg gacaccgcta cctactactg cgccaggagg | 300 |
| gagaccgtct tctactggta cttcgacgtg tggggaaggg gcacactagt gaccgtgtcc | 360 |
| agcgccagca ccaagggccc cagcgtgttc cccctggccc ccagcagcaa gagcaccagc | 420 |
| ggcggcacag ccgccctggg ctgcctggtg aaggactact cccccgaacc ggtgaccgtg | 480 |
| tcctggaaca gcggagccct gaccagcggc gtgcacacct tcccgccgt gctgcagagc | 540 |
| agcggcctgt acagcctgag cagcgtggtg accgtgccca gcagcagcct gggcacccag | 600 |
| acctacatct gtaacgtgaa ccacaagccc agcaacacca aggtggacaa gaaggtggag | 660 |
| cccaagagct gtgacaagac ccacacctgc ccccccctgcc ctgccccga gctgctggga | 720 |
| ggccccagcg tgttcctgtt ccccccaag cctaaggaca ccctgatgat cagcagaacc | 780 |
| cccgaggtga cctgtgtggt ggtggatgtg agccacgagg accctgaggt gaagttcaac | 840 |
| tggtacgtgg acggcgtgga ggtgcacaat gccaagacca gcccaggga ggagcagtac | 900 |
| aacagcacct accgggtggt gtccgtgctg accgtgctgc accaggattg gctgaacggc | 960 |
| aaggagtaca agtgtaaggt gtccaacaag gccctgcctg cccctatcga gaaaaccatc | 1020 |
| agcaaggcca agggccagcc cagagagccc caggtgtaca ccctgccccc tagcagagat | 1080 |
| gagctgacca agaaccaggt gtccctgacc tgcctggtga agggcttcta ccccagcgac | 1140 |
| atcgccgtgg agtgggagag caacggccag cccgagaaca actacaagac caccccccct | 1200 |
| gtgctggaca gcgatggcag cttcttcctg tacagcaagc tgaccgtgga caagagcaga | 1260 |
| tggcagcagg gcaacgtgtt cagctgctcc gtgatgcacg aggccctgca caatcactac | 1320 |
| acccagaaga gcctgagcct gtcccctggc aagggatcta ccgtggcagc accatcagga | 1380 |
| tctaccgtgg cagcaccatc aggttcaaca gtagctgctc cttctggttc aacagtagct | 1440 |
| gctccttctg gatccgacat ccagatgact cagagcccca gcagcctgag cgccagcgtg | 1500 |
| ggcgataggg tgaccattac ctgcagggcc agccagagca tcgacagcta cctgcactgg | 1560 |
| taccagcaga gccccggaaa ggccccaag ctcctgatct acagcgccag cgagctgcag | 1620 |
| agcggcgtgc ctagcaggtt ttctggcagc ggcagcggca ccgacttcac cctgaccatc | 1680 |
| tccagcctgc agcccgagga cttcgccacc tactactgcc agcaggtcgt gtggaggccc | 1740 |
| ttcaccttcg gccagggcac caaggtggag atcaagagg | 1779 |

```
<210> SEQ ID NO 111
<211> LENGTH: 587
<212> TYPE: PRT
<213> ORGANISM: Artificial Sequence
<220> FEATURE:
<223> OTHER INFORMATION: Fusion protein

<400> SEQUENCE: 111

Gln Val Thr Leu Arg Glu Ser Gly Pro Ala Leu Val Lys Pro Thr Gln
 1               5                  10                  15

Thr Leu Thr Leu Thr Cys Thr Phe Ser Gly Phe Ser Leu Ser Thr Ser
             20                  25                  30

Gly Met Gly Val Ser Trp Ile Arg Gln Pro Pro Gly Lys Gly Leu Glu
         35                  40                  45

Trp Leu Ala His Ile Tyr Trp Asp Asp Lys Arg Tyr Asn Pro Ser
 50                  55                  60

Leu Lys Ser Arg Leu Thr Ile Ser Lys Asp Thr Ser Arg Asn Gln Val
 65                  70                  75                  80

Val Leu Thr Met Thr Asn Met Asp Pro Val Asp Thr Ala Thr Tyr Tyr
                 85                  90                  95

Cys Ala Arg Arg Glu Thr Val Phe Tyr Trp Tyr Phe Asp Val Trp Gly
            100                 105                 110

Arg Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Tyr Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
```

```
                370                 375                 380
Gly Gln Pro Glu Asn Asn Tyr Lys Thr Thr Pro Pro Val Leu Asp Ser
385                 390                 395                 400

Asp Gly Ser Phe Phe Lys Lys Leu Thr Val Asp Lys Ser Arg Trp Gln
                405                 410                 415

Gln Gly Asn Val Phe Ser Cys Ser Val Met His Glu Ala Leu His Asn
                420                 425                 430

His Tyr Thr Gln Lys Ser Leu Ser Leu Ser Pro Gly Lys Gly Ser Thr
                435                 440                 445

Val Ala Ala Pro Ser Gly Ser Thr Val Ala Ala Pro Ser Gly Ser Thr
                450                 455                 460

Val Ala Ala Pro Ser Gly Ser Thr Val Ala Ala Pro Ser Gly Ser Asp
465                 470                 475                 480

Ile Gln Met Thr Gln Ser Pro Ser Ser Leu Ser Ala Ser Val Gly Asp
                485                 490                 495

Arg Val Thr Ile Thr Cys Arg Ala Ser Gln Ser Ile Asp Ser Tyr Leu
                500                 505                 510

His Trp Tyr Gln Gln Lys Pro Gly Lys Ala Pro Lys Leu Leu Ile Tyr
                515                 520                 525

Ser Ala Ser Glu Leu Gln Ser Gly Val Pro Ser Arg Phe Ser Gly Ser
                530                 535                 540

Gly Ser Gly Thr Asp Phe Thr Leu Thr Ile Ser Ser Leu Gln Pro Glu
545                 550                 555                 560

Asp Phe Ala Thr Tyr Tyr Cys Gln Gln Val Val Trp Arg Pro Phe Thr
                565                 570                 575

Phe Gly Gln Gly Thr Lys Val Glu Ile Lys Arg
                580                 585

<210> SEQ ID NO 112
<211> LENGTH: 14
<212> TYPE: PRT
<213> ORGANISM: Artificial Sequence
<220> FEATURE:
<223> OTHER INFORMATION: Linker

<400> SEQUENCE: 112

Thr Val Ala Ala Pro Ser Thr Val Ala Ala Pro Ser Gly Ser
1               5                   10

<210> SEQ ID NO 113
<211> LENGTH: 20
<212> TYPE: PRT
<213> ORGANISM: Artificial Sequence
<220> FEATURE:
<223> OTHER INFORMATION: Linker

<400> SEQUENCE: 113

Thr Val Ala Ala Pro Ser Thr Val Ala Ala Pro Ser Thr Val Ala Ala
1               5                   10                  15

Pro Ser Gly Ser
            20

<210> SEQ ID NO 114
<211> LENGTH: 26
<212> TYPE: PRT
<213> ORGANISM: Artificial Sequence
<220> FEATURE:
<223> OTHER INFORMATION: Linker

<400> SEQUENCE: 114
```

-continued

```
Thr Val Ala Ala Pro Ser Thr Val Ala Ala Pro Ser Thr Val Ala Ala
1               5                   10                  15
Pro Ser Thr Val Ala Ala Pro Ser Gly Ser
            20                  25
```

ANTIGEN-BINDING PROTEINS

This application is a 371 of International Application No. PCT/EP2010/057231, filed 26 May 2010, which claims the benefit of U.S. Provisional Application No. 61/181,893, filed 28 May 2009, which are both incorporated by reference in their entireties.

BACKGROUND

Antibodies are well known for use in therapeutic applications.

Antibodies are heteromultimeric glycoproteins comprising at least two heavy and two light chains. Aside from IgM, intact antibodies are usually heterotetrameric glycoproteins of approximately 150 Kda, composed of two identical light (L) chains and two identical heavy (H) chains. Typically, each light chain is linked to a heavy chain by one covalent disulfide bond while the number of disulfide linkages between the heavy chains of different immunoglobulin isotypes varies. Each heavy and light chain also has intrachain disulfide bridges. Each heavy chain has at one end a variable domain (VH) followed by a number of constant regions. Each light chain has a variable domain (VL) and a constant region at its other end; the constant region of the light chain is aligned with the first constant region of the heavy chain and the light chain variable domain is aligned with the variable domain of the heavy chain. The light chains of antibodies from most vertebrate species can be assigned to one of two types called Kappa and Lambda based on the amino acid sequence of the constant region. Depending on the amino acid sequence of the constant region of their heavy chains, human antibodies can be assigned to five different classes, IgA, IgD, IgE, IgG and IgM. IgG and IgA can be further subdivided into subclasses, IgG1, IgG2, IgG3 and IgG4; and IgA1 and IgA2. Species variants exist with mouse and rat having at least IgG2a, IgG2b. The variable domain of the antibody confers binding specificity upon the antibody with certain regions displaying particular variability called complementarity determining regions (CDRs). The more conserved portions of the variable region are called Framework regions (FR). The variable domains of intact heavy and light chains each comprise four FR connected by three CDRs. The CDRs in each chain are held together in close proximity by the FR regions and with the CDRs from the other chain contribute to the formation of the antigen binding site of antibodies. The constant regions are not directly involved in the binding of the antibody to the antigen but exhibit various effector functions such as participation in antibody dependent cell-mediated cytotoxicity (ADCC), phagocytosis via binding to Fcγ receptor, half-life/clearance rate via neonatal Fc receptor (FcRn) and complement dependent cytotoxicity via the C1q component of the complement cascade.

The nature of the structure of an IgG antibody is such that there are two antigen-binding sites, both of which are specific for the same epitope. They are therefore, monospecific.

A bispecific antibody is an antibody having binding specificities for at least two different epitopes. Methods of making such antibodies are known in the art. Traditionally, the recombinant production of bispecific antibodies is based on the coexpression of two immunoglobulin H chain-L chain pairs, where the two H chains have different binding specificities see Millstein et al, Nature 305 537-539 (1983), WO93/08829 and Traunecker et al EMBO, 10, 1991, 3655-3659. Because of the random assortment of H and L chains, a potential mixture of ten different antibody structures are produced of which only one has the desired binding specificity. An alternative approach involves fusing the variable domains with the desired binding specificities to heavy chain constant region comprising at least part of the hinge region, CH2 and CH3 regions. It is preferred to have the CH1 region containing the site necessary for light chain binding present in at least one of the fusions. DNA encoding these fusions, and if desired the L chain are inserted into separate expression vectors and are then cotransfected into a suitable host organism. It is possible though to insert the coding sequences for two or all three chains into one expression vector. In one approach, a bispecific antibody is composed of a H chain with a first binding specificity in one arm and a H-L chain pair, providing a second binding specificity in the other arm, see WO94/04690. Also see Suresh et al Methods in Enzymology 121, 210, 1986. Other approaches include antibody molecules which comprise single domain binding sites which is set out in WO2007/095338.

SUMMARY OF INVENTION

The present invention relates to an antigen-binding protein comprising a protein scaffold which is linked to one or more epitope-binding domains wherein the antigen-binding protein has at least two antigen binding sites at least one of which is from an epitope binding domain and at least one of which is from a paired VH/VL domain.

The invention further relates to antigen-binding proteins comprising at least one homodimer comprising two or more structures of formula I:

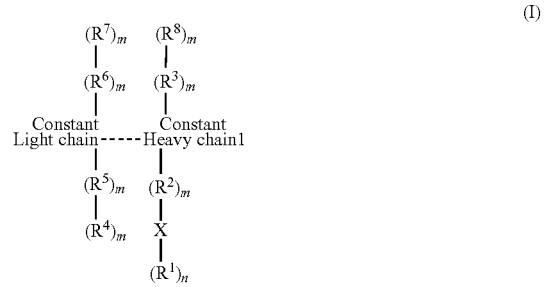

wherein
X represents a constant antibody region comprising constant heavy domain 2 and constant heavy domain 3;
$R^1$, $R^4$, $R^7$ and $R^8$ represent a domain independently selected from an epitope-binding domain;
$R^2$ represents a domain selected from the group consisting of constant heavy chain 1, and an epitope-binding domain;
$R^3$ represents a domain selected from the group consisting of a paired VH and an epitope-binding domain;
$R^5$ represents a domain selected from the group consisting of constant light chain, and an epitope-binding domain;
$R^6$ represents a domain selected from the group consisting of a paired VL and an epitope-binding domain;
n represents an integer independently selected from: 0, 1, 2, 3 and 4;
m represents an integer independently selected from: 0 and 1, wherein the Constant Heavy chain 1 and the Constant Light chain domains are associated;
wherein at least one epitope binding domain is present;
wherein when $R^3$ represents a paired VH domain, $R^6$ represents a paired VL domain, so that the two domains are together capable of binding antigen;

and wherein the epitope binding domains are linked to the rest of the molecule by the linkers of the present invention.

The invention relates to IgG based structures which comprise monoclonal antibodies, or fragments linked to one or more domain antibodies, and to methods of making such proteins and uses thereof, particularly uses in therapy.

The invention also provides a polynucleotide sequence encoding a heavy chain of any of the antigen binding proteins described herein, and a polynucleotide encoding a light chain of any of the antigen binding proteins described herein. Such polynucleotides represent the coding sequence which corresponds to the equivalent polypeptide sequences, however it will be understood that such polynucleotide sequences could be cloned into an expression vector along with a start codon, an appropriate signal sequence and a stop codon.

The invention also provides a recombinant transformed or transfected host cell comprising one or more polynucleotides encoding a heavy chain and a light chain of any of the antigen binding proteins described herein.

The invention further provides a method for the production of any of the antigen binding proteins described herein which method comprises the step of culturing a host cell comprising a first and second vector, said first vector comprising a polynucleotide encoding a heavy chain of any of the antigen binding proteins described herein and said second vector comprising a polynucleotide encoding a light chain of any of the antigen binding proteins described herein, in a serum-free culture media.

The invention further provides a pharmaceutical composition comprising an antigen binding protein as described herein a pharmaceutically acceptable carrier.

The invention also provides a mAbdAb comprising the heavy chain sequence set out in SEQ ID NO:85 and the light chain sequence set out in SEQ ID NO: 3, or the heavy chain sequence set out in SEQ ID NO:86 and the light chain sequence set out in SEQ ID NO: 3, or the heavy chain sequence set out in SEQ ID NO 2. and the light chain sequence set out in SEQ ID NO: 87, or the heavy chain sequence set out in SEQ ID NO:2. and the light chain sequence set out in SEQ ID NO: 88, or the heavy chain sequence set out in SEQ ID NO:85. and the light chain sequence set out in SEQ ID NO: 87, or the heavy chain sequence set out in SEQ ID NO:85. and the light chain sequence set out in SEQ ID NO: 88, or the heavy chain sequence set out in SEQ ID NO:86. and the light chain sequence set out in SEQ ID NO: 87, or the heavy chain sequence set out in SEQ ID NO:86. and the light chain sequence set out in SEQ ID NO: 88.

DEFINITIONS

The term 'Protein Scaffold' as used herein includes but is not limited to an immunoglobulin (Ig) scaffold, for example an IgG scaffold, which may be a four chain or two chain antibody, or which may comprise only the Fc region of an antibody, or which may comprise one or more constant regions from an antibody, which constant regions may be of human or primate origin, or which may be an artificial chimera of human and primate constant regions. Such protein scaffolds may comprise antigen-binding sites in addition to the one or more constant regions, for example where the protein scaffold comprises a full IgG. Such protein scaffolds will be capable of being linked to other protein domains, for example protein domains which have antigen-binding sites, for example epitope-binding domains or ScFv domains.

A "domain" is a folded protein structure which has tertiary structure independent of the rest of the protein. Generally, domains are responsible for discrete functional properties of proteins and in many cases may be added, removed or transferred to other proteins without loss of function of the remainder of the protein and/or of the domain. A "single antibody variable domain" is a folded polypeptide domain comprising sequences characteristic of antibody variable domains. It therefore includes complete antibody variable domains and modified variable domains, for example, in which one or more loops have been replaced by sequences which are not characteristic of antibody variable domains, or antibody variable domains which have been truncated or comprise N- or C-terminal extensions, as well as folded fragments of variable domains which retain at least the binding activity and specificity of the full-length domain.

The phrase "immunoglobulin single variable domain" refers to an antibody variable domain ($V_H$, $V_{HH}$, $V_L$) that specifically binds an antigen or epitope independently of a different V region or domain. An immunoglobulin single variable domain can be present in a format (e.g., homo- or hetero-multimer) with other, different variable regions or variable domains where the other regions or domains are not required for antigen binding by the single immunoglobulin variable domain (i.e., where the immunoglobulin single variable domain binds antigen independently of the additional variable domains). A "domain antibody" or "dAb" is the same as an "immunoglobulin single variable domain" which is capable of binding to an antigen as the term is used herein. An immunoglobulin single variable domain may be a human antibody variable domain, but also includes single antibody variable domains from other species such as rodent (for example, as disclosed in WO 00/29004), nurse shark and Camelid $V_{HH}$ dAbs. Camelid $V_{HH}$ are immunoglobulin single variable domain polypeptides that are derived from species including camel, llama, alpaca, dromedary, and guanaco, which produce heavy chain antibodies naturally devoid of light chains. Such $V_{HH}$ domains may be humanised according to standard techniques available in the art, and such domains are still considered to be "domain antibodies" according to the invention. As used herein "$V_H$ includes camelid $V_{HH}$ domains. NARV are another type of immunoglobulin single variable domain which were identified in cartilaginous fish including the nurse shark. These domains are also known as Novel Antigen Receptor variable region (commonly abbreviated to V(NAR) or NARV). For further details see Mol. Immunol. 44, 656-665 (2006) and US20050043519A.

The term "Epitope-binding domain" refers to a domain that specifically binds an antigen or epitope independently of a different V region or domain, this may be an immunoglobulin single variable domain for example a human, camelid (nanobody) or shark immunoglobulin single variable domain or it may be a non-immunoglobulin domain, for example a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to a ligand other than the natural ligand.

CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies. For further details see Journal of Immunological Methods 248 (1-2), 31-45 (2001)

Lipocalins are a family of extracellular proteins which transport small hydrophobic molecules such as steroids, bilins, retinoids and lipids. They have a rigid β-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633

An affibody is a scaffold derived from Protein A of *Staphylococcus aureus* which can be engineered to bind to antigen. The domain consists of a three-helical bundle of approximately 58 amino acids. Libraries have been generated by randomisation of surface residues. For further details see Protein Eng. Des. Sel. 17, 455-462 (2004) and EP1641818A1

Avimers are multidomain proteins derived from the A-domain scaffold family. The native domains of approximately 35 amino acids adopt a defined disulphide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007)

A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999).

Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two α-helices and a β-turn. They can be engineered to bind different target antigens by randomising residues in the first α-helix and a β-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1.

Fibronectin is a scaffold which can be engineered to bind to antigen. Adnectins consists of a backbone of the natural amino acid sequence of the 10th domain of the repeating units of human fibronectin type III (FN3). Three loops at one end of the β-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1.

Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005).

Microbodies are derived from naturally occurring microproteins of 25-50 amino acids in length which contain 3-4 cysteine bridges—examples of microproteins include KalataB1 and conotoxin and knottins. The microproteins have a loop which can be engineered to include upto 25 amino acids without affecting the overall fold of the microprotein. For further details of engineered knottin domains, see WO2008098796.

Other epitope binding domains include proteins which have been used as a scaffold to engineer different target antigen binding properties include human γ-crystallin and human ubiquitin (affilins), kunitz type domains of human protease inhibitors, PDZ-domains of the Ras-binding protein AF-6, scorpion toxins (charybdotoxin), C-type lectin domain (tetranectins) are reviewed in Chapter 7—Non-Antibody Scaffolds from Handbook of Therapeutic Antibodies (2007, edited by Stefan Dubel) and Protein Science 15:14-27 (2006). Epitope binding domains of the present invention could be derived from any of these alternative protein domains.

As used herein, the terms "paired VH domain", "paired VL domain", and "paired VH/VL domains" refer to antibody variable domains which specifically bind antigen only when paired with their partner variable domain. There is always one VH and one VL in any pairing, and the term "paired VH domain" refers to the VH partner, the term "paired VL domain" refers to the VL partner, and the term "paired VH/VL domains" refers to the two domains together.

In one embodiment of the invention the antigen binding site binds to antigen with a Kd of at least 1 mM, for example a Kd of 10 nM, 1 nM, 500 pM, 200 pM, 100 pM, to each antigen as measured by Biacore™, such as the Biacore™ method as described in Example 7.

As used herein, the term "antigen binding site" refers to a site on a protein which is capable of specifically binding to antigen, this may be a single domain, for example an epitope-binding domain, or it may be paired VH/VL domains as can be found on a standard antibody. In some aspects of the invention single-chain Fv (ScFv) domains can provide antigen-binding sites.

The terms "mAb/dAb" and dAb/mAb" are used herein to refer to antigen-binding proteins of the present invention. The two terms can be used interchangeably, and are intended to have the same meaning as used herein.

The term "constant heavy chain 1" is used herein to refer to the CH1 domain of an immunoglobulin heavy chain.

The term "constant light chain" is used herein to refer to the constant domain of an immunoglobulin light chain.

DETAILED DESCRIPTION OF INVENTION

The present invention relates to an antigen-binding protein comprising a protein scaffold which is linked to one or more epitope-binding domains wherein the antigen-binding protein has at least two antigen binding sites at least one of which is from an epitope binding domain and at least one of which is from a paired VH/VL domain.

Such antigen-binding proteins comprise a protein scaffold, for example an Ig scaffold such as IgG, for example a monoclonal antibody, which is linked to one or more epitope-binding domains, for example a domain antibody, wherein the binding protein has at least two antigen binding sites, at least one of which is from an epitope binding domain, and to methods of producing and uses thereof, particularly uses in therapy.

The antigen-binding proteins of the present invention are also referred to as mAbdAbs or dAbmAbs.

In one embodiment the protein scaffold of the antigen-binding protein of the present invention is an Ig scaffold, for example an IgG scaffold or IgA scaffold. The IgG scaffold may comprise all the domains of an antibody (i.e. CH1, CH2, CH3, VH, VL). The antigen-binding protein of the present invention may comprise an IgG scaffold selected from IgG1, IgG2, IgG3, IgG4 or IgG4PE.

The antigen-binding protein of the present invention has at least two antigen binding sites, for examples it has two binding sites, for example where the first binding site has specificity for a first epitope on an antigen and the second binding site has specificity for a second epitope on the same antigen. In a further embodiment there are 4 antigen binding sites, or 6 antigen binding sites, or 8 antigen binding sites, or 10 or more antigen-binding sites. In one embodiment the antigen binding protein has specificity for more than one antigen, for example two antigens, or for three antigens, or for four antigens.

In another aspect the invention relates to an antigen-binding protein comprising at least one homodimer comprising two or more structures of formula I:

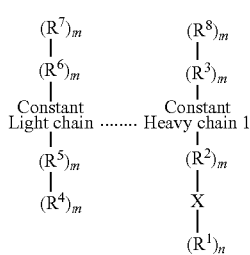

wherein
X represents a constant antibody region comprising constant heavy domain 2 and constant heavy domain 3;
$R^1$, $R^4$, $R^7$ and $R^8$ represent a domain independently selected from an epitope-binding domain;
$R^2$ represents a domain selected from the group consisting of constant heavy chain 1, and an epitope-binding domain;
$R^3$ represents a domain selected from the group consisting of a paired VH and an epitope-binding domain;
$R^5$ represents a domain selected from the group consisting of constant light chain, and an epitope-binding domain;
$R^6$ represents a domain selected from the group consisting of a paired VL and an epitope-binding domain;
n represents an integer independently selected from: 0, 1, 2, 3 and 4;
m represents an integer independently selected from: 0 and 1,
wherein the Constant Heavy chain 1 and the Constant Light chain domains are associated;
wherein at least one epitope binding domain is present;
and when $R^3$ represents a paired VH domain, $R^6$ represents a paired VL domain, so that the two domains are together capable of binding antigen.
In one embodiment $R^6$ represents a paired VL and $R^3$ represents a paired VH.
In a further embodiment either one or both of $R^7$ and $R^8$ represent an epitope binding domain.
In yet a further embodiment either one or both of $R^1$ and $R^4$ represent an epitope binding domain.
In one embodiment $R^4$ is present.
In one embodiment $R^1$, $R^7$ and $R^8$ represent an epitope binding domain.
In one embodiment $R^1$ $R^7$ and $R^8$, and $R^4$ represent an epitope binding domain.
In one embodiment $(R^1)_n$, $(R^2)_m$, $(R^4)_m$ and $(R^5)_m$=0, i.e. are not present, $R^3$ is a paired VH domain, $R^6$ is a paired VL domain, $R^8$ is a VH dAb, and $R^7$ is a VL dAb.
In another embodiment $(R^1)_n$, $(R^2)_m$, $(R^4)_m$ and $(R^5)_m$ are 0, i.e. are not present, $R^3$ is a paired VH domain, $R^6$ is a paired VL domain, $R^8$ is a VH dAb, and $(R^7)_m$=0 i.e. not present.

In another embodiment $(R^2)_m$, and $(R^6)_m$ are 0, i.e. are not present, $R^1$ is a dAb, $R^4$ is a dAb, $R^3$ is a paired VH domain, $R^6$ is a paired VL domain, $(R^8)_m$ and $(R^7)_m$=0 i.e. not present.

In one embodiment of the present invention the epitope binding domain is an immunoglobulin single variable domain.

It will be understood that any of the antigen-binding proteins described herein will be capable of neutralising one or more antigens.

The term "neutralises" and grammatical variations thereof as used throughout the present specification in relation to antigen binding proteins of the invention means that a biological activity of the target is reduced, either totally or partially, in the presence of the antigen binding proteins of the present invention in comparison to the activity of the target in the absence of such antigen binding proteins. Neutralisation may be due to but not limited to one or more of blocking ligand binding, preventing the ligand activating the receptor, down regulating the receptor or affecting effector functionality.

Levels of neutralisation can be measured in several ways, for example by use of any of the assays as set out in the examples and methods below, for example in an assay which measures inhibition of ligand binding to receptor. The neutralisation of ligand in such assays can be measured by assessing the decreased binding between the ligand and its receptor in the presence of neutralising antigen binding protein.

Levels of neutralisation can also be measured, for example in a TF1 assay which may be carried out for example as described in Example 4.3 or 4.4. The neutralisation of IL-4, IL-13 or both of these cytokines in this assay is measured by assessing the inhibition of TF1 cell proliferation in the presence of neutralising antigen binding protein.

Other methods of assessing neutralisation, for example, by assessing the decreased binding between the ligand and its receptor in the presence of neutralising antigen binding protein are known in the art, and include, for example ELISA ligand receptor inhibition assays or Biacore™ assays.

In an alternative aspect of the present invention there is provided antigen binding proteins which have at least substantially equivalent neutralising activity to the antibodies exemplified herein, for example antigen binding proteins which retain the neutralising activity of BPC2201, BPC2202, BPC2203, BPC2209, BPC2210, BPC2204 to BPC2208 and BPC2220 in the IL-13/4 binding assay as set out in Example 2.

The antigen binding proteins of the invention include those which have specificity for IL-13, for example which comprise an epitope-binding domain which is capable of binding to IL-13, or which comprise a paired VH/VL which binds to IL-13. The antigen binding protein may comprise an antibody which is capable of binding to IL-13. The antigen binding protein may comprise an immunoglobulin single variable domain which is capable of binding to IL-13.

In one embodiment the antigen-binding protein of the present invention has specificity for more than one antigen, for example where it is capable of binding two or more antigens selected from IL-13, IL-5, and IL-4, for example where it is capable of binding IL-13 and IL-4, or where it is capable of binding IL-13 and IL-5, or where it is capable of binding IL-5 and IL-4.

In one embodiment the antigen-binding protein of the present invention has specificity for more than one antigen, for example where it is capable of binding two or more antigens selected from IL-13, IL-5, and IL-4, for example where it is capable of binding IL-13 and IL-4 simultaneously, or where it is capable of binding IL-13 and IL-5 simultaneously, or where it is capable of binding IL-5 and IL-4 simultaneously.

It will be understood that any of the antigen-binding proteins described herein may be capable of binding two or more antigens simultaneously, for example, as determined by stochiometry analysis by using a suitable assay such as that described in Example 3.

Examples of antigen-binding proteins of the invention include IL-13 antibodies which have an epitope binding domain with a specificity for IL-4, for example an anti-IL-4 immunoglobulin single variable domain, attached to the c-terminus or the n-terminus of the heavy chain or the c-terminus or n-terminus of the light chain. Antigen binding proteins of the present invention include IL-13 antibodies with an IL-4 epitope binding domain attached to the n-terminus of the heavy chain. Antigen binding proteins of the present invention include IL-13 antibodies with an IL-4 epitope binding domain attached to the n-terminus of the light chain. Antigen binding proteins of the present invention include IL-13 antibodies with an IL-4 epitope binding domain attached to the c-terminus of the heavy chain. Antigen binding proteins of the present invention include IL-13 antibodies with an IL-4 epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain. IL-13 antibodies of use in the present invention include those comprising a heavy chain sequences as set out in SEQ ID NO: 28 and a light chain sequence as set out in SEQ ID NO: 27.

Examples of such antigen-binding proteins include IL-4 antibodies which have an epitope binding domain with a specificity for IL-13, for example an anti-IL-13 immunoglobulin single variable domain, attached to the c-terminus or the n-terminus of the heavy chain or the c-terminus or n-terminus of the light chain.

Antigen binding proteins of the present invention include IL-4 antibodies with an IL-13 epitope binding domain attached to the n-terminus of the heavy chain. Antigen binding proteins of the present invention include IL-4 antibodies with an IL-13 epitope binding domain attached to the n-terminus of the light chain. Antigen binding proteins of the present invention include IL-4 antibodies with an IL-13 epitope binding domain attached to the c-terminus of the heavy chain. Antigen binding proteins of the present invention include IL-4 antibodies with an IL-13 epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

IL-4 antibodies of use in the present invention include those comprising a heavy chain sequences as set out in SEQ ID NO:2 and a light chain sequence as set out in SEQ ID NO:3.

Examples of such antigen-binding proteins include IL-13 antibodies which have an epitope binding domain with a specificity for IL-5, for example an anti-IL-5 immunoglobulin single variable domain, attached to the c-terminus or the n-terminus of the heavy chain or the c-terminus or n-terminus of the light chain. Antigen binding proteins of the present invention include IL-13 antibodies with an IL-5 epitope binding domain attached to the n-terminus of the heavy chain. Antigen binding proteins of the present invention include IL-13 antibodies with an IL-5 epitope binding domain attached to the n-terminus of the light chain. Antigen binding proteins of the present invention include IL-13 antibodies with an IL-5 epitope binding domain attached to the c-terminus of the heavy chain. Antigen binding proteins of the present invention include IL-13 antibodies with an IL-5 epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

Examples of such antigen-binding proteins include IL-5 antibodies which have an epitope binding domain with a specificity for IL-13, for example an anti-IL-13 immunoglobulin single variable domain, attached to the c-terminus or the n-terminus of the heavy chain or the c-terminus or n-terminus of the light chain.

Antigen binding proteins of the present invention include IL-5 antibodies with an IL-13 epitope binding domain attached to the n-terminus of the heavy chain. Antigen binding proteins of the present invention include IL-5 antibodies with an IL-13 epitope binding domain attached to the n-terminus of the light chain. Antigen binding proteins of the present invention include IL-5 antibodies with an IL-13 epitope binding domain attached to the c-terminus of the heavy chain. Antigen binding proteins of the present invention include IL-5 antibodies with an IL-13 epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain. IL-5 antibodies of use in the present invention include those comprising a heavy chain sequences as set out in SEQ ID NO: 91 and a light chain sequence as set out in SEQ ID NO: 92

Examples of such antigen-binding proteins include IL-4 antibodies which have an epitope binding domain with a specificity for IL-5, for example an anti-IL-5 immunoglobulin single variable domain, attached to the c-terminus or the n-terminus of the heavy chain or the c-terminus or n-terminus of the light chain. Antigen binding proteins of the present invention include IL-4 antibodies with an IL-5 epitope binding domain attached to the n-terminus of the heavy chain. Antigen binding proteins of the present invention include IL-4 antibodies with an IL-5 epitope binding domain attached to the n-terminus of the light chain. Antigen binding proteins of the present invention include IL-4 antibodies with an IL-5 epitope binding domain attached to the c-terminus of the heavy chain. Antigen binding proteins of the present invention include IL-4 antibodies with an IL-5 epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

Examples of such antigen-binding proteins include IL-5 antibodies which have an epitope binding domain with a specificity for IL-4, for example an anti-IL-4 immunoglobulin single variable domain, attached to the c-terminus or the n-terminus of the heavy chain or the c-terminus or n-terminus of the light chain.

Antigen binding proteins of the present invention include IL-5 antibodies with an IL-4 epitope binding domain attached to the n-terminus of the heavy chain. Antigen binding proteins of the present invention include IL-5 antibodies with an IL-4 epitope binding domain attached to the n-terminus of the light chain. Antigen binding proteins of the present invention include IL-5 antibodies with an IL-4 epitope binding domain attached to the c-terminus of the heavy chain. Antigen binding proteins of the present invention include IL-5 antibodies with an IL-4 epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

The invention also provides a trispecific binding protein which is capable of binding to IL-4, IL-13 and IL-5.

Examples of such antigen-binding proteins include IL-5 antibodies which have an epitope binding domain with a specificity for IL-4, for example an anti-IL-4 immunoglobulin single variable domain, attached to the c-terminus or the n-terminus of the heavy chain or the c-terminus or n-terminus of the light chain and an epitope binding domain with a specificity for IL-13, for example an anti-IL-13 immunoglobulin single variable domain, attached to the c-terminus or the n-terminus of the heavy chain or the c-terminus or n-terminus of the light chain.

Antigen binding proteins of the present invention include IL-5 antibodies with an IL-4 epitope binding domain attached to the n-terminus of the heavy chain and an IL-13 epitope binding domain attached to the n-terminus of the light chain.

Antigen binding proteins of the present invention include IL-5 antibodies with an IL-4 epitope binding domain attached to the n-terminus of the heavy chain and an IL-13 epitope binding domain attached to the c-terminus of the light chain.

Antigen binding proteins of the present invention include IL-5 antibodies with an IL-4 epitope binding domain attached to the n-terminus of the heavy chain and an IL-13 epitope binding domain attached to the c-terminus of the heavy chain.

Antigen binding proteins of the present invention include IL-5 antibodies with an IL-4 epitope binding domain attached to the n-terminus of the light chain and an IL-13 epitope binding domain attached to the c-terminus of the light chain.

Antigen binding proteins of the present invention include IL-5 antibodies with an IL-4 epitope binding domain attached to the n-terminus of the light chain and an IL-13 epitope binding domain attached to the c-terminus of the heavy chain.

Antigen binding proteins of the present invention include IL-5 antibodies with an IL-4 epitope binding domain attached to the n-terminus of the light chain and an IL-13 epitope binding domain attached to the n-terminus of the heavy chain.

Antigen binding proteins of the present invention include IL-5 antibodies with an IL-4 epitope binding domain attached to the c-terminus of the heavy chain and an IL-13 epitope binding domain attached to the c-terminus of the light chain.

Antigen binding proteins of the present invention include IL-5 antibodies with an IL-4 epitope binding domain attached to the c-terminus of the heavy chain and an IL-13 epitope binding domain attached to the n-terminus of the light chain.

Antigen binding proteins of the present invention include IL-5 antibodies with an IL-4 epitope binding domain attached to the c-terminus of the heavy chain and an IL-13 epitope binding domain attached to the n-terminus of the heavy chain.

Antigen binding proteins of the present invention include IL-5 antibodies with an IL-4 epitope binding domain attached to the c-terminus of the light chain and an IL-13 epitope binding domain attached to the c-terminus of the heavy chain.

Antigen binding proteins of the present invention include IL-5 antibodies with an IL-4 epitope binding domain attached to the c-terminus of the light chain and an IL-13 epitope binding domain attached to the n-terminus of the heavy chain.

Antigen binding proteins of the present invention include IL-5 antibodies with an IL-4 epitope binding domain attached to the c-terminus of the light chain and an IL-13 epitope binding domain attached to the n-terminus of the light chain.

Such antigen-binding proteins may also have one or more further epitope binding domains with the same or different antigen-specificity attached to the c-terminus and/or the n-terminus of the heavy chain and/or the c-terminus and/or n-terminus of the light chain.

The antigen binding proteins of the invention include those which have specificity for IL-18, for example which comprises an epitope-binding domain which is capable of binding to IL-18, or which comprises a paired VH/VL which binds to IL-18.

The antigen binding protein may comprise an antibody which is capable of binding to IL-18. The antigen binding protein may comprise an immunoglobulin single variable domain which is capable of binding to IL-18.

The invention also provides a trispecific binding protein which is capable of binding to IL-4, IL-13 and IL-18.

Examples of such antigen-binding proteins include IL-18 antibodies which have an epitope binding domain with a specificity for IL-4, for example an anti-IL-4 immunoglobulin single variable domain, attached to the c-terminus or the n-terminus of the heavy chain or the c-terminus or n-terminus of the light chain and an epitope binding domain with a specificity for IL-13, for example an anti-IL-13 immunoglobulin single variable domain, attached to the c-terminus or the n-terminus of the heavy chain or the c-terminus or n-terminus of the light chain.

Antigen binding proteins of the present invention include IL-18 antibodies with an IL-4 epitope binding domain attached to the n-terminus of the heavy chain and an IL-13 epitope binding domain attached to the n-terminus of the light chain.

Antigen binding proteins of the present invention include IL-18 antibodies with an IL-4 epitope binding domain attached to the n-terminus of the heavy chain and an IL-13 epitope binding domain attached to the c-terminus of the light chain.

Antigen binding proteins of the present invention include IL-18 antibodies with an IL-4 epitope binding domain attached to the n-terminus of the heavy chain and an IL-13 epitope binding domain attached to the c-terminus of the heavy chain.

Antigen binding proteins of the present invention include IL-18 antibodies with an IL-4 epitope binding domain attached to the n-terminus of the light chain and an IL-13 epitope binding domain attached to the c-terminus of the light chain.

Antigen binding proteins of the present invention include IL-18 antibodies with an IL-4 epitope binding domain attached to the n-terminus of the light chain and an IL-13 epitope binding domain attached to the c-terminus of the heavy chain.

Antigen binding proteins of the present invention include IL-18 antibodies with an IL-4 epitope binding domain attached to the n-terminus of the light chain and an IL-13 epitope binding domain attached to the n-terminus of the heavy chain.

Antigen binding proteins of the present invention include IL-18 antibodies with an IL-4 epitope binding domain attached to the c-terminus of the heavy chain and an IL-13 epitope binding domain attached to the c-terminus of the light chain.

Antigen binding proteins of the present invention include IL-18 antibodies with an IL-4 epitope binding domain attached to the c-terminus of the heavy chain and an IL-13 epitope binding domain attached to the n-terminus of the light chain.

Antigen binding proteins of the present invention include IL-18 antibodies with an IL-4 epitope binding domain attached to the c-terminus of the heavy chain and an IL-13 epitope binding domain attached to the n-terminus of the heavy chain.

Antigen binding proteins of the present invention include IL-18 antibodies with an IL-4 epitope binding domain attached to the c-terminus of the light chain and an IL-13 epitope binding domain attached to the c-terminus of the heavy chain.

Antigen binding proteins of the present invention include IL-18 antibodies with an IL-4 epitope binding domain attached to the c-terminus of the light chain and an IL-13 epitope binding domain attached to the n-terminus of the heavy chain.

Antigen binding proteins of the present invention include IL-18 antibodies with an IL-4 epitope binding domain attached to the c-terminus of the light chain and an IL-13 epitope binding domain attached to the n-terminus of the light chain.

Such antigen-binding proteins may also have one or more further epitope binding domains with the same or different antigen-specificity attached to the c-terminus and/or the n-terminus of the heavy chain and/or the c-terminus and/or n-terminus of the light chain.

The antigen binding proteins of the invention include those which have specificity for TNFα, for example which comprises an epitope-binding domain which is capable of binding to TNFα, or which comprises a paired VH/VL which binds to TNFα.

The antigen binding protein may comprise an antibody which is capable of binding to TNFα. The antigen binding protein may comprise an immunoglobulin single variable domain which is capable of binding to TNFα.

In one embodiment the antigen-binding protein of the present invention has specificity for more than one antigen, for example where it is capable of binding two or more antigens selected from TNFα, EGFR and VEGF, for example where it is capable of binding TNFα and EGFR, or where it is capable of binding TNFα and VEGF, or where it is capable of binding EGFR and VEGF. Examples of such antigen-binding proteins include TNFα antibodies which have an epitope binding domain with a specificity for EGFR, for example an anti-EGFR immunoglobulin single variable domain, attached to the c-terminus or the n-terminus of the heavy chain or the c-terminus or n-terminus of the light chain.

Antigen binding proteins of the present invention include TNFα antibodies with an EGFR epitope binding domain attached to the n-terminus of the heavy chain. Antigen binding proteins of the present invention include TNFα antibodies with an EGFR epitope binding domain attached to the n-terminus of the light chain. Antigen binding proteins of the present invention include TNFα antibodies with an EGFR epitope binding domain attached to the c-terminus of the heavy chain. Antigen binding proteins of the present invention include TNFα antibodies with an EGFR epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

Antigen binding proteins of the present invention include EGFR antibodies with an TNFα epitope binding domain attached to the n-terminus of the heavy chain. Antigen binding proteins of the present invention include EGFR antibodies with an TNFα epitope binding domain attached to the n-terminus of the light chain. Antigen binding proteins of the present invention include EGFR antibodies with an TNFα epitope binding domain attached to the c-terminus of the heavy chain. Antigen binding proteins of the present invention include EGFR antibodies with an TNFα epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

Examples of such antigen-binding proteins include TNFα antibodies which have an epitope binding domain with a specificity for VEGF, for example an anti-VEGF immunoglobulin single variable domain, attached to the c-terminus or the n-terminus of the heavy chain or the c-terminus or n-terminus of the light chain.

The antigen-binding protein of the present invention may have specificity for more than one antigen, for example where it is capable of binding TNFα, and one or both antigens selected from IL-4 and IL-13, for example where it is capable of binding TNFα and IL-4, or where it is capable of binding TNFα and IL-13, or where it is capable of binding TNFα and IL-13 and IL-4. Examples of such antigen-binding proteins include IL-13 antibodies which have an epitope binding domain with a specificity for TNFα, for example an anti-TNFα adnectin, attached to the c-terminus or the n-terminus of the heavy chain or the c-terminus or n-terminus of the light chain. Other examples of such antigen-binding proteins include IL-4 antibodies which have an epitope binding domain with a specificity for TNFα, for example an anti-TNFα adnectin, attached to the c-terminus or the n-terminus of the heavy chain or the c-terminus or n-terminus of the light chain.

Antigen binding proteins of the present invention include TNFα antibodies with an VEGF epitope binding domain attached to the n-terminus of the heavy chain. Antigen binding proteins of the present invention include TNFα antibodies with an VEGF epitope binding domain attached to the n-terminus of the light chain. Antigen binding proteins of the present invention include TNFα antibodies with an VEGF epitope binding domain attached to the c-terminus of the heavy chain. Antigen binding proteins of the present invention include TNFα antibodies with an VEGF epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

Antigen binding proteins of the present invention include VEGF antibodies with an TNFα epitope binding domain attached to the n-terminus of the heavy chain. Antigen binding proteins of the present invention include VEGF antibodies with an TNFα epitope binding domain attached to the n-terminus of the light chain. Antigen binding proteins of the present invention include VEGF antibodies with an TNFα epitope binding domain attached to the c-terminus of the heavy chain. Antigen binding proteins of the present invention include VEGF antibodies with an TNFα epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

The antigen binding proteins of the invention include those which have specificity for CD-20, for example which comprises an epitope-binding domain which is capable of binding to CD-20, or which comprises a paired VH/VL which binds to CD-20.

The antigen binding protein may comprise an antibody which is capable of binding to CD-20. The antigen binding protein may comprise an immunoglobulin single variable domain which is capable of binding to CD-20.

Such antigen-binding proteins may also have one or more further epitope binding domains with the same or different antigen-specificity attached to the c-terminus and/or the n-terminus of the heavy chain and/or the c-terminus and/or n-terminus of the light chain.

The antigen binding proteins of the invention include those which have specificity for IL1R1, for example which comprise an epitope-binding domain which is capable of binding to IL1R1, or which comprises a paired VH/VL which binds to IL1R1.

The antigen binding protein may comprise an antibody which is capable of binding to IL1R1. The antigen binding protein may comprise an immunoglobulin single variable domain which is capable of binding to IL1R1.

In one embodiment the antigen-binding protein of the present invention has specificity for more than one antigen, for example where it is capable of binding IL1R1 and a second antigen, for example where it is capable of binding IL1R1 and VEGF. Examples of such antigen-binding proteins include IL1R1 antibodies which have an epitope binding domain with a specificity for VEGF, for example an anti-VEGF immunoglobulin single variable domain, attached to the c-terminus or the n-terminus of the heavy chain or the c-terminus or n-terminus of the light chain.

Antigen binding proteins of the present invention include IL1R1 antibodies with an VEGF epitope binding domain attached to the n-terminus of the heavy chain. Antigen binding proteins of the present invention include IL1R1 antibodies with an VEGF epitope binding domain attached to the n-terminus of the light chain. Antigen binding proteins of the present invention include IL1R1 antibodies with an VEGF epitope binding domain attached to the c-terminus of the heavy chain. Antigen binding proteins of the present invention include IL1R1 antibodies with an VEGF epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

Antigen binding proteins of the present invention include VEGF antibodies with an IL1R1 epitope binding domain attached to the n-terminus of the heavy chain. Antigen binding proteins of the present invention include VEGF antibodies with an IL1R1 epitope binding domain attached to the n-terminus of the light chain. Antigen binding proteins of the present invention include VEGF antibodies with an IL1R1 epitope binding domain attached to the c-terminus of the heavy chain. Antigen binding proteins of the present invention include VEGF antibodies with an IL1R1 epitope binding domain attached to the c-terminus of the light chain. Such antigen-binding proteins may also have one or more further epitope binding domains with the same or different antigen-specificity attached to the c-terminus and/or the n-terminus of the heavy chain and/or the c-terminus and/or n-terminus of the light chain.

The antigen binding proteins of the invention include those which have specificity for EGFR, for example which comprises an epitope-binding domain which is capable of binding to EGFR, or which comprises a paired VH/VL which binds to EGFR.

The antigen binding protein may comprise an antibody which is capable of binding to EGFR. The antigen binding protein may comprise an immunoglobulin single variable domain which is capable of binding to EGFR.

In one embodiment the antigen-binding protein of the present invention has specificity for more than one antigen, for example where it is capable of binding two or more antigens selected from EGFR, IGF-1R, VEGFR2 and VEGF, for example where it is capable of binding EGFR and IGF-1R, or where it is capable of binding EGFR and VEGF, or where it is capable of binding VEGF and IGF-1R, or where it is capable of binding EGFR and VEGFR2, or where it is capable of binding IGF-1R and VEGFR2, or where it is capable of binding VEGF and VEGFR2, or where it is capable of binding EGFR, IGF-1R and VEGFR2, or where it is capable of binding VEGF, IGF-1R and VEGFR2, or where it is capable of binding EGFR, VEGF and VEGFR2, or where it is capable of binding EGFR, VEGF and IGF1R. Examples of such antigen-binding proteins include EGFR antibodies which have an epitope binding domain with a specificity for VEGFR2, for example an anti-VEGFR2 adnectin, attached to the c-terminus or the n-terminus of the heavy chain or the c-terminus or n-terminus of the light chain.

Examples of such antigen-binding proteins include EGFR antibodies which have an epitope binding domain with a specificity for VEGF, for example an anti-VEGF immunoglobulin single variable domain, attached to the c-terminus or the n-terminus of the heavy chain or the c-terminus or n-terminus of the light chain.

Examples of such antigen-binding proteins include VEGF antibodies which have an epitope binding domain with a specificity for EGFR, for example an anti-EGFR immunoglobulin single variable domain, attached to the c-terminus or the n-terminus of the heavy chain or the c-terminus or n-terminus of the light chain.

Examples of such antigen-binding proteins include IGF-1R antibodies which have an epitope binding domain with a specificity for VEGF, for example an anti-VEGF lipocalin, attached to the c-terminus or the n-terminus of the heavy chain or the c-terminus or n-terminus of the light chain.

Examples of such antigen-binding proteins include IGF-1R antibodies which have an epitope binding domain with a specificity for VEGFR2, for example an anti-VEGFR2 adnectin, attached to the c-terminus or the n-terminus of the heavy chain or the c-terminus or n-terminus of the light chain.

The antigen binding proteins of the invention include those which have specificity for IL-23, for example which comprises an epitope-binding domain which is capable of binding to IL-23, or which comprises a paired VH/VL which binds to IL-23.

The antigen binding protein may comprise an antibody which is capable of binding to IL-23. The antigen binding protein may comprise an immunoglobulin single variable domain which is capable of binding to IL-23.

In one embodiment the antigen-binding protein of the present invention has specificity for more than one antigen, for example where it is capable of binding two or more antigens selected from TH17 type cytokines, for example. IL-17, IL-22, or IL-21, for example where it is capable of binding IL-23 and IL-17, or where it is capable of binding IL-23 and IL-21, or where it is capable of binding IL-23 and IL-22.

Examples of such antigen-binding proteins include IL-23 antibodies which have an epitope binding domain with a specificity for IL-17, for example an anti-IL-17 immunoglobulin single variable domain, attached to the c-terminus or the n-terminus of the heavy chain or the c-terminus or n-terminus of the light chain.

The antigen binding proteins of the invention include those which have specificity for PDGFRα, for example which comprises an epitope-binding domain which is capable of binding to PDGFRα, or which comprises a paired VH/VL which binds to PDGFRα. The antigen binding protein may comprise an antibody which is capable of binding to PDGFRα. The antigen binding protein may comprise an immunoglobulin single variable domain which is capable of binding to PDGFRα.

The antigen binding proteins of the invention include those which have specificity for FGFR1, for example which comprises an epitope-binding domain which is capable of binding to FGFR1, or which comprises a paired VH/VL which binds to FGFR1. The antigen binding protein may comprise an antibody which is capable of binding to FGFR1. The antigen binding protein may comprise an immunoglobulin single variable domain which is capable of binding to FGFR1.

The antigen binding proteins of the invention include those which have specificity for FGFR3, for example which comprises an epitope-binding domain which is capable of binding to FGFR3, or which comprises a paired VH/VL which binds to FGFR3. The antigen binding protein may comprise an antibody which is capable of binding to FGFR3. The antigen binding protein may comprise an immunoglobulin single variable domain which is capable of binding to FGFR3.

The antigen binding proteins of the invention include those which have specificity for VEGFR2, for example which comprises an epitope-binding domain which is capable of binding to VEGFR2, or which comprises a paired VH/VL which binds to VEGFR2.

The antigen binding protein may comprise an antibody which is capable of binding to VEGFR2. The antigen binding protein may comprise an immunoglobulin single variable domain which is capable of binding to VEGFR2.

The antigen binding proteins of the invention include those which have specificity for VEGFR3, for example which comprises an epitope-binding domain which is capable of binding to VEGFR3, or which comprises a paired VH/VL which binds to VEGFR3. The antigen binding protein may comprise an antibody which is capable of binding to VEGFR3. The antigen binding protein may comprise an immunoglobulin single variable domain which is capable of binding to VEGFR3.

The antigen binding proteins of the invention include those which have specificity for VE cadherin, for example which comprises an epitope-binding domain which is capable of binding to VE cadherin, or which comprises a paired VH/VL which binds to VE cadherin.

The antigen binding protein may comprise an antibody which is capable of binding to VE cadherin. The antigen binding protein may comprise an immunoglobulin single variable domain which is capable of binding to VE cadherin.

The antigen binding proteins of the invention include those which have specificity for neuropilin, for example which comprises an epitope-binding domain which is capable of binding to neuropilin, or which comprises a paired VH/VL which binds to neuropilin. The antigen binding protein may comprise an antibody which is capable of binding to neuropilin. The antigen binding protein may comprise an immunoglobulin single variable domain which is capable of binding to neuropilin.

The antigen binding proteins of the invention include those which have specificity for Flt-3, for example which comprises an epitope-binding domain which is capable of binding to Flt-3, or which comprises a paired VH/VL which binds to Flt-3.

The antigen binding protein may comprise an antibody which is capable of binding to Flt-3. The antigen binding protein may comprise an immunoglobulin single variable domain which is capable of binding to Flt-3.

The antigen binding proteins of the invention include those which have specificity for ron, for example which comprises an epitope-binding domain which is capable of binding ron, or which comprises a paired VH/VL which binds to ron.

The antigen binding protein may comprise an antibody which is capable of binding to ron. The antigen binding protein may comprise an immunoglobulin single variable domain which is capable of binding to ron.

The antigen binding proteins of the invention include those which have specificity for Trp-1, for example which comprises an epitope-binding domain which is capable of binding Trp-1, or which comprises a paired VH/VL which binds to Trp-1.

The antigen binding protein may comprise an antibody which is capable of binding to Trp-1. The antigen binding protein may comprise an immunoglobulin single variable domain which is capable of binding to Trp-1.

In one embodiment the antigen-binding protein of the present invention has specificity for more than one antigen, for example where it is capable of binding two or more antigens which are implicated in cancer, for example where it is capable of binding two or more antigens selected from PDGFRα, FGFR1, FGFR3, VEGFR2, VEGFR3, IGF1R, EGFR and VEGF, VE cadherin, neuropilin, Flt-3, ron, Trp-1, CD-20 for example where it is capable of binding PDGFRα and FGFR1, or where it is capable of binding PDGFRα and VEGF, or where it is capable of binding PDGFRα and FGFR3, or where it is capable of binding PDGFRα and VEGFR2, or where it is capable of binding PDGFRα and VEGFR3, or where it is capable of binding PDGFRα and IGF1R, or where it is capable of binding PDGFRα and EGFR, or where it is capable of binding PDGFRα and VEGF, or where it is capable of binding PDGFRα and VE cadherin, or where it is capable of binding PDGFRα and neuropilin, or where it is capable of binding PDGFRα and Flt-3, or where it is capable of binding PDGFRα and ron, or where it is capable of binding PDGFRα and Trp1, or where it is capable of binding PDGFRα and CD-20, or where it is capable of binding FGFR1 and FGFR3, or where it is capable of binding FGFR1 and VEGFR2, or where it is capable of binding FGFR1 and VEGR3, or where it is capable of binding FGFR1 and IGF1R, or where it is capable of binding FGFR1 and EGFR, or where it is capable of binding FGFR1 and VEGF, or where it is capable of binding FGFR1 and VE cadherin, or where it is capable of binding FGFR1 and neuropilin, or where it is capable of binding FGFR1 and Flt-3, or where it is capable of binding FGFR1 and ron, or where it is capable of binding FGFR1 and Trp-1, or where it is capable of binding FGFR1 and CD-20, or where it is capable of binding FGFR3 and VEGFR2, or where it is capable of binding FGFR3 and VEGFR3, or where it is capable of binding FGFR3 and IGF1R, or where it is capable of binding FGFR3 and EGFR, or where it is capable of binding FGFR3 and VEGF, or where it is capable of binding FGFR3 and VE cadherin, or where it is capable of binding FGFR3 and neuropilin, or where it is capable of binding FGFR3 and Flt-3, or where it is capable of binding FGFR3 and ron, or where it is capable of binding FGFR3 and Trp-1, or where it is capable of binding FGFR3 and CD-20, or where it is capable of binding VEGFR2 and VEGFR3, or where it is capable of binding VEGFR2 and IGF1R, or where it is capable of binding VEGFR2 and EGFR, or where it is capable of binding VEGFR2 and VEGF, or where it is capable of binding VEGFR2 and VE cadherin, or where it is capable of binding VEGFR2 and neuropilin, or where it is capable of binding VEGFR2 and Flt-3, or where it is capable of binding VEGFR2 and ron, or where it is capable of binding VEGFR2 and Trp-1, or where it is capable of binding VEGFR2 and CD-20, or where it is capable of binding VEGFR3 and IGF-1R, or where it is capable of binding VEGFR3 and EGFR, or where it is capable of binding VEGFR3 and VEGF, or where it is capable of binding VEGFR3 and VE cadherin, or where it is capable of binding VEGFR3 and neuropilin, or where it is capable of binding VEGFR3 and Flt-3, or where it is capable of binding VEGFR3 and Trp-1, or where it is capable of binding VEGFR3 and CD-20, or where it is capable of binding IGF1R and EGFR, or where it is capable of binding IGF1R and VEGF, or where it is capable of binding IGF1R and VE cadherin, or where it is capable of binding IGF1R and neuropilin, or where it is capable of binding IGF1R and Flt-3, or where it is capable of binding IGF1R and ron, or where it is capable of binding IGF1R and Trp-1, or where it is capable of binding IGF1R and CD-20, or where it is capable of binding EGFR and VEGF, or where it is capable of binding EGFR and VE cadherin, or where it is capable of binding EGFR and neuropilin, or where it is capable of binding EGFR and Flt-3, or where it is capable of binding EGFR and ron, or where it is capable of binding EGFR and Trp-1, or where it is capable of binding EGFR and CD-20, or where it is capable of binding VEGF and VE cadherin, or where it is capable of binding VEGF and neuropilin, or where it is capable of binding VEGF and Flt-3, or where it is capable of binding VEGF and ron, or where it is capable of binding VEGF and Trp-1, or where it is capable of binding VEGF and CD-20, or where it is capable of binding VE cadherin and neuropilin, or where it is capable of binding VE cadherin and Flt-3, or where it is capable of binding VE cadherin and ron, or where it is capable of binding VE cadherin and Trp-1, or where it is capable of binding VE cadherin and CD-20, or where it is capable of binding neuropilin and Flt-3, or where it is capable of binding neuropilin and ron, or where it is capable of binding neuropilin and Trp-1, or where it is capable of binding neuropilin and CD-20, or where it is capable of binding Flt-3 and ron, or where it is capable of binding Flt-3 and Trp-1, or where it is capable of binding Flt-3 and CD-20, or where it is capable of binding ron and Trp-1, or where it is capable of binding ron and CD-20, and or where it is capable of binding Trp-1 and CD-20.

Such antigen-binding proteins may also have one or more further epitope binding domains with the same or different antigen-specificity attached to the c-terminus and/or the n-terminus of the heavy chain and/or the c-terminus and/or n-terminus of the light chain.

The antigen binding proteins of the invention include those which have specificity for beta-amyloid, for example which comprise an epitope-binding domain which is capable of binding to beta-amyloid, or which comprises a paired VH/VL which binds to beta-amyloid.

The antigen binding protein may comprise an antibody which is capable of binding to beta-amyloid. The antigen binding protein may comprise an immunoglobulin single variable domain which is capable of binding to beta-amyloid.

The antigen binding proteins of the invention include those which have specificity for CD-3, for example which comprise an epitope-binding domain which is capable of binding to CD-3, or which comprises a paired VH/VL which binds to CD-3.

The antigen binding protein may comprise an antibody which is capable of binding to CD-3. The antigen binding protein may comprise an immunoglobulin single variable domain which is capable of binding to CD-3.

The antigen binding proteins of the invention include those which have specificity for gpIIIb/IIa, for example which comprise an epitope-binding domain which is capable of binding to gpIIIb/IIa, or which comprises a paired VH/VL which binds to gpIIIb/IIa.

The antigen binding protein may comprise an antibody which is capable of binding to gpIIIb/IIa. The antigen binding protein may comprise an immunoglobulin single variable domain which is capable of binding to gpIIIb/IIa.

The antigen binding proteins of the invention include those which have specificity for TGFbeta, for example which comprise an epitope-binding domain which is capable of binding to TGFbeta, or which comprises a paired VH/VL which binds to TGFbeta. The antigen binding protein may comprise an antibody which is capable of binding to TGFbeta. The antigen binding protein may comprise an immunoglobulin single variable domain which is capable of binding to TGFbeta.

In one embodiment of the present invention there is provided an antigen binding protein according to the invention described herein and comprising a constant region such that the antibody has reduced ADCC and/or complement activation or effector functionality. In one such embodiment the heavy chain constant region may comprise a naturally disabled constant region of IgG2 or IgG4 isotype or a mutated IgG1 constant region. Examples of suitable modifications are described in EP0307434. One example comprises the substitutions of alanine residues at positions 235 and 237 (EU index numbering).

In one embodiment the antigen-binding proteins of the present invention will retain Fc functionality for example will be capable of one or both of ADCC and CDC activity. Such antigen-binding proteins may comprise an epitope-binding domain located on the light chain, for example on the c-terminus of the light chain.

The invention also provides a method of maintaining ADCC and CDC function of antigen-binding proteins by positioning of the epitope binding domain on the light chain of the antibody in particular, by positioning the epitope binding domain on the c-terminus of the light chain. Such ADCC and CDC function can be measured by any suitable assay which will be known to the person skilled in the art.

The invention also provides a method of reducing CDC function of antigen-binding proteins by positioning of the epitope binding domain on the heavy chain of the antibody, in particular, by positioning the epitope binding domain on the c-terminus of the heavy chain. Such CDC function can be measured by any suitable assay, which will be known to the person skilled in the art.

In a further embodiment the antigen-binding protein of the present invention is capable of binding two or more antigens selected from VEGF, IGF-1R and EGFR, for example it is capable of binding EGFR and VEGF, or EGFR and IGF1R, or IGF1R and VEGF, or for example it is capable of binding to TNF and IL1-R. In embodiments of the invention which comprise an IGF-1R binding site, the IGF-1R binding site of the antigen-binding protein of the invention may comprise a paired VH/VL domain in the protein scaffold.

In one embodiment, the antigen binding proteins comprise an epitope-binding domain which is an immunoglobulin single variable domain for example the epitope binding domain may be a human VH or human VL, or a camelid $V_{HH}$ (nanobody) or a shark dAb (NARV).

In one embodiment the antigen binding proteins comprise an epitope-binding domain which is a derivative of a non-immunoglobulin scaffold, for example a non-immunoglobulin domain selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to a ligand other than the natural ligand.

The antigen binding proteins of the present invention may comprise a protein scaffold attached to an epitope binding domain which is an adnectin, for example an IgG scaffold with an adnectin attached to the c-terminus of the heavy chain, or it may comprise a protein scaffold attached to an adnectin, for example an IgG scaffold with an adnectin attached to the n-terminus of the heavy chain, or it may comprise a protein scaffold attached to an adnectin, for example an IgG scaffold with an adnectin attached to the c-terminus of the light chain, or it may comprise a protein scaffold attached to an adnectin, for example an IgG scaffold with an adnectin attached to the n-terminus of the light chain.

In other embodiments it may comprise a protein scaffold, for example an IgG scaffold, attached to an epitope binding domain which is CTLA-4, for example an IgG scaffold with CTLA-4 attached to the n-terminus of the heavy chain, or it may comprise for example an IgG scaffold with CTLA-4 attached to the c-terminus of the heavy chain, or it may comprise for example an IgG scaffold with CTLA-4 attached to the n-terminus of the light chain, or it may comprise an IgG scaffold with CTLA-4 attached to the c-terminus of the light chain.

In other embodiments it may comprise a protein scaffold, for example an IgG scaffold, attached to an epitope binding domain which is a lipocalin, for example an IgG scaffold with a lipocalin attached to the n-terminus of the heavy chain, or it may comprise for example an IgG scaffold with a lipocalin attached to the c-terminus of the heavy chain, or it may comprise for example an IgG scaffold with a lipocalin attached to the n-terminus of the light chain, or it may comprise an IgG scaffold with a lipocalin attached to the c-terminus of the light chain.

In other embodiments it may comprise a protein scaffold, for example an IgG scaffold, attached to an epitope binding domain which is an SpA, for example an IgG scaffold with an SpA attached to the n-terminus of the heavy chain, or it may comprise for example an IgG scaffold with an SpA attached to the c-terminus of the heavy chain, or it may comprise for example an IgG scaffold with an SpA attached to the n-terminus of the light chain, or it may comprise an IgG scaffold with an SpA attached to the c-terminus of the light chain.

In other embodiments it may comprise a protein scaffold, for example an IgG scaffold, attached to an epitope binding domain which is an affibody, for example an IgG scaffold with an affibody attached to the n-terminus of the heavy chain, or it may comprise for example an IgG scaffold with an affibody attached to the c-terminus of the heavy chain, or it may comprise for example an IgG scaffold with an affibody attached to the n-terminus of the light chain, or it may comprise an IgG scaffold with an affibody attached to the c-terminus of the light chain.

In other embodiments it may comprise a protein scaffold, for example an IgG scaffold, attached to an epitope binding domain which is an affimer, for example an IgG scaffold with an affimer attached to the n-terminus of the heavy chain, or it may comprise for example an IgG scaffold with an affimer attached to the c-terminus of the heavy chain, or it may comprise for example an IgG scaffold with an affimer attached to the n-terminus of the light chain, or it may comprise an IgG scaffold with an affimer attached to the c-terminus of the light chain.

In other embodiments it may comprise a protein scaffold, for example an IgG scaffold, attached to an epitope binding domain which is a GroEI, for example an IgG scaffold with a GroEI attached to the n-terminus of the heavy chain, or it may comprise for example an IgG scaffold with a GroEI attached to the c-terminus of the heavy chain, or it may comprise for example an IgG scaffold with a GroEI attached to the n-terminus of the light chain, or it may comprise an IgG scaffold with a GroEI attached to the c-terminus of the light chain.

In other embodiments it may comprise a protein scaffold, for example an IgG scaffold, attached to an epitope binding domain which is a transferrin, for example an IgG scaffold with a transferrin attached to the n-terminus of the heavy chain, or it may comprise for example an IgG scaffold with a transferrin attached to the c-terminus of the heavy chain, or it may comprise for example an IgG scaffold with a transferrin attached to the n-terminus of the light chain, or it may comprise an IgG scaffold with a transferrin attached to the c-terminus of the light chain.

In other embodiments it may comprise a protein scaffold, for example an IgG scaffold, attached to an epitope binding domain which is a GroES, for example an IgG scaffold with a GroES attached to the n-terminus of the heavy chain, or it may comprise for example an IgG scaffold with a GroES attached to the c-terminus of the heavy chain, or it may comprise for example an IgG scaffold with a GroES attached to the n-terminus of the light chain, or it may comprise an IgG scaffold with a GroES attached to the c-terminus of the light chain.

In other embodiments it may comprise a protein scaffold, for example an IgG scaffold, attached to an epitope binding domain which is a DARPin, for example an IgG scaffold with a DARPin attached to the n-terminus of the heavy chain, or it may comprise for example an IgG scaffold with a DARPin attached to the c-terminus of the heavy chain, or it may comprise for example an IgG scaffold with a DARPin attached to the n-terminus of the light chain, or it may comprise an IgG scaffold with a DARPin attached to the c-terminus of the light chain.

In other embodiments it may comprise a protein scaffold, for example an IgG scaffold, attached to an epitope binding domain which is a peptide aptamer, for example an IgG scaffold with a peptide aptamer attached to the n-terminus of the heavy chain, or it may comprise for example an IgG scaffold with a peptide aptamer attached to the c-terminus of the heavy chain, or it may comprise for example an IgG scaffold with a peptide aptamer attached to the n-terminus of the light chain, or it may comprise an IgG scaffold with a peptide aptamer attached to the c-terminus of the light chain.

In one embodiment of the present invention there are four epitope binding domains, for example four domain antibodies, two of the epitope binding domains may have specificity for the same antigen, or all of the epitope binding domains present in the antigen-binding protein may have specificity for the same antigen.

Protein scaffolds of the present invention are linked to epitope-binding domains by the use of linkers. Examples of suitable linkers include amino acid sequences which may be from 1 amino acid to 150 amino acids in length, or from 1 amino acid to 140 amino acids, for example, from 1 amino acid to 130 amino acids, or from 1 to 120 amino acids, or from 1 to 80 amino acids, or from 1 to 50 amino acids, or from 1 to 20 amino acids, or from 1 to 10 amino acids, or from 5 to 18 amino acids. Such sequences may have their own tertiary structure, for example, a linker of the present invention may comprise a single variable domain. The size of a linker in one embodiment is equivalent to a single variable domain. Suitable linkers may be of a size from 1 to 20 angstroms, for example less than 15 angstroms, or less than 10 angstroms, or less than 5 angstroms.

In one embodiment of the present invention at least one of the epitope binding domains is directly attached to the Ig scaffold with a linker comprising any one of those set out in SEQ ID NO: 51-78, 112-114, or multiples of such linkers.

In another embodiment at least one of the epitope binding domains is directly attached to the Ig scaffold with a linker comprising any one of those set out in SEQ ID NO: 53-60, SEQ ID NO: 62-72, SEQ ID NO: 74, SEQ ID NO: 76-78, SEQ ID NO: 112-114, or multiples of such linkers.

Linkers of use in the antigen-binding proteins of the present invention may comprise alone or in addition to other linkers, one or more sets of GS residues, for example 'GSPAS' or 'PASGS' or 'GSPASGS'.

In one embodiment the epitope binding domain is linked to the Ig scaffold by the linker '$(PAS)_n(GS)_m$'. In another embodiment the epitope binding domain is linked to the Ig scaffold by the linker '$(GGGGS)_p(GS)_m$'. In another embodiment the epitope binding domain is linked to the Ig scaffold by the linker '$(TVAAPS)_p(GS)_m$'. In another embodiment the epitope binding domain is linked to the Ig scaffold by the linker '$(GS)_m(TVAAPSGS)_p$'. In another embodiment the epitope binding domain is linked to the Ig scaffold by the linker '$(PAVPPP)_n(GS)_m$'. In another embodiment the epitope binding domain is linked to the Ig scaffold by the linker '$(TVSDVP)_n(GS)_m$'. In another embodiment the epitope binding domain is linked to the Ig scaffold by the linker '$(TGLDSP)_n(GS)_m$'. In all such embodiments, n=1-10, and m=0-4, and p=2-10.

Examples of such linkers include $(PAS)_n(GS)_m$ wherein n=1 and m=1 (SEQ ID NO: 58), $(PAS)_n(GS)_m$ wherein n=2 and m=1 (SEQ ID NO: 59), $(PAS)_n(GS)_m$ wherein n=3 and m=1 (SEQ ID NO:60), $(PAS)_n(GS)_m$ wherein n=4 and m=1, $(PAS)_n(GS)_m$ wherein n=2 and m=0, $(PAS)_n(GS)_m$ wherein n=3 and m=0, $(PAS)_n(GS)_m$ wherein n=4 and m=0.

Examples of such linkers include $(GGGGS)_p(GS)_m$ wherein p=2 and m=0 (SEQ ID NO: 62), $(GGGGS)_p(GS)_m$ wherein p=3 and m=0 (SEQ ID NO:63), $(GGGGS)_p(GS)_m$ wherein p=4 and m=0.

Examples of such linkers include $(TVAAPS)_p(GS)_m$ wherein p=2 and m=1 (SEQ ID NO: 112), $(TVAAPS)_p(GS)_m$ wherein p=3 and m=1 (SEQ ID NO:113), $(TVAAPS)_p(GS)_m$ wherein p=4 and m=1 (SEQ ID NO:114), $(TVAAPS)_p(GS)_m$ wherein p=2 and m=0, $(TVAAPS)_p(GS)_m$ wherein p=3 and m=0, $(TVAAPS)_p(GS)_m$ wherein p=4 and m=0.

Examples of such linkers include $(GS)_m(TVAAPSGS)_p$ wherein p=2 and m=1 (SEQ ID NO:53), $(GS)_m(TVAAPSGS)_p$ wherein p=3 and m=1 (SEQ ID NO:54), or $(GS)_m(TVAAPSGS)_p$ wherein p=4 and m=1 (SEQ ID NO:55), $(GS)_m(TVAAPSGS)_p$ wherein p=5 and m=1 (SEQ ID NO:56), $(GS)_m(TVAAPSGS)_p$ wherein p=6 and m=1 (SEQ ID NO:57).

Examples of such linkers include $(PAVPPP)_n(GS)_m$ wherein n=1 and m=1 (SEQ ID NO: 64), $(PAVPPP)_n(GS)_m$ wherein n=2 and m=1 (SEQ ID NO: 65), $(PAVPPP)_n(GS)_m$ wherein n=3 and m=1 (SEQ ID NO:66), $(PAVPPP)_n(GS)_m$ wherein n=4 and m=1, $(PAVPPP)_n(GS)_m$ wherein n=2 and m=0, $(PAVPPP)_n(GS)_m$ wherein n=3 and m=0, $(PAVPPP)_n(GS)_m$ wherein n=4 and m=0.

Examples of such linkers include $(TVSDVP)_n(GS)_m$ wherein n=1 and m=1 (SEQ ID NO: 67), $(TVSDVP)_n(GS)_m$ wherein n=2 and m=1 (SEQ ID NO: 68), $(TVSDVP)_n(GS)_m$ wherein n=3 and m=1 (SEQ ID NO:69), $(TVSDVP)_n(GS)_m$ wherein n=4 and m=1, $(TVSDVP)_n(GS)_m$ wherein n=2 and m=0, $(TVSDVP)_n(GS)_m$ wherein n=3 and m=0, $(TVSDVP)_n(GS)_m$ wherein n=4 and m=0.

Examples of such linkers include $(TGLDSP)_n(GS)_m$ wherein n=1 and m=1 (SEQ ID NO: 70), $(TGLDSP)_n(GS)_m$ wherein n=2 and m=1 (SEQ ID NO: 71), $(TGLDSP)_n(GS)_m$ wherein n=3 and m=1 (SEQ ID NO:72), $(TGLDSP)_n(GS)_m$ wherein n=4 and m=1, $(TGLDSP)_n(GS)_m$ wherein n=2 and m=0, $(TGLDSP)_n(GS)_m$ wherein n=3 and m=0, $(TGLDSP)_n(GS)_m$ wherein n=4 and m=0.

In one embodiment, the antigen-binding protein of the present invention comprises at least one epitope binding domain which is capable of binding human serum albumin.

In one embodiment, there are at least 3 antigen binding sites, for example there are 4, or 5 or 6 or 8 or 10 antigen binding sites and the antigen binding protein is capable of binding at least 3 or 4 or 5 or 6 or 8 or 10 antigens, for example it is capable of binding 3 or 4 or 5 or 6 or 8 or 10 antigens simultaneously.

The invention also provides a mAbdAb comprising the heavy chain sequence set out in SEQ ID NO:85 and the light chain sequence set out in SEQ ID NO: 3, or the heavy chain sequence set out in SEQ ID NO:86 and the light chain sequence set out in SEQ ID NO: 3, or the heavy chain sequence set out in SEQ ID NO 2. and the light chain sequence set out in SEQ ID NO: 87, or the heavy chain sequence set out in SEQ ID NO:2. and the light chain sequence set out in SEQ ID NO: 88, or the heavy chain sequence set out in SEQ ID NO:85. and the light chain sequence set out in SEQ ID NO: 87, or the heavy chain sequence set out in SEQ ID NO:85. and the light chain sequence set out in SEQ ID NO: 88, or the heavy chain sequence set out in SEQ ID NO:86. and the light chain sequence set out in SEQ ID NO: 87, or the heavy chain sequence set out in SEQ ID NO:86. and the light chain sequence set out in SEQ ID NO: 88. Any of the linkers used in SEQ ID NO: 85-88 could be replaced with any of the other linkers or combinations of linkers described herein, in particular the 'GS' portion of the linker could be removed.

In one embodiment the present invention provides a method for improving the potency of an epitope binding domain when attached to a protein scaffold, which epitope binding domain has reduced potency when attached directly to a protein scaffold without a linker, compared with its potency as a naked epitope binding domain, i.e. without being linked to any protein scaffold, comprising the step of adding a peptide linker between the protein scaffold and the eptiope binding domain wherein the peptide linker comprises at least 10 amino acids, or wherein the peptide linker is between 10 amino acids and 50 amino acids, or between 10 amino acids and 40 amino acids or between 10 amino acids and 36 amino acids, or between 12 amino acids and 50 amino acids, or between 12 and 40 amino acids, or between 12 and 36 amino acids. In one embodiment the peptide linker comprises one or more repeats of the linker TVAAPS', for example '(TVAAPS)$_p$(GS)$_m$' for example the linker is selected from '(GS)$_m$(TVAAPSGS)$_p$' where m=0-4, and p=2-10, '(PAS)$_n$ (GS)$_m$' wherein n=2-10, and m=0-4, '(GGGGS)$_p$(GS)$_m$' wherein m=0-4 and p=2-10, '(PAVPPP)$_n$(GS)$_m$' wherein n=2-10, and m=0-4, '(TVSDVP)$_n$(GS)$_m$' wherein n=2-10, and m=0-4 and '(TGLDSP)$_n$(GS)$_m$' wherein n=2-10, and m=0-4.

In one embodiment of this method the protein scaffold is an Ig scaffold. The Ig scaffold may comprise an Fc domain of an antibody. In one such embodiment of this method the protein scaffold is an antibody. In another such embodiment of this method the protein scaffold comprises an immunoglobulin heavy chain and an immunoglobulin light chain, wherein the heavy chain comprises CH1-CH2-CH3, and the light chain comprises CL. In yet another such embodiment of this method the protein scaffold is a soluble receptor, i.e. a receptor fused to the Fc domain of an antibody for example the soluble receptor may be selected from Abatacept (marketed as Orencia) which is a fusion protein composed of an immunoglobulin fused to the extracellular domain of CTLA-4, a molecule capable of binding B7; Etanercept (Enbrel) which is a soluble recombinant human p75 tumour necrosis factor TNF receptor (TNFR2) and human IgG1 Fc portion fusion protein produced in a mammalian cell expression system, which is being developed for use in treating rheumatoid arthritis (RA) and other inflammatory conditions; and Atacicept which is a recombinant fusion protein that comprises the receptor portion of the B lymphocyte TACI receptor, which binds to and is activated by the cytokines BlyS and APRIL. The soluble protein comprises the fusion of the extracellular domain of the TACI receptor with the Fc portion of human IgG1. The TACI receptor is a member of the TNF receptor family. Atacicept binds to excess BlyS and APRIL, preventing their binding to B-cells, thereby regulating B-cell maturity and antibody production. It is being developed for the treatment of autoimmune disease.

In one embodiment the epitope binding domain is an immunoglobulin single variable domain, for example a human dAb, or a camelid VHH single variable domain (nanobody). In another embodiment, the epitope binding domain is a non-Ig domain, for example the non-Ig domains described herein.

In one embodiment the method for improving potency of an epitope binding domain in the context of a fusion protein comprises the following steps:
 (i) Determine the original potency of the naked epitope binding domain,
 (ii) Attach binding domain to the protein scaffold for example, an antibody,
 (iii) Determine potency of epitope binding domain whilst attached directly to protein scaffold
 (iv) If potency is lower when attached to a protein scaffold than the original potency then add a peptide linker comprising at least 10 amino acids between the epitope binding domain and the protein scaffold.

In another embodiment the method for improving potency of a human dAb in the context of a fusion protein comprises the following steps:

(i) Determine the original potency of naked human dAb
(ii) Genetically fuse the human dAb to an antibody,
(iii) Determine potency of epitope binding domain whilst attached directly to the protein scaffold
(iv) If potency is lower when attached to a protein scaffold than the original potency then add a peptide linker comprising at least 10 amino acids between the epitope binding domain and the protein scaffold.

The potency of the epitope binding domain can be measured by assays known in the art, for example by assessing the binding affinity i.e. the ability of the epitope binding domain to bind to antigen, which may be assessed by BIAcore™ assays such as those described in Example 7. Alternatively the potency of the epitope binding domain can be measured by a suitable cell-based neutralisation assay for example a TF1 assay which may be carried out for example as described in Example 4.3 or 4.4. The neutralisation of IL-4, IL-13 or both of these cytokines in this assay is measured by assessing the inhibition of TF1 cell proliferation in the presence of neutralising antigen binding protein.

In one embodiment the method described herein is capable of repairing the potency of the epitope binding domain so that the potency when attached to a protein scaffold is within 50% of the original potency as measured by BIAcore or by a suitable cell-based neutralisation assay. In another embodiment the repaired potency is within 40% of the original potency, or within 30% of the original potency or within 20% of the original potency, or within 20% of the original potency, or within 15% of the original potency, or within 10% of the original potency. In another embodiment the binding affinity when attached to a protein scaffold is substantially the same as that of the original binding affinity.

The invention also provides the antigen-binding proteins for use in medicine, for example for use in the manufacture of a medicament for treating cancer or inflammatory diseases such as asthma, rheumatoid arthritis, or osteoarthritis.

The invention provides a method of treating a patient suffering from cancer or inflammatory diseases such as asthma, rheumatoid arthritis, or osteoarthritis, comprising administering a therapeutic amount of an antigen-binding protein of the invention.

The antigen-binding proteins of the invention may be used for the treatment of cancer or inflammatory diseases such as asthma, rheumatoid arthritis, or osteoarthritis.

The antigen-binding proteins of the invention may have some effector function. For example if the protein scaffold contains an Fc region derived from an antibody with effector function, for example if the protein scaffold comprises CH2 and CH3 from IgG1. Levels of effector function can be varied according to known techniques, for example by mutations in the CH2 domain, for example wherein the IgG1 CH2 domain has one or more mutations at positions selected from 239 and 332 and 330, for example the mutations are selected from S239D and I332E and A330L such that the antibody has enhanced effector function, and/or for example altering the glycosylation profile of the antigen-binding protein of the invention such that there is a reduction in fucosylation of the Fc region.

Protein scaffolds of use in the present invention include full monoclonal antibody scaffolds comprising all the domains of an antibody, or protein scaffolds of the present invention may comprise a non-conventional antibody structure, such as a monovalent antibody. Such monovalent antibodies may comprise a paired heavy and light chain wherein the hinge region of the heavy chain is modified so that the heavy chain does not homodimerise, such as the monovalent antibody described in WO2007059782. Other monovalent antibodies may comprise a paired heavy and light chain which dimerises with a second heavy chain which is lacking a functional variable region and CH1 region, wherein the first and second heavy chains are modified so that they will form heterodimers rather than homodimers, resulting in a monovalent antibody with two heavy chains and one light chain such as the monovalent antibody described in WO2006015371. Such monovalent antibodies can provide the protein scaffold of the present invention to which epitope binding domains can be linked.

Epitope-binding domains of use in the present invention are domains that specifically bind an antigen or epitope independently of a different V region or domain, this may be a domain antibody or may be a domain which is a derivative of a scaffold selected from the group consisting of CTLA-4 (Evibody); lipocalin; Protein A derived molecules such as Z-domain of Protein A (Affibody, SpA), A-domain (Avimer/Maxibody); Heat shock proteins such as GroEI and GroES; transferrin (trans-body); ankyrin repeat protein (DARPin); peptide aptamer; C-type lectin domain (Tetranectin); human γ-crystallin and human ubiquitin (affilins); PDZ domains; scorpion toxinkunitz type domains of human protease inhibitors; and fibronectin (adnectin); which has been subjected to protein engineering in order to obtain binding to a ligand other than the natural ligand. In one embodiment this may be an domain antibody or other suitable domains such as a domain selected from the group consisting of CTLA-4, lipocallin, SpA, an Affibody, an avimer, GroEI, transferrin, GroES and fibronectin. In one embodiment this may be selected from an immunoglobulin single variable domain, an Affibody, an ankyrin repeat protein (DARPin) and an adnectin. In another embodiment this may be selected from an Affibody, an ankyrin repeat protein (DARPin) and an adnectin. In another embodiment this may be a domain antibody, for example a domain antibody selected from a human, camelid or shark (NARV) domain antibody.

Epitope-binding domains can be linked to the protein scaffold at one or more positions. These positions include the C-terminus and the N-terminus of the protein scaffold, for example at the C-terminus of the heavy chain and/or the C-terminus of the light chain of an IgG, or for example the N-terminus of the heavy chain and/or the N-terminus of the light chain of an IgG.

In one embodiment, a first epitope binding domain is linked to the protein scaffold and a second epitope binding domain is linked to the first epitope binding domain, for example where the protein scaffold is an IgG scaffold, a first epitope binding domain may be linked to the c-terminus of the heavy chain of the IgG scaffold, and that epitope binding domain can be linked at its c-terminus to a second epitope binding domain, or for example a first epitope binding domain may be linked to the c-terminus of the light chain of the IgG scaffold, and that first epitope binding domain may be further linked at its c-terminus to a second epitope binding domain, or for example a first epitope binding domain may be linked to the n-terminus of the light chain of the IgG scaffold, and that first epitope binding domain may be further linked at its n-terminus to a second epitope binding domain, or for example a first epitope binding domain may be linked to the n-terminus of the heavy chain of the IgG scaffold, and that first epitope binding domain may be further linked at its n-terminus to a second epitope binding domain.

When the epitope-binding domain is a domain antibody, some domain antibodies may be suited to particular positions within the scaffold.

Domain antibodies of use in the present invention can be linked at the C-terminal end of the heavy chain and/or the light chain of conventional IgGs. In addition some immunoglobulin single variable domains can be linked to the C-terminal ends of both the heavy chain and the light chain of conventional antibodies.

In antigen binding proteins where the N-terminus of immunoglobulin single variable domains are fused to an antibody constant domain (either $C_H3$ or CL), a peptide linker may help the immunoglobulin single variable domain to bind to antigen. Indeed, the N-terminal end of an immunoglobulin single variable domain is located closely to the complementarity-determining regions (CDRS) involved in antigen-binding activity. Thus a short peptide linker acts as a spacer between the epitope-binding, and the constant domain of the protein scaffold, which may allow the immunoglobulin single variable domain CDRs to more easily reach the antigen, which may therefore bind with high affinity.

The surroundings in which immunoglobulin single variable domains are linked to the IgG will differ depending on which antibody chain they are fused to:

When fused at the C-terminal end of the antibody light chain of an IgG scaffold, each immunoglobulin single variable domain is expected to be located in the vicinity of the antibody hinge and the Fc portion. It is likely that such immunoglobulin single variable domains will be located far apart from each other. In conventional antibodies, the angle between Fab fragments and the angle between each Fab fragment and the Fc portion can vary quite significantly. It is likely that—with mAbdAbs—the angle between the Fab fragments will not be widely different, whilst some angular restrictions may be observed with the angle between each Fab fragment and the Fc portion.

When fused at the C-terminal end of the antibody heavy chain of an IgG scaffold, each immunoglobulin single variable domain is expected to be located in the vicinity of the $C_H3$ domains of the Fc portion. This is not expected to impact on the Fc binding properties to Fc receptors (e.g. FcγRI, II, III an FcRn) as these receptors engage with the $C_H2$ domains (for the FcγRI, II and III class of receptors) or with the hinge between the $C_H2$ and $C_H3$ domains (e.g. FcRn receptor). Another feature of such antigen-binding proteins is that both immunoglobulin single variable domains are expected to be spatially close to each other and provided that flexibility is provided by provision of appropriate linkers, these immunoglobulin single variable domains may even form homodimeric species, hence propagating the 'zipped' quaternary structure of the Fc portion, which may enhance stability of the antigen binding protein.

Such structural considerations can aid in the choice of the most suitable position to link an epitope-binding domain, for example an immunoglobulin single variable domain, on to a protein scaffold, for example an antibody.

The size of the antigen, its localization (in blood or on cell surface), its quaternary structure (monomeric or multimeric) can vary. Conventional antibodies are naturally designed to function as adaptor constructs due to the presence of the hinge region, wherein the orientation of the two antigen-binding sites at the tip of the Fab fragments can vary widely and hence adapt to the molecular feature of the antigen and its surroundings. In contrast immunoglobulin single variable domains linked to an antibody or other protein scaffold, for example a protein scaffold which comprises an antibody with no hinge region, may have less structural flexibility either directly or indirectly.

Understanding the solution state and mode of binding at the immunoglobulin single variable domain is also helpful. Evidence has accumulated that in vitro dAbs can predominantly exist in monomeric, homo-dimeric or multimeric forms in solution (Reiter et al. (1999) J Mol Biol 290 p 685-698; Ewert et al (2003) J Mol Biol 325, p 531-553, Jespers et al (2004) J Mol Biol 337 p 893-903; Jespers et al (2004) Nat Biotechnol 22 p 1161-1165; Martin et al (1997) Protein Eng. 10 p 607-614; Sepulvada et al (2003) J Mol Biol 333 p 355-365). This is fairly reminiscent to multimerisation events observed in vivo with Ig domains such as Bence-Jones proteins (which are dimers of immunoglobulin light chains (Epp et al (1975) Biochemistry 14 p 4943-4952; Huan et al (1994) Biochemistry 33 p 14848-14857; Huang et al (1997) Mol immunol 34 p 1291-1301) and amyloid fibers (James et al. (2007) *J Mol Biol.* 367:603-8).

For example, it may be desirable to link dAbs that tend to dimerise in solution to the C-terminal end of the Fc portion in preference to the C-terminal end of the light chain as linking to the C-terminal end of the Fc will allow those dAbs to dimerise in the context of the antigen-binding protein of the invention.

The antigen-binding proteins of the present invention may comprise antigen-binding sites specific for a single antigen, or may have antigen-binding sites specific for two or more antigens, or for two or more epitopes on a single antigen, or there may be antigen-binding sites each of which is specific for a different epitope on the same or different antigens.

The antigen-binding sites can each have binding specificity for an antigen, such as human or animal proteins, including cytokines, growth factors, cytokine receptors, growth factor receptors, enzymes (e.g., proteases), co-factors for enzymes, DNA binding proteins, lipids and carbohydrates. Suitable targets, including cytokines, growth factors, cytokine receptors, growth factor receptors and other proteins include but are not limited to: ApoE, Apo-SAA, BDNF, Cardiotrophin-1, CEA, CD40, CD40 Ligand, CD56, CD38, CD138, EGF, EGF receptor, ENA-78, Eotaxin, Eotaxin-2, Exodus-2, FAPα, FGF-acidic, FGF-basic, fibroblast growth factor-10, FLT3 ligand, Fractalkine (CX3C), GDNF, G-CSF, GM-CSF, GF-β1, human serum albumin, insulin, IFN-γ, IGF-I, IGF-II, IL-1α, IL-1β, IL-1 receptor, IL-1 receptor type 1, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, c-fms, v-fmsMDC (67 a.a.), MDC (69 a.a.), MCP-1 (MCAF), MCP-2, MCP-3, MCP-4, MDC (67 a.a.), MDC (69 a.a.), MIG, MIP-1α, MIP-1β, MIP-3α, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1α, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF A, VEGF B, VEGF C, VEGF D, VEGF receptor 1, VEGF receptor 2, VEGF receptor 3, GCP-2, GRO/MGSA, GRO-β, GRO-γ, HCC1, 1-309, HER 1, HER 2, HER 3, HER 4, serum albumin, vWF, amyloid proteins (e.g., amyloid alpha), MMP12, PDK1, IgE, and other targets disclosed herein. It will be appreciated that this list is by no means exhaustive.

In some embodiments, the protease resistant peptide or polypeptide binds a target in pulmonary tissue, such as a target selected from the group consisting of TNFR1, IL-1, IL-1R, IL-4, IL-4R, IL-5, IL-6, IL-6R, IL-8, IL-8R, IL-9, IL-9R, IL-10, IL-12 IL-12R, IL-13, IL-13Rα1, IL-13Rα2, IL-15, IL-15R, IL-16, IL-17R, IL-17, IL-18, IL-18R, IL-23 IL-23R, IL-25, CD2, CD4, CD11a, CD23, CD25, CD27, CD28, CD30, CD40, CD40L, CD56, CD138, ALK5, EGFR, FcER1, TGFb, CCL2, CCL18, CEA, CR8, CTGF, CXCL12 (SDF-1), chymase, FGF, Furin, Endothelin-1, Eotaxins (e.g., Eotaxin, Eotaxin-2, Eotaxin-3), GM-CSF, ICAM-1, ICOS, IgE, IFNa, I-309, integrins, L-selectin, MIF, MIP4, MDC, MCP-1, MMPs, neutrophil elastase, osteopontin, OX-40, PARC, PD-1, RANTES, SCF, SDF-1, siglec8, TARC, TGFb, Thrombin, Tim-1, TNF, TRANCE, Tryptase, VEGF, VLA-4, VCAM, α4β7, CCR2, CCR3, CCR4, CCR5, CCR7, CCR8, alphavbeta6, alphavbeta8, cMET, CD8, vWF, amyloid proteins (e.g., amyloid alpha), MMP12, PDK1, and IgE.

In particular, the antigen-binding proteins of the present invention may be useful in treating diseases associated with IL-13, IL-5 and IL-4, for example atopic dermatitis, allergic rhinitis, crohn's disease, COPD, fibrotic diseases or disorders such as idiopathic pulmonary fibrosis, progressive systemic sclerosis, hepatic fibrosis, hepatic granulomas, schistosomiasis, leishmaniasis, diseases of cell cycle regulation such as Hodgkins disease, B cell chronic lymphocytic leukaemia, for example the proteins may be useful in treating asthma.

Antigen-binding proteins of the present invention may be useful in treating diseases associated with growth factors such as IGF-1R, VEGF, and EGFR, for example cancer or rheumatoid arthritis, examples of types of cancer in which such therapies may be useful are breast cancer, prostrate cancer, lung cancer and myeloma.

Antigen-binding proteins of the present invention may be useful in treating diseases associated with TNF, for example arthritis, for example rheumatoid arthritis or osteoarthritis.

Antigen-binding proteins of the present invention may be useful in treating diseases associated with IL1-R, for example arthritis, for example rheumatoid arthritis or osteoarthritis.

Antigen-binding proteins of the present invention may be useful in treating diseases associated with CD-20, for example autoimmune diseases such as psoriasis, inflammatory bowel disease, ulcerative colitis, crohns disease, rheumatoid arthritis, juvenile rheumatoid arthritis, systemic lupus erythematosus, neurodegenerative diseases, for example multiple sclerosis, neutrophil driven diseases, for example COPD, Wegeners vasculitis, cystic fibrosis, Sjogrens syndrome, chronic transplant rejection, type 1 diabetes graft versus host disease, asthma, allergic diseases atoptic dermatitis, eczematous dermatitis, allergic rhinitis, autoimmune diseases other including thyroiditis, spondyloarthropathy, ankylosing spondylitis, uveitis, polychonritis or scleroderma, or cancer e.g. B-cell lymphomas or mature B cell neoplasm such as CLL or SLL.

Antigen-binding proteins of the present invention may be useful in treating diseases associated with IL-17 and IL-23, for example psoriasis, inflammatory bowel disease, ulcerative colitis, crohns disease, rheumatoid arthritis, juvenile rheumatoid arthritis, systemic lupus erythematosus, neurodegenerative diseases, for example multiple sclerosis, neutrophil driven diseases, for example COPD, Wegeners vasculitis, cystic fibrosis, Sjogrens syndrome, chronic transplant rejection, type 1 diabetes graft versus host disease, asthma, allergic diseases atoptic dermatitis, eczematous dermatitis, allergic rhinitis, autoimmune diseases other including thyroiditis, spondyloarthropathy, ankylosing spondylitis, uveitis, polychonritis or scleroderma.

The antigen binding proteins of the present invention may be produced by transfection of a host cell with an expression vector comprising the coding sequence for the antigen binding protein of the invention. An expression vector or recombinant plasmid is produced by placing these coding sequences for the antigen binding protein in operative association with conventional regulatory control sequences capable of controlling the replication and expression in, and/or secretion from, a host cell. Regulatory sequences include promoter sequences, e.g., CMV promoter, and signal sequences which can be derived from other known antibodies. Similarly, a second expression vector can be produced having a DNA sequence which encodes a complementary antigen binding protein light or heavy chain. In certain embodiments this second expression vector is identical to the first except insofar as the coding sequences and selectable markers are concerned, so to ensure as far as possible that each polypeptide chain is functionally expressed. Alternatively, the heavy and light chain coding sequences for the antigen binding protein may reside on a single vector, for example in two expression cassettes in the same vector.

A selected host cell is co-transfected by conventional techniques with both the first and second vectors (or simply transfected by a single vector) to create the transfected host cell of the invention comprising both the recombinant or synthetic light and heavy chains. The transfected cell is then cultured by conventional techniques to produce the engineered antigen binding protein of the invention. The antigen binding protein which includes the association of both the recombinant heavy chain and/or light chain is screened from culture by appropriate assay, such as ELISA or RIA. Similar conventional techniques may be employed to construct other antigen binding proteins.

Suitable vectors for the cloning and subcloning steps employed in the methods and construction of the compositions of this invention may be selected by one of skill in the art. For example, the conventional pUC series of cloning vectors may be used. One vector, pUC19, is commercially available from supply houses, such as Amersham (Buckinghamshire, United Kingdom) or Pharmacia (Uppsala, Sweden). Additionally, any vector which is capable of replicating readily, has an abundance of cloning sites and selectable genes (e.g., antibiotic resistance), and is easily manipulated may be used for cloning. Thus, the selection of the cloning vector is not a limiting factor in this invention.

The expression vectors may also be characterized by genes suitable for amplifying expression of the heterologous DNA sequences, e.g., the mammalian dihydrofolate reductase gene (DHFR). Other vector sequences include a poly A signal sequence, such as from bovine growth hormone (BGH) and the betaglobin promoter sequence (betaglopro). The expression vectors useful herein may be synthesized by techniques well known to those skilled in this art.

The components of such vectors, e.g. replicons, selection genes, enhancers, promoters, signal sequences and the like, may be obtained from commercial or natural sources or synthesized by known procedures for use in directing the expression and/or secretion of the product of the recombinant DNA in a selected host. Other appropriate expression vectors of which numerous types are known in the art for mammalian, bacterial, insect, yeast, and fungal expression may also be selected for this purpose.

The present invention also encompasses a cell line transfected with a recombinant plasmid containing the coding sequences of the antigen binding proteins of the present invention. Host cells useful for the cloning and other manipulations of these cloning vectors are also conventional. However, cells from various strains of *E. coli* may be used for replication of the cloning vectors and other steps in the construction of antigen binding proteins of this invention.

Suitable host cells or cell lines for the expression of the antigen binding proteins of the invention include mammalian cells such as NS0, Sp2/0, CHO (e.g. DG44), COS, HEK, a fibroblast cell (e.g., 3T3), and myeloma cells, for example it may be expressed in a CHO or a myeloma cell. Human cells may be used, thus enabling the molecule to be modified with human glycosylation patterns. Alternatively, other eukaryotic cell lines may be employed. The selection of suitable mammalian host cells and methods for transformation, culture, amplification, screening and product production and purification are known in the art. See, e.g., Sambrook et al., cited above.

Bacterial cells may prove useful as host cells suitable for the expression of the recombinant Fabs or other embodiments of the present invention (see, e.g., Plückthun, A., Immunol. Rev., 130:151-188 (1992)). However, due to the tendency of proteins expressed in bacterial cells to be in an unfolded or improperly folded form or in a non-glycosylated form, any recombinant Fab produced in a bacterial cell would have to be screened for retention of antigen binding ability. If the molecule expressed by the bacterial cell was produced in a properly folded form, that bacterial cell would be a desirable host, or in alternative embodiments the molecule may express in the bacterial host and then be subsequently re-folded. For example, various strains of *E. coli* used for expression are well-known as host cells in the field of biotechnology. Various strains of *B. subtilis, Streptomyces*, other bacilli and the like may also be employed in this method.

Where desired, strains of yeast cells known to those skilled in the art are also available as host cells, as well as insect cells, e.g. *Drosophila* and *Lepidoptera* and viral expression systems. See, e.g. Miller et al., Genetic Engineering, 8:277-298, Plenum Press (1986) and references cited therein.

The general methods by which the vectors may be constructed, the transfection methods required to produce the host cells of the invention, and culture methods necessary to produce the antigen binding protein of the invention from such host cell may all be conventional techniques. Typically, the culture method of the present invention is a serum-free culture method, usually by culturing cells serum-free in suspension. Likewise, once produced, the antigen binding proteins of the invention may be purified from the cell culture contents according to standard procedures of the art, including ammonium sulfate precipitation, affinity columns, column chromatography, gel electrophoresis and the like. Such techniques are within the skill of the art and do not limit this invention. For example, preparation of altered antibodies are described in WO 99/58679 and WO 96/16990.

Yet another method of expression of the antigen binding proteins may utilize expression in a transgenic animal, such as described in U.S. Pat. No. 4,873,316. This relates to an expression system using the animal's casein promoter which when transgenically incorporated into a mammal permits the female to produce the desired recombinant protein in its milk.

In a further aspect of the invention there is provided a method of producing an antibody of the invention which method comprises the step of culturing a host cell transformed or transfected with a vector encoding the light and/or heavy chain of the antibody of the invention and recovering the antibody thereby produced.

In accordance with the present invention there is provided a method of producing an antigen binding protein of the present invention which method comprises the steps of;
 (a) providing a first vector encoding a heavy chain of the antigen binding protein,
 (b) providing a second vector encoding a light chain of the antigen binding protein,
 (c) transforming a mammalian host cell (e.g. CHO) with said first and second vectors;
 (d) culturing the host cell of step (c) under conditions conducive to the secretion of the antigen binding protein from said host cell into said culture media;
 (e) recovering the secreted antigen binding protein of step (d).

Once expressed by the desired method, the antigen binding protein is then examined for in vitro activity by use of an appropriate assay. Presently conventional ELISA assay formats are employed to assess qualitative and quantitative binding of the antigen binding protein to its target. Additionally, other in vitro assays may also be used to verify neutralizing efficacy prior to subsequent human clinical studies performed to evaluate the persistence of the antigen binding protein in the body despite the usual clearance mechanisms.

The dose and duration of treatment relates to the relative duration of the molecules of the present invention in the human circulation, and can be adjusted by one of skill in the art depending upon the condition being treated and the general health of the patient. It is envisaged that repeated dosing (e.g. once a week or once every two weeks) over an extended time period (e.g. four to six months) may be required to achieve maximal therapeutic efficacy.

The mode of administration of the therapeutic agent of the invention may be any suitable route which delivers the agent to the host. The antigen binding proteins, and pharmaceutical compositions of the invention are particularly useful for parenteral administration, i.e., subcutaneously (s.c.), intrathecally, intraperitoneally, intramuscularly (i.m.), intravenously (i.v.), or intranasally.

Therapeutic agents of the invention may be prepared as pharmaceutical compositions containing an effective amount of the antigen binding protein of the invention as an active ingredient in a pharmaceutically acceptable carrier. In the prophylactic agent of the invention, an aqueous suspension or solution containing the antigen binding protein, may be buffered at physiological pH, in a form ready for injection. The compositions for parenteral administration will commonly comprise a solution of the antigen binding protein of the invention or a cocktail thereof dissolved in a pharmaceutically acceptable carrier, for example an aqueous carrier. A variety of aqueous carriers may be employed, e.g., 0.9% saline, 0.3% glycine, and the like. These solutions may be made sterile and generally free of particulate matter. These solutions may be sterilized by conventional, well known sterilization techniques (e.g., filtration). The compositions may contain pharmaceutically acceptable auxiliary substances as required to approximate physiological conditions such as pH adjusting and buffering agents, etc. The concentration of the antigen binding protein of the invention in such pharmaceutical formulation can vary widely, i.e., from less than about 0.5%, usually at or at least about 1% to as much as 15 or 20% by weight and will be selected primarily based on fluid volumes, viscosities, etc., according to the particular mode of administration selected.

Thus, a pharmaceutical composition of the invention for intramuscular injection could be prepared to contain 1 mL sterile buffered water, and between about 1 ng to about 100 mg, e.g. about 50 ng to about 30 mg, or about 5 mg to about 25 mg, of an antigen binding protein of the invention. Similarly, a pharmaceutical composition of the invention for intravenous infusion could be made up to contain about 250 ml of sterile Ringer's solution, and about 1 to about 30 or about 5 mg to about 25 mg of an antigen binding protein of the invention per ml of Ringer's solution. Actual methods for preparing parenterally administrable compositions are well known or will be apparent to those skilled in the art and are described in more detail in, for example, Remington's Pharmaceutical Science, 15th ed., Mack Publishing Company, Easton, Pa. For the preparation of intravenously administrable antigen binding protein formulations of the invention see Lasmar U and Parkins D "The formulation of Biopharmaceutical products", Pharma. Sci. Tech. today, page 129-137, Vol. 3 (3 Apr. 2000), Wang, W "Instability, stabilisation and formulation of liquid protein pharmaceuticals", Int. J. Pharm 185 (1999) 129-188, Stability of Protein Pharmaceuticals Part A and B ed Ahern T. J., Manning M. C., New York, N.Y.: Plenum Press (1992), Akers, M. J. "Excipient-Drug interactions in renteral Formulations", J. Pharm Sci 91 (2002) 2283-2300, Imamura, K et al "Effects of types of sugar on stabilization of Protein in the dried state", J Pharm Sci 92 (2003) 266-274, Izutsu, Kkojima, S. "Excipient crystallinity and its protein-structure-stabilizing effect during freeze-drying", J. Pharm. Pharmacol, 54 (2002) 1033-1039, Johnson, R, "Mannitol-sucrose mixtures-versatile formulations for protein lyophilization", J. Pharm. Sci, 91 (2002) 914-922.

Ha, E Wang W, Wang Y. j. "Peroxide formation in polysorbate 80 and protein stability", J. Pharm Sci, 91, 2252-2264, (2002) the entire contents of which are incorporated herein by reference and to which the reader is specifically referred.

In one embodiment the therapeutic agent of the invention, when in a pharmaceutical preparation, is present in unit dose forms. The appropriate therapeutically effective dose will be determined readily by those of skill in the art. Suitable doses may be calculated for patients according to their weight, for example suitable doses may be in the range of 0.01 to 20 mg/kg, for example 0.1 to 20 mg/kg, for example 1 to 20 mg/kg, for example 10 to 20 mg/kg or for example 1 to 15 mg/kg, for example 10 to 15 mg/kg. To effectively treat conditions of use in the present invention in a human, suitable doses may be within the range of 0.01 to 1000 mg, for example 0.1 to 1000 mg, for example 0.1 to 500 mg, for example 500 mg, for example 0.1 to 100 mg, or 0.1 to 80 mg, or 0.1 to 60 mg, or 0.1 to 40 mg, or for example 1 to 100 mg, or 1 to 50 mg, of an antigen binding protein of this invention, which may be administered parenterally, for example subcutaneously, intravenously or intramuscularly. Such dose may, if necessary, be repeated at appropriate time intervals selected as appropriate by a physician.

The antigen binding proteins described herein can be lyophilized for storage and reconstituted in a suitable carrier prior to use. This technique has been shown to be effective with conventional immunoglobulins and art-known lyophilization and reconstitution techniques can be employed.

There are several methods known in the art which can be used to find epitope-binding domains of use in the present invention.

The term "library" refers to a mixture of heterogeneous polypeptides or nucleic acids. The library is composed of members, each of which has a single polypeptide or nucleic acid sequence. To this extent, "library" is synonymous with "repertoire." Sequence differences between library members are responsible for the diversity present in the library. The library may take the form of a simple mixture of polypeptides or nucleic acids, or may be in the form of organisms or cells, for example bacteria, viruses, animal or plant cells and the like, transformed with a library of nucleic acids. In one example, each individual organism or cell contains only one or a limited number of library members. Advantageously, the nucleic acids are incorporated into expression vectors, in order to allow expression of the polypeptides encoded by the nucleic acids. In a one aspect, therefore, a library may take the form of a population of host organisms, each organism containing one or more copies of an expression vector containing a single member of the library in nucleic acid form which can be expressed to produce its corresponding polypeptide member. Thus, the population of host organisms has the potential to encode a large repertoire of diverse polypeptides.

A "universal framework" is a single antibody framework sequence corresponding to the regions of an antibody conserved in sequence as defined by Kabat ("Sequences of Proteins of Immunological Interest", US Department of Health and Human Services) or corresponding to the human germline immunoglobulin repertoire or structure as defined by Chothia and Lesk, (1987) J. Mol. Biol. 196:910-917. There may be a single framework, or a set of such frameworks, which has been found to permit the derivation of virtually any binding specificity though variation in the hypervariable regions alone.

Amino acid and nucleotide sequence alignments and homology, similarity or identity, as defined herein are in one embodiment prepared and determined using the algorithm BLAST 2 Sequences, using default parameters (Tatusova, T. A. et al., *FEMS Microbiol Lett,* 174:187-188 (1999)).

The epitope binding domain(s) and antigen binding sites can each have binding specificity for a generic ligand or any desired target ligand, such as human or animal proteins, including cytokines, growth factors, cytokine receptors, growth factor receptors, enzymes (e.g., proteases), co-factors for enzymes, DNA binding proteins, lipids and carbohydrates. Suitable targets, including cytokines, growth factors, cytokine receptors, growth factor receptors and other proteins include but are not limited to: ApoE, Apo-SAA, BDNF, Cardiotrophin-1, CEA, CD40, CD40 Ligand, CD56, CD38, CD138, EGF, EGF receptor, ENA-78, Eotaxin, Eotaxin-2, Exodus-2, FAPα, FGF-acidic, FGF-basic, fibroblast growth factor-10, FLT3 ligand, Fractalkine (CX3C), GDNF, G-CSF, GM-CSF, GF-β1, human serum albumin, insulin, IFN-γ, IGF-I, IGF-II, IL-1α, IL-1β, IL-1 receptor, IL-1 receptor type 1, IL-2, IL-3, IL-4, IL-5, IL-6, IL-7, IL-8 (72 a.a.), IL-8 (77 a.a.), IL-9, IL-10, IL-11, IL-12, IL-13, IL-15, IL-16, IL-17, IL-18 (IGIF), Inhibin α, Inhibin β, IP-10, keratinocyte growth factor-2 (KGF-2), KGF, Leptin, LIF, Lymphotactin, Mullerian inhibitory substance, monocyte colony inhibitory factor, monocyte attractant protein, M-CSF, c-fms, v-fmsMDC (67 a.a.), MDC (69 a.a.), MCP-1 (MCAF), MCP-2, MCP-3, MCP-4, MDC (67 a.a.), MDC (69 a.a.), MIG, MIP-1a, MIP-1β, MIP-3a, MIP-3β, MIP-4, myeloid progenitor inhibitor factor-1 (MPIF-1), NAP-2, Neurturin, Nerve growth factor, β-NGF, NT-3, NT-4, Oncostatin M, PDGF-AA, PDGF-AB, PDGF-BB, PF-4, RANTES, SDF1a, SDF1β, SCF, SCGF, stem cell factor (SCF), TARC, TGF-α, TGF-β, TGF-β2, TGF-β3, tumour necrosis factor (TNF), TNF-α, TNF-β, TNF receptor I, TNF receptor II, TNIL-1, TPO, VEGF, VEGF A, VEGF B, VEGF C, VEGF D, VEGF receptor 1, VEGF receptor 2, VEGF receptor 3, GCP-2, GRO/MGSA, GRO-β, GRO-γ, HCC1, 1-309, HER 1, HER 2, HER 3, HER 4, serum albumin, vWF, amyloid proteins (e.g., amyloid alpha), MMP12, PDK1, IgE, and other targets disclosed herein. It will be appreciated that this list is by no means exhaustive.

In some embodiments, binding is to a target in pulmonary tissue, such as a target selected from the group consisting of TNFR1, IL-1, IL-1R, IL-4, IL-4R, IL-5, IL-6, IL-6R, IL-8, IL-8R, IL-9, IL-9R, IL-10, IL-12 IL-12R, IL-13, IL-13Rα1, IL-13Ra2, IL-15, IL-15R, IL-16, IL-17R, IL-17, IL-18, IL-18R, IL-23 IL-23R, IL-25, CD2, CD4, CD11a, CD23, CD25, CD27, CD28, CD30, CD40, CD40L, CD56, CD138, ALK5, EGFR, FcER1, TGFb, CCL2, CCL18, CEA, CR8, CTGF, CXCL12 (SDF-1), chymase, FGF, Furin, Endothelin-1, Eotaxins (e.g., Eotaxin, Eotaxin-2, Eotaxin-3), GM-CSF, ICAM-1, ICOS, IgE, IFNa, I-309, integrins, L-selectin, MIF, MIP4, MDC, MCP-1, MMPs, neutrophil elastase, osteopontin, OX-40, PARC, PD-1, RANTES, SCF, SDF-1, siglec8, TARC, TGFb, Thrombin, Tim-1, TNF, TRANCE, Tryptase, VEGF, VLA-4, VCAM, α4β7, CCR2, CCR3, CCR4, CCR5, CCR7, CCR8, alphavbeta6, alphavbeta8, cMET, CD8, vWF, amyloid proteins (e.g., amyloid alpha), MMP12, PDK1, and IgE.

When a display system (e.g., a display system that links coding function of a nucleic acid and functional characteristics of the peptide or polypeptide encoded by the nucleic acid) is used in the methods described herein, eg in the selection of a dAb or other epitope binding domain, it is frequently advantageous to amplify or increase the copy number of the nucleic acids that encode the selected peptides or polypeptides. This provides an efficient way of obtaining sufficient quantities of nucleic acids and/or peptides or polypeptides for additional rounds of selection, using the methods described herein or other suitable methods, or for preparing additional repertoires (e.g., affinity maturation repertoires). Thus, in some embodiments, the methods of selecting epitope binding domains comprises using a display system (e.g., that links coding function of a nucleic acid and functional characteristics of the peptide or polypeptide encoded by the nucleic acid, such as phage display) and further comprises amplifying or increasing the copy number of a nucleic acid that encodes a selected peptide or polypeptide. Nucleic acids can be amplified using any suitable methods, such as by phage amplification, cell growth or polymerase chain reaction.

In one example, the methods employ a display system that links the coding function of a nucleic acid and physical, chemical and/or functional characteristics of the polypeptide encoded by the nucleic acid. Such a display system can comprise a plurality of replicable genetic packages, such as bacteriophage or cells (bacteria). The display system may comprise a library, such as a bacteriophage display library. Bacteriophage display is an example of a display system.

A number of suitable bacteriophage display systems (e.g., monovalent display and multivalent display systems) have been described. (See, e.g., Griffiths et al., U.S. Pat. No. 6,555, 313 B1 (incorporated herein by reference); Johnson et al., U.S. Pat. No. 5,733,743 (incorporated herein by reference); McCafferty et al., U.S. Pat. No. 5,969,108 (incorporated herein by reference); Mulligan-Kehoe, U.S. Pat. No. 5,702, 892 (Incorporated herein by reference); Winter, G. et al., *Annu. Rev. Immunol.* 12:433-455 (1994); Soumillion, P. et al., *Appl. Biochem. Biotechnol.* 47(2-3):175-189 (1994); Castagnoli, L. et al., *Comb. Chem. High Throughput Screen,* 4(2): 121-133 (2001).) The peptides or polypeptides displayed in a bacteriophage display system can be displayed on any suitable bacteriophage, such as a filamentous phage (e.g., fd, M13, F1), a lytic phage (e.g., T4, T7, lambda), or an RNA phage (e.g., MS2), for example.

Generally, a library of phage that displays a repertoire of peptides or phagepolypeptides, as fusion proteins with a suitable phage coat protein (e.g., fd pIII protein), is produced or provided. The fusion protein can display the peptides or polypeptides at the tip of the phage coat protein, or if desired at an internal position. For example, the displayed peptide or polypeptide can be present at a position that is amino-terminal to domain 1 of pIII. (Domain 1 of pIII is also referred to as N1.) The displayed polypeptide can be directly fused to pIII (e.g., the N-terminus of domain 1 of pIII) or fused to pIII using a linker. If desired, the fusion can further comprise a tag (e.g., myc epitope, His tag). Libraries that comprise a repertoire of peptides or polypeptides that are displayed as fusion proteins with a phage coat protein, can be produced using any suitable methods, such as by introducing a library of phage vectors or phagemid vectors encoding the displayed peptides or polypeptides into suitable host bacteria, and culturing the resulting bacteria to produce phage (e.g., using a suitable helper phage or complementing plasmid if desired). The library of phage can be recovered from the culture using any suitable method, such as precipitation and centrifugation.

The display system can comprise a repertoire of peptides or polypeptides that contains any desired amount of diversity. For example, the repertoire can contain peptides or polypeptides that have amino acid sequences that correspond to naturally occurring polypeptides expressed by an organism, group of organisms, desired tissue or desired cell type, or can contain peptides or polypeptides that have random or randomized amino acid sequences. If desired, the polypeptides can share a common core or scaffold. For example, all polypeptides in the repertoire or library can be based on a scaffold selected from protein A, protein L, protein G, a fibronectin domain, an anticalin, CTLA4, a desired enzyme (e.g., a polymerase, a cellulase), or a polypeptide from the immunoglobulin superfamily, such as an antibody or antibody fragment (e.g., an antibody variable domain). The polypeptides in such a repertoire or library can comprise defined regions of random or randomized amino acid sequence and regions of common amino acid sequence. In certain embodiments, all or substantially all polypeptides in a repertoire are of a desired type, such as a desired enzyme (e.g., a polymerase) or a desired antigen-binding fragment of an antibody (e.g., human $V_H$ or human $V_L$). In some embodiments, the polypeptide display system comprises a repertoire of polypeptides wherein each polypeptide comprises an antibody variable domain. For example, each polypeptide in the repertoire can contain a $V_H$, a $V_L$ or an Fv (e.g., a single chain Fv).

Amino acid sequence diversity can be introduced into any desired region of a peptide or polypeptide or scaffold using any suitable method. For example, amino acid sequence diversity can be introduced into a target region, such as a complementarity determining region of an antibody variable domain or a hydrophobic domain, by preparing a library of nucleic acids that encode the diversified polypeptides using any suitable mutagenesis methods (e.g., low fidelity PCR, oligonucleotide-mediated or site directed mutagenesis, diversification using NNK codons) or any other suitable method. If desired, a region of a polypeptide to be diversified can be randomized. The size of the polypeptides that make up the repertoire is largely a matter of choice and uniform polypeptide size is not required. The polypeptides in the repertoire may have at least tertiary structure (form at least one domain).

Selection/Isolation/Recovery

An epitope binding domain or population of domains can be selected, isolated and/or recovered from a repertoire or library (e.g., in a display system) using any suitable method. For example, a domain is selected or isolated based on a selectable characteristic (e.g., physical characteristic, chemical characteristic, functional characteristic). Suitable selectable functional characteristics include biological activities of the peptides or polypeptides in the repertoire, for example, binding to a generic ligand (e.g., a superantigen), binding to a target ligand (e.g., an antigen, an epitope, a substrate), binding to an antibody (e.g., through an epitope expressed on a peptide or polypeptide), and catalytic activity. (See, e.g., Tomlinson et al., WO 99/20749; WO 01/57065; WO 99/58655.)

In some embodiments, the protease resistant peptide or polypeptide is selected and/or isolated from a library or repertoire of peptides or polypeptides in which substantially all domains share a common selectable feature. For example, the domain can be selected from a library or repertoire in which substantially all domains bind a common generic ligand, bind a common target ligand, bind (or are bound by) a common antibody, or possess a common catalytic activity. This type of selection is particularly useful for preparing a repertoire of domains that are based on a parental peptide or polypeptide that has a desired biological activity, for example, when performing affinity maturation of an immunoglobulin single variable domain.

Selection based on binding to a common generic ligand can yield a collection or population of domains that contain all or substantially all of the domains that were components of the original library or repertoire. For example, domains that bind a target ligand or a generic ligand, such as protein A, protein L or an antibody, can be selected, isolated and/or recovered by panning or using a suitable affinity matrix. Panning can be accomplished by adding a solution of ligand (e.g., generic ligand, target ligand) to a suitable vessel (e.g., tube, petri dish) and allowing the ligand to become deposited or coated onto the walls of the vessel. Excess ligand can be washed away and domains can be added to the vessel and the vessel maintained under conditions suitable for peptides or polypeptides to bind the immobilized ligand. Unbound domains can be washed away and bound domains can be recovered using any suitable method, such as scraping or lowering the pH, for example.

Suitable ligand affinity matrices generally contain a solid support or bead (e.g., agarose) to which a ligand is covalently or noncovalently attached. The affinity matrix can be combined with peptides or polypeptides (e.g., a repertoire that has been incubated with protease) using a batch process, a column process or any other suitable process under conditions suitable for binding of domains to the ligand on the matrix. domains that do not bind the affinity matrix can be washed away and bound domains can be eluted and recovered using any suitable method, such as elution with a lower pH buffer, with a mild denaturing agent (e.g., urea), or with a peptide or domain that competes for binding to the ligand. In one example, a biotinylated target ligand is combined with a repertoire under conditions suitable for domains in the repertoire to bind the target ligand. Bound domains are recovered using immobilized avidin or streptavidin (e.g., on a bead).

In some embodiments, the generic or target ligand is an antibody or antigen binding fragment thereof. Antibodies or antigen binding fragments that bind structural features of peptides or polypeptides that are substantially conserved in the peptides or polypeptides of a library or repertoire are particularly useful as generic ligands. Antibodies and antigen binding fragments suitable for use as ligands for isolating, selecting and/or recovering protease resistant peptides or polypeptides can be monoclonal or polyclonal and can be prepared using any suitable method.

Libraries/Repertoires

Libraries that encode and/or contain protease epitope binding domains can be prepared or obtained using any suitable method. A library can be designed to encode domains based on a domain or scaffold of interest (e.g., a domain selected from a library) or can be selected from another library using the methods described herein. For example, a library enriched in domains can be prepared using a suitable polypeptide display system.

Libraries that encode a repertoire of a desired type of domain can readily be produced using any suitable method. For example, a nucleic acid sequence that encodes a desired type of polypeptide (e.g., an immunoglobulin variable domain) can be obtained and a collection of nucleic acids that each contain one or more mutations can be prepared, for example by amplifying the nucleic acid using an error-prone polymerase chain reaction (PCR) system, by chemical mutagenesis (Deng et al., *J. Biol. Chem.*, 269:9533 (1994)) or using bacterial mutator strains (Low et al., *J. Mol. Biol.*, 260:359 (1996)).

In other embodiments, particular regions of the nucleic acid can be targeted for diversification. Methods for mutating selected positions are also well known in the art and include, for example, the use of mismatched oligonucleotides or degenerate oligonucleotides, with or without the use of PCR. For example, synthetic antibody libraries have been created by targeting mutations to the antigen binding loops. Random or semi-random antibody H3 and L3 regions have been appended to germline immunoblulin V gene segments to produce large libraries with unmutated framework regions (Hoogenboom and Winter (1992) supra; Nissim et al. (1994) supra; Griffiths et al. (1994) supra; DeKruif et al. (1995) supra). Such diversification has been extended to include some or all of the other antigen binding loops (Crameri et al. (1996) Nature Med., 2:100; Riechmann et al. (1995) Bio/Technology, 13:475; Morphosys, WO 97/08320, supra). In other embodiments, particular regions of the nucleic acid can be targeted for diversification by, for example, a two-step PCR strategy employing the product of the first PCR as a "mega-primer." (See, e.g., Landt, O. et al., Gene 96:125-128 (1990).) Targeted diversification can also be accomplished, for example, by SOE PCR. (See, e.g., Horton, R. M. et al., Gene 77:61-68 (1989).)

Sequence diversity at selected positions can be achieved by altering the coding sequence which specifies the sequence of the polypeptide such that a number of possible amino acids (e.g., all 20 or a subset thereof) can be incorporated at that position. Using the IUPAC nomenclature, the most versatile codon is NNK, which encodes all amino acids as well as the TAG stop codon. The NNK codon may be used in order to introduce the required diversity. Other codons which achieve the same ends are also of use, including the NNN codon, which leads to the production of the additional stop codons TGA and TAA. Such a targeted approach can allow the full sequence space in a target area to be explored.

Some libraries comprise domains that are members of the immunoglobulin superfamily (e.g., antibodies or portions thereof). For example the libraries can comprise domains that have a known main-chain conformation. (See, e.g., Tomlinson et al., WO 99/20749.) Libraries can be prepared in a suitable plasmid or vector. As used herein, vector refers to a discrete element that is used to introduce heterologous DNA into cells for the expression and/or replication thereof. Any suitable vector can be used, including plasmids (e.g., bacterial plasmids), viral or bacteriophage vectors, artificial chromosomes and episomal vectors. Such vectors may be used for simple cloning and mutagenesis, or an expression vector can be used to drive expression of the library. Vectors and plasmids usually contain one or more cloning sites (e.g., a polylinker), an origin of replication and at least one selectable marker gene. Expression vectors can further contain elements to drive transcription and translation of a polypeptide, such as an enhancer element, promoter, transcription termination signal, signal sequences, and the like. These elements can be arranged in such a way as to be operably linked to a cloned insert encoding a polypeptide, such that the polypeptide is expressed and produced when such an expression vector is maintained under conditions suitable for expression (e.g., in a suitable host cell).

Cloning and expression vectors generally contain nucleic acid sequences that enable the vector to replicate in one or more selected host cells. Typically in cloning vectors, this sequence is one that enables the vector to replicate independently of the host chromosomal DNA and includes origins of replication or autonomously replicating sequences. Such sequences are well known for a variety of bacteria, yeast and viruses. The origin of replication from the plasmid pBR322 is suitable for most Gram-negative bacteria, the 2 micron plasmid origin is suitable for yeast, and various viral origins (e.g. SV40, adenovirus) are useful for cloning vectors in mammalian cells. Generally, the origin of replication is not needed for mammalian expression vectors, unless these are used in mammalian cells able to replicate high levels of DNA, such as COS cells.

Cloning or expression vectors can contain a selection gene also referred to as selectable marker. Such marker genes encode a protein necessary for the survival or growth of transformed host cells grown in a selective culture medium. Host cells not transformed with the vector containing the selection gene will therefore not survive in the culture medium. Typical selection genes encode proteins that confer resistance to antibiotics and other toxins, e.g. ampicillin, neomycin, methotrexate or tetracycline, complement auxotrophic deficiencies, or supply critical nutrients not available in the growth media.

Suitable expression vectors can contain a number of components, for example, an origin of replication, a selectable marker gene, one or more expression control elements, such as a transcription control element (e.g., promoter, enhancer, terminator) and/or one or more translation signals, a signal sequence or leader sequence, and the like. Expression control elements and a signal or leader sequence, if present, can be provided by the vector or other source. For example, the transcriptional and/or translational control sequences of a cloned nucleic acid encoding an antibody chain can be used to direct expression.

A promoter can be provided for expression in a desired host cell. Promoters can be constitutive or inducible. For example, a promoter can be operably linked to a nucleic acid encoding an antibody, antibody chain or portion thereof, such that it directs transcription of the nucleic acid. A variety of suitable promoters for procaryotic (e.g., the β-lactamase and lactose promoter systems, alkaline phosphatase, the tryptophan (trp) promoter system, lac, tac, T3, T7 promoters for E. coli) and eucaryotic (e.g., simian virus 40 early or late promoter, Rous sarcoma virus long terminal repeat promoter, cytomegalovirus promoter, adenovirus late promoter, EG-1a promoter) hosts are available.

In addition, expression vectors typically comprise a selectable marker for selection of host cells carrying the vector, and, in the case of a replicable expression vector, an origin of replication. Genes encoding products which confer antibiotic or drug resistance are common selectable markers and may be used in procaryotic (e.g., β-lactamase gene (ampicillin resistance), Tet gene for tetracycline resistance) and eucaryotic cells (e.g., neomycin (G418 or geneticin), gpt (mycophenolic acid), ampicillin, or hygromycin resistance genes). Dihydrofolate reductase marker genes permit selection with methotrexate in a variety of hosts. Genes encoding the gene product of auxotrophic markers of the host (e.g., LEU2, URA3, HIS3) are often used as selectable markers in yeast. Use of viral (e.g., baculovirus) or phage vectors, and vectors which are capable of integrating into the genome of the host cell, such as retroviral vectors, are also contemplated.

Suitable expression vectors for expression in prokaryotic (e.g., bacterial cells such as E. coli) or mammalian cells include, for example, a pET vector (e.g., pET-12a, pET-36, pET-37, pET-39, pET-40, Novagen and others), a phage vector (e.g., pCANTAB 5 E, Pharmacia), pRIT2T (Protein A fusion vector, Pharmacia), pCDM8, pcDNA1.1/amp, pcDNA3.1, pRc/RSV, pEF-1 (Invitrogen, Carlsbad, Calif.), pCMV-SCRIPT, pFB, pSG5, pXT1 (Stratagene, La Jolla, Calif.), pCDEF3 (Goldman, L. A., et al., Biotechniques, 21:1013-1015 (1996)), pSVSPORT (GibcoBRL, Rockville, Md.), pEF-Bos (Mizushima, S., et al., Nucleic Acids Res., 18:5322 (1990)) and the like. Expression vectors which are suitable for use in various expression hosts, such as prokaryotic cells (E. coli), insect cells (Drosophila Schnieder S2 cells, Sf9), yeast (P. methanolica, P. pastoris, S. cerevisiae) and mammalian cells (eg, COS cells) are available.

Some examples of vectors are expression vectors that enable the expression of a nucleotide sequence corresponding to a polypeptide library member. Thus, selection with generic and/or target ligands can be performed by separate propagation and expression of a single clone expressing the polypeptide library member. As described above, a particular selection display system is bacteriophage display. Thus, phage or phagemid vectors may be used, for example vectors may be phagemid vectors which have an *E. coli*. origin of replication (for double stranded replication) and also a phage origin of replication (for production of single-stranded DNA). The manipulation and expression of such vectors is well known in the art (Hoogenboom and Winter (1992) supra; Nissim et al. (1994) supra). Briefly, the vector can contain a β-lactamase gene to confer selectivity on the phagemid and a lac promoter upstream of an expression cassette that can contain a suitable leader sequence, a multiple cloning site, one or more peptide tags, one or more TAG stop codons and the phage protein pIII. Thus, using various suppressor and non-suppressor strains of *E. coli* and with the addition of glucose, iso-propyl thio-β-D-galactoside (IPTG) or a helper phage, such as VCS M13, the vector is able to replicate as a plasmid with no expression, produce large quantities of the polypeptide library member only or product phage, some of which contain at least one copy of the polypeptide-pIII fusion on their surface.

Antibody variable domains may comprise a target ligand binding site and/or a generic ligand binding site. In certain embodiments, the generic ligand binding site is a binding site for a superantigen, such as protein A, protein L or protein G. The variable domains can be based on any desired variable domain, for example a human VH (e.g., $V_H1a$, $V_H1b$, $V_H2$, $V_H3$, $V_H4$, $V_H5$, $V_H6$), a human Vλ (e.g., VλI, VλII, VλIII, VλIV, VλV, VλVI or Vκ1) or a human Vκ(e.g., Vκ2, Vκ3, Vκ4, Vκ5, Vκ6, Vκ7, Vκ8, Vκ9 or Vκ10).

A still further category of techniques involves the selection of repertoires in artificial compartments, which allow the linkage of a gene with its gene product. For example, a selection system in which nucleic acids encoding desirable gene products may be selected in microcapsules formed by water-in-oil emulsions is described in WO99/02671, WO00/40712 and Tawfik & Griffiths (1998) *Nature Biotechnol* 16(7), 652-6. Genetic elements encoding a gene product having a desired activity are compartmentalised into microcapsules and then transcribed and/or translated to produce their respective gene products (RNA or protein) within the microcapsules. Genetic elements which produce gene product having desired activity are subsequently sorted. This approach selects gene products of interest by detecting the desired activity by a variety of means.

Characterisation of the Epitope Binding Domains.

The binding of a domain to its specific antigen or epitope can be tested by methods which will be familiar to those skilled in the art and include ELISA. In one example, binding is tested using monoclonal phage ELISA.

Phage ELISA may be performed according to any suitable procedure: an exemplary protocol is set forth below.

Populations of phage produced at each round of selection can be screened for binding by ELISA to the selected antigen or epitope, to identify "polyclonal" phage antibodies. Phage from single infected bacterial colonies from these populations can then be screened by ELISA to identify "monoclonal" phage antibodies. It is also desirable to screen soluble antibody fragments for binding to antigen or epitope, and this can also be undertaken by ELISA using reagents, for example, against a C- or N-terminal tag (see for example Winter et al. (1994) Ann. Rev. Immunology 12, 433-55 and references cited therein.

The diversity of the selected phage monoclonal antibodies may also be assessed by gel electrophoresis of PCR products (Marks et al. 1991, supra; Nissim et al. 1994 supra), probing (Tomlinson et al., 1992) J. Mol. Biol. 227, 776) or by sequencing of the vector DNA.

E. Structure of dAbs

In the case that the dAbs are selected from V-gene repertoires selected for instance using phage display technology as herein described, then these variable domains comprise a universal framework region, such that is they may be recognised by a specific generic ligand as herein defined. The use of universal frameworks, generic ligands and the like is described in WO99/20749.

Where V-gene repertoires are used variation in polypeptide sequence may be located within the structural loops of the variable domains. The polypeptide sequences of either variable domain may be altered by DNA shuffling or by mutation in order to enhance the interaction of each variable domain with its complementary pair. DNA shuffling is known in the art and taught, for example, by Stemmer, 1994, Nature 370: 389-391 and U.S. Pat. No. 6,297,053, both of which are incorporated herein by reference. Other methods of mutagenesis are well known to those of skill in the art.

Scaffolds for Use in Constructing dAbs i. Selection of the Main-Chain Conformation The members of the immunoglobulin superfamily all share a similar fold for their polypeptide chain. For example, although antibodies are highly diverse in terms of their primary sequence, comparison of sequences and crystallographic structures has revealed that, contrary to expectation, five of the six antigen binding loops of antibodies (H1, H2, L1, L2, L3) adopt a limited number of main-chain conformations, or canonical structures (Chothia and Lesk (1987) *J. Mol. Biol.*, 196: 901; Chothia et al. (1989) *Nature*, 342: 877). Analysis of loop lengths and key residues has therefore enabled prediction of the main-chain conformations of H1, H2, L1, L2 and L3 found in the majority of human antibodies (Chothia et al. (1992) *J. Mol. Biol.*, 227: 799; Tomlinson et al. (1995) *EMBO J.*, 14: 4628; Williams et al. (1996) *J. Mol. Biol.*, 264: 220). Although the H3 region is much more diverse in terms of sequence, length and structure (due to the use of D segments), it also forms a limited number of main-chain conformations for short loop lengths which depend on the length and the presence of particular residues, or types of residue, at key positions in the loop and the antibody framework (Martin et al. (1996) *J. Mol. Biol.*, 263: 800; Shirai et al. (1996) *FEBS Letters*, 399: 1).

The dAbs are advantageously assembled from libraries of domains, such as libraries of $V_H$ domains and/or libraries of $V_L$ domains. In one aspect, libraries of domains are designed in which certain loop lengths and key residues have been chosen to ensure that the main-chain conformation of the members is known. Advantageously, these are real conformations of immunoglobulin superfamily molecules found in nature, to minimise the chances that they are non-functional, as discussed above. Germline V gene segments serve as one suitable basic framework for constructing antibody or T-cell receptor libraries; other sequences are also of use. Variations may occur at a low frequency, such that a small number of functional members may possess an altered main-chain conformation, which does not affect its function.

Canonical structure theory is also of use to assess the number of different main-chain conformations encoded by ligands, to predict the main-chain conformation based on ligand sequences and to chose residues for diversification which do not affect the canonical structure. It is known that, in the human $V_K$ domain, the L1 loop can adopt one of four canonical structures, the L2 loop has a single canonical structure and that 90% of human $V_K$ domains adopt one of four or five canonical structures for the L3 loop (Tomlinson et al. (1995) supra); thus, in the $V_K$ domain alone, different canonical structures can combine to create a range of different main-chain conformations. Given that the Vλ domain encodes a different range of canonical structures for the L1, L2 and L3 loops and that $V_K$ and Vλ domains can pair with any $V_H$ domain which can encode several canonical structures for the H1 and H2 loops, the number of canonical structure combinations observed for these five loops is very large. This implies that the generation of diversity in the main-chain conformation may be essential for the production of a wide range of binding specificities. However, by constructing an antibody library based on a single known main-chain conformation it has been found, contrary to expectation, that diversity in the main-chain conformation is not required to generate sufficient diversity to target substantially all antigens. Even more surprisingly, the single main-chain conformation need not be a consensus structure—a single naturally occurring conformation can be used as the basis for an entire library. Thus, in a one particular aspect, the dAbs possess a single known main-chain conformation.

The single main-chain conformation that is chosen may be commonplace among molecules of the immunoglobulin superfamily type in question. A conformation is commonplace when a significant number of naturally occurring molecules are observed to adopt it. Accordingly, in one aspect, the natural occurrence of the different main-chain conformations for each binding loop of an immunoglobulin domain are considered separately and then a naturally occurring variable domain is chosen which possesses the desired combination of main-chain conformations for the different loops. If none is available, the nearest equivalent may be chosen. The desired combination of main-chain conformations for the different loops may be created by selecting germline gene segments which encode the desired main-chain conformations. In one example, the selected germline gene segments are frequently expressed in nature, and in particular they may be the most frequently expressed of all natural germline gene segments.

In designing libraries the incidence of the different main-chain conformations for each of the six antigen binding loops may be considered separately. For H1, H2, L1, L2 and L3, a given conformation that is adopted by between 20% and 100% of the antigen binding loops of naturally occurring molecules is chosen. Typically, its observed incidence is above 35% (i.e. between 35% and 100%) and, ideally, above 50% or even above 65%. Since the vast majority of H3 loops do not have canonical structures, it is preferable to select a main-chain conformation which is commonplace among those loops which do display canonical structures. For each of the loops, the conformation which is observed most often in the natural repertoire is therefore selected. In human antibodies, the most popular canonical structures (CS) for each loop are as follows: H1-CS1 (79% of the expressed repertoire), H2-CS 3 (46%), L1-CS 2 of $V_K$(39%), L2-CS1 (100%), L3-CS1 of $V_K$(36%) (calculation assumes a κ:λ ratio of 70:30, Hood et al. (1967) *Cold Spring Harbor Symp. Quant. Biol.*, 48: 133). For H3 loops that have canonical structures, a CDR3 length (Kabat et al. (1991) *Sequences of proteins of immunological interest*, U.S. Department of Health and Human Services) of seven residues with a salt-bridge from residue 94 to residue 101 appears to be the most common. There are at least 16 human antibody sequences in the EMBL data library with the required H3 length and key residues to form this conformation and at least two crystallographic structures in the protein data bank which can be used as a basis for antibody modelling (2cgr and 1tet). The most frequently expressed germline gene segments that this combination of canonical structures are the $V_H$ segment 3-23 (DP-47), the $J_H$ segment JH4b, the $V_K$ segment O2/O12 (DPK9) and the $J_K$ segment $J_K1$. $V_H$ segments DP45 and DP38 are also suitable. These segments can therefore be used in combination as a basis to construct a library with the desired single main-chain conformation.

Alternatively, instead of choosing the single main-chain conformation based on the natural occurrence of the different main-chain conformations for each of the binding loops in isolation, the natural occurrence of combinations of main-chain conformations is used as the basis for choosing the single main-chain conformation. In the case of antibodies, for example, the natural occurrence of canonical structure combinations for any two, three, four, five, or for all six of the antigen binding loops can be determined. Here, the chosen conformation may be commonplace in naturally occurring antibodies and may be observed most frequently in the natural repertoire. Thus, in human antibodies, for example, when natural combinations of the five antigen binding loops, H1, H2, L1, L2 and L3, are considered, the most frequent combination of canonical structures is determined and then combined with the most popular conformation for the H3 loop, as a basis for choosing the single main-chain conformation.

Diversification of the Canonical Sequence

Having selected several known main-chain conformations or a single known main-chain conformation, dAbs can be constructed by varying the binding site of the molecule in order to generate a repertoire with structural and/or functional diversity. This means that variants are generated such that they possess sufficient diversity in their structure and/or in their function so that they are capable of providing a range of activities.

The desired diversity is typically generated by varying the selected molecule at one or more positions. The positions to be changed can be chosen at random or they may be selected. The variation can then be achieved either by randomisation, during which the resident amino acid is replaced by any amino acid or analogue thereof, natural or synthetic, producing a very large number of variants or by replacing the resident amino acid with one or more of a defined subset of amino acids, producing a more limited number of variants.

Various methods have been reported for introducing such diversity. Error-prone PCR (Hawkins et al. (1992) *J. Mol. Biol.*, 226: 889), chemical mutagenesis (Deng et al. (1994) *J. Biol. Chem.*, 269: 9533) or bacterial mutator strains (Low et al. (1996) *J. Mol. Biol.*, 260: 359) can be used to introduce random mutations into the genes that encode the molecule. Methods for mutating selected positions are also well known in the art and include the use of mismatched oligonucleotides or degenerate oligonucleotides, with or without the use of PCR. For example, several synthetic antibody libraries have been created by targeting mutations to the antigen binding loops. The H3 region of a human tetanus toxoid-binding Fab has been randomised to create a range of new binding specificities (Barbas et al. (1992) *Proc. Natl. Acad. Sci. USA*, 89: 4457). Random or semi-random H3 and L3 regions have been appended to germline V gene segments to produce large libraries with unmutated framework regions (Hoogenboom & Winter (1992) *J. Mol. Biol.*, 227: 381; Barbas et al. (1992) *Proc. Natl. Acad. Sci. USA*, 89: 4457; Nissim et al. (1994) *EMBO J.*, 13: 692; Griffiths et al. (1994) *EMBO J.*, 13: 3245; De Kruif et al. (1995) *J. Mol. Biol.*, 248: 97). Such diversification has been extended to include some or all of the other antigen binding loops (Crameri et al. (1996) *Nature Med.,* 2: 100; Riechmann et al. (1995) *Bio/Technology,* 13: 475; Morphosys, WO97/08320, supra).

Since loop randomisation has the potential to create approximately more than $10^{15}$ structures for H3 alone and a similarly large number of variants for the other five loops, it is not feasible using current transformation technology or even by using cell free systems to produce a library representing all possible combinations. For example, in one of the largest libraries constructed to date, $6 \times 10^{10}$ different antibodies, which is only a fraction of the potential diversity for a library of this design, were generated (Griffiths et al. (1994) supra).

In a one embodiment, only those residues which are directly involved in creating or modifying the desired function of the molecule are diversified. For many molecules, the function will be to bind a target and therefore diversity should be concentrated in the target binding site, while avoiding changing residues which are crucial to the overall packing of the molecule or to maintaining the chosen main-chain conformation.

In one aspect, libraries of dAbs are used in which only those residues in the antigen binding site are varied. These residues are extremely diverse in the human antibody repertoire and are known to make contacts in high-resolution antibody/antigen complexes. For example, in L2 it is known that positions 50 and 53 are diverse in naturally occurring antibodies and are observed to make contact with the antigen. In contrast, the conventional approach would have been to diversify all the residues in the corresponding Complementarity Determining Region (CDR1) as defined by Kabat et al. (1991, supra), some seven residues compared to the two diversified in the library. This represents a significant improvement in terms of the functional diversity required to create a range of antigen binding specificities.

In nature, antibody diversity is the result of two processes: somatic recombination of germline V, D and J gene segments to create a naive primary repertoire (so called germline and junctional diversity) and somatic hypermutation of the resulting rearranged V genes. Analysis of human antibody sequences has shown that diversity in the primary repertoire is focused at the centre of the antigen binding site whereas somatic hypermutation spreads diversity to regions at the periphery of the antigen binding site that are highly conserved in the primary repertoire (see Tomlinson et al. (1996) *J. Mol. Biol.,* 256: 813). This complementarity has probably evolved as an efficient strategy for searching sequence space and, although apparently unique to antibodies, it can easily be applied to other polypeptide repertoires. The residues which are varied are a subset of those that form the binding site for the target. Different (including overlapping) subsets of residues in the target binding site are diversified at different stages during selection, if desired.

In the case of an antibody repertoire, an initial 'naive' repertoire is created where some, but not all, of the residues in the antigen binding site are diversified. As used herein in this context, the term "naive" or "dummy" refers to antibody molecules that have no pre-determined target. These molecules resemble those which are encoded by the immunoglobulin genes of an individual who has not undergone immune diversification, as is the case with fetal and newborn individuals, whose immune systems have not yet been challenged by a wide variety of antigenic stimuli. This repertoire is then selected against a range of antigens or epitopes. If required, further diversity can then be introduced outside the region diversified in the initial repertoire. This matured repertoire can be selected for modified function, specificity or affinity.

It will be understood that the sequences described herein include sequences which are substantially identical, for example sequences which are at least 90% identical, for example which are at least 91%, or at least 92%, or at least 93%, or at least 94% or at least 95%, or at least 96%, or at least 97% or at least 98%, or at least 99% identical to the sequences described herein.

For nucleic acids, the term "substantial identity" indicates that two nucleic acids, or designated sequences thereof, when optimally aligned and compared, are identical, with appropriate nucleotide insertions or deletions, in at least about 80% of the nucleotides, usually at least about 90% to 95%, or at least about 98% to 99.5% of the nucleotides. Alternatively, substantial identity exists when the segments will hybridize under selective hybridization conditions, to the complement of the strand.

For nucleotide and amino acid sequences, the term "identical" indicates the degree of identity between two nucleic acid or amino acid sequences when optimally aligned and compared with appropriate insertions or deletions. Alternatively, substantial identity exists when the DNA segments will hybridize under selective hybridization conditions, to the complement of the strand.

The percent identity between two sequences is a function of the number of identical positions shared by the sequences (i.e., % identity=# of identical positions/total # of positions times 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below.

The percent identity between two nucleotide sequences can be determined using the GAP program in the GCG software package, using a NWSgapdna.CMP matrix and a gap weight of 40, 50, 60, 70, or 80 and a length weight of 1, 2, 3, 4, 5, or 6. The percent identity between two nucleotide or amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol. Biol. 48:444-453 (1970)) algorithm which has been incorporated into the GAP program in the GCG software package, using either a Blossum 62 matrix or a PAM250 matrix, and a gap weight of 16, 14, 12, 10, 8, 6, or 4 and a length weight of 1, 2, 3, 4, 5, or 6.

By way of example, a polynucleotide sequence of the present invention may be identical to the reference sequence, that is be 100% identical, or it may include up to a certain integer number of nucleotide alterations as compared to the reference sequence. Such alterations are selected from the group consisting of at least one nucleotide deletion, substitution, including transition and transversion, or insertion, and wherein said alterations may occur at the 5' or 3' terminal positions of the reference nucleotide sequence or anywhere between those terminal positions, interspersed either individually among the nucleotides in the reference sequence or in one or more contiguous groups within the reference sequence. The number of nucleotide alterations is determined by multiplying the total number of nucleotides in the reference sequence by the numerical percent of the respective percent identity (divided by 100) and subtracting that product from said total number of nucleotides in the reference sequence, or:

$$nn \leq xn - (xn \cdot y),$$

wherein nn is the number of nucleotide alterations, xn is the total number of nucleotides in the reference sequence, and y is 0.50 for 50%, 0.60 for 60%, 0.70 for 70%, 0.80 for 80%, 0.85 for 85%, 0.90 for 90%, 0.95 for 95%, 0.97 for 97% or 1.00 for 100%, and wherein any non-integer product of xn and y is rounded down to the nearest integer prior to subtracting it from xn. Alterations of the polynucleotide sequence of the reference sequence may create nonsense, missense or frameshift mutations in this coding sequence and thereby alter the polypeptide encoded by the polynucleotide following such alterations.

Similarly, in another example, a polypeptide sequence of the present invention may be identical to the reference sequence encoded by SEQ ID NO: 5, that is be 100% identical, or it may include up to a certain integer number of amino acid alterations as compared to the reference sequence such that the % identity is less than 100%. Such alterations are selected from the group consisting of at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the polypeptide sequence encoded by SEQ ID NO: 5 by the numerical percent of the respective percent identity (divided by 100) and then subtracting that product from said total number of amino acids in the polypeptide sequence encoded by SEQ ID NO: 5, or:

$$na \leq xa - (xa \cdot y),$$

wherein na is the number of amino acid alterations, xa is the total number of amino acids in the polypeptide sequence encoded by SEQ ID NO: 5, and y is, for instance 0.70 for 70%, 0.80 for 80%, 0.85 for 85% etc., and wherein any non-integer product of xa and y is rounded down to the nearest integer prior to subtracting it from xa.

EXAMPLES

Example 1

Design and Construction of Bispecific Antigen Binding Proteins with Various Linkers An anti-IL-13 dAb DNA sequence (DOM10-53-616, SEQ ID NO: 1) was modified by PCR to include a BamHI site at the 5' end and an EcoRI site at the 3' end in order to facilitate cloning. The PCR product was cloned into a mammalian expression vector encoding the heavy chain of an anti-IL4 antibody, allowing the anti IL-13 dAb to be fused onto the C-terminus of the heavy chain via a GS linker (SEQ ID NO: 4, heavy chain of bispecific antibody BPC 2201).

Forward and reverse primers encoding the TVAAPS linker were designed with BglII and BamHI cohesive ends to facilitate cloning into the BamHI site of the vector described above. This method allowed the sequential introduction of TVAAPSGS linker sequences between the C-terminus of the CH3 domain and the N-terminus of the DOM-10-53-616 anti-IL-13 domain antibody. The resulting expression vectors encode SEQ ID NO: 5 and SEQ ID NO: 6 (the heavy chains of BPC2202 and BPC2203 respectively).

The DNA sequence of an anti-IL-4 mAb heavy chain was modified at the 3' end by PCR in order to incorporate various linker sequences. The resulting PCR fragments were restricted with HindIII and BamHI and cloned into an expression vector encoding SEQ ID NO: 4 also restricted with HindIII and BamHI. The resulting mammalian expression vectors encode the heavy chain of the anti-IL-4 mAb fused to DOM-10-53-616 with various linkers between the C-terminus of the CH3 domain and the N-terminus of the DOM10-53-616 anti IL-13 dAb. This method generated expression vectors encoding the heavy chains of BPC2204-2215 and BPC2217-2220 (SEQ ID NOs: 7-8 and 11-21 and 23-25).

Plasmids encoding heavy chains of BPC2201-2210 and BPC2220 (SEQ ID NO's 4-8 and 11-16) were used as base constructs to generate alternative constructs. In the first stage, the DNA sequence encoding the DOM-10-53-616 anti-IL-13 domain antibody (SEQ ID NO: 1) was replaced with a DNA sequence encoding the DOM-9-155-154 anti IL-4 dAb (SEQ ID NO: 26) by restriction cloning using BamHI and EcoRI. In the second stage, the DNA sequence encoding the variable heavy domain of the anti-IL4 antibody was replaced with a DNA sequence encoding the variable domain of an anti-IL13 antibody by restriction cloning using HindIII and SpeI. The resulting expression vectors encode the heavy chain-domain antibody fusion proteins SEQ ID NOs: 29-33 and 36-41.

Plasmids encoding heavy chains of BPC2211-2214, 2218 and 2219 (SEQ ID NO's 17-20, 24 and 25), were used as base constructs to generate alternative constructs. In the first stage, the DNA sequence encoding the DOM-10-53-616 anti-IL-13 domain antibody (SEQ ID NO:1) was replaced with a DNA sequence encoding the DOM-9-155-154 anti IL-4 dAb (SEQ ID NO: 26) by restriction cloning using BamHI and EcoRI. In the second stage, the DNA sequence encoding the variable heavy domain of the anti-IL4 antibody was replaced with a DNA sequence encoding the variable domain of an anti-IL13 antibody by restriction cloning using HindIII and SpeI. The resulting expression vectors encode the heavy chain-domain antibody fusion proteins SEQ ID NOs: 42-45, 49 and 50.

Alternative heavy chain-domain antibody fusion proteins containing different linkers between the CH3 domain of the heavy chain and the domain antibody were designed and are listed in SEQ ID NOs: 9, 10, 22, 34-35 and 42-50. An alternative anti-IL-4 domain antibody sequence is given in SEQ ID NO. 80-82. An alternative anti-IL-13 domain antibody sequence is given in SEQ ID NO: 83. Linkers are listed in SEQ ID NOs: 51-78 and 112-114.

TABLE 1 summary of the antibodies and bispecific antigen binding proteins that have been designed. All of these have been constructed and expressed except for those identified with * i.e. BPC2232, 2233, 2243, 2244, 2245, 2238, 2239 and 2240.

| Identifier | SEQ ID NO: of Heavy Chain | SEQ ID NO: of light chain | Linker |
|---|---|---|---|
| anti-IL-4 mAb | 3 | 2 | None |
| anti-IL-13 mAb (also described as 586 or A1L1) | 28 | 27 | None |

TABLE 1-continued summary of the antibodies and bispecific antigen binding proteins that have been designed. All of these have been constructed and expressed except for those identified with * i.e. BPC2232, 2233, 2243, 2244, 2245, 2238, 2239 and 2240.

| Identifier | SEQ ID NO: of Heavy Chain | SEQ ID NO: of light chain | Linker |
|---|---|---|---|
| BPC 2201 | 4 | 2 | GS |
| BPC 2202 | 5 | 2 | GS(TVAAPSGS)$_1$ |
| BPC 2203 | 6 | 2 | GS(TVAAPSGS)$_2$ |
| BPC 2209 | 7 | 2 | GS(TVAAPSGS)$_3$ |
| BPC 2210 | 8 | 2 | GS(TVAAPSGS)$_4$ |
| BPC 2232* | 9 | 2 | GS(TVAAPSGS)$_5$ |
| BPC 2233* | 10 | 2 | GS(TVAAPSGS)$_6$ |
| BPC 2208 | 11 | 2 | (PAS)$_1$GS |
| BPC 2204 | 12 | 2 | (PAS)$_2$GS |
| BPC 2205 | 13 | 2 | (PAS)$_3$GS |
| BPC 2206 | 14 | 2 | (G4S)$_1$ |
| BPC 2207 | 15 | 2 | (G4S)$_2$ |
| BPC 2220 | 16 | 2 | (G4S)$_3$ |
| BPC 2211 | 17 | 2 | (PAVPPP)$_1$GS |
| BPC 2212 | 18 | 2 | (PAVPPP)$_2$GS |
| BPC 2213 | 19 | 2 | (PAVPPP)$_3$GS |
| BPC 2214 | 20 | 2 | (TVSDVP)$_1$GS |
| BPC 2215 | 21 | 2 | (TVSDVP)$_2$GS |
| BPC 2243* | 22 | 2 | (TVSDVP)$_3$GS |
| BPC 2217 | 23 | 2 | (TGLDSP)$_1$GS |
| BPC 2218 | 24 | 2 | (TGLDSP)$_2$GS |
| BPC 2219 | 25 | 2 | (TGLDSP)$_3$GS |
| BPC2221 | 29 | 27 | GS |
| BPC2222 | 30 | 27 | GS(TVAAPSGS)$_1$ |
| BPC2223 | 31 | 27 | GS(TVAAPSGS)$_2$ |
| BPC2230 | 32 | 27 | GS(TVAAPSGS)$_3$ |
| BPC2231 | 33 | 27 | GS(TVAAPSGS)$_4$ |
| BPC2244* | 34 | 27 | GS(TVAAPSGS)$_5$ |
| BPC2245* | 35 | 27 | GS(TVAAPSGS)$_6$ |
| BPC2229 | 36 | 27 | (PAS)$_1$GS |
| BPC2224 | 37 | 27 | (PAS)$_2$GS |
| BPC2225 | 38 | 27 | (PAS)$_3$GS |
| BPC2226 | 39 | 27 | (G$_4$S)$_1$ |
| BPC2227 | 40 | 27 | (G$_4$S)$_2$ |
| BPC2228 | 41 | 27 | (G$_4$S)$_3$ |
| BPC 2234 | 42 | 27 | (PAVPPP)$_1$GS |

TABLE 1-continued

Summary of the antibodies and bispecific antigen binding proteins that have been designed. All of these have been constructed and expressed except for those identified with * i.e. BPC2232, 2233, 2243, 2244, 2245, 2238, 2239 and 2240.

| Identifier | SEQ ID NO: of Heavy Chain | SEQ ID NO: of light chain | Linker |
|---|---|---|---|
| BPC 2235 | 43 | 27 | $(PAVPPP)_2GS$ |
| BPC 2236 | 44 | 27 | $(PAVPPP)_3GS$ |
| BPC 2237 | 45 | 27 | $(TVSDVP)_1GS$ |
| BPC 2238* | 46 | 27 | $(TVSDVP)_2GS$ |
| BPC 2239* | 47 | 27 | $(TVSDVP)_3GS$ |
| BPC 2240* | 48 | 27 | $(TGLDSP)_1GS$ |
| BPC 2241 | 49 | 27 | $(TGLDSP)_2GS$ |
| BPC 2242 | 50 | 27 | $(TGLDSP)_3GS$ |
| BPC 2246 | 29 | 2 | GS |
| BPC 2247 | 30 | 2 | $GS(TVAAPSGS)_1$ |
| BPC 2248 | 31 | 2 | $GS(TVAAPSGS)_2$ |
| BPC 2249 | 32 | 2 | $GS(TVAAPSGS)_3$ |
| BPC 2250 | 33 | 2 | $GS(TVAAPSGS)_4$ |
| BPC 2251 | 36 | 2 | $(PAS)_1GS$ |
| BPC 2252 | 37 | 2 | $(PAS)_2GS$ |
| BPC 2253 | 38 | 2 | $(PAS)_3GS$ |
| BPC 2254 | 39 | 2 | $(G_4S)_1$ |
| BPC 2255 | 40 | 2 | $(G_4S)_2$ |
| BPC 2256 | 41 | 2 | $(G_4S)_3$ |

Expression plasmids encoding heavy chain and corresponding light chain of the bispecific antigen binding proteins shown in Table 1 were transiently co-transfected into HEK 293-6E cells using 293-fectin (Invitrogen, 12347019). A tryptone feed was added to each cell culture up to 24 hours after transfection and the cells were harvested after 3 to 7 days. In some instances the supernatant was used as the test article in binding assays and BIAcore. In other instances, the bispecific antigen binding protein was purified using a Protein A column before being run in binding assays.

The supernatants were quantified with Gyros or the Beckman Coulter IMMAGE nephelometer.

Example 2

IL-4 and IL-13 Binding ELISA 96-well high binding plates were coated with 5 µg/ml of either IL-4 or IL-13 in bicarbonate water and stored overnight at 4° C. The plates were washed twice with Phosphate Buffered Saline (PBS) or Tris-buffered saline (TBS) containing 0.05% of Tween-20. 200 µL of blocking solution (3% BSA in PBS buffer) was added in each well and the plate was incubated for at least 1 hour at room temperature. Another wash step was then performed. The supernatants or purified antibodies (mAbs) were successively diluted across the plates in blocking solution. After 1 hour incubation, the plates were washed. Goat anti-human kappa light chain specific peroxidase conjugated antibody (Sigma, A7164) was diluted in blocking solution to 1 µg/mL and 50 µL was added to each well. The plates were incubated between one to one and a half hours. After another wash step, 50 µl of OPD (o-phenylene-diamine dihydrochloride) SigmaFast substrate solution was added to each well and the reaction was stopped 15 minutes later by addition of 25 µL of 3M sulphuric acid. Absorbance was read at 490 nm using the VersaMax Tunable Microplate Reader (Molecular Devices) using a basic endpoint protocol.

FIG. 1 and FIG. 2 show the results of the binding of several separate assays of purified bispecific antigen binding proteins with GS and $GS(TVAAPSGS)_{n=1-4}$ linker (BPC 2201, 2202, 2203, 2209 and BPC 2210) to human IL-4 and human IL-13 respectively as determined by ELISA. BPC1001 (a positive control bispecific antigen binding protein which binds IL-13 and IL-4) showed binding to IL-4 and IL-13. In contrast a negative control antibody (labelled hybrid which does not recognise either IL-4 or IL-13) showed no binding to human IL-4 or IL-13. In this experiment the bispecific antigen binding proteins all show similar binding activity to human IL-4 and human IL-13.

FIG. 3 and FIG. 4 show the results of the binding of several separate assays of purified bispecific antigen binding proteins with (PAS)$_{n=1-3}$GS and (G$_4$S)$_{n=1-3}$ linkers (BPC 2204 to BPC 2208 and BPC 2220) to human IL-4 and human IL-13 respectively as determined by ELISA. BPC1001 (a positive control bispecific antigen binding protein which binds IL-13 and IL-4) showed binding to IL-4 and IL-13. In contrast a negative control antibody (labelled hybrid which does not recognise either IL-4 or IL-13) showed no binding to human IL-4 or IL-13. In this experiment the bispecific antigen binding proteins all show similar binding activity to human IL-4 and human IL-13.

FIG. 5 and FIG. 6 show the results of the binding of purified bispecific antigen binding proteins with (PAVPPP)$_{n=1-3}$GS, (TVSDVP)$_{n=1-2}$GS and (TGLDSP)$_{n=1-3}$GS linkers (BPC 2211 to BPC 2215 and BPC 2217 to BPC 2219) to human IL-4 and human IL-13 respectively as determined by ELISA. BPC1001 (a positive control bispecific antigen binding protein which binds IL-13 and IL-4) showed binding to IL-4 and IL-13. In contrast a negative control antibody (labelled hybrid which does not recognise either IL-4 or IL-13) showed no binding to human IL-4 or IL-13. In this experiment the bispecific antigen binding proteins all show similar binding activity to human IL-4 and human IL-13.

FIGS. 7 and 8 show the results of the binding of purified bispecific antigen binding proteins with GS and GS(TVAAPSGS)$_{n=1-4}$, (PAS)$_{n=1-3}$GS and (G$_4$S)$_{n=1-3}$ linker (BPC 2221-2231) to human IL-4 and human IL-13 respectively as determined by ELISA. BPC1001 (a positive control bispecific antigen binding protein which binds IL-13 and IL-4) showed binding to IL-4 and IL-13. In contrast a negative control antibody (labelled hybrid which does not recognise either IL-4 or IL-13) showed no binding to human IL-4 or IL-13. In this experiment the bispecific antigen binding proteins all show similar binding activity to human IL-13. In comparison, a significant increase in the binding of the dAb portion to IL-4 was observed on increasing the linker size from the GS(TVAAPSGS)$_1$ linker to the GS(TVAAPSGS)$_{2-4}$ linkers.

FIGS. 9 and 10 show the results of the binding of purified bispecific antigen binding proteins with (PAVPPP)$_{n=1-3}$GS and TVSDVPGS and (TGLDSP)$_{n=2-3}$GS linkers (BPC 2234 to BPC 2237, BPC 2241 and BPC 2242) to human IL-4 and human IL-13 respectively as determined by ELISA. BPC1001 (a positive control bispecific antigen binding protein which binds IL-13 and IL-4) showed binding to IL-4 and IL-13. In contrast a negative control antibody (labelled hybrid which does not recognise either IL-4 or IL-13) showed no binding to human IL-4 or IL-13. In this experiment the bispecific antigen binding proteins all show similar binding activity to human IL-13. In comparison, a trend was observed in the human IL-4 binding ELISA: as linker length increased, the binding activity of the dAb portion of the bispecific antigen binding proteins to IL-4 improved.

Example 3

Stoichiometry Assessment of Antigen Binding Proteins (Using Biacore™)

This example is prophetic. It provides guidance for carrying out an additional assay in which the antigen binding proteins of the invention can be tested, Anti-human IgG is immobilised onto a CM5 biosensor chip by primary amine coupling. Antigen binding proteins are captured onto this surface after which a single concentration of IL-13 or IL-4 is passed over, this concentration is enough to saturate the binding surface and the binding signal observed reached full R-max. Stoichiometries are then calculated using the given formula:

Stoich=$R$max*$Mw$ (ligand)/$Mw$ (analyte)*$R$ (ligand immobilised or captured)

Where the stoichiometries are calculated for more than one analyte binding at the same time, the different antigens are passed over sequentially at the saturating antigen concentration and the stoichiometries calculated as above. The work can be carried out on the Biacore 3000, at 25° C. using HBS-EP running buffer.

Example 4

Construction and Testing of Antigen Binding Proteins Comprising the CDRH3 Variant Anti-IL-13 mAb and a Mutated dAb (BPC1085, BPC1086 & BPC1087)

4.1 Construction and Expression

Plasmids encoding heavy chains consisting of an anti-IL-13 mAb and an anti-IL-4 dAb were used as base constructs to generate alternative plasmid constructs. A two step cloning strategy was required. In step 1, the DNA sequence encoding the VH of the anti-IL13 mAb component of the H chain was replaced with the DNA sequence encoding the VH of another humanized anti-IL13 antibody (SEQ ID NO:93) by restriction cloning using HindIII and SpeI. In step 2, the codon encoding the leucine at Kabat position 89 in the anti-IL4 dAb (DOM9-155-154, SEQ ID NO: 26) component of the mAbdAb was mutated by site directed mutagenesis to glutamine. All of the resulting heavy chain DNA sequences generated are given in SEQ ID NOs: 98-100. Table 2 provides a list of the molecules constructed and expressed.

TABLE 2

Summary of the antibodies constructed and expressed

| Identifier | Alternative names | Linker | Molecule description | Protein SEQ ID NO: |
|---|---|---|---|---|
| BPC1085 | 829H-GS(TVAAPSGS)$_2$-154 (89Q) or 829H-GS(TVAAPSGS)$_2$-256 | GS(TVAAPSGS)$_2$ | H chain: Anti-human IL-13 mAb heavy chain Y100B_V_GS(TVAAPSGS)$_2$-DOM9-155-256 | 98 |
| | | | L chain: Anti-human IL-13 mAb light chain | 27 |
| BPC1086 | 829H-GS(TVAAPSGS)$_3$-154 (89Q) or 829H-GS(TVAAPSGS)$_3$-256 | GS(TVAAPSGS)$_3$ | H chain: Anti-human IL-13 mAb heavy chain Y100B_V_GS(TVAAPSGS)$_3$-DOM9-155-256 | 99 |
| | | | Light chain: Anti-human IL-13 mAb light chain | 27 |

TABLE 2-continued

Summary of the antibodies constructed and expressed

| Identifier | Alternative names | Linker | Molecule description | Protein SEQ ID NO: |
|---|---|---|---|---|
| BPC1087 | 829H-GS(TVAAPSGS)$_4$-154 (89Q) or 829H-GS(TVAAPSGS)$_4$-256 | GS(TVAAPSGS)$_4$ | H chain: Anti-human IL-13 mAb heavy chain Y100B_V_GS(TVAAPSGS)$_4$-DOM9-155-256 | 100 |
| | | | L chain: Anti-human IL-13 mAb light chain | 27 |

Heavy and light chain expression plasmids encoding BPC1085, BPC1086 and BPC1087 mAbdAbs were co-transfected into HEK 2936E cells using 293fectin (Invitrogen, 12347019). A tryptone feed was added to each of the cell cultures after 24 hours and the cells were harvested after 72 hours. The antibodies were purified using a Protein A column before being tested in binding assays.

BPC1085, BPC1086 and BPC1087 mAbdAbs were purified using Protein A affinity. 1 ml Protein A columns were used (GE Healthcare) on the AKTA Xpress system, columns were equilibrated in PBS (Gibco/Invitrogen) and the antibodies eluted using Pierce IgG elute. Eluted fractions were neutralised using 1M Tris(Hydroxymethyl) Aminomethane buffer (in general 5-10% v/v). Eluted antibody fractions were pooled and analysed for aggregation by size exclusion chromatography and quantified by reading at OD$_{280}$ nm using a spectrophotometer.

These were compared to equivalent mAbdAbs (2222, 2223, 2230 and 2231) which are described in Table 3. These comprise:
i) a dAb which is identical to that used in BPC1085, BPC1086 and BPC1087 except for position 89 which is 'L' in BPC2222, BPC2223, BPC2230 & BPC2231 and 'Q' in BPC1085, BPC1086 & BPC1087).
ii) same linkers
iii) an IL-13 mAb sequence which is identical to that used BPC1085, BPC1086 and BPC1087 except for position 100B which is 'Y' in BPC2222, BPC2223, BPC2230 & BPC2231 and 'V' in BPC1085, BPC1086 & BPC1087).

TABLE 3

| Identifier | mAb | Linker | dAb | Heavy chain | Light chain |
|---|---|---|---|---|---|
| BPC2222 | A1L1 | GS(TVAAPSGS)$_1$ | DOM9-155-154 | 30 | 27 |
| BPC2223 | A1L1 | GS(TVAAPSGS)$_2$ | DOM9-155-154 | 31 | 27 |
| BPC2230 | A1L1 | GS(TVAAPSGS)$_3$ | DOM9-155-154 | 32 | 27 |
| BPC2231 | A1L1 | GS(TVAAPSGS)$_4$ | DOMP-155-154 | 33 | 27 |

BPC2222, 2223, 2230 and 2231 mAbdAbs were purified using Protein A affinity. 1 ml Protein A columns were used (GE Healthcare) on the AKTA Xpress system, columns were equilibrated in PBS (Gibco/Invitrogen) and the antibodies eluted using Pierce IgG elute. Eluted fractions were neutralised using 1M Tris(Hydroxymethyl) Aminomethane buffer (in general 5-10% v/v). Eluted antibody fractions were pooled and analysed for aggregation by size exclusion chromatography and quantified by reading at OD$_{280}$ nm using a spectrophotometer.

BPC2222, 2223, 2230 and 2231 showed aggregation of between 30-40%, with the aggregated material eluting before 10 minutes.

Compared to BPC2222, 2223, 2230 and 2231 the constructs BPC1085, 1086 and 1087 showed lower levels of aggregation as assessed by size exclusion chromatography.

4.2 IL-4 Binding ELISA

Purified BPC1085, BPC1086 and BPC1087 mAbdAbs were tested for binding to IL-4 in a direct binding ELISA according to the following method.

96-well high binding plates were coated with 5 µg/ml human IL-4 (made at GSK) in NaHCO$_3$ and stored overnight at 4° C. The plates were washed twice with Tris-Buffered Saline with 0.05% of Tween-20 (TBST). 100 µL of blocking solution (1% BSA in TBST buffer) was added in each well and the plates were incubated for at least one hour at room temperature. The purified mAbdAbs were successively diluted across the plates in blocking solution. After one hour incubation, the plates were washed three times. Goat anti-human kappa light chain specific peroxidase conjugated antibody (Sigma A7164) was diluted in blocking solution to 1 µg/mL and 50 µL was added to each well. The plates were incubated for one hour. After another three washing steps, 50 µl of OPD (o-phenylenediamine dihydrochloride) SigmaFast substrate solution was added to each well and the reaction was stopped after about 5 minutes by addition of 25 µL of 3M sulphuric acid. Absorbance was read at 490 nm using the VersaMax Tunable Microplate Reader (Molecular Devices) using a basic endpoint protocol.

The experiment was carried out using mAbdAbs directly from tissue culture supernatants except for the positive control (anti-IL-4 mab) and the anti-IL13 negative control mAb, which were purified material.

These data are shown in FIG. 11. The results of the ELISA confirmed that these purified mAbdAbs bound to IL-4. The positive controls anti-IL-4 mAb and BPC2231 also showed binding to IL-4 whereas the negative control mAb (anti IL-13 mAb) showed no binding to IL-4. This indicated in this ELISA the dAb potency increased when the linker length was increased from GS(TVAAPSGS) to GS(TVAAPSGS)$_{2-4}$.

4.3 Neutralization of IL-4 in a TF-1 Cell Proliferation Bioassay

Purified BPC1085, BPC1086 and BPC1087 mAbdAbs were tested for neutralization of human IL-4 in a TF-1 cell bioassay.

TF-1 cells proliferate in response to a number of different cytokines including human IL-4. The proliferative response of these cells for IL-4 can therefore be used to measure the bioactivity of IL-4 and subsequently an assay has been developed to determine the IL-4 neutralisation potency (inhibition of IL-4 bioactivity) of mAbdAbs. The assay was performed in sterile 96-well tissue culture plates under sterile conditions and all test wells were performed in duplicate. Approximately 2.2 ng/ml recombinant *E. Coli*-expressed human IL-4 was pre-incubated with various dilutions of mAbdAbs (usually from 560 nM titrated in 3-fold dilutions to 0.009 nM) in a total volume of 120 µl for 1 hour at 37° C. An antibody of irrelevant specificity was similarly titrated as a negative control (anti-IL13 mAb). 50 µl of these samples were then added to 50 µl of TF-1 cells (at a concentration of $2\times10^5$ cells per ml) in a sterile 96-well tissue culture plate. Thus the final 100 µl assay volume contained various dilutions of mAbdAbs (at a final concentration of 270 nM titrated in 3-fold dilutions to 0.005 nM), recombinant *E. Coli*-expressed human IL-4 (at a final concentration of 1.1 ng/ml) and TF-1 cells (at a final concentration of $1\times10^5$ cells per ml). The assay plate was incubated at 37° C. for approximately 4 days in a humidified $CO_2$ incubator. The amount of cell proliferation was then determined using the 'CellTitre 96® Non-Radioactive Cell Proliferation Assay' from Promega (catalogue number G4100), as described in the manufacturers instructions. The absorbance of the samples in the 96-well plate was read in a plate reader at 570 nm. These data were entered on an Excel spreadsheet, values for duplicate test wells were averaged and the average background value (no mAb-dAb and no IL-4 test wells) was subtracted.

The capacity of the mAbdAbs to neutralise recombinant *E. Coli*-expressed human IL-4 bioactivity was expressed as that concentration of the mAb-dAb required to neutralise the bioactivity of the defined amount of human IL-4 (1.1 ng/ml) by 50% (=$ND_{50}$). The lower the concentration of the mAbdAb required, the more potent the neutralisation capacity. The $ND_{50}$ data provided herein (Table 4) were calculated using the Robosage function in Excel. These data are represented graphically in FIG. 12.

An anti-IL-4 mAb and DOM9-155-154 (SEQ ID NO: 26) were included as positive controls for neutralization of human and cynomolgus IL-4 in the TF-1 cell bioassays. Additionally, a dAb with specificity for an irrelevant antigen (dummy dAb) was also included as a negative control for neutralization of human or cynomolgus IL-4 in the TF-1 cell bioassays.

These were repeated several times and FIG. 12 shows the results for one of these experiments. $ND_{50}$ values were calculated from the dataset. The $ND_{50}$ value is the concentration of the mAbdAb or mAb or dAb, which is able to neutralise the bioactivity of IL-4 by 50%. The mean $ND_{50}$ value and the number of times tested (n) are shown in Table 4.

TABLE 4

| Molecule | Mean $ND_{50}$ value & standard deviation (nM) | Number of repeats |
|---|---|---|
| BPC1085 | 9.21 | 3 |
| BPC1086 | 4.32 | 3 |
| BPC1087 | 3.59 | 3 |
| Anti-IL-4 mAb | 1.95 | 2 |
| DOM9-155-154 | 0.98 | 2 |
| Negative control dAb | did not neutralise | 2 |

These data confirm that purified BPC1085, BPC1086 and BPC1087 mAbdAbs, neutralized the bioactivity of human and cyno IL-4. Anti-IL-4 mAb and DOM9-155-154 also neutralised the bioactivity of human and cynomolgus IL-4, whereas the negative dAb (dummy dAb) showed no neutralization in the same bioassay.

All three mAbdAbs show good potency, and there is a clear trend of increasing dAb potency with increasing linker length was apparent from the neutralisation assays, despite the more crude ELISA not picking up this difference in potency. A negative control anti-IL-4 mAb) showed no neutralization in the same bioassay.

4.4 Neutralization of Human IL-13 in a TF-1 Cell Proliferation Bioassay

Purified BPC1085, BPC1086 and BPC1087 mAbdAbs were tested for neutralization of human IL-13 in a TF-1 cell bioassay as described below.

TF-1 cells proliferate in response to a number of different cytokines including human IL-13. The proliferative response of these cells for IL-13 can therefore be used to measure the bioactivity of IL-13 and subsequently an assay has been developed to determine the IL-13 neutralisation potency (inhibition of IL-13 bioactivity) of mAbdAbs.

The assay was performed in sterile 96-well tissue culture plates under sterile conditions and all test wells were performed in duplicate. Approximately 14 ng/ml recombinant *E. Coli*-expressed human IL-13 was pre-incubated with various dilutions of mAbdAbs (usually from 560 nM titrated in 3-fold dilutions to 0.009 nM) in a total volume of 120 µl for 1 hour at 37° C. An antibody and dAb of irrelevant specificity was similarly titrated as negative controls (anti-IL-4 mAb & DOM9-155-154 respectively). 50 µl of these samples were then added to 50 µl of TF-1 cells (at a concentration of $2\times10^5$ cells per ml) in a sterile 96-well tissue culture plate. Thus the final 100 µl assay volume contained various dilutions of mAbdAbs (at a final concentration of 270 nM titrated in 3-fold dilutions to 0.005 nM), recombinant *E. Coli*-expressed human IL-13 (at a final concentration of 7 ng/ml) and TF-1 cells (at a final concentration of $1\times10^5$ cells per ml). The assay plate was incubated at 37° C. for approximately 4 days in a humidified $CO_2$ incubator. The amount of cell proliferation was then determined using the 'CellTitre 96® Non-Radioactive Cell Proliferation Assay' from Promega (catalogue number G4100), as described in the manufacturers instructions. The absorbance of the samples in the 96-well plate was read in a plate reader at 570 nm. These data were entered on an Excel spreadsheet, values for duplicate test wells were averaged and the average background value (no mAb-dAb and no IL-13 test wells) was subtracted.

The capacity of the mAbdAbs to neutralise recombinant *E. Coli*-expressed human IL-13 bioactivity was expressed as that concentration of the mAb-dAb required to neutralise the bioactivity of the defined amount of human IL-13 (7 ng/ml) by 50% (=$ND_{50}$). The lower the concentration of the mAbdAb required, the more potent the neutralisation capacity. The $ND_{50}$ data provided herein (Table 5) were calculated using the Robosage function in Excel. These data are represented graphically in FIG. 13.

An anti IL-13 mAb was included as a positive control for neutralization of human IL-13 in the TF-1 cell bioassays. Additionally, an anti-IL-4 mAb was also included as a negative control.

FIG. 13 shows the result of the TF-1 cell neutralization assay. $ND_{50}$ values were calculated from the dataset. The $ND_{50}$ value is the concentration of the mAbdAb or mAb or dAb, which is able to neutralise the bioactivity of IL-13 by 50%.

The mean $ND_{50}$ value and the number of times tested are shown in Table 5.

TABLE 5

| Molecule | Mean ND$_{50}$ value & standard deviation (nM) | Number of repeats |
|---|---|---|
| BPC1085 | 0.88 | 1 |
| BPC1086 | 1.01 | 1 |
| BPC1087 | 1.14 | 1 |
| Anti-IL-13 mAb | 5.01 | 1 |
| Anti-IL-4 mAb | did not neutralise | 1 |

These data confirm that purified BPC1085, BPC1086 and BPC1087 mAbdAbs, neutralized the bioactivity of recombinant human and cyno IL-13. A negative control anti-IL-4 mAb showed no neutralization in the same bioassay.

Example 5 mAbdAbs Comprising the DOM10-53-616 dAb 5.1 Expression Analysis of Anti-IL13 mAb-Anti-IL4 dAb Heavy and light chain expression plasmids encoding for BPC2202, BPC2203, BPC2209 and BPC2210 as described in Example 1 were co-transfected into HEK 2936E cells using 293fectin (Invitrogen, 12347019) and expressed at small scale to produce antibody molecules. Molecules were assessed directly from the tissue culture supernatant and were quantified using the Gyrolab workstation.

BPC2202, BPC2203, BPC2209 and BPC2210 all expressed well.

We attempted to make equivalent mAbdAbs using an alternative anti-IL-13 dAb sequence (DOM10-176-535—SEQ ID NO: 97). However on expression, these molecules were highly aggregated, so no there was not enough material to use for further testing.

5.2 Stressor Studies of mAbdAbs Comprising the DOM10-53-616

BPC2202, BPC2203, BPC2209, BPC2210 were placed in PBS or 50 mM acetate buffer and incubated at 37° C. for up to 14 days. They were then analysed for the presence of a visual precipitate, soluble aggregate and maintenance of the concentration of the molecule in solution.

Subsequent analysis indicated that in both PBS and acetate solutions there was a reduction in protein concentration in solution for these molecules, this was thought to be due to adsorbtion of the protein onto the eppendorf tube walls.

BPC2210 also exhibited a reduction in protein concentration in the acetate buffer solution, but had a slight increase in protein concentration after two weeks incubation in the PBS solution (and this may have been due to bacterial contamination).

Example 6

Design and Construction of Anti-IL4/Anti-TNFα mAb-dAb Constructs with Various Linker Lengths An anti-TNFα dAb DNA sequence was generated by PCR using overlapping oligonucleotide primers. The PCR product was cloned into a mammalian expression vector containing the heavy chain of an anti-IL4 antibody, allowing the anti TNFα dAb to be fused onto the C-terminus of the heavy chain via a TVAAPSGS linker (SEQ ID NO. 103 and 104, DNA and protein sequences of the heavy chain of BPC2626). The heavy chain of BPC2626 was also used as base construct to clone different linkers (TVAAPSGSx2, TVAAPSGSx3, TVAAPSGSx4) and generate the heavy chains of BPC2651, BPC2652 and BPC2653 respectively (SEQ ID. NO: 106 and 107, 108 and 109, 110 and 111, DNA and protein sequences of BPC2651, BPC2652 and BPC2653 respectively).

Expression plasmids encoding the heavy and corresponding light chains of BPC2626, BPC2651, BPC2652 and BPC2653 were transiently co-transfected into HEK 293-6E cells using 293 fectin (Invitrogen, 12347019). A tryptone feed was added to each cell culture 24 hours after transfection, and the cells were harvested after 3 to 7 days. The mAbdAbs were purified using a Protein A column before being assessed for activity. The constructs made and expressed are set out in Table 6.

TABLE 6

| ANTIBODY ID | DESCRIPTION | SEQ ID NO: Polynucleotide sequence | SEQ ID NO: Amino acid sequence |
|---|---|---|---|
| BPC2626 | PascoH-TVAAPSGS-PEP1-5-19 Heavy Chain | 104 | 103 |
|  | Light Chain | 3 | 105 |
| BPC2651 | PascoH-GS(TVAAPSGS)$_2$- PEP1-5-19 Heavy Chain | 106 | 107 |
|  | Light Chain | 3 | 105 |
| BPC2652 | PascoH-GS(TVAAPSGS)$_3$- PEP1-5-19 Heavy Chain | 108 | 109 |
|  | Light Chain | 3 | 105 |
| BPC2653 | PascoH-GS(TVAAPSGS)$_4$- PEP1-5-19 Heavy Chain | 110 | 111 |
|  | Light Chain | 3 | 105 |

6.1 TNFα Binding ELISA 96-well high binding plates were coated with 1 µg/ml of TNFα (R&D Systems, 210-TA-010/CF) in Phosphate-Buffered Saline and stored overnight at 4° C. The plates were washed three times with Tris-Buffered Saline containing 0.05% of Tween-20. 100 µL of blocking solution (1% BSA in Tris-Buffered Saline containing 0.05% of Tween-20 buffer) was added in each well and the plate was incubated for at least 1 hour at room temperature. Another wash step was then performed. Purified bispecific antibodies and a negative control antibody were successively diluted across the plates in blocking solution. After 1 hour incubation, the plates were washed. Goat anti-human kappa light chain specific peroxidase conjugated antibody H23 (Sigma, A7164) was diluted in blocking solution to 1 µg/mL and 50 µL was added to each well. The plates were incubated for one hour. After another wash step, 50 µl of OPD (o-phenylenediamine dihydrochloride) SigmaFast substrate solution was added to each well and the reaction was stopped 15 minutes later by addition of 25 µL of 3M sulphuric acid. Absorbance was read at 490 nm using the VersaMax Tunable Microplate Reader (Molecular Devices) using a basic endpoint protocol.

FIG. 14 shows the results of the TNFα binding ELISA and confirms that BPC2626, BPC2651, BPC2652 and BPC2653 bound to TNFα with an increase in the binding activity correlated to increased linker lengths. The negative control antibody did not show binding to the target. A trend of increasing dAb potency with increasing linker length was observed.

6.2—IL4 Binding ELISA

These constructs were tested for binding to IL-4 and because of a technical issue with the assay the only conclusion we can draw is that they all bound.

Example 7

Binding Affinity of mAbsdAbs with Varying Linker Length (BPC2221-2231) for IL-13 and IL-4 as Assessed by BIAcore™ Analysis Method Anti Human IgG (GE Healthcare/Biacore) was immobilised on a CM5 chip by primary amine coupling; this surface was used as a capture surface for the antibody molecules to be tested. Recombinant *E. coli*-expressed Human IL4 and human IL13 were used at 256, 64, 16, 4 and 1 nM, with 0 nM (i.e. buffer alone) used to double reference the binding curves. Regeneration the anti-human IgG surface was with an injection of 100 mM Phosphoric acid followed by an injection of 3M $MgCl_2$. The assay was run at 25° C. using HBS-EP as running buffer. The data was fitted to 1:1 model inherent to the Biacore T100 analysis software.

The results of binding to human IL13 are shown in Table 7 and the result of binding to human IL4 are shown in Table 8.

TABLE 7

| Molecule name | ka (M/s) | kd (1/s) | KD (nM) |
|---|---|---|---|
| BPC2221 | 1.049E+6 | 3.441E−4 | 0.328 |
| BPC2222 | 1.108E+6 | 3.543E−4 | 0.320 |
| BPC2223 | 1.410E+6 | 4.012E−4 | 0.285 |
| BPC2224 | 1.156E+6 | 3.053E−4 | 0.264 |
| BPC2225 | 1.178E+6 | 3.336E−4 | 0.283 |
| BPC2226 | 1.105E+6 | 2.997E−4 | 0.271 |
| BPC2227 | 1.082E+6 | 3.261E−4 | 0.301 |
| BPC2228 | 1.071E+6 | 3.364E−4 | 0.314 |
| BPC2229 | 1.066E+6 | 3.307E−4 | 0.310 |
| BPC2230 | 1.067E+6 | 3.316E−4 | 0.311 |
| BPC2231 | 1.099E+6 | 3.454E−4 | 0.314 |

TABLE 8

| Molecule name | ka (M/s) | kd (1/s) | KD (nM) |
|---|---|---|---|
| BPC2221 | 7.268E+4 | 3.444E−4 | 4.74 |
| BPC2222 | 5.723E+4 | 4.774E−4 | 8.34 |
| BPC2223 | 5.856E+6 | 8.860E−8 | 0.00002 |
| BPC2224 | 2.414E+4 | 7.553E−4 | 31.3 |
| BPC2225 | 4.811E+4 | 3.498E−5 | 0.727 |
| BPC2226 | 4.212E+6 | 3.253E−6 | 0.0008 |
| BPC2227 | 1.573E+5 | 2.552E−4 | 1.62 |
| BPC2228 | 3.199E+5 | 1.646E−4 | 0.515 |
| BPC2229 | 3.457E+4 | 2.150E−4 | 6.22 |
| BPC2230 | 2.835E+4 | 3.576E−4 | 12.6 |
| BPC2231* | 5.342E+6 | 7.332E−6 | 0.001 |

*Impossible off-rate, unable to analyse, very tight binding
**Actual kinetic values likely to be worse than calculated due to poor fitting for BPC2229

Overall run quality was poor for IL4 binding, the analysis was complicated by the fact that at highest concentrations there was non-specific binding to the chip surface Example 8

Binding Affinity of mAbdabs Comprising the 616 dAb for IL-13 and IL-4 as Assessed by BIAcore™ Analysis mAbdAbs BPC2201-2215, BPC2217-2220 and BPC2243, each of which comprise the DOM10-53-616 anti-IL-13 domain antibody (SEQ ID NO:1) were tested by BIAcore. All mAbdAbs bound to both IL-13 and IL-4 but they bound so tightly that off rates were impossible to measure.

Example 9

Binding Affinity of mAbdAbs with Varying Linker Length (BPC2211-2231 & BPC2234-2237 & BPC2241-2242) for IL-13 and IL-4 as Assessed by BIAcore™ Analysis Method Anti Human IgG (GE Healthcare/Biacore) was immobilised on a CM5 chip by primary amine coupling; this surface was used as a capture surface for the antibody molecules to be tested. Recombinant *E. coli*-expressed human IL4 was used at 256, 64, 16, 4 and 1 nM and Recombinant *E. coli*-expressed human IL13 used at 256 nM only, with 0 nM (i.e. buffer alone) used to double reference the binding curves of both IL4 and IL13 binding. Regeneration of the anti-human IgG surface was with an injection of 100 mM Phosphoric acid followed by an injection of 3M $MgCl_2$. The assay was run at 25° C. using HBS-EP as running buffer. The data was fitted to 1:1 model inherent to the Biacore T100 analysis software.

The results of binding to human IL13 and human IL4 are shown in Table 9.

TABLE 9

| Molecule name/analyte | ka (M/s) | kd (1/s) | KD (nM) | Quality of data |
|---|---|---|---|---|
| BPC2221/IL4 | 7.07E+04 | 5.92E−04 | 8.368 | Ok |
| BPC2221/IL13 | 1.29E+06 | 4.52E−04 | 0.350 | Yes |
| BPC2222/IL4 | 6.52E+04 | 1.29E−04 | 1.980 | Ok |
| BPC2222/IL13 | 2.13E+06 | 6.04E−04 | 0.284 | Ok |
| BPC2223/IL4 | 1.30E+07 | 1.07E−04 | 0.008 | No |
| BPC2223/IL13 | 1.38E+06 | 4.51E−04 | 0.327 | Yes |
| BPC2224/IL4 | 2.52E+04 | 1.55E−03 | 61.370 | Ok |
| BPC2224/IL13 | 1.43E+06 | 4.74E−04 | 0.332 | Yes |
| BPC2225/IL4 | 5.78E+04 | 1.11E−04 | 1.912 | Ok |
| BPC2225/IL13 | 1.40E+06 | 4.77E−04 | 0.341 | Yes |
| BPC2226/IL4 | 2.86E+04 | 1.44E−03 | 50.130 | Ok |
| BPC2226/IL13 | 1.37E+06 | 4.55E−04 | 0.333 | Yes |
| BPC2227/IL4 | 2.07E+05 | 3.05E−04 | 1.476 | Ok |
| BPC2227/IL13 | 1.30E+06 | 4.68E−04 | 0.360 | Yes |

TABLE 9-continued

| Molecule name/analyte | ka (M/s) | kd (1/s) | KD (nM) | Quality of data |
|---|---|---|---|---|
| BPC2228/IL4 | 4.24E+05 | 2.28E−04 | 0.539 | Ok |
| BPC2228/IL13 | 1.40E+06 | 4.82E−04 | 0.344 | Yes |
| BPC2229/IL4 | 3.17E+04 | 8.28E−04 | 26.080 | Ok |
| BPC2229/IL13 | 1.36E+06 | 4.71E−04 | 0.347 | Yes |
| BPC2230/IL4 | 1.86E+07 | 1.92E−04 | 0.010 | Ok |
| BPC2230/IL13 | 1.34E+06 | 4.51E−04 | 0.336 | Yes |
| BPC2231/IL4 | 1.92E+07 | 2.54E−04 | 0.013 | Ok |
| BPC2231/IL13 | 1.34E+06 | 4.67E−04 | 0.348 | Yes |
| BPC2234/IL4 | 2.73E+05 | 8.49E−05 | 0.312 | Ok |
| BPC2234/IL13 | 1.45E+06 | 4.49E−04 | 0.310 | Yes |
| BPC2235/IL4 | 9.71E+05 | 9.32E−05 | 0.096 | Ok |
| BPC2235/IL13 | 1.43E+06 | 4.72E−04 | 0.331 | Yes |
| BPC2236/IL4 | 5.46E+06 | 9.23E−05 | 0.017 | Ok |
| BPC2236/IL13 | 1.40E+06 | 4.73E−04 | 0.339 | Yes |
| BPC2237/IL4 | 2.06E+05 | 2.80E−04 | 1.359 | Ok |
| BPC2237/IL13 | 1.36E+06 | 4.42E−04 | 0.326 | Yes |
| BPC2241/IL4 | 6.17E+05 | 2.40E−04 | 0.389 | Ok |
| BPC2241/IL13 | 1.43E+06 | 4.37E−04 | 0.306 | Yes |
| BPC2242/IL4 | 3.45E+06 | 2.17E−04 | 0.063 | Ok |
| BPC2242/IL13 | 1.43E+06 | 4.57E−04 | 0.321 | Yes |

Some non-specific binding was seen with the highest concentrations of recombinant *E. coli*-expressed human IL4, which affected the quality of the data Example 10

Binding Affinity of mAbdAbs Comprising the Original IL-13 mAb CDRH3 with Varying Linker Lengths (BPC2222, BPC2223 & BPC2230-2231) for IL-13 and IL-4 as Assessed by BIAcore™ Analysis Method Protein A was immobilised on a C1 chip by primary amine coupling; this surface was used as a capture surface for the antibody molecules to be tested. Recombinant *E. coli*-expressed human IL13 was used at 256, 64, 16, 4, and 1 nM, recombinant *E. coli*-expressed human IL4 was used at 64, 16, 4, 1 and 0.25 nM, with 0 nM (i.e. buffer alone) used to double reference the binding curves of both IL4 and IL13 binding. Regeneration the Protein A surface was with 100 mM Phosphoric acid. The assay was run at 25° C. using HBS-EP as running buffer. The data was fitted to 1:1 model inherent to the Biacore T100 analysis software.

The results of binding to human IL13 are shown in Table 10 and the result of binding to human IL4 are shown in Table 11.

TABLE 10

| Molecule name | ka(M/s) | kd(1/s) | KD (nM) |
|---|---|---|---|
| BPC2222 | 1.31E+06 | 4.93E−04 | 0.376 |
| BPC2223 | 1.32E+06 | 4.90E−04 | 0.372 |
| BPC2230 | 1.31E+06 | 4.88E−04 | 0.373 |
| BPC2231 | 1.30E+06 | 5.13E−04 | 0.394 |

TABLE 11

| Molecule name | ka(M/s) | kd(1/s) | KD (nM) |
|---|---|---|---|
| BPC2222 | 1.06E+05 | 1.09E−04 | 1.027 |
| BPC2223 | 8.59E+06 | 1.56E−04 | 0.018 |
| BPC2230* | 2.48E+07 | 2.48E−04 | 0.010 |
| BPC2231* | 4.03E+07 | 2.31E−04 | 0.006 |

*The on-rate for BPC2230 and 2231 are beyond the sensitivity of Biacore, but the fact that we cannot accurately analyse this data does indicate that the interaction with IL4 is likely to be of high affinity with a fast on-rate.

Example 11

Binding Affinity of mAbdAbs Comprising the Original IL-13 mAb CDRH3 with Varying Linker Lengths (BPC2222, BPC2231) & Variant Anti-IL-13 mAb CDRH3 with Varying Linker Lengths (BPC1085-1087) for IL-13 and IL-4 as Assessed by BIAcore™ Analysis Method Protein A was immobilised on a CM5 chip by primary amine coupling; this surface was used as a capture surface for the antibody molecules to be tested. Recombinant *E. coli*-expressed human IL13 was used at 256 nM only, Recombinant *E. coli*-expressed human IL4 was used at 64, 16, 4 and 1 nM, with 0 nM (i.e. buffer alone) used to double reference the binding curves for both IL4 and IL13 binding. Regeneration the Protein A surface was with 50 mM NaOH. The assay was run at 25° C. using HBS-EP as running buffer. The data was fitted to 1:1 model inherent to the Biacore T100 analysis software.

The results of binding to human IL13 are shown in Table 12, and the results of binding to human IL4 are shown in Table 13.

TABLE 12

| Molecule name | ka(M/s) | kd(1/s) | KD (nM) |
|---|---|---|---|
| BPC2222 | 1.64E+05 | 5.15E−05 | 0.314 |
| BPC2231 | 5.36E+08 | 1.16E−03 | 0.002 |
| BPC1085 | 1.87E+07 | 8.97E−04 | 0.048 |
| BPC1086 | 7.99E+07 | 1.64E−03 | 0.021 |
| BPC1087 | 9.86E+07 | 1.79E−03 | 0.018 |

On-rate for BPC1086 and BPC1087 are beyond the sensitivity of Biacore, but the fact that we cannot accurately analyse this data does indicate that the interaction with IL4 is likely to be of high affinity with a fast on-rate.

TABLE 13

| Molecule name | ka(M/s) | kd(1/s) | KD (nM) |
|---|---|---|---|
| BPC2222 | 1.44E+06 | 4.44E−04 | 0.308 |
| BPC2231 | 1.56E+06 | 4.95E−04 | 0.316 |
| BPC1085 | 1.20E+06 | 6.39E−05 | 0.053 |
| BPC1086 | 1.28E+06 | 6.57E−05 | 0.051 |
| BPC1087 | 1.13E+06 | 6.42E−05 | 0.057 |

Example 12

Stressor Studies of mAbdAbs

A number of mAbdAbs were placed in PBS or 50 mM acetate buffer and incubated at 37° C. for up to 14 days. They were then analysed for presence of a visual precipitate, soluble aggregate and maintenance of the concentration of the molecule in solution.

The results indicate that the mAbdAbs comprising the mutated dAb (BPC1085, 1086, 1087) behaved similarly to the non-mutated dAb (BPC2222, 2223, 2230, 2231) both categories of mAbdAb appeared to be stable in both PBS and acetate buffers over the two week incubation period at 37° C., as indicated by no change in the protein concentration in the solutions. In addition none or very little change was noted for the levels of aggregates in the solutions and no precipitation was observed.

Example 13

Effect of Linker Length on Rat and Cyno PK

The pharmacokinetics of BPC1085, BPC1086, and BPC1087 were investigated in separate studies following IV administration to rats. The PK of BPC1085 was also investigated in cynomologus monkeys following IV administration.

The PK of all three molecules in rat and BPC1085 in monkey were found to be consistent with that of a standard mAb.

Example 14

A panel of mAbdabs to a different target with a number of differing length linkers were expressed. Uncharacterised supernatants were put through some ELISA binding experiments and these preliminary results indicate similar trends to those described herein across different linker lengths.

A second panel of mAbdabs to a different target with a number of differing length linkers were expressed. Uncharacterised supernatants were put through some ELISA binding experiments and these preliminary results indicate variability across different dAbs and linker lengths.

TABLE 14

Sequence listing

Figure 1:
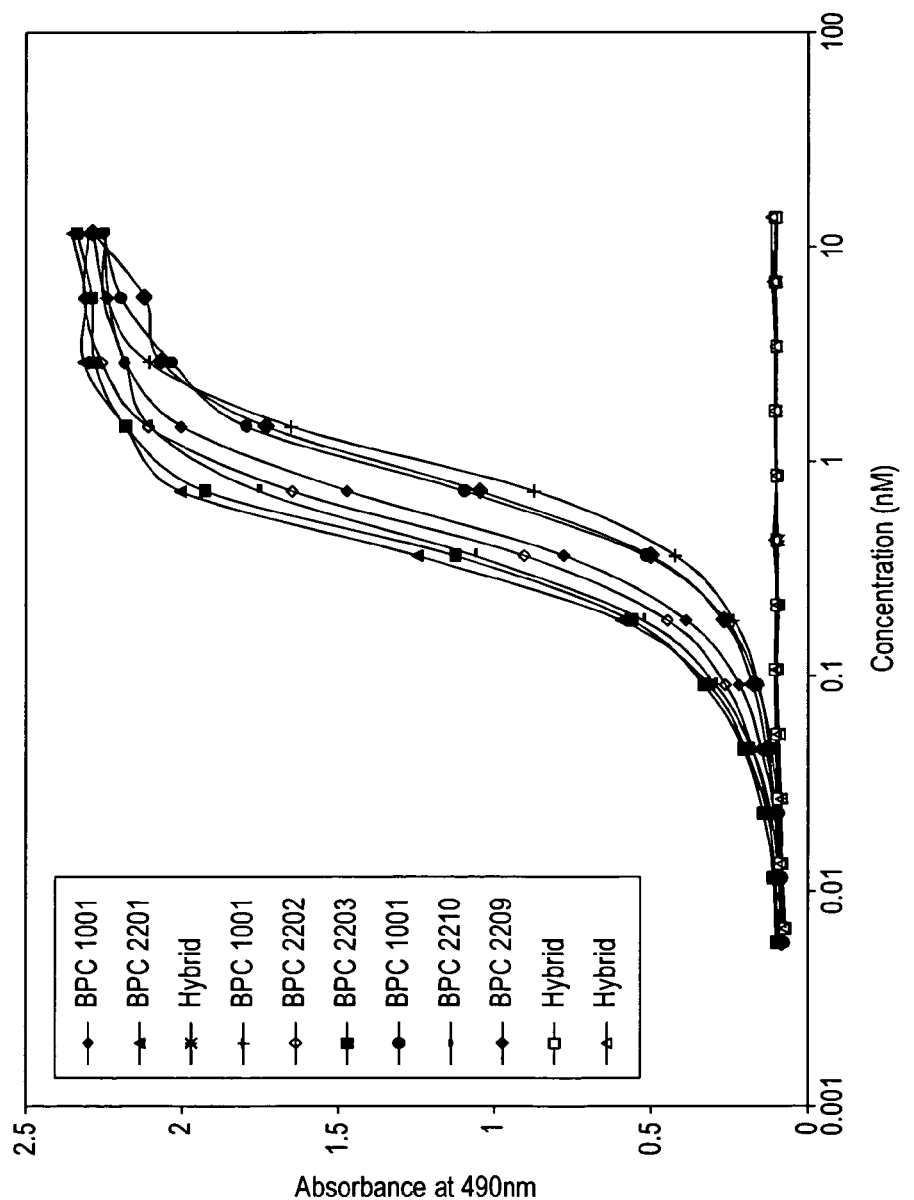
FIG. 1: A graph showing binding of purified bispecific antigen binding proteins with GS and GS(TVAAPSGS)$_{n=1-4}$ linker (BPC 2201, 2202, 2203, 2209 and BPC 2210) to human IL-4 as determined by ELISA.
Figure 2:
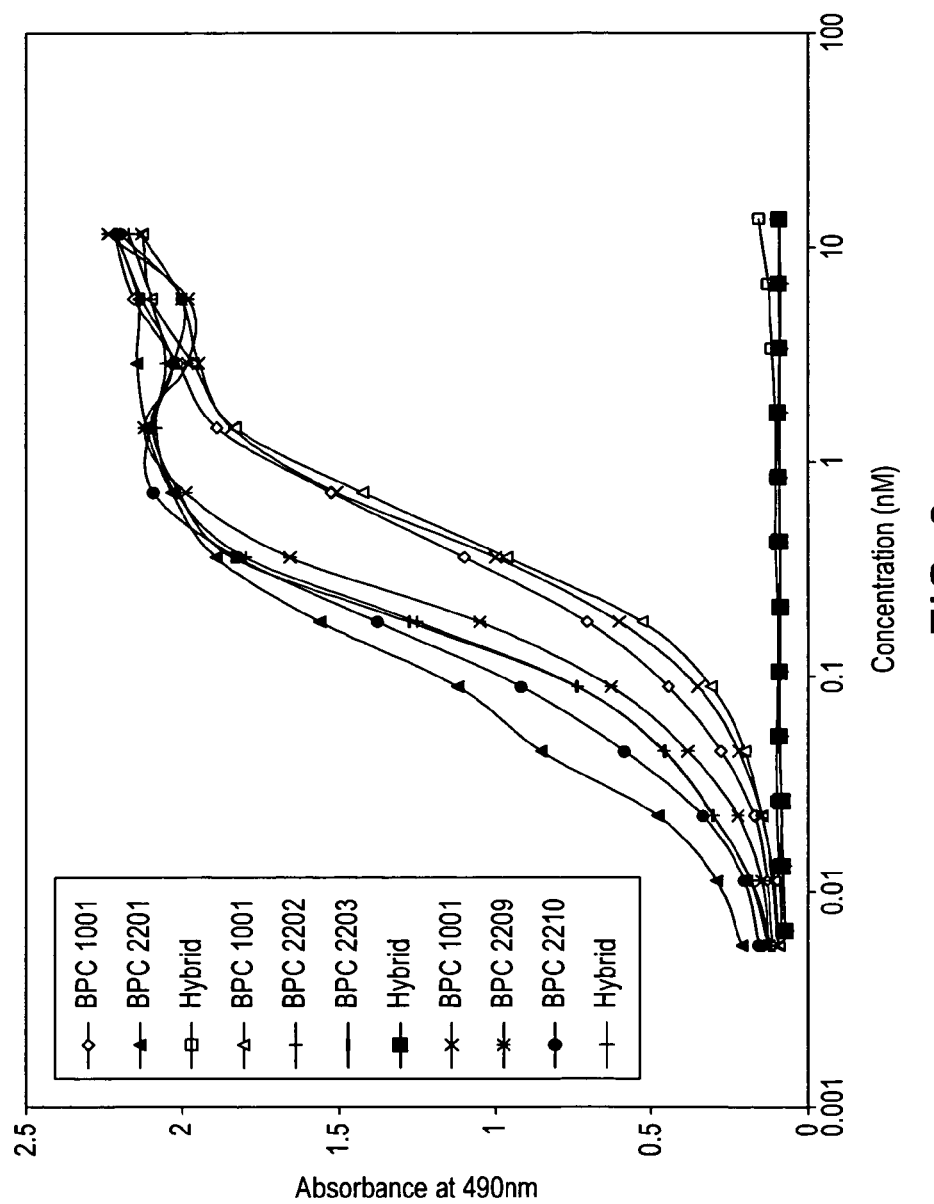
FIG. 2: A graph showing binding of purified bispecific antigen binding proteins with GS and GS(TVAAPSGS)$_{n=1-4}$ linker (BPC 2201, 2202, 2203, 2209 and BPC 2210) to human IL-13 as determined by ELISA.
Figure 3:
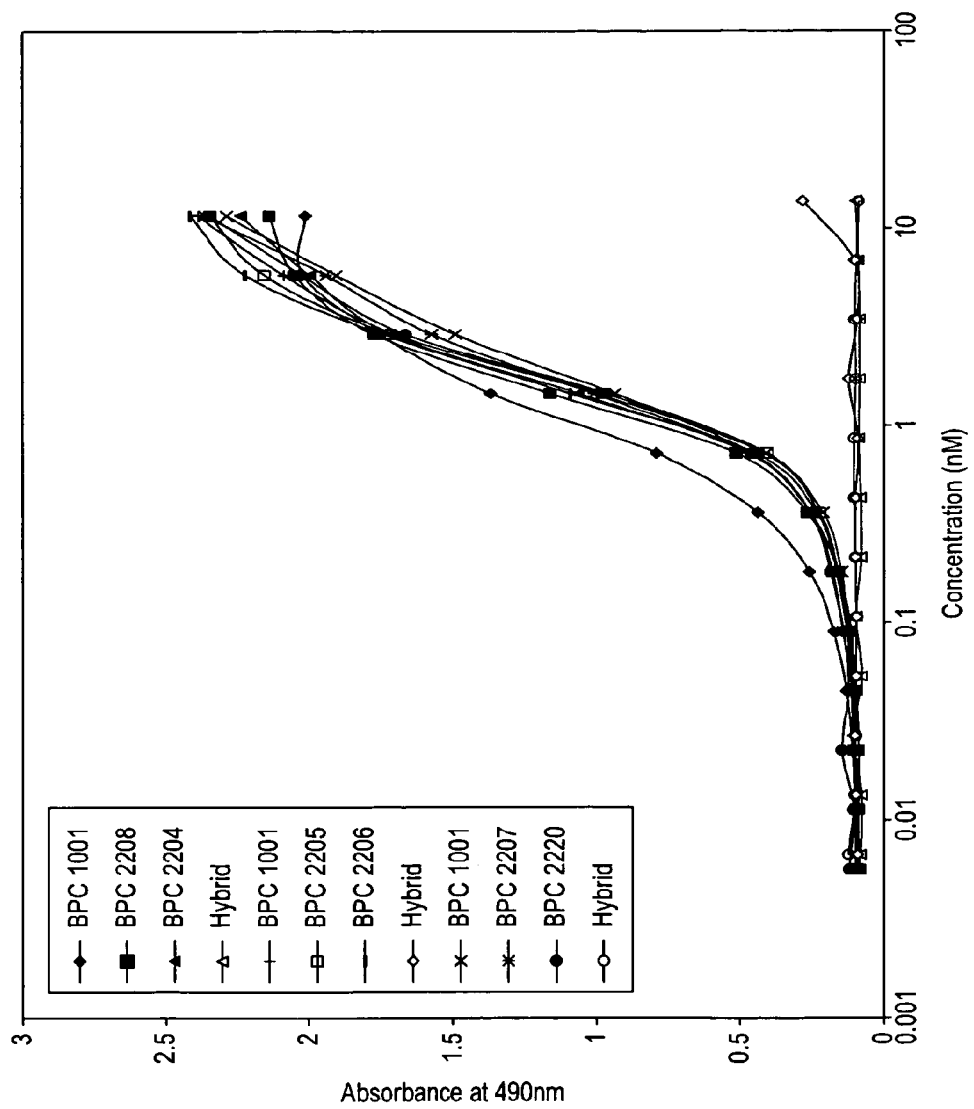
FIG. 3: A graph showing binding of purified bispecific antigen binding proteins with (PAS)$_{n=1-3}$GS and (G$_4$S)$_{n=1-3}$ linkers (BPC 2204 to BPC 2208 and BPC 2220) to human IL-4 as determined by ELISA.
Figure 4:
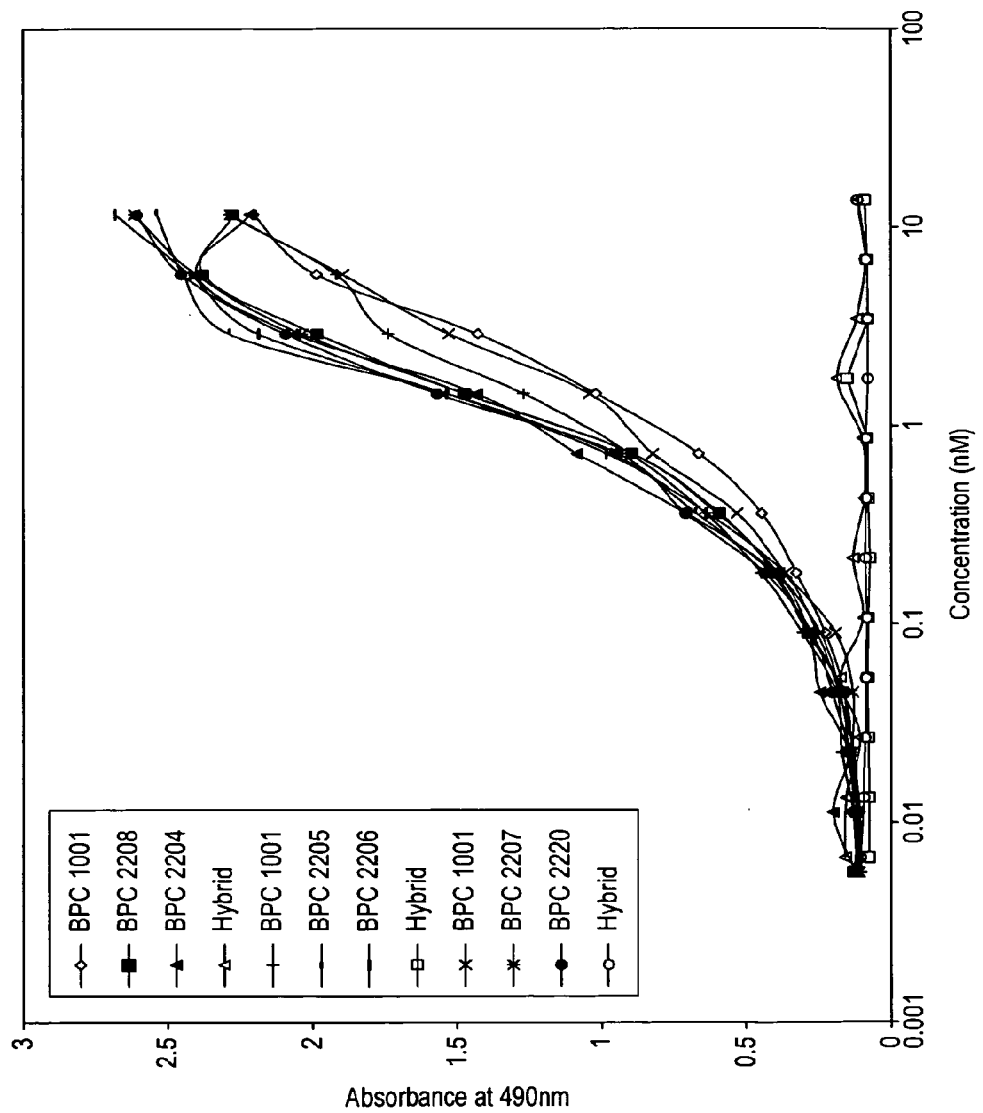
FIG. 4: A graph showing binding of purified bispecific antigen binding proteins with (PAS)$_{n=1-3}$GS and (G$_4$S)$_{n=1-3}$ linkers (BPC 2204 to BPC 2208 and BPC 2220) to human IL-13 as determined by ELISA.
Figure 5:
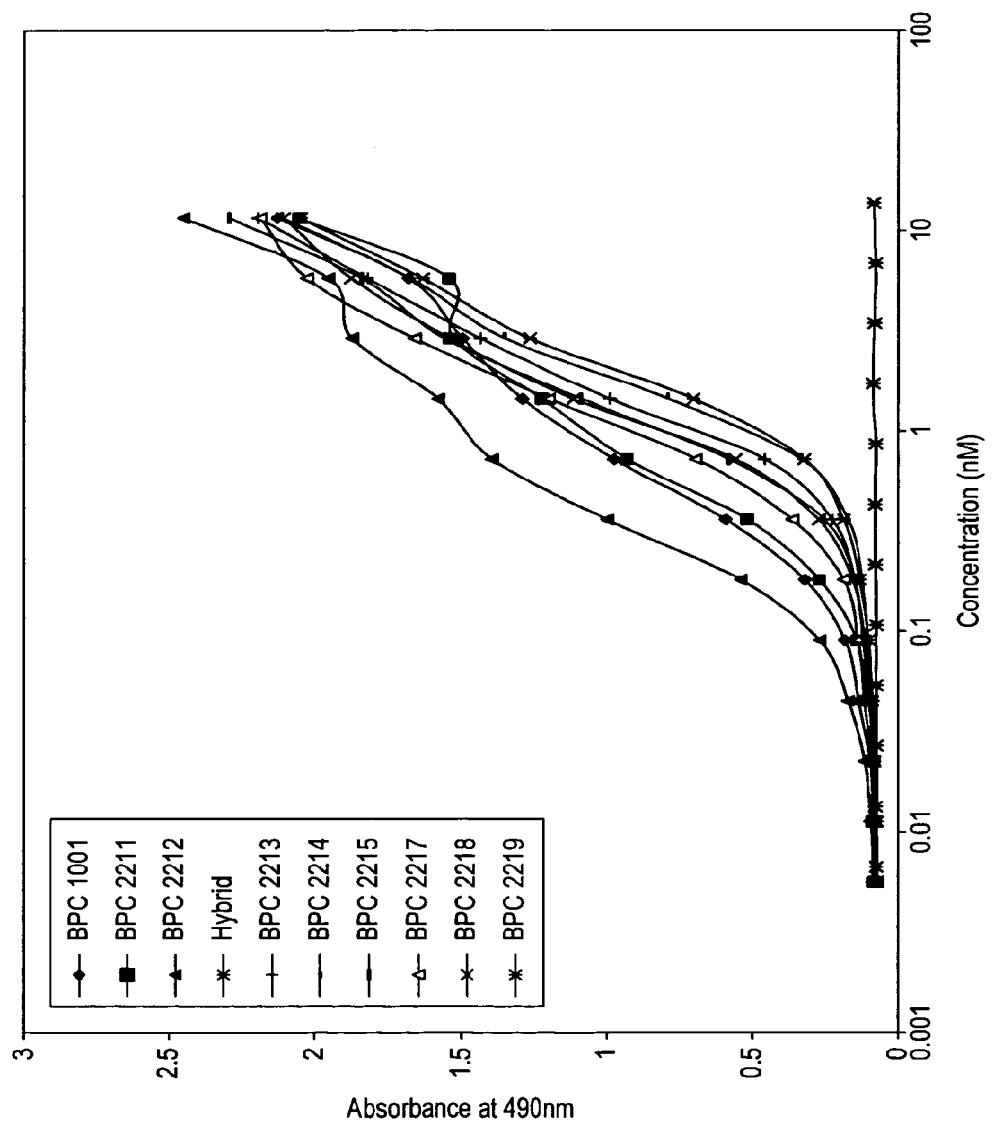
FIG. 5: A graph showing binding of purified bispecific antigen binding proteins with (PAVPPP)$_{n=1-3}$GS, (TVSDVP)$_{n=1-2}$GS and (TGLDSP)$_{n=1-3}$GS linkers (BPC 2211 to BPC 2215 and BPC 2217 to BPC 2219) to human IL-4 as determined by ELISA.
Figure 6:
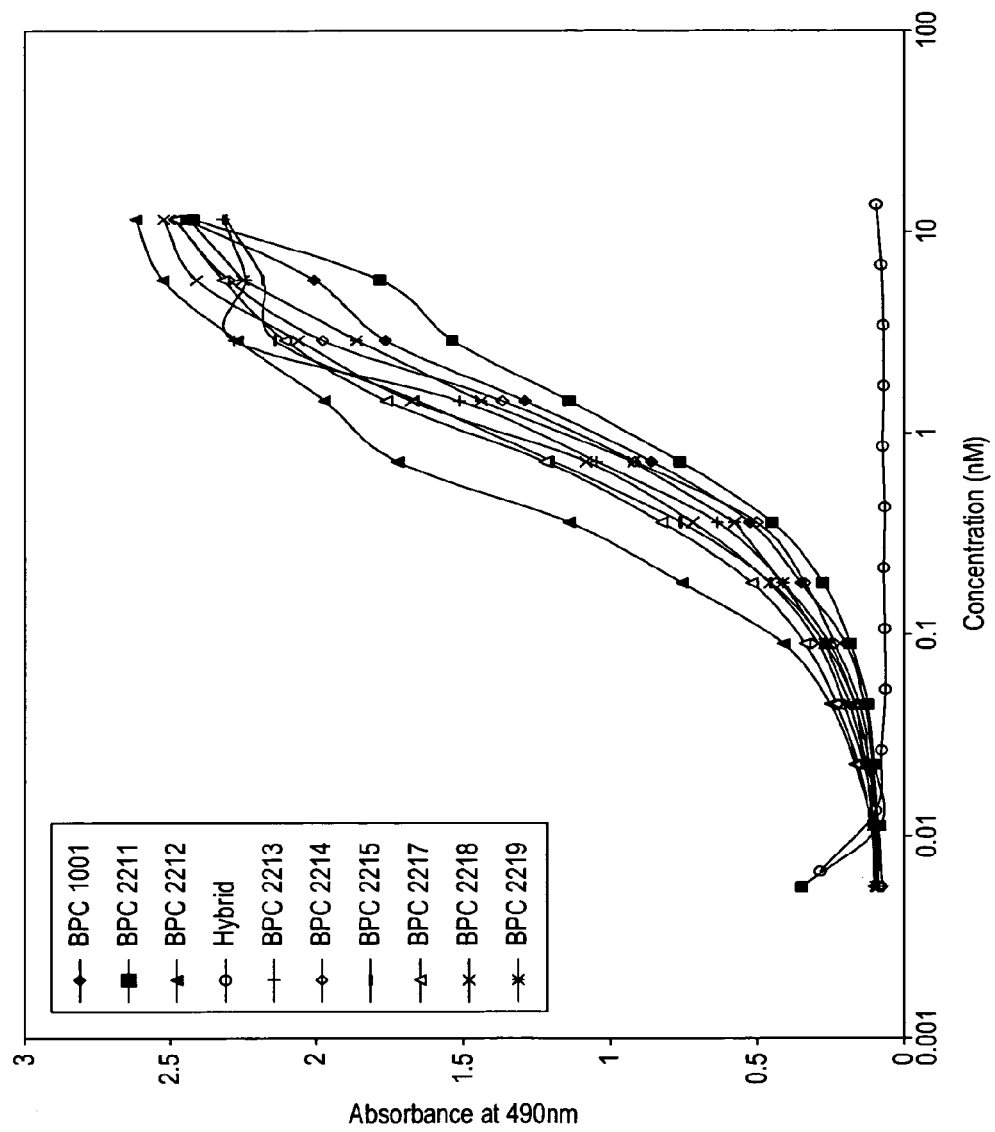
FIG. 6: A graph showing binding of purified bispecific antigen binding proteins with (PAVPPP)$_{n=1-3}$GS, (TVSDVP)$_{n=1-2}$GS and (TGLDSP)$_{n=1-3}$GS linkers (BPC 2211 to BPC 2215 and BPC 2217 to BPC 2219) to human IL-13 as determined by ELISA.
Figure 7:
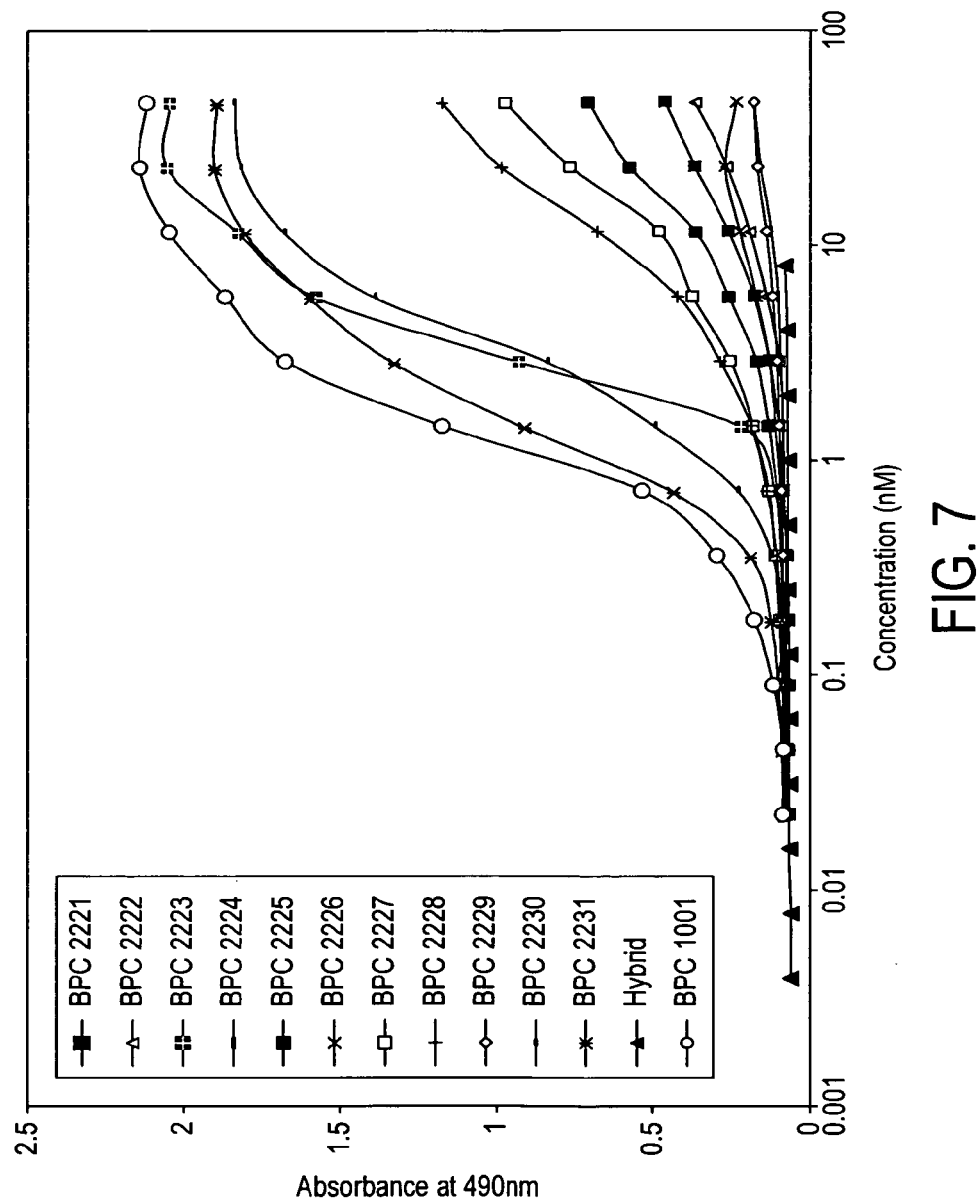
FIG. 7: A graph showing binding of purified bispecific antigen binding proteins with GS and GS(TVAAPSGS)$_{n=1-4}$, (PAS)$_{n=1-3}$GS and (G$_4$S)$_{n=1-3}$ linker (BPC 2221 to BPC 2231) to human IL-4 as determined by ELISA.
Figure 8:
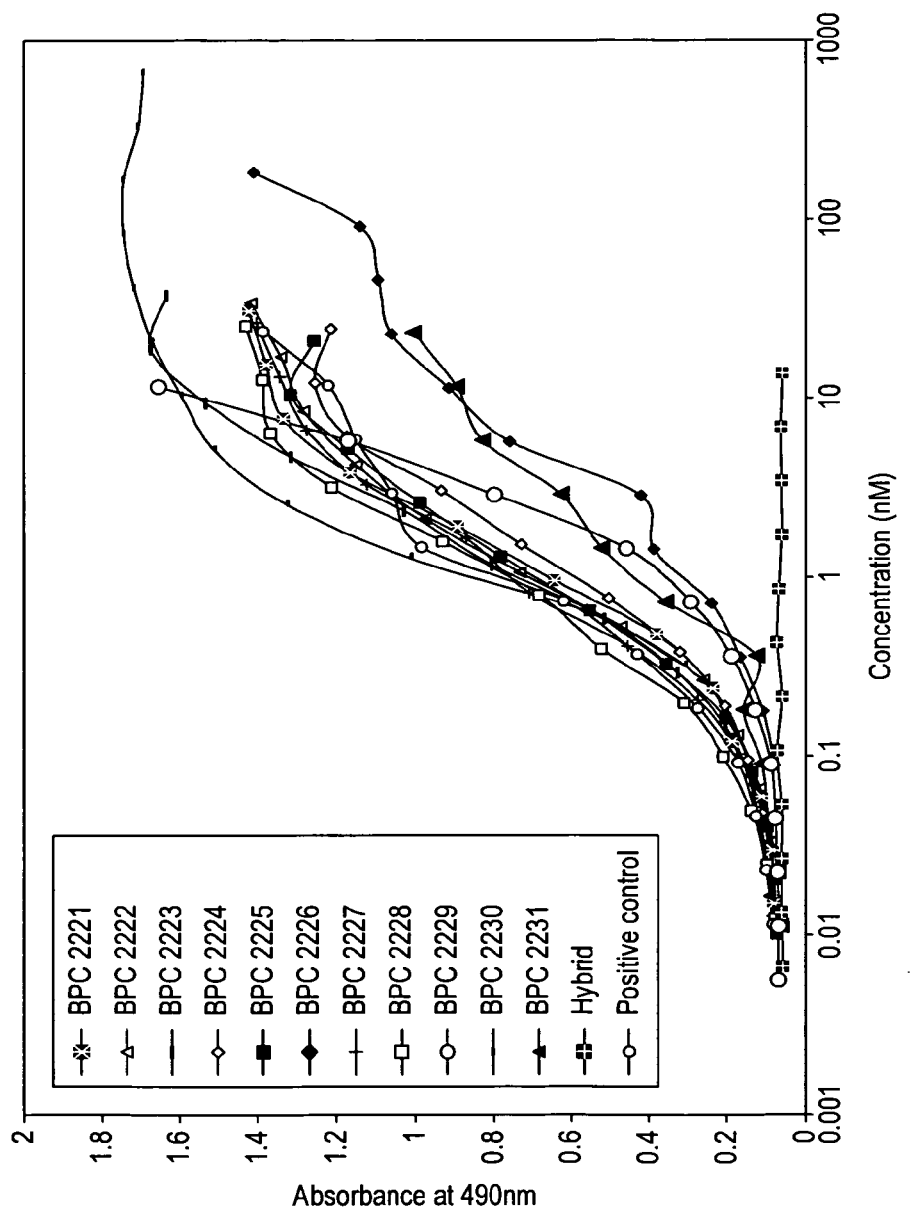
FIG. 8: A graph showing binding of purified bispecific antigen binding proteins with GS and GS(TVAAPSGS)$_{n=1-4}$, (PAS)$_{n=1-3}$GS and (G$_4$S)$_{n=1-3}$ linker (BPC 2221 to BPC 2231) to human IL-13 as determined by ELISA.
Figure 9:
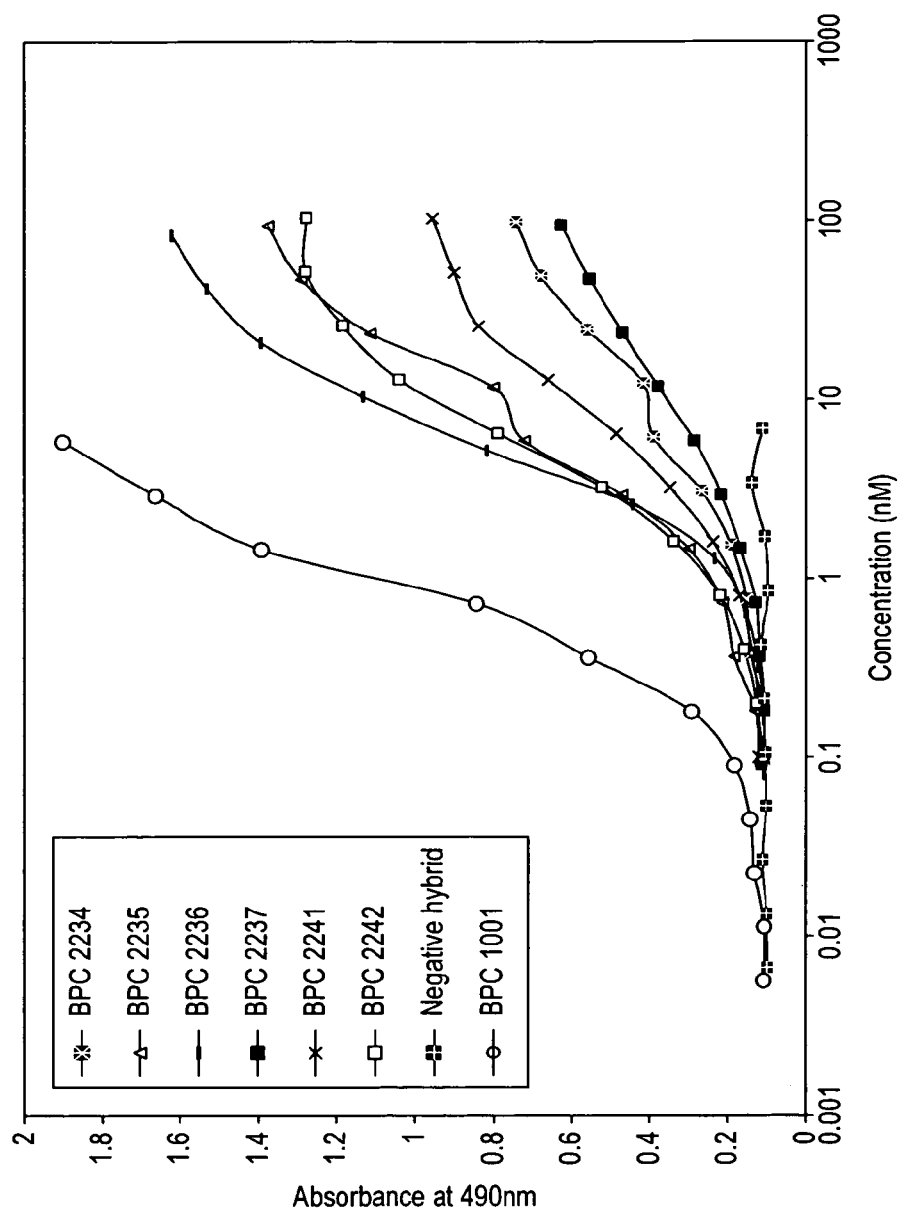
FIG. 9: A graph showing binding of purified bispecific antigen binding proteins with (PAVPPP)$_{n=1-3}$GS and TVSDVPGS and (TGLDSP)$_{n=2-3}$GS linkers (BPC 2234 to BPC 2237, BPC 2241 and BPC 2242) to human IL-4 as determined by ELISA.
Figure 10:
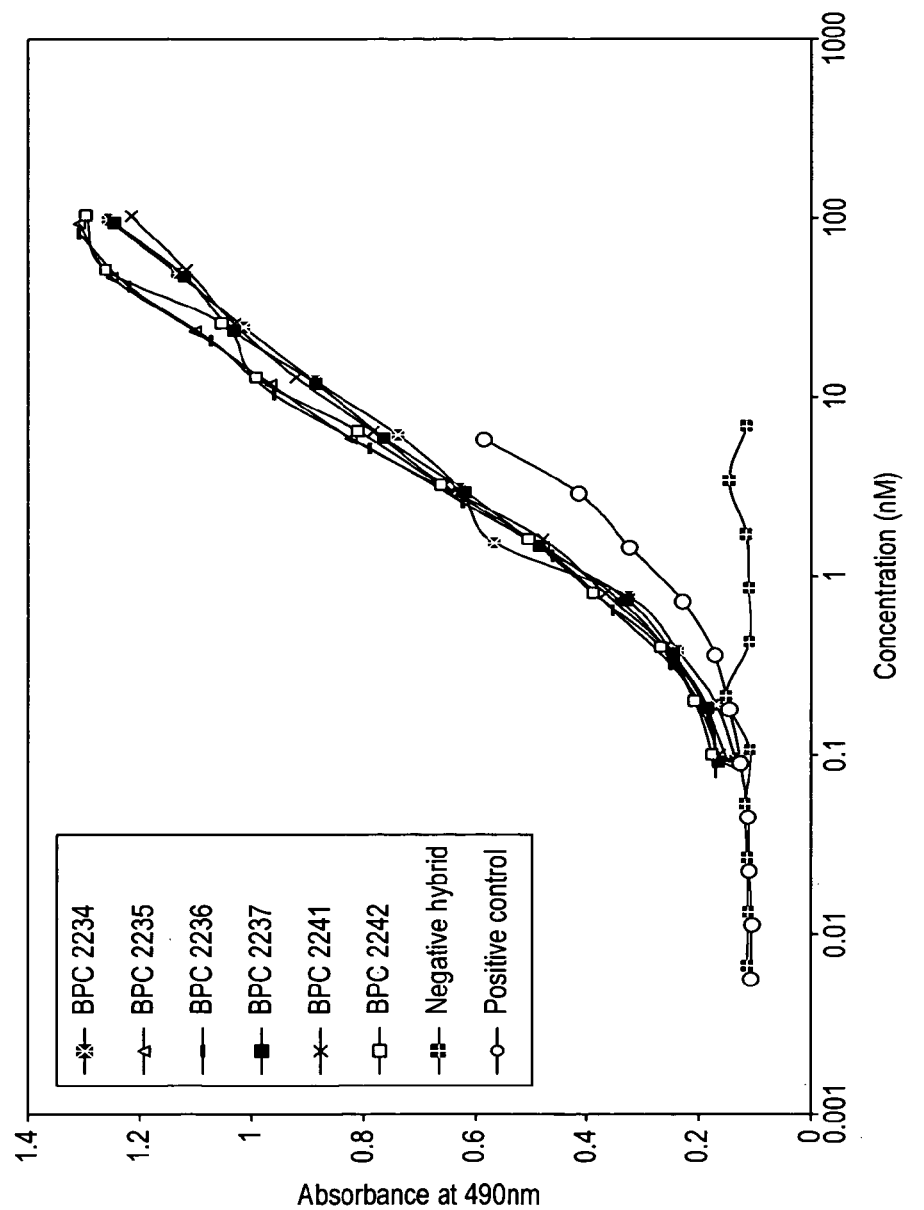
FIG. 10: A graph showing binding of purified bispecific antigen binding proteins with (PAVPPP)$_{n=1-3}$GS and TVSDVPGS and (TGLDSP)$_{n=2-3}$GS linkers (BPC 2234 to BPC 2237, BPC 2241 and BPC 2242) to human IL-13 as determined by ELISA.
Figure 11:
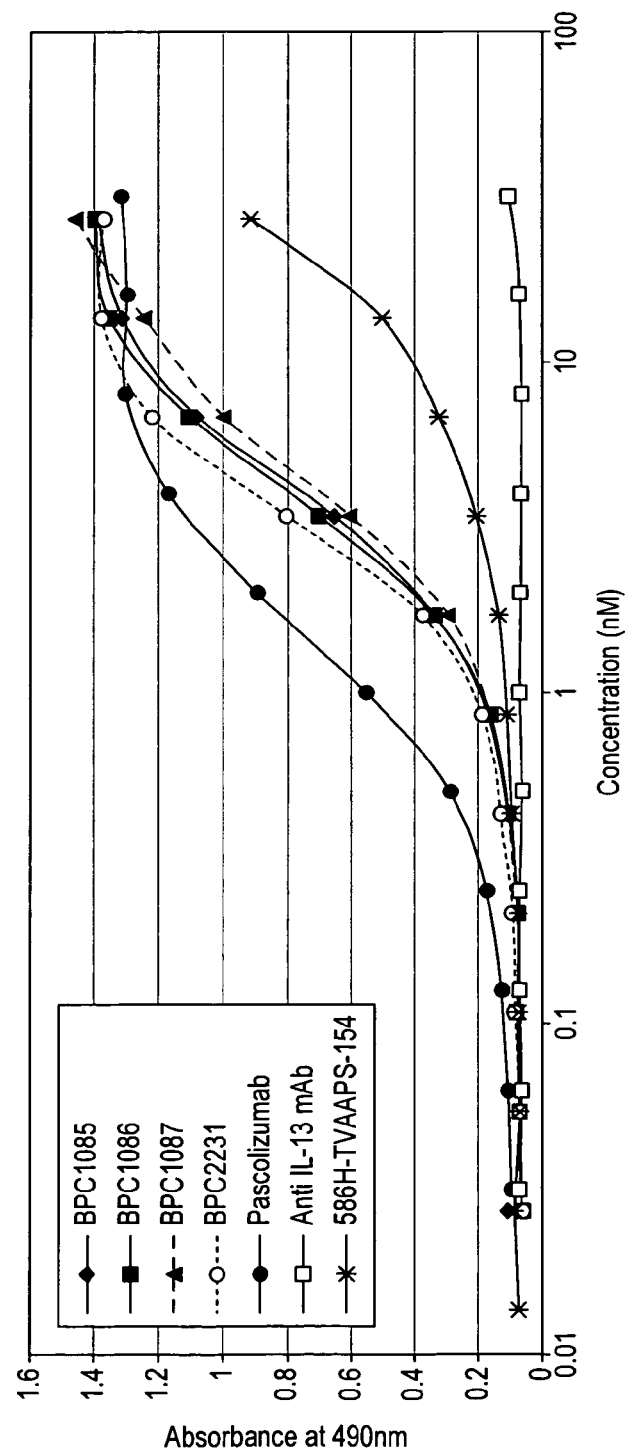
FIG. 11: A graph showing binding of purified mAbdAbs (BPC1085, BPC1086 and BPC1087) to human IL-4 as determined by ELISA. The IL-4 control mAb is labelled as 'pascolizumab'.
Figure 12:
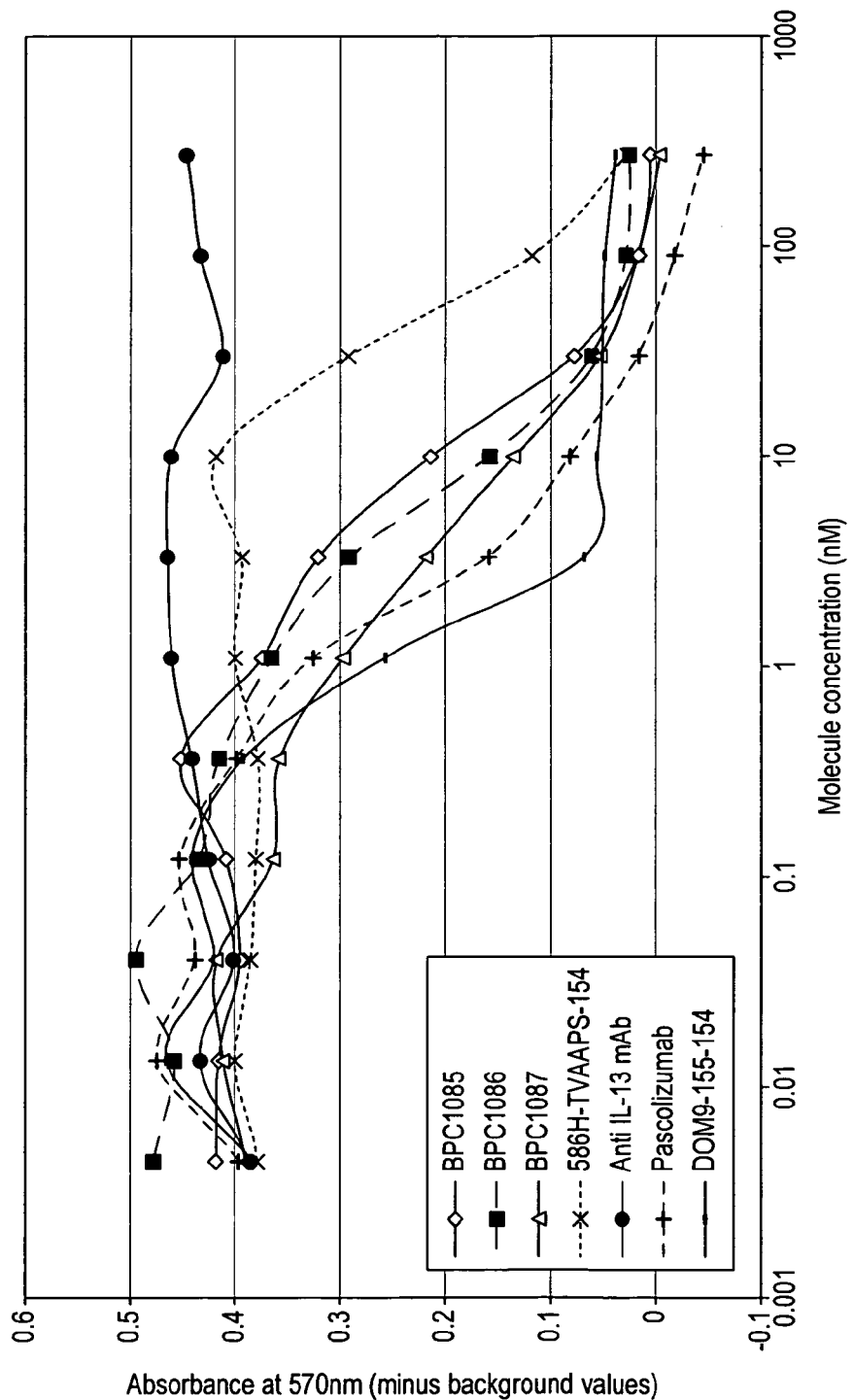
FIG. 12: A graph showing neutralization of human IL-4 by purified mAbdAbs (BPC1085, BPC1086 and BPC1087) to human IL-4 in the TF-1 cell bioassay. The IL-4 control mAb is labelled as 'pascolizumab'.
Figure 13:
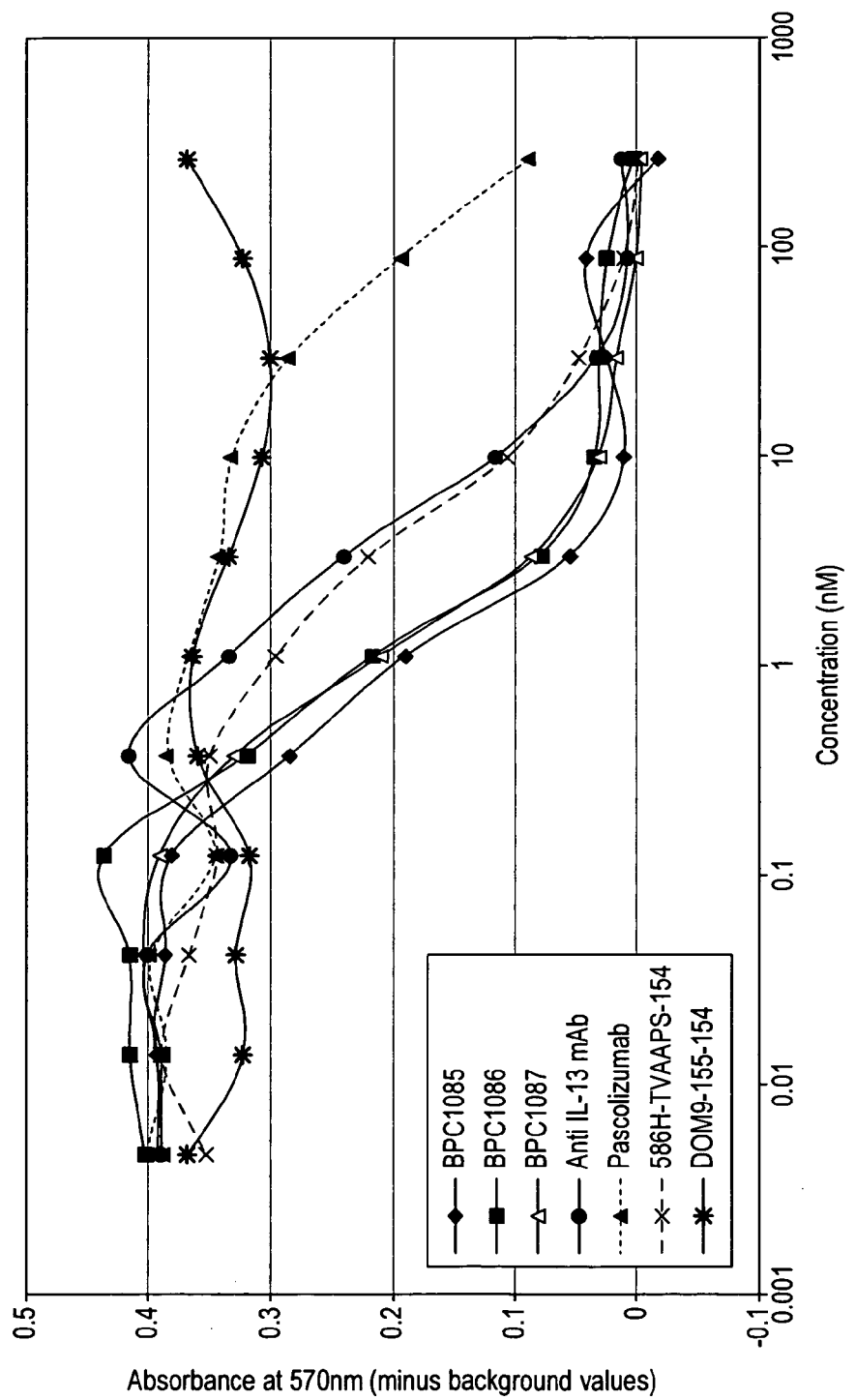
FIG. 13: A graph showing neutralization of human IL-13 by purified mAbdAbs (BPC1085, BPC1086 and BPC1087) to human IL-13 in the TF-1 cell bioassay. The IL-4 control mAb is labelled as 'pascolizumab'.
Figure 14:
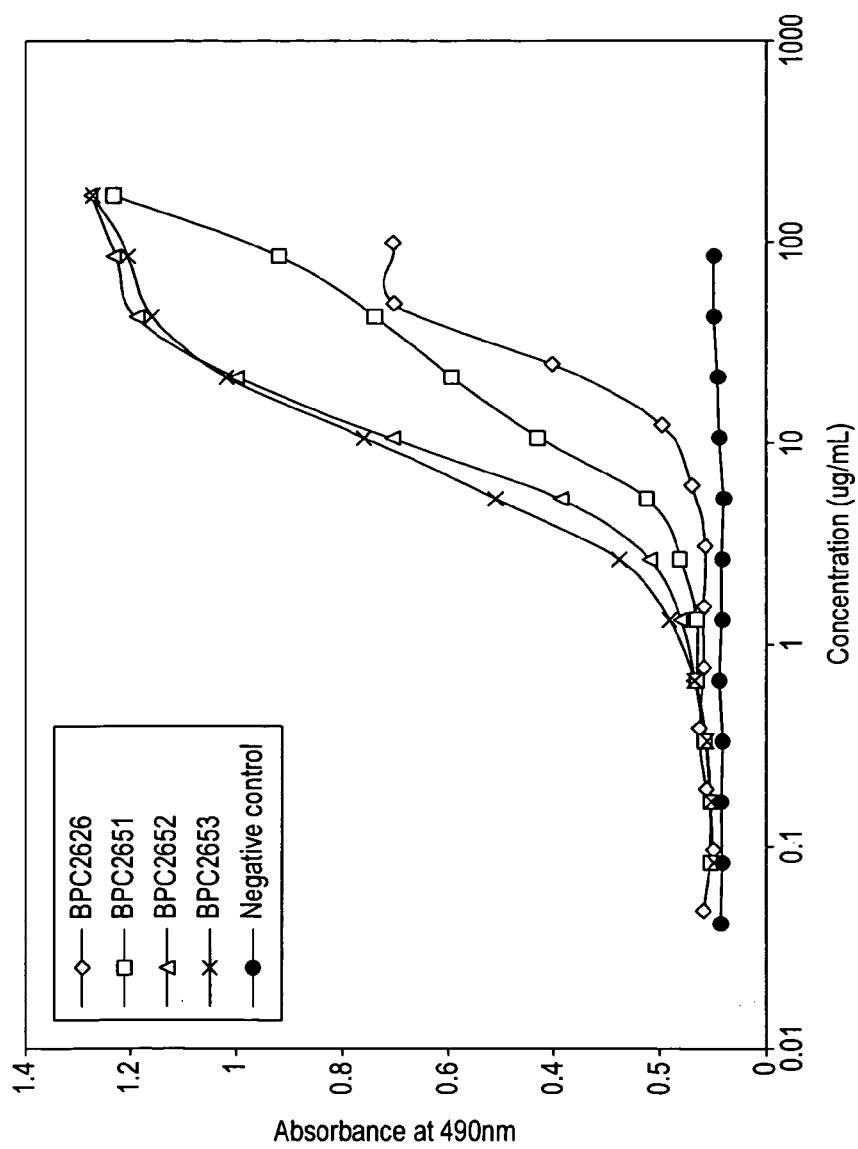
FIG. 14: A graph showing the binding of BPC2651, BPC2652 and BPC2653 to TNFα as determined by ELISA.

| Description | Sequence identifier (SEQ ID NO) | |
|---|---|---|
| | amino acid sequence | DNA sequence |
| DOM10-53-616 anti-IL-13 domain antibody | 1 | |
| anti-IL-4 mAb heavy chain | 2 | |
| anti-IL-4 mAb light chain | 3 | 105 |
| PascoH-GS-DOM10-53-616 | 4 | |
| Anti-human IL-4 mAb heavy chain-GS(TVAAPSGS)$_1$-DOM10-53-616 | 5 | |
| Anti-human IL-4 mAb heavy chain-GS(TVAAPSGS)$_2$-DOM10-53-616 | 6 | |
| Anti-human IL-4 mAb heavy chain-GS(TVAAPSGS)$_3$-DOM10-53-616 | 7 | |

TABLE 14-continued

| Sequence listing | |
|---|---|
| Anti-human IL-4 mAb heavy chain-GS(TVAAPSGS)$_4$-DOM10-53-616 | 8 |
| Anti-human IL-4 mAb heavy chain-GS(TVAAPSGS)$_5$-DOM10-53-616 | 9 |
| Anti-human IL-4 mAb heavy chain-GS(TVAAPSGS)$_6$-DOM10-53-616 | 10 |
| Anti-human IL-4 mAb heavy chain-(PAS)$_1$GS-DOM10-53-616 | 11 |
| Anti-human IL-4 mAb heavy chain-(PAS)$_2$GS-DOM10-53-616 | 12 |
| Anti-human IL-4 mAb heavy chain-(PAS)$_3$GS-DOM10-53-616 | 13 |
| Anti-human IL-4 mAb heavy chain-(G$_4$S)$_1$-DOM10-53-616 | 14 |
| Anti-human IL-4 mAb heavy chain-(G$_4$S)$_2$-DOM10-53-616 | 15 |
| Anti-human IL-4 mAb heavy chain-(G$_4$S)$_3$-DOM10-53-616 | 16 |
| Anti-human IL-4 mAb heavy chain-(PAVPPP)$_1$GS-DOM10-53-616 | 17 |
| Anti-human IL-4 mAb heavy chain-(PAVPPP)$_2$GS-DOM10-53-616 | 18 |
| Anti-human IL-4 mAb heavy chain-(PAVPPP)$_3$GS-DOM10-53-616 | 19 |
| Anti-human IL-4 mAb heavy chain-(TVSDVP)$_1$GS-DOM10-53-616 | 20 |
| Anti-human IL-4 mAb heavy chain-(TVSDVP)$_2$GS-DOM10-53-616 | 21 |
| Anti-human IL-4 mAb heavy chain-(TVSDVP)$_3$GS-DOM10-53-616 | 22 |
| Anti-human IL-4 mAb heavy chain-(TGLDSP)$_1$GS-DOM10-53-616 | 23 |
| Anti-human IL-4 mAb heavy chain-(TGLDSP)$_2$GS-DOM10-53-616 | 24 |
| Anti-human IL-4 mAb heavy chain-(TGLDSP)$_3$GS-DOM10-53-616 | 25 |
| DOM9-155-154 anti-IL-4 domain antibody | 26 |
| Anti-IL-13 antibody (586) light chain | 27 |
| Anti-IL-13 antibody (586) heavy chain | 28 |
| Anti-IL-13 mAb heavy chain-GS-DOM9-155-154 | 29 |
| Anti-IL-13 mAb heavy chain-GS(TVAAPSGS)$_1$-DOM9-155-154 | 30 |
| Anti-IL-13 mAb heavy chain-GS(TVAAPSGS)$_2$-DOM9-155-154 | 31 |
| Anti-IL-13 mAb heavy chain-GS(TVAAPSGS)$_3$-DOM9-155-154 | 32 |
| Anti-IL-13 mAb heavy chain-GS(TVAAPSGS)$_4$-DOM9-155-154 | 33 |
| Anti-IL-13 mAb heavy chain-GS(TVAAPSGS)$_5$-DOM9-155-154 | 34 |

TABLE 14-continued

| Sequence listing | |
|---|---|
| Anti-IL-13 mAb heavy chain-GS(TVAAPSGS)$_6$-DOM9-155-154 | 35 |
| Anti-IL-13 mAb heavy chain-(PAS)$_1$GS-DOM9-155-154 | 36 |
| Anti-IL-13 mAb heavy chain-(PAS)$_2$GS-DOM9-155-154 | 37 |
| Anti-IL-13 mAb heavy chain-(PAS)$_3$GS-DOM9-155-154 | 38 |
| Anti-IL-13 mAb heavy chain-(G$_4$S)$_1$-DOM9-155-154 | 39 |
| Anti-IL-13 mAb heavy chain-(G$_4$S)$_2$-DOM9-155-154 | 40 |
| Anti-IL-13 mAb heavy chain-(G$_4$S)$_3$-DOM9-155-154 | 41 |
| Anti-IL-13 mAb heavy chain-(PAVPPP)$_1$GS-DOM9-155-154 | 42 |
| Anti-IL-13 mAb heavy chain-(PAVPPP)$_2$GS-DOM9-155-154 | 43 |
| Anti-IL-13 mAb heavy chain-(PAVPPP)$_3$GS-DOM9-155-154 | 44 |
| Anti-IL-13 mAb heavy chain-(TVSDVP)$_1$GS-DOM9-155-154 | 45 |
| Anti-IL-13 mAb heavy chain-(TVSDVP)$_2$GS-DOM9-155-154 | 46 |
| Anti-IL-13 mAb heavy chain-(TVSDVP)$_3$GS-DOM9-155-154 | 47 |
| Anti-IL-13 mAb heavy chain-(TGLDSP)$_1$GS-DOM9-155-154 | 48 |
| Anti-IL-13 mAb heavy chain-(TGLDSP)$_2$GS-DOM9-155-154 | 49 |
| Anti-IL-13 mAb heavy chain-(TGLDSP)$_3$GS-DOM9-155-154 | 50 |
| GS | 51 |
| GS(TVAAPSGS)$_1$ | 52 |
| GS(TVAAPSGS)$_2$ | 53 |
| GS(TVAAPSGS)$_3$ | 54 |
| GS(TVAAPSGS)$_4$ | 55 |
| GS(TVAAPSGS)$_5$ | 56 |
| GS(TVAAPSGS)$_6$ | 57 |
| (PAS)$_1$GS | 58 |
| (PAS)$_2$GS | 59 |
| (PAS)$_3$GS | 60 |
| (G$_4$S)$_1$ | 61 |
| (G$_4$S)$_2$ | 62 |
| (G$_4$S)$_3$ | 63 |
| (PAVPPP)$_1$GS | 64 |
| (PAVPPP)$_2$GS | 65 |

TABLE 14-continued

| Sequence listing | |
|---|---|
| (PAVPPP)$_3$GS | 66 |
| (TVSDVP)$_1$GS | 67 |
| (TVSDVP)$_2$GS | 68 |
| (TVSDVP)$_3$GS | 69 |
| (TGLDSP)$_1$GS | 70 |
| (TGLDSP)$_2$GS | 71 |
| (TGLDSP)$_3$GS | 72 |
| TVAAPSGS linker | 73 |
| PAS linker | 74 |
| TVAAPS linker | 75 |
| PAVPPP linker | 76 |
| TVSDVP linker | 77 |
| TGLDSP linker | 78 |
| 586H-TVAAPSGS-154 Heavy chain | 79 |
| DOM9-155-25 | 80 |
| DOM9-155-147 | 81 |
| DOM9-112-210 | 82 |
| DOM10-53-474 | 83 |
| Example signal peptide | 84 |
| DOM10-53-616 dAb-GSTVAAPS-Anti-human IL-4 mAb heavy chain | 85 |
| DOM10-53-616 dAb-GSASTKGPS-Anti-human IL-4 mAb heavy chain | 86 |
| DOM10-53-616 dAb-GSTVAAPS-Anti-human IL-4 mAb light chain | 87 |
| DOM10-53-616 dAb-GSASTKGPS-Anti-human IL-4 mAb light chain | 88 |
| Anti-human IL-4 mAb light chain-TVAAPS-DOM10-53-616 dAb | 89 |
| Anti-human IL-4 mAb heavy chain-TVAAPS-DOM10-53-616 dAb | 90 |
| IL-5 mAb Heavy chain | 91 |
| IL-5 mAb Light chain | 92 |
| Anti IL13 humanised variant A1 Y100B Val (Heavy Chain) | 93 |
| 829H-(TVAAPS)$_2$GS-154 L89Q | 94 |
| 829H-(TVAAPS)$_3$GS-154 L89Q | 95 |
| 829H-(TVAAPS)$_4$GS-154 L89Q | 96 |
| DOM10-176-535 | 97 |
| 829H-GS(TVAAPSGS)$_2$-154 L89Q | 98 |
| 829H-GS(TVAAPSGS)$_3$-154 L89Q | 99 |
| 829H-GS(TVAAPSGS)$_4$-154 L89Q | 100 |
| Anti-human IL-4 DOM9-155-256 | 101 |

TABLE 14-continued

| Sequence listing | | |
|---|---|---|
| Anti-human IL-4 DOM9-155-256, CDRH3 | 102 | |
| PascoH-TVAAPSGS-PEP1-5-19 Heavy Chain | 104 | 103 |
| PascoH-GS(TVAAPS)$_2$- PEP1-5-19 Heavy Chain | 107 | 106 |
| PascoH-GS(TVAAPS)$_3$- PEP1-5-19 Heavy Chain | 109 | 108 |
| PascoH-GS(TVAAPS)$_4$- PEP1-5-19 Heavy Chain | 111 | 110 |
| (TVAAPS)$_2$GS linker | 112 | |
| (TVAAPS)$_3$GS linker | 113 | |
| (TVAAPS)$_4$GS linker | 114 | |

SEQ ID NO: 1

GVQLLESGGGLVQPGGSLRLSCAASGFVFPWYDMGWVRQAPGKGLEWVSSIDWHGKITYYAD
SVKGRFTISRDNSKNTLYLQMNSLRAEDTAVYYCATAEDEPGYDYWGQGTLVTVSS

SEQ ID NO: 2

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGK

SEQ ID NO: 3

DIVLTQSPSSLSASVGDRVTITCKASQSVDYDGDSYMNWYQQKPGKAPKLLIYAASNLESGI
PSRFSGSGSGTDFTFTISSLQPEDIATYYCQQSNEDPPTFGQGTKVEIKRTVAAPSVFIFPP
SDEQLKSGTASVVCLLNNFYPREAKVQWKVDNALQSGNSQESVTEQDSKDSTYSLSSTLTLS
KADYEKHKVYACEVTHQGLSSPVTKSFNRGEC

SEQ ID NO: 4

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSGVQLLESGGGLVQPGGSLRLSCAASGFVFPWYDMGWVRQAPGK
GLEWVSSIDWHGKITYYADSVKGRFTISRDNSKNTLYLQMNSLRAEDTAVYYCATAEDEPGY
DYWGQGTLVTVSS

SEQ ID NO: 5

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSTVAAPSGSGVQLLESGGGLVQPGGSLRLSCAASGFVFPWYDMG
WVRQAPGKGLEWVSSIDWHGKITYYADSVKGRFTISRDNSKNTLYLQMNSLRAEDTAVYYCA
TAEDEPGYDYWGQGTLVTVSS

SEQ ID NO: 6

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSTVAAPSGSTVAAPSGSGVQLLESGGGLVQPGGSLRLSCAASGF
VFPWYDMGWVRQAPGKGLEWVSSIDWHGKITYYADSVKGRFTISRDNSKNTLYLQMNSLRAE
DTAVYYCATAEDEPGYDYWGQGTLVTVSS

SEQ ID NO: 7

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST

TABLE 14-continued

Sequence listing

```
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSTVAAPSGSTVAAPSGSTVAAPSGSGVQLLESGGGLVQPGGSLR
LSCAASGFVFPWYDMGWVRQAPGKGLEWVSSIDWHGKITYYADSVKGRFTISRDNSKNTLYL
QMNSLRAEDTAVYYCATAEDEPGYDYWGQGTLVTVSS
```

SEQ ID NO: 8

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSTVAAPSGSTVAAPSGSTVAAPSGSTVAAPSGSGVQLLESGGGL
VQPGGSLRLSCAASGFVFPWYDMGWVRQAPGKGLEWVSSIDWHGKITYYADSVKGRFTISRD
NSKNTLYLQMNSLRAEDTAVYYCATAEDEPGYDYWGQGTLVTVSS
```

SEQ ID NO: 9

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSTVAAPSGSTVAAPSGSTVAAPSGSTVAAPSGSTVAAPSGSGVQ
LLESGGGLVQPGGSLRLSCAASGFVFPWYDMGWVRQAPGKGLEWVSSIDWHGKITYYADSVK
GRFTISRDNSKNTLYLQMNSLRAEDTAVYYCATAEDEPGYDYWGQGTLVTVSS
```

SEQ ID NO: 10

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSTVAAPSGSTVAAPSGSTVAAPSGSTVAAPSGSTVAAPSGSTVA
APSGSGVQLLESGGGLVQPGGSLRLSCAASGFVFPWYDMGWVRQAPGKGLEWVSSIDWHGKI
TYYADSVKGRFTISRDNSKNTLYLQMNSLRAEDTAVYYCATAEDEPGYDYWGQGTLVTVSS
```

SEQ ID NO: 11

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKPASGSGVQLLESGGGLVQPGGSLRLSCAASGFVFPWYDMGWVRQA
PGKGLEWVSSIDWHGKITYYADSVKGRFTISRDNSKNTLYLQMNSLRAEDTAVYYCATAEDE
PGYDYWGQGTLVTVSS
```

SEQ ID NO: 12

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKPASPSGSGVQLLESGGGLVQPGGSLRLSCAASGFVFPWYDMGWV
RQAPGKGLEWVSSIDWHGKITYYADSVKGRFTISRDNSKNTLYLQMNSLRAEDTAVYYCATA
EDEPGYDYWGQGTLVTVSS
```

SEQ ID NO: 13

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKPASPASPASGSGVQLLESGGGLVQPGGSLRLSCAASGFVFPWYDM
```

TABLE 14-continued

Sequence listing

GWVRQAPGKGLEWVSSIDWHGKITYYADSVKGRFTISRDNSKNTLYLQMNSLRAEDTAVYYC
ATAEDEPGYDYWGQGTLVTVSS

SEQ ID NO: 14

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGGGGSGVQLLESGGGLVQPGGSLRLSCAASGFVFPWYDMGWVRQA
PGKGLEWVSSIDWHGKITYYADSVKGRFTISRDNSKNTLYLQMNSLRAEDTAVYYCATAEDE
PGYDYWGQGTLVTVSS

SEQ ID NO: 15

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGGGGSGGGGSGVQLLESGGGLVQPGGSLRLSCAASGFVFPWYDMG
WVRQAPGKGLEWVSSIDWHGKITYYADSVKGRFTISRDNSKNTLYLQMNSLRAEDTAVYYCA
TAEDEPGYDYWGQGTLVTVSS

SEQ ID NO: 16

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGGGGSGGGGSGGGGSGVQLLESGGGLVQPGGSLRLSCAASGFVFP
WYDMGWVRQAPGKGLEWVSSIDWHGKITYYADSVKGRFTISRDNSKNTLYLQMNSLRAEDTA
VYYCATAEDEPGYDYWGQGTLVTVSS

SEQ ID NO: 17

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKPAVPPPGSGVQLLESGGGLVQPGGSLRLSCAASGFVFPWYDMGWV
RQAPGKGLEWVSSIDWHGKITYYADSVKGRFTISRDNSKNTLYLQMNSLRAEDTAVYYCATA
EDEPGYDYWGQGTLVTVSS

SEQ ID NO: 18

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKPAVPPPPAVPPPGSGVQLLESGGGLVQPGGSLRLSCAASGFVFPW
YDMGWVRQAPGKGLEWVSSIDWHGKITYYADSVKGRFTISRDNSKNTLYLQMNSLRAEDTAV
YYCATAEDEPGYDYWGQGTLVTVSS

SEQ ID NO: 19

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKPAVPPPPAVPPPPAVPPPGSGVQLLESGGGLVQPGGSLRLSCAAS
GFVFPWYDMGWVRQAPGKGLEWVSSIDWHGKITYYADSVKGRFTISRDNSKNTLYLQMNSLR
AEDTAVYYCATAEDEPGYDYWGQGTLVTVSS

SEQ ID NO: 20

QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST

TABLE 14-continued

Sequence listing

```
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKTVSDVPGSGVQLLESGGGLVQPGGSLRLSCAASGFVFPWYDMGWV
RQAPGKGLEWVSSIDWHGKITYYADSVKGRFTISRDNSKNTLYLQMNSLRAEDTAVYYCATA
EDEPGYDYWGQGTLVTVSS
```

SEQ ID NO: 21

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKTVSDVPTVSDVPGSGVQLLESGGGLVQPGGSLRLSCAASGFVFPW
YDMGWVRQAPGKGLEWVSSIDWHGKITYYADSVKGRFTISRDNSKNTLYLQMNSLRAEDTAV
YYCATAEDEPGYDYWGQGTLVTVSS
```

SEQ ID NO: 22

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKTVSDVPTVSDVPTVSDVPGSGVQLLESGGGLVQPGGSLRLSCAAS
GFVFPWYDMGWVRQAPGKGLEWVSSIDWHGKITYYADSVKGRFTISRDNSKNTLYLQMNSLR
AEDTAVYYCATAEDEPGYDYWGQGTLVTVSS
```

SEQ ID NO: 23

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKTGLDSPGSGVQLLESGGGLVQPGGSLRLSCAASGFVFPWYDMGWV
RQAPGKGLEWVSSIDWHGKITYYADSVKGRFTISRDNSKNTLYLQMNSLRAEDTAVYYCATA
EDEPGYDYWGQGTLVTVSS
```

SEQ ID NO: 24

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKTGLDSPTGLDSPGSGVQLLESGGGLVQPGGSLRLSCAASGFVFPW
YDMGWVRQAPGKGLEWVSSIDWHGKITYYADSVKGRFTISRDNSKNTLYLQMNSLRAEDTAV
YYCATAEDEPGYDYWGQGTLVTVSS
```

SEQ ID NO: 25

```
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKTGLDSPTGLDSPTGLDSPGSGVQLLESGGGLVQPGGSLRLSCAAS
GFVFPWYDMGWVRQAPGKGLEWVSSIDWHGKITYYADSVKGRFTISRDNSKNTLYLQMNSLR
AEDTAVYYCATAEDEPGYDYWGQGTLVTVSS
```

SEQ ID NO: 26

```
DIQMTQSPSSLSASVGDRVTITCRASRPISDWLHWYQQKPGKAPKLLIAWASSLQGGVPSRF
SGSGSGTDFTLTISSLQPEDFATYYCLQEGWGPPTFGQGTKVEIKR
```

SEQ ID NO: 27

```
DIVMTQSPLSLPVTPGEPASISCRSSQNIVHINGNTYLEWYLQKPGQSPRLLIYKISDRFSG
VPDRFSGSGSGTDFTLKISRVEADDVGIYYCFQGSHVPWTFGQGTKLEIKRTVAAPSVFIFP
PSDEQLKSGTASVVCLLNNFYPREAKVQWKVDNALQSGNSQESVTEQDSKDSTYSLSSTLTL
SKADYEKHKVYACEVTHQGLSSPVTKSFNRGEC
```

TABLE 14-continued

Sequence listing

SEQ ID NO: 28
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGK

SEQ ID NO: 29
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGSDIQMTQSPSSLSASVGDRVTITCRASRPISDWLHWYQQK
PGKAPKLLIAWASSLQGGVPSRFSGSGSGTDFTLTISSLQPEDFATYYCLQEGWGPPTFGQG
TKVEIKR

SEQ ID NO: 30
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGSTVAAPSGSDIQMTQSPSSLSASVGDRVTITCRASRPISD
WLHWYQQKPGKAPKLLIAWASSLQGGVPSRFSGSGSGTDFTLTISSLQPEDFATYYCLQEGW
GPPTFGQGTKVEIKR

SEQ ID NO: 31
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGSTVAAPSGSTVAAPSGSDIQMTQSPSSLSASVGDRVTITC
RASRPISDWLHWYQQKPGKAPKLLIAWASSLQGGVPSRFSGSGSGTDFTLTISSLQPEDFAT
YYCLQEGWGPPTFGQGTKVEIKR

SEQ ID NO: 32
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGSTVAAPSGSTVAAPSGSTVAAPSGSDIQMTQSPSSLSASV
GDRVTITCRASRPISDWLHWYQQKPGKAPKLLIAWASSLQGGVPSRFSGSGSGTDFTLTISS
LQPEDFATYYCLQEGWGPPTFGQGTKVEIKR

SEQ ID NO: 33
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGSTVAAPSGSTVAAPSGSTVAAPSGSTVAAPSGSDIQMTQS
PSSLSASVGDRVTITCRASRPISDWLHWYQQKPGKAPKLLIAWASSLQGGVPSRFSGSGSGT
DFTLTISSLQPEDFATYYCLQEGWGPPTFGQGTKVEIKR

SEQ ID NO: 34
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS

TABLE 14-continued

Sequence listing

VMHEALHNHYTQKSLSLSPGKGSTVAAPS**GSTVAAPSGSTVAAPSGSTVAAPSGSTVAAPSG
S**DIQMTQSPSSLSASVGDRVTITCRASRPISDWLHWYQQKPGKAPKLLIAWASSLQGGVPSR
FSGSGSGTDFTLTISSLQPEDFATYYCLQEGWGPPTFGQGTKVEIKR

SEQ ID NO: 35

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGK**GSTVAAPSGSTVAAPSGSTVAAPSGSTVAAPSGSTVAAPSG
STVAAPSGS**DIQMTQSPSSLSASVGDRVTITCRASRPISDWLHWYQQKPGKAPKLLIAWASS
LQGGVPSRFSGSGSGTDFTLTISSLQPEDFATYYCLQEGWGPPTFGQGTKVEIKR

SEQ ID NO: 36

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKPASGSDIQMTQSPSSLSASVGDRVTITCRASRPISDWLHWY
QQKPGKAPKLLIAWASSLQGGVPSRFSGSGSGTDFTLTISSLQPEDFATYYCLQEGWGPPTF
GQGTKVEIKR

SEQ ID NO: 37

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKPASPASGSDIQMTQSPSSLSASVGDRVTITCRASRPISDWL
HWYQQKPGKAPKLLIAWASSLQGGVPSRFSGSGSGTDFTLTISSLQPEDFATYYCLQEGWGP
PTFGQGTKVEIKR

SEQ ID NO: 38

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKPASPASPASGSDIQMTQSPSSLSASVGDRVTITCRASRPIS
DWLHWYQQKPGKAPKLLIAWASSLQGGVPSRFSGSGSGTDFTLTISSLQPEDFATYYCLQEG
WGPPTFGQGTKVEIKR

SEQ ID NO: 39

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGGGGSDIQMTQSPSSLSASVGDRVTITCRASRPISDWLHWY
QQKPGKAPKLLIAWASSLQGGVPSRFSGSGSGTDFTLTISSLQPEDFATYYCLQEGWGPPTF
GQGTKVEIKR

SEQ ID NO: 40

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGGGGSGGGGSDIQMTQSPSSLSASVGDRVTITCRASRPISD
WLHWYQQKPGKAPKLLIAWASSLQGGVPSRFSGSGSGTDFTLTISSLQPEDFATYYCLQEGW
GPPTFGQGTKVEIKR

TABLE 14-continued

Sequence listing

SEQ ID NO: 41

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGGGGSGGGGSGGGGSDIQMTQSPSSLSASVGDRVTITCRAS
RPISDWLHWYQQKPGKAPKLLIAWASSLQGGVPSRFSGSGSGTDFTLTISSLQPEDFATYYC
LQEGWGPPTFGQGTKVEIKR

SEQ ID NO: 42

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKPAVPPPGSDIQMTQSPSSLSASVGDRVTITCRASRPISDWL
HWYQQKPGKAPKLLIAWASSLQGGVPSRFSGSGSGTDFTLTISSLQPEDFATYYCLQEGWGP
PTFGQGTKVEIKR

SEQ ID NO: 43

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKPAVPPPPAVPPPGSDIQMTQSPSSLSASVGDRVTITCRASR
PISDWLHWYQQKPGKAPKLLIAWASSLQGGVPSRFSGSGSGTDFTLTISSLQPEDFATYYCL
QEGWGPPTFGQGTKVEIKR

SEQ ID NO: 44

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKPAVPPPPAVPPPPAVPPPGSDIQMTQSPSSLSASVGDRVTI
TCRASRPISDWLHWYQQKPGKAPKLLIAWASSLQGGVPSRFSGSGSGTDFTLTISSLQPEDF
ATYYCLQEGWGPPTFGQGTKVEIKR

SEQ ID NO: 45

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTVSDVPGSDIQMTQSPSSLSASVGDRVTITCRASRPISDWL
HWYQQKPGKAPKLLIAWASSLQGGVPSRFSGSGSGTDFTLTISSLQPEDFATYYCLQEGWGP
PTFGQGTKVEIKR

SEQ ID NO: 46

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTVSDVPTVSDVPGSDIQMTQSPSSLSASVGDRVTITCRASR
PISDWLHWYQQKPGKAPKLLIAWASSLQGGVPSRFSGSGSGTDFTLTISSLQPEDFATYYCL
QEGWGPPTFGQGTKVEIKR

SEQ ID NO: 47

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV

TABLE 14-continued

Sequence listing

VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTVSDVPTVSDVPTVSDVPGSDIQMTQSPSSLSASVGDRVTI
TCRASRPISDWLHWYQQKPGKAPKLLIAWASSLQGGVPSRFSGSGSGTDFTLTISSLQPEDF
ATYYCLQEGWGPPTFGQGTKVEIKR

SEQ ID NO: 48

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTGLDSPGSDIQMTQSPSSLSASVGDRVTITCRASRPISDWL
HWYQQKPGKAPKLLIAWASSLQGGVPSRFSGSGSGTDFTLTISSLQPEDFATYYCLQEGWGP
PTFGQGTKVEIKR

SEQ ID NO: 49

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTGLDSPTGLDSPGSDIQMTQSPSSLSASVGDRVTITCRASR
PISDWLHWYQQKPGKAPKLLIAWASSLQGGVPSRFSGSGSGTDFTLTISSLQPEDFATYYCL
QEGWGPPTFGQGTKVEIKR

SEQ ID NO: 50

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTGLDSPTGLDSPTGLDSPGSDIQMTQSPSSLSASVGDRVTI
TCRASRPISDWLHWYQQKPGKAPKLLIAWASSLQGGVPSRFSGSGSGTDFTLTISSLQPEDF
ATYYCLQEGWGPPTFGQGTKVEIKR

SEQ ID NO: 51

GS

SEQ ID NO: 52

GSTVAAPSGS

SEQ ID NO: 53

GSTVAAPSGSTVAAPSGS

SEQ ID NO: 54

GSTVAAPSGSTVAAPSGSTVAAPSGS

SEQ ID NO: 55

GSTVAAPSGSTVAAPSGSTVAAPSGSTVAAPSGS

SEQ ID NO: 56

GSTVAAPSGSTVAAPSGSTVAAPSGSTVAAPSGSTVAAPSGS

SEQ ID NO: 57

GSTVAAPSGSTVAAPSGSTVAAPSGSTVAAPSGSTVAAPSGSTVAAPSGS

SEQ ID NO: 58

PASGS

SEQ ID NO: 59

PASPASGS

SEQ ID NO: 60

PASPASPASGS

SEQ ID NO: 61

GGGGS

SEQ ID NO: 62

GGGGSGGGGS

TABLE 14-continued

| Sequence listing | |
|---|---|
| GGGGSGGGGSGGGGS | SEQ ID NO: 63 |
| PAVPPPGS | SEQ ID NO: 64 |
| PAVPPPPAVPPPGS | SEQ ID NO: 65 |
| PAVPPPPAVPPPPAVPPPGS | SEQ ID NO: 66 |
| TVSDVPGS | SEQ ID NO: 67 |
| TVSDVPTVSDVPGS | SEQ ID NO: 68 |
| TVSDVPTVSDVPTVSDVPGS | SEQ ID NO: 69 |
| TGLDSPGS | SEQ ID NO: 70 |
| TGLDSPTGLDSPGS | SEQ ID NO: 71 |
| TGLDSPTGLDSPTGLDSPGS | SEQ ID NO: 72 |
| TVAAPSGS | SEQ ID NO: 73 |
| PAS | SEQ ID NO: 74 |
| TVAAPS | SEQ ID NO: 75 |
| PAVPPP | SEQ ID NO: 76 |
| TVSDVP | SEQ ID NO: 77 |
| TGLDSP | SEQ ID NO: 78 |

SEQ ID NO: 79 = 586H-TVAAPS-154 (H chain)
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHYDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTVAAPSGSDIQMTQSPSSLSASVGDRVTITCRASRPISDWL
HWYQQKPGKAPKLLIAWASSLQGGVPSRFSGSGSGTDFTLTISSLQPEDFATYYCLQEGWGP
PTFGQGTKVEIKR SEQ ID NO: 80 = DOM9-155-25
DIQMTQSPSSLSASVGDRVTITCRASRPISDWLHWYQQKPGKAPKLLIAWASTLDSGVPSRF
SGSGSGTDFTLTISSLQPEDFATYYCLQEGWGPPTFGQGTKVEIKR SEQ ID NO: 81 = DOM9-155-147
DIQMTQSPSSLSASVGDRVTITCRASRPISDWLHWYQQKPGKAPKLLIAWASSLYEGVPSRF
SGSGSGTDFTLTISSLQPEDFATYYCLQEGWGPPTFGQGTKVEIKR SEQ ID NO: 82 = DOM9-112-210
EVQLLESGGGLVQPGGSLRLSCAASGFTFRNFGMGWVRQAPGKGLEWVSWIISSGTETYYAD
SVKGRFTISRDNSKNTLYLQMNSLRAEDTAVYYCAKSLGRFDYWGQGTLVTVSS SEQ ID NO: 83 = DOM10-53-474
GVQLLESGGGLVQPGGSLRLSCAASGFTFAWYDMGWVRQAPGKGLEWVSSIDWHGEVTYYAD
SVKGRFTISRDNSKNTLYLQMNSLRAEDTAVYYCATAEDEPGYDYWGQGTLVTVSS TABLE 14-continued Sequence listing SEQ ID NO: 84
(Example signal peptide sequence)
MGWSCIILFLVATATGVHS SEQ ID NO: 85 = 616-TVAAPS-Anti-human IL-4 mAb heavy chain
GVQLLESGGGLVQPGGSLRLSCAASGFVFPWYDMGWVRQAPGKGLEWVSSIDWHGKITYYAD
SVKGRFTISRDNSKNTLYLQMNSLRAEDTAVYYCATAEDEPGYDYWGQGTLVTVSSGSTVAA
PSQVTLRESGPALVKPTQTLTLTCTFSGFSLSTSGMGVSWIRQPPGKGLEWLAHIYWDDDKR
YNPSLKSRLTISKDTSRNQVVLTMTNMDPVDTATYYCARRETVFYWYFDVWGRGTLVTVSSA
STKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFL
FPPKPKDTLMISRTPEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSRWQQGNVFSCSVM
HEALHNHYTQKSLSLSPGK SEQ ID NO: 86 = 616-ASTKG-Anti-human IL-4 mAb heavy chain
GVQLLESGGGLVQPGGSLRLSCAASGFVFPWYDMGWVRQAPGKGLEWVSSIDWHGKITYYAD
SVKGRFTISRDNSKNTLYLQMNSLRAEDTAVYYCATAEDEPGYDYWGQGTLVTVSSGSASTK
GPSQVTLRESGPALVKPTQTLTLTCTFSGFSLSTSGMGVSWIRQPPGKGLEWLAHIYWDDDK
RYNPSLKSRLTISKDTSRNQVVLTMTNMDPVDTATYYCARRETVFYWYFDVWGRGTLVTVSS
ASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKKVEPKSCDKTHTCPPCPAPELLGGPSVF
LFPPKPKDTLMISRTPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTLPPSRDELTKNQVSL
TCLVKGFYPSDIAVEWESNGQPENNYKTTPPVLDSDGSFFLYSKLTVDKSRWQQGNVFSCSV
MHEALHNHYTQKSLSLSPGK SEQ ID NO: 87 = 616-GSTVAAPS-Anti-human IL-4 mAb Light chain
GVQLLESGGGLVQPGGSLRLSCAASGFVFPWYDMGWVRQAPGKGLEWVSSIDWHGKITYYAD
SVKGRFTISRDNSKNTLYLQMNSLRAEDTAVYYCATAEDEPGYDYWGQGTLVTVSSGSTVAA
PSDIVLTQSPSSLSASVGDRVTITCKASQSVDYDGDSYMNWYQQKPGKAPKLLIYAASNLES
GIPSRFSGSGSGTDFTFTISSLQPEDIATYYCQQSNEDPPTFGQGTKVEIKRTVAAPSVFIF
PPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC SEQ ID NO: 88 = 616-GSASTKG- Anti-human IL-4 mAb Light chain
GVQLLESGGGLVQPGGSLRLSCAASGFVFPWYDMGWVRQAPGKGLEWVSSIDWHGKITYYAD
SVKGRFTISRDNSKNTLYLQMNSLRAEDTAVYYCATAEDEPGYDYWGQGTLVTVSSGSASTK
GPSDIVLTQSPSSLSASVGDRVTITCKASQSVDYDGDSYMNWYQQKPGKAPKLLIYAASNLE
SGIPSRFSGSGSGTDFTFTISSLQPEDIATYYCQQSNEDPPTFGQGTKVEIKRTVAAPSVFI
FPPSDEQLKSGTASVVCLLNNFYPREAKVQWKVDNALQSGNSQESVTEQDSKDSTYSLSSTL
TLSKADYEKHKVYACEVTHQGLSSPVTKSFNRGEC SEQ ID NO: 89 = Anti-human IL-4 mAb Light chain-TVAAPS-616
DIVLTQSPSSLSASVGDRVTITCKASQSVDYDGDSYMNWYQQKPGKAPKLLIYAASNLESGI
PSRFSGSGSGTDFTFTISSLQPEDIATYYCQQSNEDPPTFGQGTKVEIKRTVAAPSVFIFPP
SDEQLKSGTASVVCLLNNFYPREAKVQWKVDNALQSGNSQESVTEQDSKDSTYSLSSTLTLS
KADYEKHKVYACEVTHQGLSSPVTKSFNRGECTVAAPSGVQLLESGGGLVQPGGSLRLSCAA
SGFVFPWYDMGWVRQAPGKGLEWVSSIDWHGKITYYADSVKGRFTISRDNSKNTLYLQMNSL
RAEDTAVYYCATAEDEPGYDYWGQGTLVTVSS SEQ ID NO: 90 = Anti-human IL-4 mAb heavy chain-TVAAPS-616
(Heavy chain)
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKTVAAPSGVQLLESGGGLVQPGGSLRLSCAASGFVFPWYDMGWVRQ
APGKGLEWVSSIDWHGKITYYADSVKGRFTISRDNSKNTLYLQMNSLRAEDTAVYYCATAED
EPGYDYWGQGTLVTVSS SEQ ID NO: 91 = Anti-IL-5 mAb Heavy chain
QVTLRESGPALVKPTQTLTLTCTVSGFSLTSYSVHWVRQPPGKGLEWLGVIWASGGTDYNSA
LMSRLSISKDTSRNQVVLTMTNMDPVDTATYYCARDPPSSLLRLDYWGRGTLVTVSSASTKG
PSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPELLGGPSVFLFPPK
PKDTLMISRTPEVTCVVVDVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPGK SEQ ID NO: 92 = Anti-IL-5 mAb Light chain
DIVMTQSPDSLAVSLGERATINCKSSQSLLNSGNQKNYLAWYQQKPGQPPKLLIYGASTRES
GVPDRFSGSGSGTDFTLTISSLQAEDVAVYYCQNVHSFPFTFGGGTKLEIKRTVAAPSVFIF

TABLE 14-continued

Sequence listing

PPSDEQLKSGTASVVCLLNNFYPREAKVQWKVDNALQSGNSQESVTEQDSKDSTYSLSSTLT
LSKADYEKHKVYACEVTHQGLSSPVTKSFNRGEC

SEQ ID NO: 93

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHVDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGK

SEQ ID NO: 94

(829H-(TVAAPS)$_2$GS-154 L89Q)
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHVDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTVAAPSTVAAPSGSDIQMTQSPSSLSASVGDRVTITCRASR
PISDWLHWYQQKPGKAPKLLIAWASSLQGGVPSRFSGSGSGTDFTLTISSLQPEDFATYYCQ
QEGWGPPTFGQGTKVEIKR

SEQ ID NO: 95

829H-(TVAAPS)$_3$GS-154 L89Q
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHVDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTVAAPSTVAAPSGSDIQMTQSPSSLSASVGDRVTI
TCRASRPISDWLHWYQQKPGKAPKLLIAWASSLQGGVPSRFSGSGSGTDFTLTISSLQPEDF
ATYYCQQEGWGPPTFGQGTKVEIKR

SEQ ID NO: 96

829H-(TVAAPS)$_4$GS-154 L89Q
QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHVDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKTVAAPSTVAAPSTVAAPSGSDIQMTQSPSSLSASV
GDRVTITCRASRPISDWLHWYQQKPGKAPKLLIAWASSLQGGVPSRFSGSGSGTDFTLTISS
LQPEDFATYYCQQEGWGPPTFGQGTKVEIKR

SEQ ID NO: 97

DIQMTQSPSSLSASVGDRVTITCRASQWIGPYLNWYQQKPGKAPKPLIYMGYWAPSGVPSRF
SGSGSGTDFTLTISSLQPEDFATYYCQQDLYPPFTFGQGTKVEIKR

SEQ ID NO: 98

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHVDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGSTVAAPSGSTVAAPSGSDIQMTQSPSSLSASVGDRVTITC
RASRPISDWLHWYQQKPGKAPKLLIAWASSLQGGVPSRFSGSGSGTDFTLTISSLQPEDFAT
YYCQQEGWGPPTFGQGTKVEIKR

SEQ ID NO: 99

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHVDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS

TABLE 14-continued

Sequence listing

VMHEALHNHYTQKSLSLSPGKGSTVAAPSGSTVAAPSGSTVAAPSGSDIQMTQSPSSLSASV
GDRVTITCRASRPISDWLHWYQQKPGKAPKLLIAWASSLQGGVPSRFSGSGSGTDFTLTISS
LQPEDFATYYCQQEGWGPPTFGQGTKVEIKR

SEQ ID NO: 100

QVQLVQSGAEVKKPGSSVKVSCKASGFYIKDTYMHWVRQAPGQGLEWMGTIDPANGNTKYVP
KFQGRVTITADESTSTAYMELSSLRSEDTAVYYCARSIYDDYHVDDYYAMDYWGQGTLVTVS
SASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGPSV
FLFPPKPKDTLMISRTPEVTCVVVDVSHEDPEVKFNWYVDGVEVHNAKTKPREEQYNSTYRV
VSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCS
VMHEALHNHYTQKSLSLSPGKGSTVAAPSGSTVAAPSGSTVAAPSGSTVAAPSGSDIQMTQS
PSSLSASVGDRVTITCRASRPISDWLHWYQQKPGKAPKLLIAWASSLQGGVPSRFSGSGSGT
DFTLTISSLQPEDFATYYCQQEGWGPPTFGQGTKVEIKR

SEQ ID NO: 101

DIQMTQSPSSLSASVGDRVTITCRASRPISDWLHWYQQKPGKAPKLLIAWASSLQGGVPSRF
SGSGSGTDFTLTISSLQPEDFATYYCQQEGWGPPTFGQGTKVEIKR

SEQ ID NO: 102

QQEGWGPPT

SEQ ID NO: 103
- polynucleotide sequence of BPC2626 heavy chain
CAGGTGACCCTGAGGGAGAGCGGCCCCGCCCTGGTGAAGCCCACCCAGACCCTGACCCTGAC
CTGCACCTTCAGCGGCTTTAGCCTCAGCACCTCCGGCATGGGCGTGAGCTGGATCAGGCAG
CACCCGGCAAAGGCCTGGAGTGGCTGGCCCACATCTACTGGGACGACGACAAGAGGTACAAC
CCCAGCCTGAAGAGCCGGCTGACCATCAGCAAGGATACCAGCAGGAACCAGGTGGTGCTGAC
CATGACCAACATGGACCCCGTGGACACCGCTACCTACTACTGCGCCAGGAGGGAGACCGTCT
TCTACTGGTACTTCGACGTGTGGGGAAGGGGCACACTAGTGACCGTGTCCAGCGCCAGCACC
AAGGGCCCCAGCGTGTTCCCCCTGGCCCCCAGCAGCAAGAGCACCAGCGGCGGCACAGCCGC
CCTGGGCTGCCTGGTGAAGGACTACTTCCCCGAACCGGTGACCGTGTCCTGGAACAGCGGAG
CCCTGACCAGCGGCGTGCACACCTTCCCCGCCGTGCTGCAGAGCAGCGGCCTGTACAGCCTG
AGCAGCGTGGTGACCGTGCCCAGCAGCAGCCTGGGCACCCAGACCTACATCTGTAACGTGAA
CCACAAGCCCAGCAACACCAAGGTGGACAAGAAGGTGGAGCCCAAGAGCTGTGACAAGACCC
ACACCTGCCCCCCCTGCCCTGCCCCCGAGCTGCTGGGAGGCCCCAGCGTGTTCCTGTTCCCC
CCCAAGCCTAAGGACACCCTGATGATCAGCAGAACCCCCGAGGTGACCTGTGTGGTGGTGGA
TGTGAGCCACGAGGACCCTGAGGTGAAGTTCAACTGGTACGTGGACGGCGTGGAGGTGCACA
ATGCCAAGACCAAGCCCAGGGAGGAGCAGTACAACAGCACCTACCGGGTGGTGTCCGTGCTG
ACCGTGCTGCACCAGGATTGGCTGAACGGCAAGGAGTACAAGTGTAAGGTGTCCAACAAGGC
CCTGCCTGCCCCTATCGAGAAAACCATCAGCAAGGCCAAGGGCCAGCCCAGAGAGCCCCAGG
TGTACACCCTGCCCCCTAGCAGAGATGAGCTGACCAAGAACCAGGTGTCCCTGACCTGCCTG
GTGAAGGGCTTCTACCCCAGCGACATCGCCGTGGAGTGGGAGAGCAACGGCCAGCCCGAGAA
CAACTACAAGACCACCCCCCCTGTGCTGGACAGCGATGGCAGCTTCTTCCTGTACAGCAAGC
TGACCGTGGACAAGAGCAGATGGCAGCAGGGCAACGTGTTCAGCTGCTCCGTGATGCACGAG
GCCCTGCACAATCACTACACCCAGAAGAGCCTGAGCCTGTCCCCTGGCAAGACCGTGGCCGC
CCCCTCGGGATCCGACATCCAGATGACTCAGAGCCCCAGCAGCCTGAGCGCCAGCGTGGGCG
ATAGGGTGACCATTACCTGCAGGGCCAGCCAGAGCATCGACAGCTACCTGCACTGGTACCAG
CAGAAGCCCGGAAAGGCCCCAAGCTCCTGATCTACAGCGCCAGCGAGCTGCAGAGCGGCGT
GCCTAGCAGGTTTTCTGGCAGCGGCAGCGGCACCGACTTCACCCTGACCATCTCCAGCCTGC
AGCCCGAGGACTTCGCCACCTACTACTGCCAGCAGGTCGTGTGGAGGCCCTTCACCTTCGGC
CAGGGCACCAAGGTGGAGATCAAGAGG SEQ ID NO: 104
- protein sequence of BPC2626 heavy chain
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKTVAAPSGSDIQMTQSPSSLSASVGDRVTITCRASQSIDSYLHWYQ
QKPGKAPKLLIYSASELQSGVPSRFSGSGSGTDFTLTISSLQPEDFATYYCQQVVWRPFTFG
QGTKVEIKR SEQ ID NO: 105
- polynucleotide sequence of light chain
GACATCGTGCTGACCCAGAGCCCCTCTTCCCTGAGCGCAAGCGTGGGCGATAGGGTGACCAT
CACCTGCAAGGCCAGCCAGAGCGTGGACTACGACGGCGACAGCTACATGAACTGGTACCAGC
AGAAGCCCGGCAAGGCCCCCAAACTGCTGATCTACGCCGCCAGCAACCTCGAGTCAGGCATT
CCCAGCAGGTTTAGCGGCAGCGGCAGCGGCACCGACTTCACCTTCACAATCAGCAGCCTGCA
GCCCGAGGACATCGCCACCTACTACTGCCAGCAGAGCAACGAGGACCCTCCCACCTTCGGAC
AGGGCACCAAGGTCGAGATCAAGCGTACGGTGGCCGCCCCCAGCGTGTTCATCTTCCCCCCC
AGCGATGAGCAGCTGAAGAGCGGCACCGCCAGCGTGGTGTGTCTGCTGAACAACTTCTACCC
CCGGGAGGCCAAGGTGCAGTGGAAGGTGGACAATGCCCTGCAGAGCGGCAACAGCCAGGAGA
GCGTGACCGAGCAGGACAGCAAGGACTCCACCTACAGCCTGAGCAGCACCCTGACCCTGAGC TABLE 14-continued Sequence listing AAGGCCGACTACGAGAAGCACAAGGTGTACGCCTGTGAGGTGACCCACCAGGGCCTGTCCAG
CCCCGTGACCAAGAGCTTCAACCGGGGCGAGTGC SEQ ID NO: 106
- polynucleotide sequence of BPC2651 heavy chain
CAGGTGACCCTGAGGGAGAGCGGCCCCGCCCTGGTGAAGCCCACCCAGACCCTGACCCTGAC
CTGCACCTTCAGCGGCTTTAGCCTCAGCACCTCCGGCATGGGCGTGAGCTGGATCAGGCAGC
CACCCGGCAAAGGCCTGGAGTGGCTGGCCCACATCTACTGGGACGACGACAAGAGGTACAAC
CCCAGCCTGAAGAGCCGGCTGACCATCAGCAAGGATACCAGCAGGAACCAGGTGGTGCTGAC
CATGACCAACATGGACCCCGTGGACACCGCTACCTACTACTGCGCCAGGAGGGAGACCGTCT
TCTACTGGTACTTCGACGTGTGGGGAAGGGGCACACTAGTGACCGTGTCCAGCGCCAGCACC
AAGGGCCCCAGCGTGTTCCCCCTGGCCCCCAGCAGCAAGAGCACCAGCGGCGGCACAGCCGC
CCTGGGCTGCCTGGTGAAGGACTACTTCCCCGAACCGGTGACCGTGTCCTGGAACAGCGGAG
CCCTGACCAGCGGCGTGCACACCTTCCCCGCCGTGCTGCAGAGCAGCGGCCTGTACAGCCTG
AGCAGCGTGGTGACCGTGCCCAGCAGCAGCCTGGGCACCCAGACCTACATCTGTAACGTGAA
CCACAAGCCCAGCAACACCAAGGTGGACAAGAAGGTGGAGCCCAAGAGCTGTGACAAGACCC
ACACCTGCCCCCCCTGCCCTGCCCCCGAGCTGCTGGGAGGCCCCAGCGTGTTCCTGTTCCCC
CCCAAGCCTAAGGACACCCTGATGATCAGCAGAACCCCCGAGGTGACCTGTGTGGTGGTGGA
TGTGAGCCACGAGGACCCTGAGGTGAAGTTCAACTGGTACGTGGACGGCGTGGAGGTGCACA
ATGCCAAGACCAAGCCCAGGGAGGAGCAGTACAACAGCACCTACCGGGTGGTGTCCGTGCTG
ACCGTGCTGCACCAGGATTGGCTGAACGGCAAGGAGTACAAGTGTAAGGTGTCCAACAAGGC
CCTGCCTGCCCCTATCGAGAAAACCATCAGCAAGGCCAAGGGCCAGCCCAGAGAGCCCCAGG
TGTACACCCTGCCCCCTAGCAGAGATGAGCTGACCAAGAACCAGGTGTCCCTGACCTGCCTG
GTGAAGGGCTTCTACCCCAGCGACATCGCCGTGGAGTGGGAGAGCAACGGCCAGCCCGAGAA
CAACTACAAGACCACCCCCCCTGTGCTGGACAGCGATGGCAGCTTCTTCCTGTACAGCAAGC
TGACCGTGGACAAGAGCAGATGGCAGCAGGGCAACGTGTTCAGCTGCTCCGTGATGCACGAG
GCCCTGCACAATCACTACACCCAGAAGAGCCTGAGCCTGTCCCCTGGCAAGGGATCTACCGT
GGCAGCACCATCCGGATCTACCGTAGCAGCACCATCCGGATCCGACATCCAGATGACTCAGA
GCCCCAGCAGCCTGAGCGCCAGCGTGGGCGATAGGGTGACCATTACCTGCAGGGCCAGCCAG
AGCATCGACAGCTACCTGCACTGGTACCAGCAGAAGCCCGGAAAGGCCCCCAAGCTCCTGAT
CTACAGCGCCAGCGAGCTGCAGAGCGGCGTGCCTAGCAGGTTTTCTGGCAGCGGCAGCGGCA
CCGACTTCACCCTGACCATCTCCAGCCTGCAGCCCGAGGACTTCGCCACCTACTACTGCCAG
CAGGTCGTGTGGAGGCCCTTCACCTTCGGCCAGGGCACCAAGGTGGAGATCAAGAGG SEQ ID NO: 107
- protein sequence of BPC2651 heavy chain
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSTVAAPSGSTVAAPSGSDIQMTQSPSSLSASVGDRVTITCRASQ
SIDSYLHWYQQKPGKAPKLLIYSASELQSGVPSRFSGSGSGTDFTLTISSLQPEDFATYYCQ
QVVWRPFTFGQGTKVEIKR SEQ ID NO: 108
- polynucleotide sequence of BPC2652 heavy chain
CAGGTGACCCTGAGGGAGAGCGGCCCCGCCCTGGTGAAGCCCACCCAGACCCTGACCCTGAC
CTGCACCTTCAGCGGCTTTAGCCTCAGCACCTCCGGCATGGGCGTGAGCTGGATCAGGCAGC
CACCCGGCAAAGGCCTGGAGTGGCTGGCCCACATCTACTGGGACGACGACAAGAGGTACAAC
CCCAGCCTGAAGAGCCGGCTGACCATCAGCAAGGATACCAGCAGGAACCAGGTGGTGCTGAC
CATGACCAACATGGACCCCGTGGACACCGCTACCTACTACTGCGCCAGGAGGGAGACCGTCT
TCTACTGGTACTTCGACGTGTGGGGAAGGGGCACACTAGTGACCGTGTCCAGCGCCAGCACC
AAGGGCCCCAGCGTGTTCCCCCTGGCCCCCAGCAGCAAGAGCACCAGCGGCGGCACAGCCGC
CCTGGGCTGCCTGGTGAAGGACTACTTCCCCGAACCGGTGACCGTGTCCTGGAACAGCGGAG
CCCTGACCAGCGGCGTGCACACCTTCCCCGCCGTGCTGCAGAGCAGCGGCCTGTACAGCCTG
AGCAGCGTGGTGACCGTGCCCAGCAGCAGCCTGGGCACCCAGACCTACATCTGTAACGTGAA
CCACAAGCCCAGCAACACCAAGGTGGACAAGAAGGTGGAGCCCAAGAGCTGTGACAAGACCC
ACACCTGCCCCCCCTGCCCTGCCCCCGAGCTGCTGGGAGGCCCCAGCGTGTTCCTGTTCCCC
CCCAAGCCTAAGGACACCCTGATGATCAGCAGAACCCCCGAGGTGACCTGTGTGGTGGTGGA
TGTGAGCCACGAGGACCCTGAGGTGAAGTTCAACTGGTACGTGGACGGCGTGGAGGTGCACA
ATGCCAAGACCAAGCCCAGGGAGGAGCAGTACAACAGCACCTACCGGGTGGTGTCCGTGCTG
ACCGTGCTGCACCAGGATTGGCTGAACGGCAAGGAGTACAAGTGTAAGGTGTCCAACAAGGC
CCTGCCTGCCCCTATCGAGAAAACCATCAGCAAGGCCAAGGGCCAGCCCAGAGAGCCCCAGG
TGTACACCCTGCCCCCTAGCAGAGATGAGCTGACCAAGAACCAGGTGTCCCTGACCTGCCTG
GTGAAGGGCTTCTACCCCAGCGACATCGCCGTGGAGTGGGAGAGCAACGGCCAGCCCGAGAA
CAACTACAAGACCACCCCCCCTGTGCTGGACAGCGATGGCAGCTTCTTCCTGTACAGCAAGC
TGACCGTGGACAAGAGCAGATGGCAGCAGGGCAACGTGTTCAGCTGCTCCGTGATGCACGAG
GCCCTGCACAATCACTACACCCAGAAGAGCCTGAGCCTGTCCCCTGGCAAGGGATCTACCGT
GGCAGCACCATCAGGATCTACCGTGGCAGCACCATCAGGTTCAACAGTAGCTGCTCCTTCTG
GATCCGACATCCAGATGACTCAGAGCCCCAGCAGCCTGAGCGCCAGCGTGGGCGATAGGGTG
ACCATTACCTGCAGGGCCAGCCAGAGCATCGACAGCTACCTGCACTGGTACCAGCAGAAGCC
CGGAAAGGCCCCCAAGCTCCTGATCTACAGCGCCAGCGAGCTGCAGAGCGGCGTGCCTAGCA
GGTTTTCTGGCAGCGGCAGCGGCACCGACTTCACCCTGACCATCTCCAGCCTGCAGCCCGAG
GACTTCGCCACCTACTACTGCCAGCAGGTCGTGTGGAGGCCCTTCACCTTCGGCCAGGGCAC
CAAGGTGGAGATCAAGAGG TABLE 14-continued Sequence listing SEQ ID NO: 109
- protein sequence of BPC2652 heavy chain
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSTVAAPSGSTVAAPSGSTVAAPSGSDIQMTQSPSSLSASVGDRV
TITCRASQSIDSYLHWYQQKPGKAPKLLIYSASELQSGVPSRFSGSGSGTDFTLTISSLQPE
DFATYYCQQVVWRPFTFGQGTKVEIKR SEQ ID NO: 110
- polynucleotide sequence of BPC2653 heavy chain
CAGGTGACCCTGAGGGAGAGCGGCCCCGCCCTGGTGAAGCCCACCCAGACCCTGACCCTGAC
CTGCACCTTCAGCGGCTTTAGCCTCAGCACCTCCGGCATGGGCGTGAGCTGGATCAGGCAGC
CACCCGGCAAAGGCCTGGAGTGGCTGGCCCACATCTACTGGGACGACGACAAGAGGTACAAC
CCCAGCCTGAAGAGCCGGCTGACCATCAGCAAGGATACCAGCAGGAACCAGGTGGTGCTGAC
CATGACCAACATGGACCCCGTGGACACCGCTACCTACTACTGCGCCAGGAGGGAGACCGTCT
TCTACTGGTACTTCGACGTGTGGGGAAGGGGCACACTAGTGACCGTGTCCAGCGCCAGCACC
AAGGGCCCCAGCGTGTTCCCCCTGGCCCCCAGCAGCAAGAGCACCAGCGGCGGCACAGCCGC
CCTGGGCTGCCTGGTGAAGGACTACTTCCCCGAACCGGTGACCGTGTCCTGGAACGGGGA
CCCTGACCAGCGGCGTGCACACCTTCCCCGCCGTGCTGCAGAGCAGCGGCCTGTACAGCCTG
AGCAGCGTGGTGACCGTGCCCAGCAGCAGCCTGGGCACCCAGACCTACATCTGTAACGTGAA
CCACAAGCCCAGCAACACCAAGGTGGACAAGAAGGTGGAGCCCAAGAGCTGTGACAAGACCC
ACACCTGCCCCCCCTGCCCTGCCCCCGAGCTGCTGGGAGGCCCCAGCGTGTTCCTGTTCCCC
CCCAAGCCTAAGGACACCCTGATGATCAGCAGAACCCCCGAGGTGACCTGTGTGGTGGTGGA
TGTGAGCCACGAGGACCCTGAGGTGAAGTTCAACTGGTACGTGGACGGCGTGGAGGTGCACA
ATGCCAAGACCAAGCCCAGGGAGGAGCAGTACAACAGCACCTACCGGGTGGTGTCCGTGCTG
ACCGTGCTGCACCAGGATTGGCTGAACGGCAAGGAGTACAAGTGTAAGGTGTCCAACAAGGC
CCTGCCTGCCCCTATCGAGAAAACCATCAGCAAGGCCAAGGGCCAGCCCAGAGAGCCCCAGG
TGTACACCCTGCCCCCTAGCAGAGATGAGCTGACCAAGAACCAGGTGTCCCTGACCTGCCTG
GTGAAGGGCTTCTACCCCAGCGACATCGCCGTGGAGTGGGAGAGCAACGGCCAGCCCGAGAA
CAACTACAAGACCACCCCCCCTGTGCTGGACAGCGATGGCAGCTTCTTCCTGTACAGCAAGC
TGACCGTGGACAAGAGCAGATGGCAGCAGGGCAACGTGTTCAGCTGCTCCGTGATGCACGAG
GCCCTGCACAATCACTACACCCAGAAGAGCCTGAGCCTGTCCCCTGGCAAGGGATCTACCGT
GGCAGCACCATCAGGATCTACCGTGGCAGCACCATCAGGTTCAACAGTAGCTGCTCCTTCTG
GTTCAACAGTAGCTGCTCCTTCTGGATCCGACATCCAGATGACTCAGAGCCCCAGCAGCCTG
AGCGCCAGCGTGGGCGATAGGGTGACCATTACCTGCAGGGCCAGCCAGAGCATCGACAGGTA
CCTGCACTGGTACCAGCAGAAGCCCGGAAAGGCCCCCAAGCTCCTGATCTACAGCGCCAGCG
AGCTGCAGAGCGGCGTGCCTAGCAGGTTTTCTGGCAGCGGCAGCGGCACCGACTTCACCCTG
ACCATCTCCAGCCTGCAGCCCGAGGACTTCGCCACCTACTACTGCCAGCAGGTCGTGTGGAG
GCCCTTCACCTTCGGCCAGGGCACCAAGGTGGAGATCAAGAGG SEQ ID NO: 111
- protein sequence of BPC2653 heavy chain
QVTLRESGPALVKPTQTLTLTCTFSGFSLSTSGMGVSWIRQPPGKGLEWLAHIYWDDDKRYN
PSLKSRLTISKDTSRNQVVLTMTNMDPVDTATYYCARRETVFYWYFDVWGRGTLVTVSSAST
KGPSVFPLAPSSKSTSGGTAALGCLVKDYFPEPVTVSWNSGALTSGVHTFPAVLQSSGLYSL
SSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSVL
TVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPGKGSTVAAPSGSTVAAPSGSTVAAPSGSTVAAPSGSDIQMTQSPSSL
SASVGDRVTITCRASQSIDSYLHWYQQKPGKAPKLLIYSASELQSGVPSRFSGSGSGTDFTL
TISSLQPEDFATYYCQQVVWRPFTFGQGTKVEIKR

SEQ ID NO: 112
TVAAPSTVAAPSGS

SEQ ID NO: 113
TVAAPSTVAAPSTVAAPSGS

SEQ ID NO: 114
TVAAPSTVAAPSTVAAPSTVAAPSGS

The invention claimed is:

1. An antigen-binding protein comprising a protein scaffold which is linked to one or more epitope-binding domains wherein the antigen-binding protein has at least two antigen binding sites at least one of which is from an epitope binding domain and at least one of which is from a paired VH/VL domain wherein the epitope binding domain is linked to the protein scaffold by a linker comprising SEQ ID NO: 78.

2. An antigen-binding protein according to claim 1 wherein the linker is (TGLDSP)$_n$(GS)$_m$, wherein n=1-10, and m=0-4.

3. The antigen-binding protein according to claim 1 wherein at least one epitope binding domain is an immunoglobulin single variable domain.

4. The antigen-binding protein according to claim 3 wherein the immunoglobulin single variable domain is a human dAb.

5. The antigen-binding protein of claim 1 wherein the antigen binding protein has specificity for more than one antigen.

6. The antigen-binding protein according to claim 1 wherein the first binding site has specificity for a first epitope on an antigen and the second binding site has specificity for a second epitope on the same antigen.

7. The antigen-binding protein according to claim 1 wherein the antigen-binding protein is capable of binding IL-13 or TNFα or IL1-R.

8. The antigen-binding protein according to claim 1 wherein the antigen-binding protein is capable of binding two or more antigens selected from IL-13, IL-5, and IL-4, VEGF, IGF-1R and EGFR.

9. The antigen-binding protein according to claim 1 wherein the protein scaffold is an Ig scaffold.

10. The antigen-binding protein according to claim 1 wherein at least one of the epitope binding domains binds human serum albumin.

11. A pharmaceutical composition comprising an antigen binding protein of claim 1 and a pharmaceutically acceptable carrier.

12. The antigen-binding protein according to claim 2 wherein at least one epitope binding domain is an immunoglobulin single variable domain.

13. The antigen-binding protein according to claim 12 wherein the immunoglobulin single variable domain is a human dAb.

14. The antigen-binding protein of claim 2 wherein the antigen binding protein has specificity for more than one antigen.

15. The antigen-binding protein according to claim 2 wherein the first binding site has specificity for a first epitope on an antigen and the second binding site has specificity for a second epitope on the same antigen.

16. The antigen-binding protein according to claim 2 wherein the antigen-binding protein is capable of binding IL-13 or TNFα or IL1-R.

17. The antigen-binding protein according to claim 2 wherein the antigen-binding protein is capable of binding two or more antigens selected from IL-13, IL-5, and IL-4, VEGF, IGF-1R and EGFR.

18. The antigen-binding protein according to claim 2 wherein the protein scaffold is an Ig scaffold.

19. The antigen-binding protein according to claim 2 wherein at least one of the epitope binding domains binds human serum albumin.

20. A pharmaceutical composition comprising an antigen binding protein of claim 2 and a pharmaceutically acceptable carrier.

21. An antigen-binding protein comprising a protein scaffold which is linked to one or more epitope-binding domains wherein the antigen-binding protein has at least two antigen binding sites at least one of which is from an epitope binding domain and at least one of which is from a paired VH/VL domain wherein the epitope binding domain is linked to the protein scaffold by a linker comprising SEQ ID NO: 77.

22. An antigen-binding protein according to claim 21 wherein the linker is (TVSDVP)$_n$(GS)$_m$, wherein n=1-10, and m=0-4.

23. The antigen-binding protein according to claim 21 wherein at least one epitope binding domain is an immunoglobulin single variable domain.

24. The antigen-binding protein according to claim 23 wherein the immunoglobulin single variable domain is a human dAb.

25. The antigen-binding protein of claim 21 wherein the antigen binding protein has specificity for more than one antigen.

26. The antigen-binding protein according to claim 21 wherein the first binding site has specificity for a first epitope on an antigen and the second binding site has specificity for a second epitope on the same antigen.

27. The antigen-binding protein according to claim 21 wherein the antigen-binding protein is capable of binding IL-13 or TNFα or IL1-R.

28. The antigen-binding protein according to claim 21 wherein the antigen-binding protein is capable of binding two or more antigens selected from IL-13, IL-5, and IL-4, VEGF, IGF-1R and EGFR.

29. The antigen-binding protein according to claim 21 wherein the protein scaffold is an Ig scaffold.

30. The antigen-binding protein according to claim 21 wherein at least one of the epitope binding domains binds human serum albumin.

31. A pharmaceutical composition comprising an antigen binding protein of claim 21 and a pharmaceutically acceptable carrier.

32. The antigen-binding protein according to claim 22 wherein at least one epitope binding domain is an immunoglobulin single variable domain.

33. The antigen-binding protein according to claim 22 wherein the immunoglobulin single variable domain is a human dAb.

34. The antigen-binding protein of claim 22 wherein the antigen binding protein has specificity for more than one antigen.

35. The antigen-binding protein according to claim 22 wherein the first binding site has specificity for a first epitope on an antigen and the second binding site has specificity for a second epitope on the same antigen.

36. The antigen-binding protein according to claim 22 wherein the antigen-binding protein is capable of binding IL-13 or TNFα or IL1-R.

37. The antigen-binding protein according to claim 22 wherein the antigen-binding protein is capable of binding two or more antigens selected from IL-13, IL-5, and IL-4, VEGF, IGF-1R and EGFR.

38. The antigen-binding protein according to claim 22 wherein the protein scaffold is an Ig scaffold.

39. The antigen-binding protein according to claim 22 wherein at least one of the epitope binding domains binds human serum albumin.

40. A pharmaceutical composition comprising an antigen binding protein of claim 22 and a pharmaceutically acceptable carrier.

\* \* \* \* \*